(12) United States Patent
Guo et al.

(10) Patent No.: US 7,329,673 B2
(45) Date of Patent: Feb. 12, 2008

(54) ACYLATED SPIROPIPERIDINE DERIVATIVES AS MELANOCORTIN-4 RECEPTOR AGONISTS

(75) Inventors: Liangqin Guo, Edison, NJ (US); Shuwen He, Edison, NJ (US); Tianying Jian, Westfield, NJ (US); Yingjie Lai, Edison, NJ (US); Jian Liu, Edison, NJ (US); Ravi P. Nargund, East Brunswick, NJ (US); Iyassu K. Sebhat, New York, NY (US); Feroze Ujjainwalla, Scotch Plains, NJ (US); Zhixiong Ye, Princeton, NJ (US); Jonathan R. Young, Kendall Park, NJ (US)

(73) Assignee: Merck & Co., Inc., Rahway, NJ (US)

( * ) Notice: Subject to any disclaimer, the term of this patent is extended or adjusted under 35 U.S.C. 154(b) by 142 days.

(21) Appl. No.: 10/548,350

(22) PCT Filed: Mar. 31, 2004

(86) PCT No.: PCT/US2004/009751

§ 371 (c)(1),
(2), (4) Date: Sep. 7, 2005

(87) PCT Pub. No.: WO2004/089307

PCT Pub. Date: Oct. 21, 2004

(65) Prior Publication Data

US 2006/0183904 A1    Aug. 17, 2006

Related U.S. Application Data

(60) filed as application No. PCT/US04/09751 on Mar. 31, 2004.

(60) Provisional application No. 60/460,293, filed on Apr. 4, 2003.

(51) Int. Cl.
*A61K 31/438* (2006.01)
*C07D 221/20* (2006.01)
*C07D 401/02* (2006.01)

(52) U.S. Cl. ............................. 514/278; 546/17; 546/18
(58) Field of Classification Search ................ 514/278; 546/17, 18
See application file for complete search history.

(56) References Cited

U.S. PATENT DOCUMENTS

| 5,804,578 | A | 9/1998 | Chakravarty et al. |
| 6,166,037 | A | 12/2000 | Budhu et al. |
| 6,410,548 | B2 * | 6/2002 | Nargund et al. ............ 514/278 |

FOREIGN PATENT DOCUMENTS

| EP | 0444945 | 4/1991 |
| EP | 0450761 | 9/1991 |
| EP | 0431943 | 12/1991 |
| EP | 1460073 | 9/2004 |
| GB | 2309458 | 7/1997 |
| WO | WO 94/07496 | 4/1994 |
| WO | WO 95/25443 | 9/1995 |
| WO | WO 99/64002 | 8/1999 |
| WO | WO 99/65494 | 12/1999 |
| WO | WO 00/51607 | 9/2000 |
| WO | WO 00/51608 | 9/2000 |
| WO | WO 01/70337 | 9/2001 |
| WO | WO 02/067869 | 9/2002 |
| WO | WO 02/068387 | 9/2002 |
| WO | WO 02/085354 | 10/2002 |
| WO | WO 03/000677 | 1/2003 |
| WO | WO 2004/069798 | 8/2004 |
| WO | WO 2004/083208 | 9/2004 |
| WO | WO 2005/030210 | 4/2005 |
| WO | WO 2005/046682 | 5/2005 |

OTHER PUBLICATIONS

Kopelman, Nature, vol. 404 (2000) pp. 635-543, "Obesity as a medical problem".
Hill et al., Science, vol. 280 (1998), pp. 1371-1374, "Environmental contributions to the obesity epidemic".
Wessells et al., J. of Urology, vol. 160(2), (1998), pp. 389-393, "Synthetic melanotropic peptide initiates erections in men with psychogenic erectile dynfunction . . . ".
Giraudo et al., Brain Research, vol. 809 (1998), pp. 302-306, "Feeding effects of hypothalamic injection of melanocortin 4 receptor ligands".
Wessells et al., Urology (2000), vol. 56, pp. 641-646, "Effect of an alpha-melanocyte stimulating hormone analog on penile erection and sexual desire in men with organic erectile dysfunction".
Dorr et al., Life Sciences, vol. 58 (1996), pp. 1777-1784, "Evaluation of melanotan-II, a superpotent cyclic melanotropic peptide in a pilot phase-I clinical study".
Moreland et al., Life Sciences, vol. 62 (1998), pp. 309-318, "Sildenafil, a novel inhibitor of phosphodiesterase type 5 in human corpus cavernosum smooth muscle cells".
Gingell et al., Exp. Opin. Ther. Patents (1999), vol. 9(12), pp. 1689-1696, "Emerging pharmacological therapies for erectile dysfunction".
Dinsmore et al., BMJ, vol. 318 (1999), pp. 387-390, "ABC of sexual health: Erectile dysfunction".
Chen et al., Cell, vol. 91 (1997), pp. 789-798, "Exocrine gland dysfunction in MC5-R-deficient mice: . . . ".

(Continued)

*Primary Examiner*—Charanjit S. Aulakh
(74) *Attorney, Agent, or Firm*—Richard C. Billups; Baerbel R. Brown; Catherine D. Fitch

(57) ABSTRACT

Certain novel N-acylated spiropiperidine derivatives are agonists of the human melanocortin receptor(s) and, in particular, are selective agonists of the human melanocortin-4 receptor (MC-4R). They are therefore useful for the treatment, control, or prevention of diseases and disorders responsive to the activation of MC-4R, such as obesity, diabetes, sexual dysfunction, including erectile dysfunction and female sexual dysfunction.

22 Claims, No Drawings

OTHER PUBLICATIONS

Kask et al., Biochem. & Biophys. Res. Comm., vol. 245 (1998), pp. 90-93, "Selective antagonist for the melanocortin 4 receptor (HS014) increases food intake in free-feeding rats".

Huszar et al., Cell, vol. 88 (1997), pp. 131-141, "Targeted disruption of the melanocortin-4 receptor results in obesity in mice".

Peptides: Frontiers of Peptide Science, Fifteenth American Peptide Symposium, Jun. 14-19, 1997 (Nashville, TN).

Heaton et al., Int'l J. of Impotence Research, vol. 9 (1997), pp. 115-121, "A therapeutic taxonomy of treatments for erectile dysfunction: An evolutionary imperative".

Corcos et al., Society for Neuroscience, vol. 23 (1997), Abstract 267.9, "HP 228 is a potent agonist of melanocortin receptor 4, and significantly attenuates obesity and diabetes in Zucker fatty rats".

* cited by examiner

ACYLATED SPIROPIPERIDINE DERIVATIVES AS MELANOCORTIN-4 RECEPTOR AGONISTS

CROSS-REFERENCE TO RELATED APPLICATIONS

This application is a U.S. National Phase application under 35 U.S.C. §371 of PCT Application No. PCT/US04/009751, filed Mar. 31, 2004, which claims priority under 35 U.S.C. §119 from U.S. Provisional Application No. 60/460,293, filed Apr. 4, 2003.

FIELD OF THE INVENTION

The present invention relates to acylated spiropiperidine derivatives, their synthesis, and their use as melanocortin receptor (MC-R) agonists. More particularly, the compounds of the present invention are selective agonists of the melanocortin-4 receptor (MC-4R) and are thereby useful for the treatment of disorders responsive to the activation of MC-4R, such as obesity, diabetes, male sexual dysfunction, and female sexual dysfunction.

BACKGROUND OF THE INVENTION

Obesity, which can be defined as a body weight more than 20% above the ideal body weight, is a major health concern in Western societies. It is estimated that about 97 million adults in the United States are overweight or obese. Obesity is the result of a positive energy balance, as a consequence of increased ratio of caloric intake to energy expenditure. Epidemiological studies have shown that increasing degrees of overweight and obesity are important predictors of decreased life expectancy. Obesity causes or exacerbates many health problems, both independently and in association with other diseases. The medical problems associated with obesity, which can be serious and life-threatening, include hypertension; type 2 diabetes mellitus; elevated plasma insulin concentrations; insulin resistance; dyslipidemias; hyperlipidemia; endometrial, breast, prostate and colon cancer; osteoarthritis; respiratory complications, such as obstructive sleep apnea; cholelithiasis; gallstones; arterioscelerosis; heart disease; abnormal heart rhythms; and heart arrythmias (Kopelman, P. G., Nature 404, 635-643 (2000)). Obesity is further associated with premature death and with a significant increase in mortality and morbidity from stroke, myocardial infarction, congestive heart failure, coronary heart disease, and sudden death.

In the vast majority of obese individuals, the cause of the excess adiposity is not immediately apparent. A currently accepted working hypothesis is that obesity is the result of a maladaptation of the innate metabolic response to environmental challenges such as unlimited availability of low cost/energy dense foods and sedentariness (Hill et al., Science 1998; 280:1371). The study of energy intake in free living humans has met with only limited success and definitive experimental evidence that hyperphagia causes most forms of human obesity is lacking. Following the discovery of leptin, the interest in the neurohormonal regulation of food intake has regained momentum. However, while much knowledge has been gained on the regulation of food intake in rodents and other animal species, the understanding of the neurophysiology of feeding behavior in humans remains extremely limited.

Pro-opiomelanocortin (POMC) derived peptides are known to affect food intake. Several lines of evidence support the notion that the G-protein coupled receptors (GPCRs) of the melanocortin receptor (MC-R) family, several of which are expressed in the brain, are the targets of POMC derived peptides involved in the control of food intake and metabolism. A specific single MC-R that may be targeted for the control of obesity has not yet been identified, although evidence has been presented that MC-4R signalling is important in mediating feed behavior (S. Q. Giraudo et al., "Feeding effects of hypothalamic injection of melanocortin-4 receptor ligands," Brain Research, 80: 302-306 (1998)).

Evidence for the involvement of MC-R's in obesity includes: i) the agouti ($A^{vy}$) mouse which ectopically expresses an antagonist of the MC-1R, MC-3R and -4R is obese, indicating that blocking the action of these three MC-R's can lead to hyperphagia and metabolic disorders; ii) MC-4R knockout mice (D. Huszar et al., Cell, 88: 131-141 (1997)) recapitulate the phenotype of the agouti mouse and these mice are obese; iii) the cyclic heptapeptide MT-II (a non-selective MC-1R, -3R, -4R, and -5R agonist) injected intracerebroventricularly (ICV) in rodents, reduces food intake in several animal feeding models (NPY, ob/ob, agouti, fasted) while ICV injected SHU-9119 (MC-3R and 4R antagonist; MC-1R and -5R agonist) reverses this effect and can induce hyperphagia; iv) chronic intraperitoneal treatment of Zucker fatty rats with an α-NDP-MSH derivative (HP228) has been reported to activate MC-1R, -3R, -4R, and -5R and to attenuate food intake and body weight gain over a 12-week period (I. Corcos et al., "HP228 is a potent agonist of melanocortin receptor-4 and significantly attenuates obesity and diabetes in Zucker fatty rats," Society for Neuroscience Abstracts, 23: 673 (1997)).

Five distinct MC-R's have thus far been identified, and these are expressed in different tissues. MC-1R was initially characterized by dominant gain of function mutations at the Extension locus, affecting coat color by controlling phaeomelanin to eumelanin conversion through control of tyrosinase. MC-1R is mainly expressed in melanocytes. MC-2R is expressed in the adrenal gland and represents the ACTH receptor. MC-3R is expressed in the brain, gut, and placenta and may be involved in the control of food intake and thermogenesis. MC-4R is uniquely expressed in the brain, and its inactivation was shown to cause obesity (A. Kask, et al., "Selective antagonist for the melanocortin-4 receptor (HS014) increases food intake in free-feeding rats," Biochem. Biophys. Res. Commun., 245: 90-93 (1998)). MC-5R is expressed in many tissues, including white fat, placenta and exocrine glands. A low level of expression is also observed in the brain. MC-5R knockout mice reveal reduced sebaceous gland lipid production (Chen et al., Cell, 91: 789-798 (1997)).

Weight loss drugs that are currently used to treat obesity have limited efficacy and significant side effects. Studies of the weight loss medications orlistat (Davidson, M. H. et al. (1999) JAMA 281:235-42), dexfenfluramine (Guy Grand, B. et al. (1989) Lancet 2:1142-5), sibutramine (Bray, G. A. et al. (1999) Obes. Res. &:189-98) and phentermine (Douglas, A. et al. (1983) Int. J. Obes. 7:591-5) have demonstrated a limited weight loss of about 5%-10% of body weight for drug compared to placebo. The side effects of these drugs and anti-obesity agents further limit their use. Dexfenfluramine was withdrawn from the market because of suspected heart valvulopathy; orlistat is limited by gastrointestinal side effects; the use of topiramate is limited by central nervous system effects; and the use of sibutramine is limited by its cardiovascular side effects which have led to reports of deaths and its withdrawal from the market in Italy.

There is a need for a weight loss treatment with enhanced efficacy and fewer undesirable side effects. The instant invention addresses this problem by providing melanocortin receptor (MC-R) agonists, and in particular selective agonists of the melanocortin-4 receptor (MC-4R), useful in the treatment and prevention of obesity and obesity-related disorders, including diabetes.

Melanocortin receptor involvement in male and female sexual dysfunction has also been reported.

Erectile dysfunction denotes the medical condition of inability to achieve penile erection sufficient for successful sexual intercourse. The term "impotence" is oftentimes employed to describe this prevalent condition. Approximately 140 million men worldwide, and, according to a National Institutes of Health study, about 30 million American men suffer from impotency or erectile dysfunction. It has been estimated that the latter number could rise to 47 million men by the year 2000. Erectile dysfunction can arise from either organic or psychogenic causes, with about 20% of such cases being purely psychogenic in origin. Erectile dysfunction increases from 40% at age 40, to 67% at age 75, with over 75% occurring in men over the age of 50. In spite of the frequent occurrence of this condition, only a small number of patients have received treatment because existing treatment alternatives, such as injection therapies, penile prosthesis implantation, and vacuum pumps, have been uniformly disagreeable [for a discussion, see "ABC of sexual health—erectile dysfunction," *Brit. Med. J.* 318: 387-390 (1999)]. Only more recently have more viable treatment modalities become available, in particular orally active agents, such as sildenafil citrate, marketed by Pfizer under the brand name of Viagra®. (See "Emerging pharmacological therapies for erectile dysfunction," *Exp. Opin. Ther. Patents* 9: 1689-1696 (1999)). Sildenafil is a selective inhibitor of type V phosphodiesterase (PDE-V), a cyclic-GMP-specific phosphodiesterase isozyme [see R. B. Moreland et al., "Sildenafil: A Novel Inhibitor of Phosphodiesterase Type 5 in Human Corpus Cavernosum Smooth Muscle Cells," *Life Sci.*, 62: 309-318 (1998)]. Prior to the introduction of Viagra on the market, less than 10% of patients suffering from erectile dysfunction received treatment. Sildenafil is also being evaluated in the clinic for the treatment of female sexual dysfunction.

The regulatory approval of Viagra® for the oral treatment of erectile dysfunction has invigorated efforts to discover even more effective methods to treat erectile dysfunction. Several additional selective PDE-V inhibitors are in clinical trials. UK-114542 is a sildenafil backup from Pfizer with supposedly improved properties. Tadalafil or IC-351 (ICOS Corp.) is claimed to have greater selectivity for PDE-V over PDE-VI than sildenafil. Other PDE-V inhibitors include vardenafil from Bayer, M-54033 and M-54018 from Mochida Pharmaceutical Co., and E-4010 from Eisai Co., Ltd.

Other pharmacological approaches to the treatment of erectile dysfunction have been described [see, e.g., "Latest Findings on the Diagnosis and Treatment of Erectile Dysfunction," *Drug News & Perspectives,* 9: 572-575 (1996); "Oral Pharmacotherapy in Erectile Dysfunction," *Current Opinion in Urology,* 7: 349-353 (1997)]. A product under clinical development by Zonagen is an oral formulation of the alpha-adrenoceptor antagonist phentolamine mesylate under the brand name of Vasomax®. Vasomax® is also being evaluated for the treatment of female sexual dysfunction.

Drugs to treat erectile dysfunction act either peripherally or centrally. They are also classified according to whether they "initiate" a sexual response or "facilitate" a sexual response to prior stimulation [for a discussion, see "A Therapeutic Taxonomy of Treatments for Erectile Dysfunction: An Evolutionary Imperative," *Int. J. Impotence Res.*, 9: 115-121 (1997)]. While sildenafil and phentolamine act peripherally and are considered to be "enhancers" or "facilitators" of the sexual response to erotic stimulation, sildenafil appears to be efficacious in both mild organic and psychogenic erectile dysfunction. Sildenafil has an onset of action of 30-60 minutes after an oral dose with the effect lasting about 4 hours, whereas phentolamine requires 5-30 minutes for onset with a duration of 2 hours. Although sildenafil is effective in a majority of patients, it takes a relatively long time for the compound to show the desired effects. The faster-acting phentolamine appears to be less effective and to have a shorter duration of action than sildenafil. Oral sildenafil is effective in about 70% of men who take it, whereas an adequate response with phentolamine is observed in only 35-40% of patients. Both compounds require erotic stimulation for efficacy. Since sildenafil indirectly increases blood flow in the systemic circulation by enhancing the smooth muscle relaxation effects of nitric oxide, it is contraindicated for patients with unstable heart conditions or cardiovascular disease, in particular patients taking nitrates, such as nitroglycerin, to treat angina. Other adverse effects associated with the clinical use of sildenafil include headache, flushing, dyspepsia, and "abnormal vision," the latter the result of inhibition of the type VI phosphodiesterase isozyme (PDE-VI), a cyclic-GMP-specific phosphodiesterase that is concentrated in the retina. "Abnormal vision" is defined as a mild and transient "bluish" tinge to vision, but also an increased sensitivity to light or blurred vision.

Synthetic melanocortin receptor agonists (melanotropic peptides) have been found to initiate erections in men with psychogenic erectile dysfunction [See H. Wessells et al. "Synthetic Melanotropic Peptide Initiates Erections in Men With Psychogenic Erectile Dysfunction: Double-Blind, Placebo Controlled Crossover Study," *J. Urol.*, 160: 389-393 (1998); *Fifteenth American Peptide Symposium*, Jun. 14-19, 1997 (Nashville Tenn.)]. Activation of melanocortin receptors of the brain appears to cause normal stimulation of sexual arousal. In the above study, the centrally acting α-melanocyte-stimulating hormone analog, melanotan-II (MT-II), exhibited a 75% response rate, similar to results obtained with apomorphine, when injected intramuscularly or subcutaneously to males with psychogenic erectile dysfunction. MT-II is a synthetic cyclic heptapeptide, Ac-Nle-c[Asp-His-DPhe-Arg-Trp-Lys]-$NH_2$, which contains the 4-10 melanocortin receptor binding region common to α-MSH and adrenocorticotropin, but with a lactam bridge. It is a non-selective MC-1R, -3R, -4R, and -5R agonist (Dorr et al., *Life Sciences*, Vol. 58, 1777-1784, 1996). MT-II (also referred to as PT-14) (Erectide®) is presently in clinical development by Palatin Technologies, Inc. and TheraTech, Inc. as a non-penile subcutaneous injection formulation. It is considered to be an "initiator" of the sexual response. The time to onset of erection with this drug is relatively short (10-20 minutes) with a duration of action approximately 2.5 hours. Adverse reactions observed with MT-II include nausea, flushing, loss of appetite, stretching, and yawning and may be the result of activation of MC-1R, MC-2R, MC-3R, and/or MC-5R. MT-II must be administered parenterally, such as by subcutaneous, intravenous, or intramuscular route, since it is not absorbed into the systemic circulation when given by the oral route.

MT-II's erectogenic properties apparently are not limited to cases of psychogenic erectile dysfunction in that men with a variety of organic risk factors developed penile erections upon subcutaneous injection of the compound; moreover, the level of sexual desire was significantly higher after MT-II administration than after placebo [see H. Wessells, "Effect of an Alpha-Melanocyte Stimulating Hormone Analog on Penile Erection and Sexual Desire in Men with Organic Erectile Dysfunction," *Urology*, 56: 641-646 (2000)].

Compositions of melanotropic peptides and methods for the treatment of psychogenic erectile dysfunction are disclosed in U.S. Pat. No. 5,576,290, assigned to Competitive Technologies. Methods of stimulating sexual response in females using melanotropic peptides have been disclosed in U.S. Pat. No. 6,051,555.

Spiropiperidine, piperidine and piperazine derivatives have been disclosed in WO 99/64002 (16 Dec. 1999); WO 00/74679 (14 Dec. 2000); WO 01/70708 (27 Sep. 2001); WO 01/70337 (27 Sep. 2001); WO 01/91752 (6 Dec. 2001); WO 02/059095 (1 Aug. 2002); WO 02/059107 (1 Aug. 2002); WO 02/059108 (1 Aug. 2002); WO 02/059117 (1 Aug. 2002); WO 02/068387 (6 Sep. 2002); WO 02/068388 (6 Sep. 2002); WO 03/007949 (30 Jan. 2003); and WO 03/009847 (6 Feb. 2003) as agonists of the melanocortin receptor(s) and particularly as selective agonists of the MC-4R receptor and thereby useful for the treatment of diseases and disorders, such as obesity, diabetes, and sexual dysfunction, including erectile dysfunction and female sexual dysfunction.

Because of the unresolved deficiencies of the various pharmacological agents discussed above, there is a continuing need in the medical arts for improved methods and compositions to treat individuals suffering from psychogenic and/or organic sexual dysfunction. Such methods should have wider applicability, enhanced convenience and ease of compliance, short onset of action, reasonably long duration of action, and minimal side effects with few contraindications, as compared to agents now available.

It is therefore an object of the present invention to provide acylated spiropiperidine derivatives which are melanocortin receptor agonists and thereby useful to treat obesity, diabetes, male sexual dysfunction, and female sexual dysfunction.

It is another object of the present invention to provide acylated spiropiperidine derivatives which are selective agonists of the melanocortin-4 (MC-4R) receptor.

It is another object of the present invention to provide pharmaceutical compositions comprising the melanocortin receptor agonists of the present invention with a pharmaceutically acceptable carrier.

It is another object of the present invention to provide methods for the treatment or prevention of disorders, diseases, or conditions responsive to the activation of the melanocortin-4 receptor in a mammal in need thereof by administering the compounds and pharmaceutical compositions of the present invention.

It is another object of the present invention to provide methods for the treatment or prevention of obesity, diabetes mellitus, male sexual dysfunction, and female sexual dysfunction by administering the compounds and pharmaceutical compositions of the present invention to a mammal in need thereof.

It is another object of the present invention to provide methods for the treatment of erectile dysfunction by administering the compounds and pharmaceutical compositions of the present invention to a mammal in need thereof.

These and other objects will become readily apparent from the detailed description that follows.

SUMMARY OF THE INVENTION

The present invention relates to novel N-acylated spiropiperidines of structural formula I and formula VI:

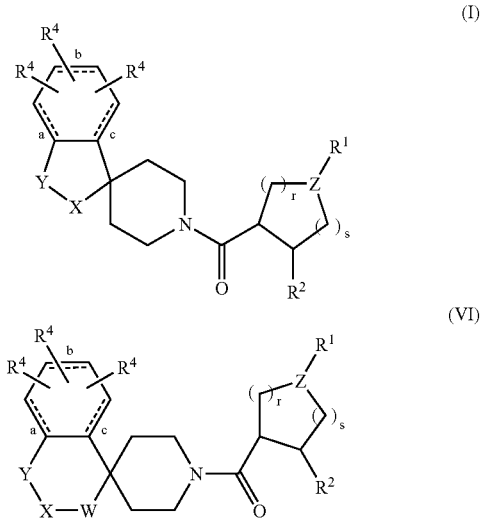

These acylated spiropiperidine derivatives are effective as melanocortin receptor agonists and are particularly effective as selective melanocortin-4 receptor (MC-4R) agonists. They are therefore useful for the treatment and/or prevention of disorders responsive to the activation of MC-4R, such as obesity, diabetes as well as male and female sexual dysfunction, in particular, male erectile dysfunction.

The present invention also relates to pharmaceutical compositions comprising the compounds of the present invention and a pharmaceutically acceptable carrier.

The present invention also relates to methods for the treatment or prevention of disorders, diseases, or conditions responsive to the activation of the melanocortin-4 receptor in a mammal in need thereof by administering the compounds and pharmaceutical compositions of the present invention.

The present invention also relates to methods for the treatment or prevention of obesity, diabetes mellitus, male sexual dysfunction, and female sexual dysfunction by administering the compounds and pharmaceutical compositions of the present invention.

The present invention also relates to methods for treating erectile dysfunction by administering the compounds and pharmaceutical compositions of the present invention.

The present invention also relates to methods for treating erectile dysfunction by administering the compounds of the present invention in combination with a therapeutically effective amount of another agent known to be useful to treat the condition.

The present invention also relates to methods for treating or preventing obesity by administering the compounds of the present invention in combination with a therapeutically effective amount of another agent known to be useful to prevent or treat the condition.

The present invention also relates to methods for treating or preventing diabetes by administering the compounds of the present invention in combination with a therapeutically effective amount of another agent known to be useful to prevent or treat the condition.

DETAILED DESCRIPTION OF THE INVENTION

The present invention relates to N-acylated spiropiperidine derivatives useful as melanocortin receptor agonists, in particular, as selective MC-4R agonists. Compounds of the present invention are described by structural formula I:

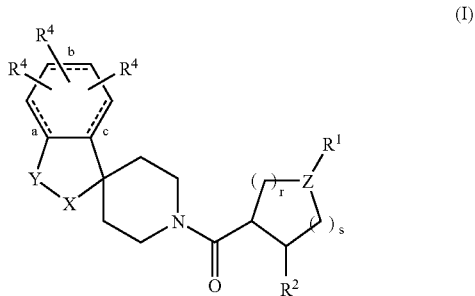

or a pharmaceutically acceptable salt thereof; wherein
a, b and c are all single bonds or all double bonds;
X and Y taken together form —C($R^6$)=C($R^6$)—, or
one of X and Y is C($R^6$)$_2$ and the other is selected from the group consisting of
 (1) C($R^6$)$_2$,
 (2) N($R^6$),
 (3) C(O),
 (4) C=N($R^6$)
 (5) oxygen,
 (6) sulfur,
 (7) S(O), and
 (8) S(O)$_2$,
or one of X and Y is N($R^9$) and the other is selected from the group consisting of
 (1) C($R^6$)$_2$,
 (2) N($R^9$),
 (3) C(O),
 (4) C=N($R^6$)
 (5) oxygen,
 (6) sulfur,
 (7) S(O), and
 (8) S(O)$_2$,
or one of X and Y is C(O) and the other is selected from the group consisting of
 (1) C($R^6$)$_2$,
 (2) N($R^6$),
 (3) C(O),
 (4) C=N($R^6$)
 (5) oxygen, and
 (6) sulfur;
Z is independently selected from the group consisting of
 (1) CH,
 (2) C($R^1$), and
 (3) N;
$R^1$ is selected from the group consisting of
 (1) hydrogen,
 (2) —(CH$_2$)$_n$—NR$^7$R$^8$,
 (3) amidino,
 (4) $C_{1-4}$ alkyliminoyl,
 (5) $C_{1-10}$ alkyl, (6) —(CH$_2$)$_n$—$C_{3-7}$ cycloalkyl,
 (7) —(CH$_2$)$_n$-phenyl,
 (8) —(CH$_2$)$_n$-naphthyl, and
 (9) —(CH$_2$)$_n$-heteroaryl,
wherein phenyl, naphthyl, and heteroaryl are unsubstituted or substituted with one to three groups independently selected from $R^3$, and wherein alkyl and cycloalkyl are unsubstituted or substituted with one to three groups independently selected from $R^3$ and oxo;
$R^2$ is selected from the group consisting of
 (1) phenyl,
 (2) naphthyl, and
 (3) heteroaryl,
wherein phenyl, naphthyl, and heteroaryl are unsubstituted or substituted with one to three groups independently selected from $R^3$;
each $R^3$ is independently selected from the group consisting of
 (1) $C_{1-6}$ alkyl,
 (2) —(CH$_2$)$_n$-phenyl,
 (3) —(CH$_2$)$_n$-naphthyl,
 (4) —(CH$_2$)$_n$-heteroaryl,
 (5) —(CH$_2$)$_n$$C_{2-7}$ heterocycloalkyl,
 (6) —(CH$_2$)$_n$$C_{3-7}$ cycloalkyl,
 (7) halogen,
 (8) OR$^5$,
 (9) —(CH$_2$)$_n$N(R$^5$)$_2$,
 (10) —(CH$_2$)$_n$C≡N,
 (11) —(CH$_2$)$_n$CO$_2$R$^5$,
 (12) NO$_2$,
 (13) —(CH$_2$)$_n$NR$^5$S(O)$_p$R$^5$
 (14) —(CH$_2$)$_n$S(O)$_p$N(R$^5$)$_2$,
 (15) —(CH$_2$)$_n$S(O)$_p$R$^5$,
 (16) —(CH$_2$)$_n$NR$^5$C(O)N(R$^5$)$_2$,
 (17) —(CH$_2$)$_n$C(O)N(R$^5$)$_2$,
 (18) —(CH$_2$)$_n$NR$^5$C(O)R$^5$,
 (19) —(CH$_2$)$_n$NR$^5$CO$_2$R$^5$,
 (20) —(CH$_2$)$_n$NR$^5$C(O)-heteroaryl,
 (21) —(CH$_2$)$_n$C(O)NR$^5$N(R$^5$)$_2$,
 (22) —(CH$_2$)$_n$C(O)NR$^5$NR$^5$C(O)R$^5$,
 (23) O(CH$_2$)$_n$C(O)N(R$^5$)$_2$,
 (24) CF$_3$,
 (25) CH$_2$CF$_3$,
 (26) OCF$_3$, and
 (27) OCH$_2$CF$_3$;
wherein phenyl, naphthyl, and heteroaryl are unsubstituted or substituted with one to three substituents independently selected from halogen, hydroxy, $C_{1-4}$ alkyl, trifluoromethyl, and $C_{1-4}$ alkoxy, and wherein alkyl, cycloalkyl, heterocycloalkyl, and (CH$_2$) are unsubstituted or substituted with one to three substituents independently selected from halogen, hydroxy, oxo, $C_{1-4}$ alkyl, trifluoromethyl, and $C_{1-4}$ alkoxy, or wherein two substituents when on the same methylene (CH$_2$) group are taken together with the carbon atom to which they are attached to form a cyclopropyl group;
each $R^4$ is independently selected from the group consisting of
 (1) hydrogen,
 (2) $C_{1-8}$ alkyl,
 (3) —(CH$_2$)$_n$-phenyl,
 (4) —(CH$_2$)$_n$-naphthyl,
 (5) —(CH$_2$)$_n$-heteroaryl,
 (6) —(CH$_2$)$_n$$C_{2-7}$ heterocycloalkyl,
 (7) —(CH$_2$)$_n$$C_{3-7}$ cycloalkyl,
 (8) halogen,
 (9) OR$^5$,

(10) —$(CH_2)_nN(R^5)_2$,
(11) —$(CH_2)_nC{\equiv}N$,
(12) —$(CH_2)_nC(O)OR^5$,
(13) —$(CH_2)_nOC(O)R^5$,
(14) $NO_2$,
(15) —$(CH_2)_nNR^5S(O)_pR^5$,
(16) —$(CH_2)_nN(S(O)_pR^5)_2$,
(17) —$(CH_2)_nS(O)_pN(R^5)_2$,
(18) —$(CH_2)_nS(O)_pR^5$,
(19) —$(CH_2)_nNR^5C(O)N(R^5)_2$,
(20) —$(CH_2)_nC(O)N(R^5)_2$,
(21) —$(CH_2)_nNR^5C(O)R^5$,
(22) —$(CH_2)_nNR^5CO_2R^5$,
(23) —$(CH_2)_nNR^5C(O)$-heteroaryl,
(24) —$(CH_2)_nC(O)NR^5N(R^5)_2$,
(25) —$(CH_2)_nC(O)NR^5NR^5C(O)R^5$,
(26) $O(CH_2)_nC(O)N(R^5)_2$,
(27) $CF_3$,
(28) $CH_2CF_3$,
(29) $OCF_3$, and
(30) $OCH_2CF_3$;

wherein phenyl, naphthyl, and heteroaryl are unsubstituted or substituted with one to three substituents independently selected from halogen, hydroxy, $C_{1-4}$ alkyl, trifluoromethyl, and $C_{1-4}$ alkoxy, and wherein alkyl, cycloalkyl, heterocycloalkyl, and ($CH_2$) are unsubstituted or substituted with one to three substituents independently selected from halogen, hydroxy, oxo, $C_{1-4}$ alkyl, trifluoromethyl, and $C_{1-4}$ alkoxy, or wherein two substituents when on the same methylene ($CH_2$) group are taken together with the carbon atom to which they are attached to form a cyclopropyl group;

each $R^5$ is independently selected from the group consisting of
(1) hydrogen,
(2) $C_{1-8}$ alkyl,
(3) —$(CH_2)_nC_{3-7}$ cycloalkyl,
(4) —$(CH_2)_nC_{2-7}$ heterocycloalkyl,
(5) —$(CH_2)_n$-phenyl,
(6) —$(CH_2)_n$-naphthyl,
(7) —$(CH_2)_n$-heteroaryl, and
(8) —$(CH_2)_nC_{3-7}$ bicycloalkyl;

wherein alkyl, phenyl, heteroaryl, heterocycloalkyl, naphthyl, cycloalkyl, bicycloalkyl and ($CH_2$) are unsubstituted or substituted with one to three groups independently selected from halogen, $C_{1-4}$ alkyl, hydroxy, and $C_{1-4}$ alkoxy, or wherein two $R^5$ groups together with the atom to which they are attached form a 4- to 8-membered mono- or bicyclic ring system optionally containing an additional heteroatom selected from O, S, and —$NC_{1-4}$ alkyl;

each $R^6$ is independently selected from the group consisting of
(1) hydrogen,
(2) $C_{1-6}$ alkyl,
(3) —$(CH_2)_nC_{3-7}$ cycloalkyl,
(4) —$(CH_2)_nC_{2-7}$ heterocycloalkyl,
(5) —$(CH_2)_n$-phenyl,
(6) —$(CH_2)_n$-naphthyl,
(7) —$(CH_2)_n$-heteroaryl,
(8) —$(CH_2)_nC(O)R^5$,
(9) —$(CH_2)_nC(O)OR^5$,
(10) —$(CH_2)_nC(OH)R^5$,
(11) —$(CH_2)_nC(O)(CH_2)_n$—$N(R^5)_2$,
(12) —$(CH_2)_nC(O)(CH_2)_n$—$NR^7R^8$,
(13) —$(CH_2)_m$—$OR^5$,
(14) —$(CH_2)_n$—$OC(O)R^5$,
(15) —$(CH_2)_n$—O—$(CH_2)_n$—$N(R^5)_2$,
(16) —$(CH_2)_n$CN,
(17) —$(CH_2)_nN(R^5)_2$,
(18) —$(CH_2)_nN(R^5)C(O)R^5$,
(19) —$(CH_2)_nN(C(O)R^5)_2$,
(20) —$(CH_2)_nN(R^5)C(O)OR^5$,
(21) —$(CH_2)_nN(C(O)OR^5)_2$,
(22) —$(CH_2)_nN(R^5)C(O)(CH_2)_nN(R^5)_2$,
(23) —$(CH_2)_nN(R^5)$—S(O)—$C_{1-8}$ alkyl,
(24) —$(CH_2)_nN(R^5)$—$S(O)_2$—$C_{1-8}$ alkyl,
(25) —$(CH_2)_n$—S—$R^5$,
(26) —$(CH_2)_n$—S(O)—$R^5$, and
(27) —$(CH_2)_n$—$S(O)_2$—$R^5$, wherein phenyl, naphthyl, and heteroaryl are unsubstituted or substituted with one to three groups independently selected from $R^3$, and wherein alkyl, cycloalkyl and heterocycloalkyl are unsubstituted or substituted with one to three groups independently selected from $R^3$ and oxo, and wherein any methylene ($CH_2$) in $R^6$ is unsubstituted or substituted with one to two groups independently selected from halogen, hydroxy, and $C_{1-4}$ alkyl; or wherein two $R^6$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from $R^3$ and oxo;

each $R^7$ and $R^8$ is independently selected from the group consisting of
(1) hydrogen,
(2) amidino,
(3) $C_{1-4}$ alkyliminoyl,
(4) $C_{1-10}$ alkyl,
(5) —$(CH_2)_n$—$C_{3-7}$ cycloalkyl,
(6) —$(CH_2)_n$-phenyl,
(7) —$(CH_2)_n$-naphthyl, and
(8) —$(CH_2)_n$-heteroaryl, wherein phenyl, naphthyl, and heteroaryl are unsubstituted or substituted with one to three groups independently selected from $R^3$, and wherein alkyl and cycloalkyl are unsubstituted or substituted with one to three groups independently selected from $R^3$ and oxo;

each $R^9$ is independently selected from the group consisting of
(1) hydrogen,
(2) $C_1$ alkyl,
(3) —$(CH_2)_nC_{3-7}$ cycloalkyl,
(4) —$(CH_2)_nC_{2-7}$ heterocycloalkyl,
(5) —$(CH_2)_n$-phenyl,
(6) —$(CH_2)_n$-naphthyl,
(7) —$(CH_2)_n$-heteroaryl,
(8) —$(CH_2)_nC(O)R^5$,
(9) —$(CH_2)_nC(O)OR^5$,
(10) —$(CH_2)_nC(OH)R^5$,
(11) —$(CH_2)_nC(O)(CH_2)_n$—$N(R^5)_2$,
(12) —$(CH_2)_nC(O)(CH_2)_n$—$NR^7R^8$,
(13) —$(CH_2)_m$—$OR^5$,
(14) —$(CH_2)_m$—$OC(O)R^5$,
(15) —$(CH_2)_m$—O—$(CH_2)_n$—$N(R^5)_2$,
(16) —$(CH_2)_m$CN,
(17) —$(CH_2)_mN(R^5)_2$,
(18) —$(CH_2)_mN(R^5)C(O)R^5$,
(19) —$(CH_2)_mN(C(O)R^5)_2$,
(20) —$(CH_2)_mN(R^5)C(O)OR^5$,
(21) —$(CH_2)_mN(C(O)OR^5)_2$,
(22) —$(CH_2)_mN(R^5)C(O)(CH_2)_nN(R^5)_2$,

(23) —$(CH_2)_mN(R^5)$—$S(O)$—$C_{1-8}$ alkyl,
(24) —$(CH_2)_mN(R^5)$—$S(O)_2$—$C_{1-8}$ alkyl,
(25) —$(CH_2)_m$—$S$—$R^5$,
(26) —$(CH_2)_n$—$S(O)$—$R^5$, and
(27) —$(CH_2)_n$—$S(O)_2$—$R^5$, wherein phenyl, naphthyl, and heteroaryl are unsubstituted or substituted with one to three groups independently selected from $R^3$, and wherein alkyl, cycloalkyl and heterocycloalkyl are unsubstituted or substituted with one to three groups independently selected from $R^3$ and oxo, and wherein any methylene ($CH_2$) in $R^9$ is unsubstituted or substituted with one to two groups independently selected from halogen, hydroxy, and $C_{1-4}$ alkyl; or wherein two $R^9$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from $R^3$ and oxo;

r is 1 or 2;
s is 1 or 2;
n is 0, 1, 2, or 3;
m is 1, 2, or 3; and
p is 0, 1, or 2.

In one embodiment of the compounds of structural formula I and formula VI, $R^1$ is selected from the group consisting of hydrogen, $C_{1-6}$ alkyl, —$(CH_2)_{0-1}$—$C_{3-6}$ cycloalkyl, —$(CH_2)_{0-1}$-phenyl, and —$(CH_2)_{0-1}$—$NR^7R^8$; wherein phenyl is unsubstituted or substituted with one to three groups independently selected from $R^3$, and wherein alkyl and cycloalkyl are optionally substituted with one to three groups independently selected from $R^3$ and oxo. In a class of this embodiment, $R^1$ is selected from the group consisting of hydrogen, and $C_{1-6}$ alkyl, and alkyl is optionally substituted with one to three groups independently selected from $R^3$ and oxo. In another class of this embodiment, $R^1$ is —$(CH_2)_{0-1}$—$NR^7R^8$.

In a second embodiment of the compounds of structural formula I and formula VI, $R^2$ is phenyl or thienyl optionally substituted with one to three groups independently selected from $R^3$. In a class of this embodiment, $R^2$ is phenyl optionally substituted with one to three groups independently selected from $R^3$.

In a third embodiment of the compounds of structural formula I and formula VI, $R^3$ is selected from the group consisting of $C_{1-6}$ alkyl, —$(CH_2)_n$-phenyl, —$(CH_2)_n$-heteroaryl, —$(CH_2)_nC_{2-7}$ heterocycloalkyl, —$(CH_2)_nC_{3-7}$ cycloalkyl, halogen, $OR^5$, —$(CH_2)_nN(R^5)_2$, —$(CH_2)_nCO_2R^5$, $NO_2$, and $CF_3$, wherein phenyl, naphthyl, and heteroaryl are unsubstituted or substituted with one to three substituents independently selected from halogen, hydroxy, $C_{1-4}$ allyl, trifluoromethyl, and $C_{1-4}$ alkoxy, and wherein alkyl, cycloalkyl, heterocycloalkyl, and ($CH_2$) are unsubstituted or substituted with one to three substituents independently selected from halogen, hydroxy, oxo, $C_{1-4}$ alkyl, trifluoromethyl, and $C_{1-4}$ alkoxy, or wherein two substituents when on the same methylene ($CH_2$) group are taken together with the carbon atom to which they are attached to form a cyclopropyl group. In a class of this embodiment, $R^3$ is selected from the group consisting of $C_{1-6}$ alkyl, halogen, and $OR^5$, wherein alkyl is unsubstituted or substituted with one to three substituents independently selected from halogen, hydroxy, oxo, $C_{1-4}$ alkyl, trifluoromethyl, and $C_{1-4}$ alkoxy.

In a fourth embodiment of the compounds of structural formula I and formula VI, $R^4$ is selected from the group consisting of hydrogen, $C_{1-6}$ alkyl, halogen, $OR^5$, —$(CH_2)_nN(R^5)_2$, —$(CH_2)_nC\equiv N$, —$(CH_2)_nNR^5SO_2R^5$, —$(CH_2)_nN(S(O)_2R^5)_2$, and —$(CH_2)_nNR^5C(O)R^5$, wherein alkyl, and ($CH_2$) are unsubstituted or substituted with one to three substituents independently selected from halogen, hydroxy, oxo, $C_{1-4}$ alkyl, trifluoromethyl, and $C_{1-4}$ alkoxy, or wherein two substituents when on the same methylene ($CH_2$) group are taken together with the carbon atom to which they are attached to form a cyclopropyl group.

In a fifth embodiment of the compounds of structural formula I and formula VI, $R^6$ is independently selected from the group consisting of
(1) hydrogen,
(2) $C_{1-6}$ alkyl,
(3) —$(CH_2)_nC_{3-7}$ cycloalkyl,
(4) —$(CH_2)_n$-phenyl,
(5) —$(CH_2)_n$-heteroaryl,
(6) —$(CH_2)_nC(O)R^5$,
(7) —$(CH_2)_nC(O)OR^5$,
(8) —$(CH_2)_nC(OH)R^5$,
(9) —$(CH_2)_nC(O)(CH_2)_n$—$N(R^5)_2$,
(10) —$(CH_2)_nC(O)(CH_2)_n$—$NR^7R^8$,
(11) —$(CH_2)_n$—$OR^5$,
(12) —$(CH_2)_nOC(O)R^5$,
(13) —$(CH_2)_nO$—$(CH_2)_n$—$N(R^5)_2$,
(14) —$(CH_2)_nCN$,
(15) —$(CH_2)_nN(R^5)_2$,
(16) —$(CH_2)_nN(R^5)C(O)R^5$,
(17) —$(CH_2)_nN(C(O)R^5)_2$,
(18) —$(CH_2)_nN(R^5)C(O)OR^5$,
(19) —$(CH_2)_nN(R^5)C(O)(CH_2)_nN(R^5)_2$,
(20) —$(CH_2)_nN(R^5)$—$S(O)_2$—$C_{1-8}$ alkyl,
(21) —$(CH_2)_n$—$S$—$R^5$,
(22) —$(CH_2)_n$—$S(O)$—$R^5$, and
(23) —$(CH_2)_n$—$S(O)_2$—$R^5$, wherein phenyl, naphthyl, and heteroaryl are unsubstituted or substituted with one to three groups independently selected from $R^3$, and wherein alkyl and cycloalkyl are unsubstituted or substituted with one to three groups independently selected from $R^3$ and oxo, and wherein any methylene ($CH_2$) in $R^6$ is unsubstituted or substituted with one to two groups independently selected from halogen, hydroxy, and $C_{1-4}$ alkyl, or wherein two $R^6$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from $R^3$ and oxo.

In a sixth embodiment of the compounds of structural formula I and formula VI, X and Y are independently selected from the group consisting of oxygen, $C(R^6)_2$, $N(R^9)$, and $C(O)$, or X and Y taken together form —$C(R^6)$=$C(R^6)$—. In a class of this embodiment, X and Y are independently selected from the group consisting of $C(R^6)_2$, $N(R^9)$, and $C(O)$, or X and Y taken together form —$C(R^6)$=$C(R^6)$—. In a subclass of this class, X is selected from the group consisting of $N(R^9)$, $C(R^6)_2$, and $C(O)$, or X and Y taken together form —$C(R^6)$=$C(R^6)$—. In another subclass of this class, Y is selected from the group consisting of $C(R^6)_2$, and $N(R^9)$, or X and Y taken together form —$C(R^6)$=$C(R^6)$—. In a seventh embodiment of compounds of formula I and formula VI, Z is N. In a class of this embodiment, Z is N and $R^1$ is selected from the group consisting of hydrogen, amidino, $C_{1-4}$ alkyliminoyl, $C_{1-10}$ alkyl, —$(CH_2)_n$—$C_{3-7}$ cycloalkyl, —$(CH_2)_n$-phenyl, —$(CH_2)_n$-naphthyl, and —$(CH_2)_n$-heteroaryl.

In an eighth embodiment of compounds of formula I and formula VI, Z is CH. In a class of this embodiment, Z is CH and $R^1$ is —$(CH_2)_n$—$NR^7R^8$.

In yet a further embodiment of the compounds of the present invention, there are provided compounds of structural formula IIa or IIb of the indicated relative stereochemical configurations having the trans orientation of the $R^2$ and piperidinecarbonyl substituents:

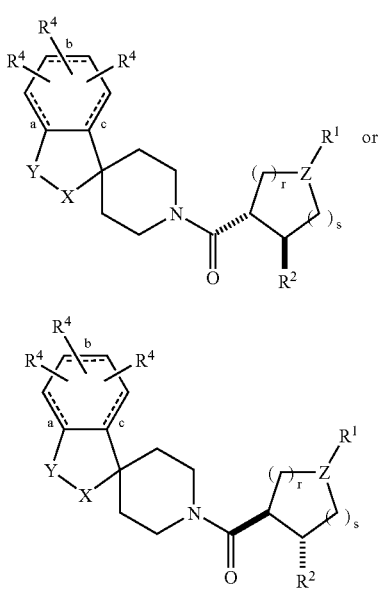

or a pharmaceutically acceptable salt thereof; wherein
a, b and c are all single bonds or all double bonds;
X and Y taken together form $C(R^6)=C(R^6)$—, or
one of X and Y is $C(R^6)_2$ and the other is selected from the group consisting of
(1) $C(R^6)_2$,
(2) $N(R^6)$,
(3) C(O),
(4) $C=N(R^6)$
(5) oxygen,
(6) sulfur,
(7) S(O), and
(8) $S(O)_2$,
or one of X and Y is $N(R^9)$ and the other is selected from the group consisting of
(1) $C(R^6)_2$,
(2) $N(R^9)$,
(3) C(O),
(4) $C=N(R^6)$
(5) oxygen,
(6) sulfur,
(7) S(O), and
(8) $S(O)_2$,
or one of X and Y is C(O) and the other is selected from the group consisting of
(1) $C(R^6)_2$,
(2) $N(R^6)$,
(3) C(O),
(4) $C=N(R^6)$
(5) oxygen, and
(6) sulfur;

Z is independently selected from the group consisting of
(1) CH,
(2) $C(R^1)$, and
(3) N;
$R^1$ is selected from the group consisting of hydrogen, amidino, $C_{1-4}$ alkyliminoyl, $C_{1-6}$ alkyl, $C_{5-6}$ cycloalkyl, —$(CH_2)_{0-1}$ phenyl, —$(CH_2)_{0-1}$ heteroaryl, and —$(CH_2)_{0-1}$—$NR^7R^8$; wherein phenyl and heteroaryl are unsubstituted or substituted with one to three groups independently selected from $R^3$, and wherein alkyl and cycloalkyl are unsubstituted or substituted with one to three groups independently selected from $R^3$ and oxo;
$R^2$ is phenyl or thienyl optionally substituted with one to three groups independently selected from $R^3$;
each $R^3$ is independently selected from the group consisting of
(1) $C_{1-6}$ alkyl,
(2) —$(CH_2)_n$-phenyl,
(3) —$(CH_2)_n$-naphthyl,
(4) —$(CH_2)_n$-heteroaryl,
(5) —$(CH_2)_nC_{2-7}$ heterocycloalkyl,
(6) —$(CH_2)_nC_{3-7}$ cycloalkyl,
(7) halogen,
(8) $OR^5$,
(9) —$(CH_2)_nN(R^5)_2$,
(10) —$(CH_2)_nC\equiv N$,
(11) —$(CH_2)_nCO_2R^5$,
(12) $NO_2$,
(13) —$(CH_2)_nNR^5S(O)_pR^5$
(14) —$(CH_2)_nS(O)_pN(R^5)_2$,
(15) —$(CH_2)_nS(O)_pR^5$,
(16) —$(CH_2)_nNR^5C(O)N(R^5)_2$,
(17) —$(CH_2)_nC(O)N(R^5)_2$,
(18) —$(CH_2)_nNR^5C(O)R^5$,
(19) —$(CH_2)_nNR^5CO_2R^5$,
(20) —$(CH_2)_nNR^5C(O)$-heteroaryl,
(21) —$(CH_2)_nC(O)NR^5N(R^5)_2$,
(22) —$(CH_2)_nC(O)NR^5NR^5C(O)R^5$,
(23) $O(CH_2)_nC(O)N(R^5)_2$,
(24) $CF_3$,
(25) $CH_2CF_3$,
(26) $OCF_3$, and
(27) $OCH_2CF_3$;
wherein phenyl, naphthyl, and heteroaryl are unsubstituted or substituted with one to three substituents independently selected from halogen, hydroxy, $C_{1-4}$ alkyl, trifluoromethyl, and $C_{1-4}$ alkoxy, and wherein alkyl, cycloalkyl, heterocycloalkyl, and ($CH_2$) are unsubstituted or substituted with one to three substituents independently selected from halogen, hydroxy, oxo, $C_{1-4}$ alkyl, trifluoromethyl, and $C_{1-4}$ alkoxy, or wherein two substituents when on the same methylene ($CH_2$) group are taken together with the carbon atom to which they are attached to form a cyclopropyl group;
each $R^4$ is independently selected from the group consisting of
(1) hydrogen,
(2) $C_{1-8}$ alkyl,
(3) —$(CH_2)_n$-phenyl,
(4) —$(CH_2)_n$-naphthyl,
(5) —$(CH_2)_n$-heteroaryl,
(6) —$(CH_2)_nC_{2-7}$ heterocycloalkyl,
(7) —$(CH_2)_nC_{3-7}$ cycloalkyl,
(8) halogen,
(9) $OR^5$,
(10) —$(CH_2)_nN(R^5)_2$,
(11) —$(CH_2)_nC\equiv N$,

(12) —$(CH_2)_nC(O)OR^5$,
(13) —$(CH_2)_nOC(O)R^5$,
(14) $NO_2$,
(15) —$(CH_2)_nNR^5S(O)_pR^5$,
(16) —$(CH_2)_nN(S(O)_pR^5)_2$,
(17) —$(CH_2)_nS(O)_pN(R^5)_2$,
(18) —$(CH_2)_nS(O)_pR^5$,
(19) —$(CH_2)_nNR^5C(O)N(R^5)_2$,
(20) —$(CH_2)_nC(O)N(R^5)_2$,
(21) —$(CH_2)_nNR^5C(O)R^5$,
(22) —$(CH_2)_nNR^5CO_2R^5$,
(23) —$(CH_2)_nNR^5C(O)$-heteroaryl,
(24) —$(CH_2)_nNR^5C(O)NR^5N(R^5)_2$,
(25) —$(CH_2)_nC(O)NR^5NR^5C(O)R^5$,
(26) $O(CH_2)_nC(O)N(R^5)_2$,
(27) $CF_3$,
(28) $CH_2CF_3$,
(29) $OCF_3$, and
(30) $OCH_2CF_3$;
wherein phenyl, naphthyl, and heteroaryl are unsubstituted or substituted with one to three substituents independently selected from halogen, hydroxy, $C_{1-4}$ alkyl, trifluoromethyl, and $C_{1-4}$ alkoxy, and wherein alkyl, cycloalkyl, heterocycloalkyl, and $(CH_2)$ are unsubstituted or substituted with one to three substituents independently selected from halogen, hydroxy, oxo, $C_{1-4}$ alkyl, trifluoromethyl, and $C_{1-4}$ alkoxy, or wherein two substituents when on the same methylene $(CH_2)$ group are taken together with the carbon atom to which they are attached to form a cyclopropyl group;

each $R^5$ is independently selected from the group consisting of
(1) hydrogen,
(2) $C_{1-8}$ alkyl,
(3) —$(CH_2)_nC_{3-7}$ cycloalkyl,
(4) —$(CH_2)_nC_{2-7}$ heterocycloalkyl,
(5) —$(CH_2)_n$-phenyl,
(6) —$(CH_2)_n$-naphthyl,
(7) —$(CH_2)_n$-heteroaryl, and
(8) —$(CH_2)_nC_{3-7}$ bicycloalkyl;
wherein alkyl, phenyl, heteroaryl, heterocycloalkyl, naphthyl, cycloalkyl, bicycloalkyl and $(CH_2)$ are unsubstituted or substituted with one to three groups independently selected from halogen, $C_{1-4}$ alkyl, hydroxy, and $C_{1-4}$ alkoxy, or wherein two $R^5$ groups together with the atom to which they are attached form a 4- to 8-membered mono- or bicyclic ring system optionally containing an additional heteroatom selected from O, S, and —$NC_{1-4}$ alkyl;

each $R^6$ is independently selected from the group consisting of
(1) hydrogen,
(2) $C_{1-6}$ alkyl,
(3) —$(CH_2)_nC_{3-7}$ cycloalkyl,
(4) —$(CH_2)_nC_{2-7}$ heterocycloalkyl,
(5) —$(CH_2)_n$-phenyl,
(6) —$(CH_2)_n$-naphthyl,
(7) —$(CH_2)_n$-heteroaryl,
(8) —$(CH_2)_nC(O)R^5$,
(9) —$(CH_2)_nC(O)OR^5$,
(10) —$(CH_2)_nC(OH)R^5$,
(11) —$(CH_2)_nC(O)(CH_2)_n$—$N(R^5)_2$,
(12) —$(CH_2)_nC(O)(CH_2)_n$—$NR^7R^8$,
(13) —$(CH_2)_n$—$OR^5$,
(14) —$(CH_2)_n$—$OC(O)R^5$,
(15) —$(CH_2)_n$—$O$—$(CH_2)_n$—$N(R^5)_2$,
(16) —$(CH_2)_nCN$,
(17) —$(CH_2)_nN(R^5)_2$,
(18) —$(CH_2)_nN(R^5)C(O)R^5$,
(19) —$(CH_2)_nN(C(O)R^5)_2$,
(20) —$(CH_2)_nN(R^5)C(O)OR^5$,
(21) —$(CH_2)_nN(C(O)OR^5)_2$,
(22) —$(CH_2)_nN(R^5)C(O)(CH_2)_nN(R^5)_2$,
(23) —$(CH_2)_nN(R^5)$—$S(O)$—$C_{1-8}$ alkyl,
(24) —$(CH_2)_nN(R^5)$—$S(O)_2$—$C_{1-8}$ alkyl,
(25) —$(CH_2)_n$—$S$—$R^5$,
(26) —$(CH_2)_n$—$S(O)$—$R^5$, and
(27) —$(CH_2)_n$—$S(O)_2$—$R^5$,
wherein phenyl, naphthyl, and heteroaryl are unsubstituted or substituted with one to three groups independently selected from $R^3$, and wherein alkyl, cycloalkyl and heterocycloalkyl are unsubstituted or substituted with one to three groups independently selected from $R^3$ and oxo, and wherein any methylene $(CH_2)$ in $R^6$ is unsubstituted or substituted with one to two groups independently selected from halogen, hydroxy, and $C_{1-4}$ alkyl, or wherein two $R^6$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from $R^3$ and oxo;

each $R^7$ and $R^8$ is independently selected from the group consisting of
(1) hydrogen,
(2) amidino,
(3) $C_{1-4}$ alkyliminoyl,
(4) $C_{1-10}$ alkyl,
(5) —$(CH_2)_n$—$C_{3-7}$ cycloalkyl,
(6) —$(CH_2)_n$-phenyl,
(7) —$(CH_2)_n$-naphthyl, and
(8) —$(CH_2)_n$-heteroaryl,
wherein phenyl, naphthyl, and heteroaryl are unsubstituted or substituted with one to three groups independently selected from $R^3$, and wherein alkyl and cycloalkyl are unsubstituted or substituted with one to three groups independently selected from $R^3$ and oxo;

each $R^9$ is independently selected from the group consisting of
(1) hydrogen,
(2) $C_{1-6}$ alkyl,
(3) —$(CH_2)_nC_{3-7}$ cycloalkyl,
(4) —$(CH_2)_nC_{2-7}$ heterocycloalkyl,
(5) —$(CH_2)_n$-phenyl,
(6) —$(CH_2)_n$-naphthyl,
(7) —$(CH_2)_n$-heteroaryl,
(8) —$(CH_2)_nC(O)R^5$,
(9) —$(CH_2)_nC(O)OR^5$,
(10) —$(CH_2)_nC(OH)R^5$,
(11) —$(CH_2)_nC(O)(CH_2)_n$—$N(R^5)_2$,
(12) —$(CH_2)_nC(O)(CH_2)_n$—$NR^7R^8$,
(13) —$(CH_2)_m$—$OR^5$,
(14) —$(CH_2)_m$—$OC(O)R^5$,
(15) —$(CH_2)_m$—$O$—$(CH_2)_n$—$N(R^5)_2$,
(16) —$(CH_2)_mCN$,
(17) —$(CH_2)_mN(R^5)_2$,
(18) —$(CH_2)_mN(R^5)C(O)R^5$,
(19) —$(CH_2)_mN(C(O)R^5)_2$,
(20) —$(CH_2)_mN(R^5)C(O)OR^5$,
(21) —$(CH_2)_mN(C(O)OR^5)_2$,
(22) —$(CH_2)_mN(R^5)C(O)(CH_2)_nN(R^5)_2$,
(23) —$(CH_2)_mN(R^5)$—(O)—$C_{1-8}$ alkyl,
(24) —$(CH_2)_mN(R^5)$—$S(O)_2$—$C_{1-18}$ alkyl,

(25) —(CH$_2$)$_m$—S—R$^5$,
(26) —(CH$_2$)$_n$—S(O)—R$^5$, and
(27) —(CH$_2$)$_n$—S(O)$_2$—R$^5$, wherein phenyl, naphthyl, and heteroaryl are unsubstituted or substituted with one to three groups independently selected from R$^3$, and wherein alkyl, cycloalkyl and heterocycloalkyl are unsubstituted or substituted with one to three groups independently selected from R$^3$ and oxo, and wherein any methylene (CH$_2$) in R$^9$ is unsubstituted or substituted with one to two groups independently selected from halogen, hydroxy, and C$_{1-4}$ alkyl; or wherein two R$^9$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from R$^3$ and oxo;

r is 1 or 2;
s is 1 or 2;
n is 0, 1, 2, or 3;
m is 1, 2, or 3; and
p is 0, 1, or 2.

In yet a further embodiment of the compounds of the present invention, there are provided compounds of structural formula IIIa or IIIb of the indicated relative stereochemical configurations having the trans orientation of the phenyl and piperidinecarbonyl substituents:

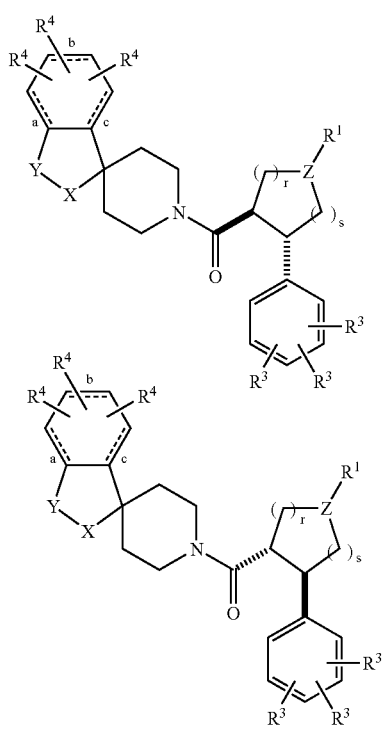

(IIIa)

(IIIb)

or a pharmaceutically acceptable salt thereof; wherein
a, b and c are all single bonds or all double bonds;
X and Y taken together form —C(R$^6$)=C(R$^6$)—, or
one of X and Y is C(R$^6$)$_2$ and the other is selected from the group consisting of
(1) C(R$^6$)$_2$,
(2) N(R$^6$),
(3) C(O),
(4) C=N(R$^6$)
(5) oxygen,
(6) sulfur,
(7) S(O), and
(8) S(O)$_2$, or one of X and Y is N(R$^9$) and the other is selected from the group consisting of
(1) C(R$^6$)$_2$,
(2) N(R$^9$),
(3) C(O),
(4) C=N(R$^6$)
(5) oxygen,
(6) sulfur,
(7) S(O), and
(8) S(O)$_2$, or one of X and Y is C(O) and the other is selected from the group consisting of
(1) C(R$^6$)$_2$,
(2) N(R$^6$),
(3) C(O),
(4) C=N(R$^6$)
(5) oxygen, and
(6) sulfur;

Z is independently selected from the group consisting of
(1) CH,
(2) C(R$^1$), and
(3) N;

R$^1$ is selected from the group consisting of hydrogen, C$_{1-4}$ alkyl, —(CH$_2$)$_{0-1}$-phenyl, and —(CH$_2$)$_{0-1}$—NR$^7$R$^8$;

each R$^3$ is independently selected from the group consisting of
(1) C$_{1-6}$ alkyl,
(2) —(CH$_2$)$_{0-1}$-phenyl,
(3) —(CH$_2$)$_{0-1}$-naphthyl,
(4) —(CH$_2$)$_{0-1}$-heteroaryl,
(5) —(CH$_2$)$_{0-1}$—C$_{2-7}$ heterocycloalkyl,
(6) —(CH$_2$)$_{0-1}$—C$_{3-7}$ cycloalkyl,
(7) halogen,
(8) OR$^5$,
(9) —(CH$_2$)$_{0-1}$—N(R$^5$)$_2$,
(10) —(CH$_2$)$_{0-1}$—C≡N,
(11) —(CH$_2$)$_{0-1}$—CO$_2$R$^5$,
(12) NO$_2$,
(13) —(CH$_2$)O—, —NR$^5$S(O)$_{1-2}$R$^5$,
(14) —(CH$_2$)$_{0-1}$—S(O)$_{1-2}$N(R$^5$)$_2$,
(15) —(CH$_2$)$_{0-1}$—S(O)$_{0-2}$R$^5$,
(16) —(CH$_2$)$_{0-1}$—NR$^5$C(O)N(R$^5$)$_2$,
(17) —(CH$_2$)$_{0-1}$—C(O)N(R$^5$)$_2$,
(18) —(CH$_2$)$_{0-1}$—NR$^5$C(O)R$^5$,
(19) —(CH$_2$)$_{0-1}$—NR$^5$CO$_2$R$^5$,
(20) —(CH$_2$)$_{0-1}$—NR$^5$C(O)-heteroaryl,
(21) —(CH$_2$)$_{0-1}$—C(O)NR$^5$N(R$^5$)$_2$,
(22) —(CH$_2$)$_{0-1}$—C(O)NR$^5$NR$^5$C(O)R$^5$,
(23) O(CH$_2$)$_{0-1}$—C(O)N(R$^5$)$_2$,
(24) CF$_3$,
(25) CH$_2$CF$_3$,
(26) OCF$_3$, and
(27) OCH$_2$CF$_3$;

wherein phenyl, naphthyl, and heteroaryl are unsubstituted or substituted with one to three substituents independently selected from halogen, hydroxy, C$_{1-4}$ alkyl, trifluoromethyl, and C$_{1-4}$ alkoxy, and wherein alkyl, cycloalkyl, heterocycloalkyl, and (CH$_2$) are unsubstituted or substituted with one to three substituents independently selected from halogen, hydroxy, oxo, C$_{1-4}$ alkyl, trifluoromethyl, and C$_{1-4}$ alkoxy, or wherein two substituents when on the same methylene (CH$_2$) group are taken together with the carbon atom to which they are attached to form a cyclopropyl group;

each $R^4$ is independently selected from the group consisting of
- (1) hydrogen,
- (2) $C_{1-8}$ alkyl,
- (3) —$(CH_2)_{0-1}$-phenyl,
- (4) —$(CH_2)_{0-1}$-naphthyl,
- (5) —$(CH_2)_{0-1}$-heteroaryl,
- (6) —$(CH_2)_{0-1}$—$C_{2-7}$ heterocycloalkyl,
- (7) —$(CH_2)_{0-1}$—$C_{3-7}$ cycloalkyl,
- (8) halogen,
- (9) $OR^5$,
- (10) —$(CH_2)_{0-1}$—$N(R^5)_2$,
- (11) —$(CH_2)_{0-1}$—C≡N,
- (12) —$(CH_2)_{0-1}$—$C(O)OR^5$,
- (13) —$(CH_2)_{0-1}$—$OC(O)R^5$,
- (14) $NO_2$,
- (15) —$(CH_2)_{0-1}$—$NR^5S(O)_{1-2}$—$R^5$,
- (16) —$(CH_2)_{0-1}$—$N(S(O)_{1-2}$—$R^5)_2$,
- (17) —$(CH_2)_{0-1}$—$S(O)_{1-2}$—$N(R^5)_2$,
- (18) —$(CH_2)_{0-1}$—$S(O)_{0-2}$—$R^5$,
- (19) —$(CH_2)_{0-1}$—$NR^5C(O)N(R^5)_2$,
- (20) —$(CH_2)_{0-1}$—$C(O)N(R^5)_2$,
- (21) —$(CH_2)_{0-1}$—$NR^5C(O)R^5$,
- (22) —$(CH_2)_{0-1}$—$NR^5CO_2R^5$,
- (23) —$(CH_2)_{0-1}$—$NR^5C(O)$-heteroaryl,
- (24) —$(CH_2)_{0-1}$—$C(O)NR^5N(R^5)_2$,
- (25) —$(CH_2)_{0-1}$—$C(O)NR^5NR^5C(O)R^5$,
- (26) $O(CH_2)_{0-1}$—$C(O)N(R^5)_2$,
- (27) $CF_3$,
- (28) $CH_2CF_3$,
- (29) $OCF_3$, and
- (30) $OCH_2CF_3$;

wherein phenyl, naphthyl, and heteroaryl are unsubstituted or substituted with one to three substituents independently selected from halogen, hydroxy, $C_{1-4}$ alkyl, trifluoromethyl, and $C_{1-4}$ alkoxy, and wherein alkyl, cycloalkyl, heterocycloalkyl, and ($CH_2$) are unsubstituted or substituted with one to three substituents independently selected from halogen, hydroxy, oxo, $C_{1-4}$ alkyl, trifluoromethyl, and $C_{1-4}$ alkoxy, or wherein two substituents when on the same methylene ($CH_2$) group are taken together with the carbon atom to which they are attached to form a cyclopropyl group;

each $R^5$ is independently selected from the group consisting of
- (1) hydrogen,
- (2) $C_{1-8}$ alkyl,
- (3) —$(CH_2)_{0-1}$—$C_{3-7}$ cycloalkyl,
- (4) —$(CH_2)_{0-1}$—$C_{2-7}$ heterocycloalkyl,
- (5) —$(CH_2)_{0-1}$-phenyl,
- (6) —$(CH_2)_{0-1}$-naphthyl,
- (7) —$(CH_2)_{0-1}$-heteroaryl, and
- (8) —$(CH_2)_{0-1}$—$C_{3-7}$ bicycloalkyl;

wherein alkyl, phenyl, heteroaryl, heterocycloalkyl, naphthyl, cycloalkyl, bicycloalkyl and ($CH_2$) are unsubstituted or substituted with one to three groups independently selected from halogen, $C_{1-4}$ alkyl, hydroxy, and $C_{1-4}$ alkoxy, or wherein two $R^5$ groups together with the atom to which they are attached form a 4- to 8-membered mono- or bicyclic ring system optionally containing an additional heteroatom selected from O, S, and —$NC_{1-4}$ alkyl;

each $R^6$ is independently selected from the group consisting of
- (1) hydrogen,
- (2) $C_{1-6}$ alkyl,
- (3) —$(CH_2)_{0-1}$—$C_{3-7}$ cycloalkyl,
- (4) —$(CH_2)_{0-1}$—$C_{2-7}$ heterocycloalkyl,
- (5) —$(CH_2)_{0-1}$-phenyl,
- (6) —$(CH_2)_{0-1}$-naphthyl,
- (7) —$(CH_2)_{0-1}$-heteroaryl,
- (8) —$(CH_2)_{0-1}$—$C(O)R^5$,
- (9) —$(CH_2)_{0-1}$—$C(O)OR^5$,
- (10) —$(CH_2)_{0-1}$—$C(OH)R^5$,
- (11) —$(CH_2)_{0-1}$—$(O)(CH_2)_{0-1}$—$N(R^5)_2$,
- (12) —$(CH_2)_{0-1}C(O)(CH_2)_{0-1}$—$NR^7R^8$,
- (13) —$(CH_2)_{0-1}$—$OR^5$,
- (14) —$(CH_2)_{0-1}$—$OC(O)R^5$,
- (15) —$(CH_2)_{0-1}$—O—$(CH_2)_{1-2}$—$N(R^5)_2$,
- (16) —$(CH_2)_{0-1}$—CN,
- (17) —$(CH_2)_{0-3}$—$N(R^5)_2$,
- (18) —$(CH_2)_{0-3}$—$N(R^5)C(O)R^5$,
- (19) —$(CH_2)_{0-3}$—$N(C(O)R^5)_2$,
- (20) —$(CH_2)_{0-3}$—$N(R^5)C(O)OR^5$,
- (21) —$(CH_2)_{0-1}$—$N(C(O)OR^5)_2$,
- (22) —$(CH_2)_{0-1}$—$N(R^5)C(O)(CH_2)_{0-1}N(R^5)_2$,
- (23) —$(CH_2)_{0-3}$—$N(R^5)$—S(O)—$C_{1-8}$ alkyl,
- (24) —$(CH_2)_{0-3}$—$N(R^5)$—$S(O)_2$—$C_{1-8}$ alkyl,
- (25) —$(CH_2)_{0-1}$—S—$R^5$,
- (26) —$(CH_2)_{0-1}$—S(O)—$R^5$, and
- (27) —$(CH_2)_{0-1}$—$S(O)_2$—$R^5$, wherein phenyl, naphthyl, and heteroaryl are unsubstituted or substituted with one to three groups independently selected from $R^3$, and wherein alkyl, cycloalkyl and heterocycloalkyl are unsubstituted or substituted with one to three groups independently selected from $R^3$ and oxo, and wherein any methylene ($CH_2$) in $R^6$ is unsubstituted or substituted with one to two groups independently selected from halogen, hydroxy, and $C_{1-4}$ alkyl, or wherein two $R^6$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from $R^3$ and oxo;

each $R^7$ and $R^8$ is independently selected from the group consisting of
- (1) hydrogen,
- (2) amidino,
- (3) $C_{1-4}$ alkyliminoyl,
- (4) $C_{1-10}$alkyl,
- (5) —$(CH_2)_{0-1}$—$C_{3-7}$ cycloalkyl,
- (6) —$(CH_2)_{0-1}$-phenyl,
- (7) —$(CH_2)_{0-1}$-naphthyl, and
- (8) —$(CH_2)_{0-1}$-heteroaryl, wherein phenyl, naphthyl, and heteroaryl are unsubstituted or substituted with one to three groups independently selected from $R^3$, and wherein alkyl and cycloalkyl are unsubstituted or substituted with one to three groups independently selected from $R^3$ and oxo;

each $R^9$ is independently selected from the group consisting of
- (1) hydrogen,
- (2) $C_{1-6}$ alkyl,
- (3) —$(CH_2)_{0-1}$—$C_{3-7}$ cycloalkyl,
- (4) —$(CH_2)_{0-1}$—$C_{2-7}$ heterocycloalkyl,
- (5) —$(CH_2)_{0-1}$-phenyl,
- (6) —$(CH_2)_{0-1}$-naphthyl,
- (7) —$(CH_2)_{0-1}$-heteroaryl,
- (8) —$(CH_2)_{0-1}$—$C(O)R^5$,
- (9) —$(CH_2)_{0-1}$—$C(O)OR^5$,
- (10) —$(CH_2)_{0-1}$—$C(OH)R^5$,
- (11) —$(CH_2)_{0-1}$—$C(O)(CH_2)_{0-1}$—$N(R^5)_2$,

(12) —(CH$_2$)$_{0-1}$—C(O)(CH$_2$)$_{0-1}$—NR$^7$R$^8$,
(13) —(CH$_2$)$_{1-3}$—OR$^5$,
(14) —(CH$_2$)$_{1-3}$—OC(O)R$^5$,
(15) —(CH$_2$)$_{1-3}$—O—(CH$_2$)$_{1-2}$—N(R$^5$)$_2$,
(16) —(CH$_2$)$_{1-3}$—CN,
(17) —(CH$_2$)$_{1-3}$—N(R$^5$)$_2$,
(18) —(CH$_2$)$_{1-3}$—N(R$^5$)C(O)R$^5$,
(19) —(CH$_2$)$_{1-3}$—N(C(O)R$^5$)$_2$,
(20) —(CH$_2$)$_{1-3}$—N(R$^5$)C(O)OR$^5$,
(21) —(CH$_2$)$_{1-3}$—N(C(O)OR$^5$)$_2$,
(22) —(CH$_2$)$_{1-3}$—N(R$^5$)C(O)(CH$_2$)$_{0-1}$N(R$^5$)$_2$,
(23) —(CH$_2$)$_{1-3}$—N(R$^5$)—S(O)—C$_{1-8}$ alkyl,
(24) —(CH$_2$)$_{1-3}$—N(R$^5$)—S(O)$_2$—C$_{1-8}$ alkyl,
(25) —(CH$_2$)$_{1-3}$—S—R$^5$,
(26) —(CH$_2$)$_{0-1}$—S(O)—R$^5$, and
(27) —(CH$_2$)$_{0-1}$—S(O)$_2$—R$^5$, wherein phenyl, naphthyl, and heteroaryl are unsubstituted or substituted with one to three groups independently selected from R$^3$, and wherein alkyl, cycloalkyl and heterocycloalkyl are unsubstituted or substituted with one to three groups independently selected from R$^3$ and oxo, and wherein any methylene (CH$_2$) in R$^9$ is unsubstituted or substituted with one to two groups independently selected from halogen, hydroxy, and C$_{1-4}$ alkyl; or wherein two R$^9$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from R$^3$ and oxo;

r is 1 or 2; and
s is 1 or 2.

In a further embodiment of the compounds of structural formula I, there are provided compounds of structural formula IVa:

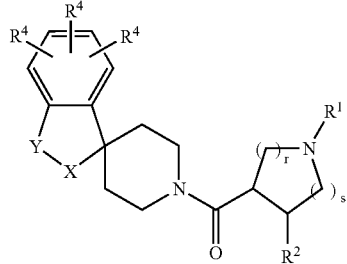

(IV)

In yet a further embodiment of the compounds of structural formula I, there are provided compounds of structural formula V:

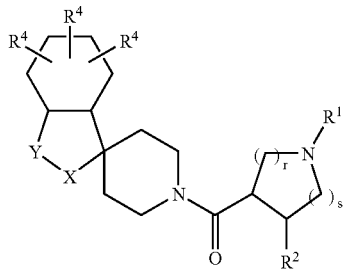

(V)

Illustrative but nonlimiting examples of compounds of the present invention that are useful as melanocortin-4 receptor agonists are the following:

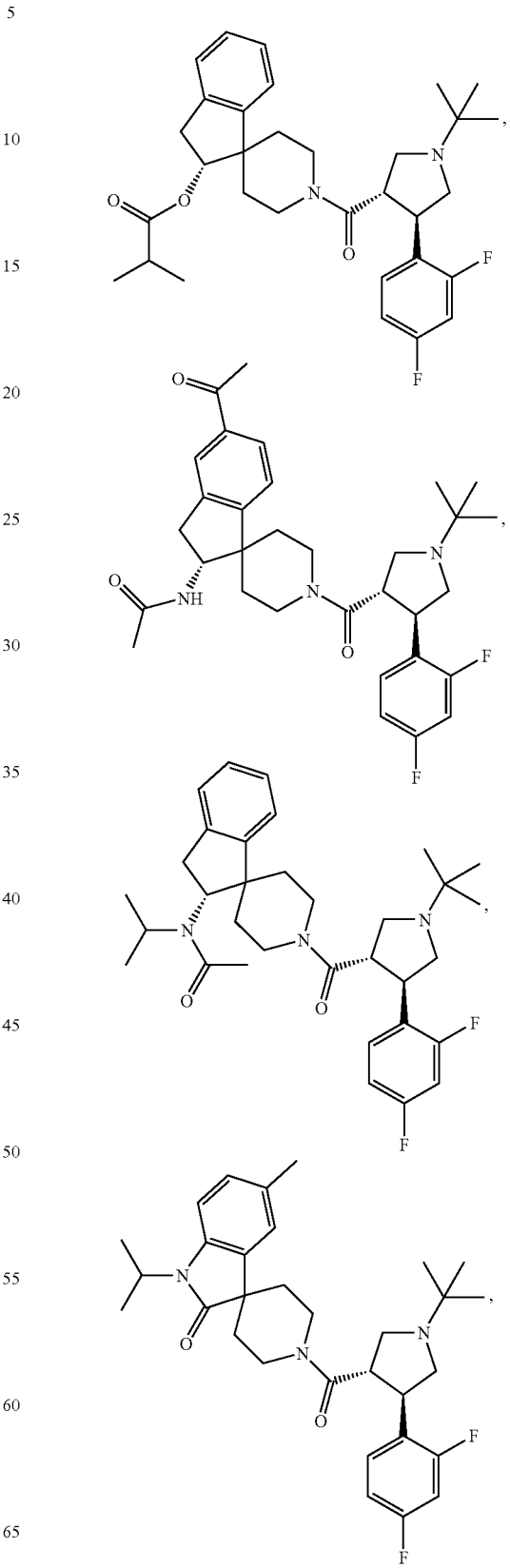

-continued
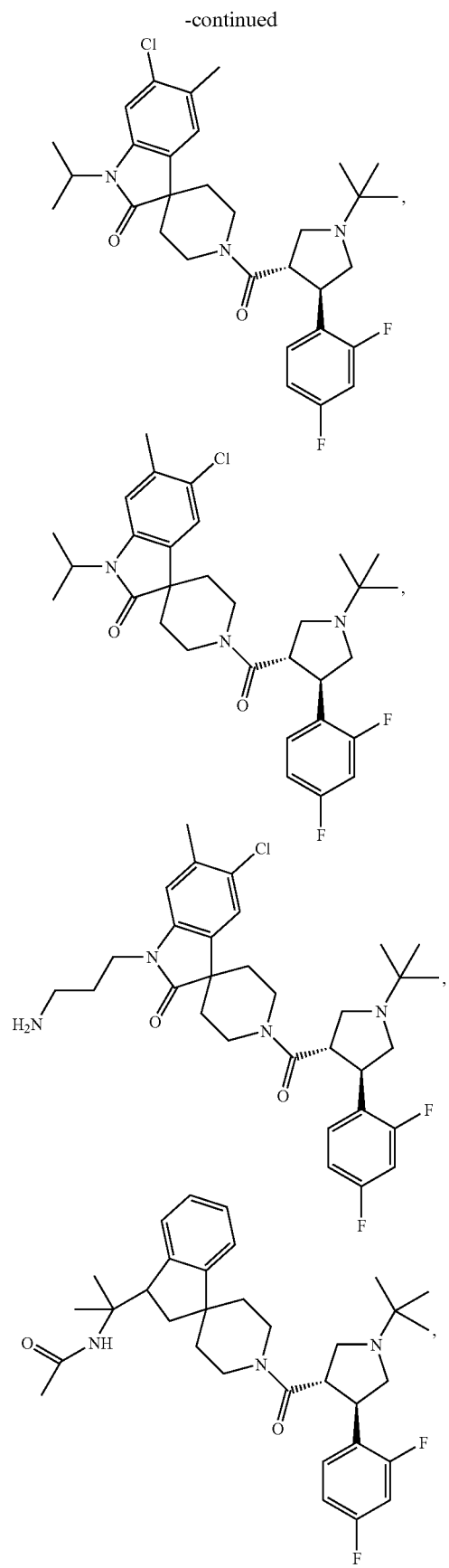

-continued
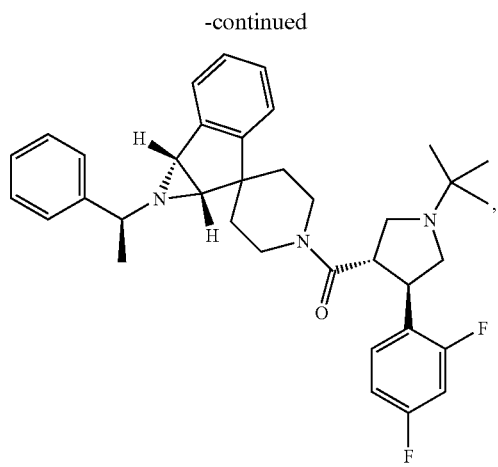
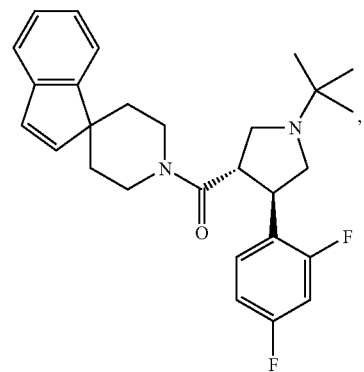
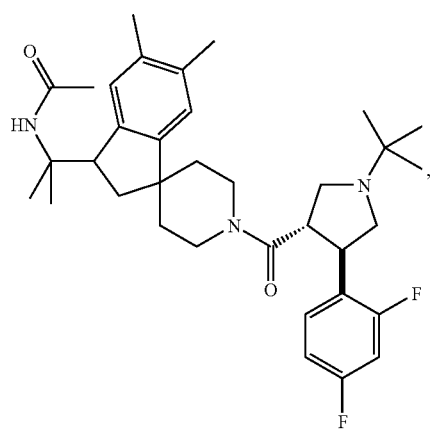
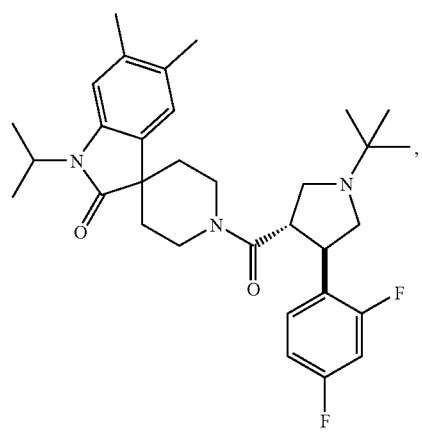
-continued
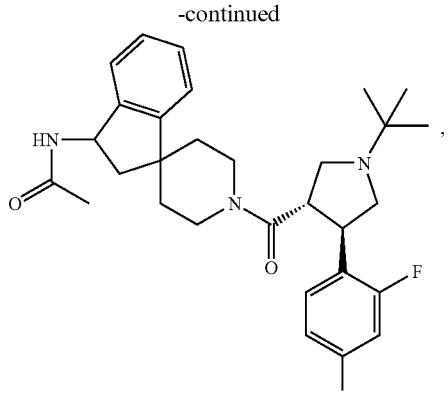
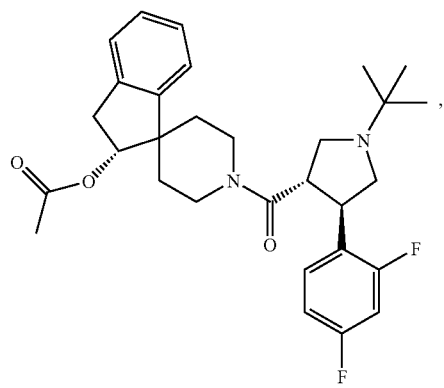
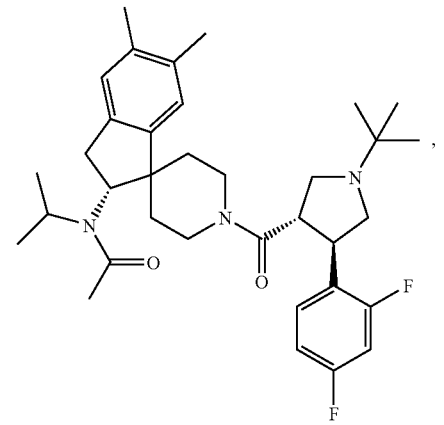
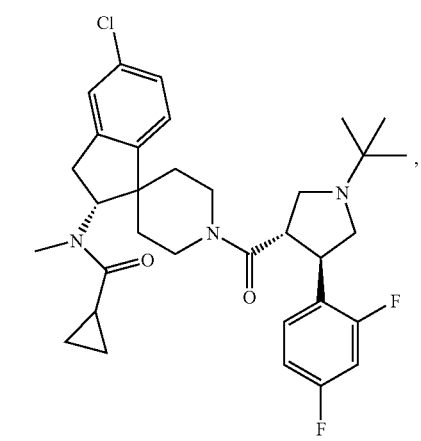

-continued
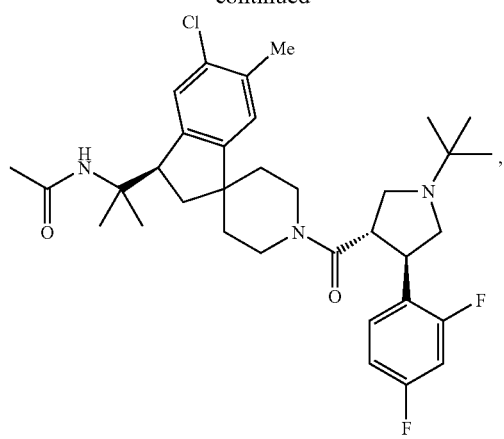
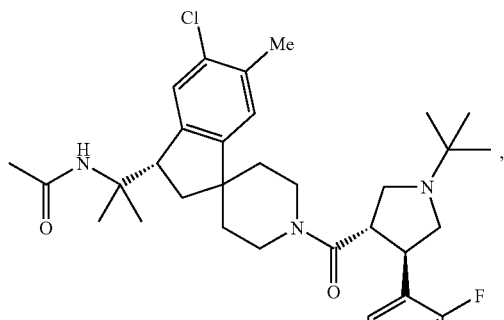
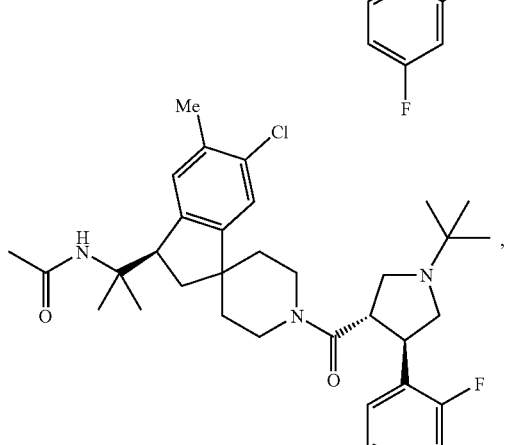
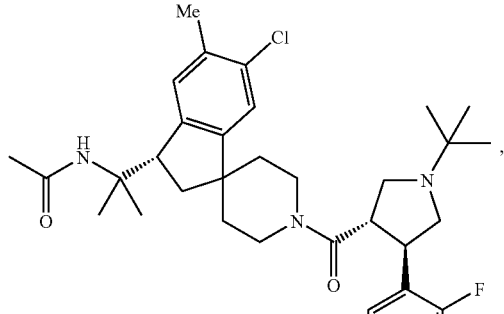
-continued
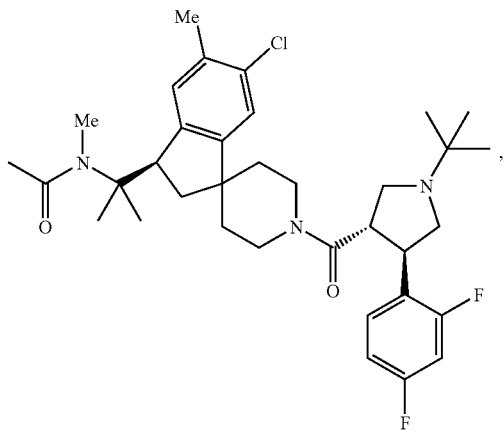
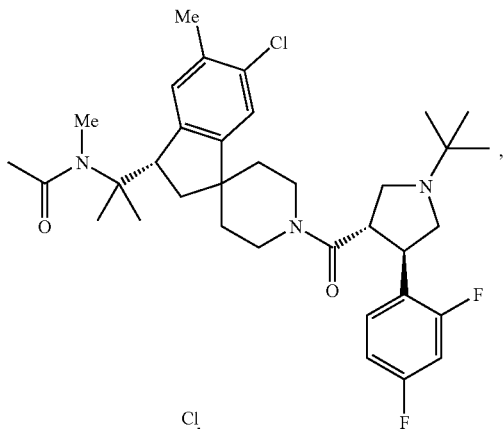
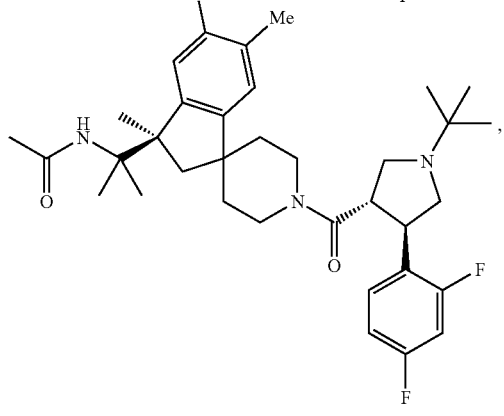
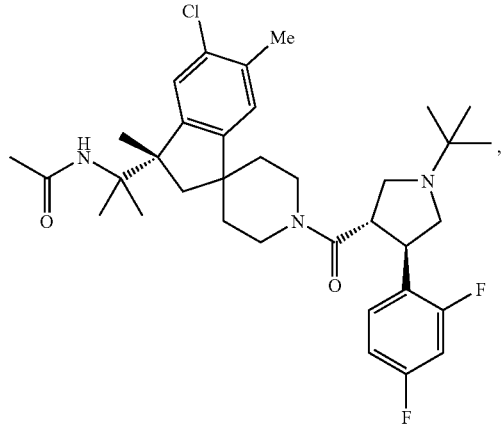

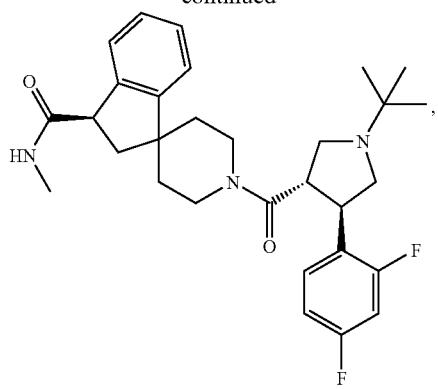
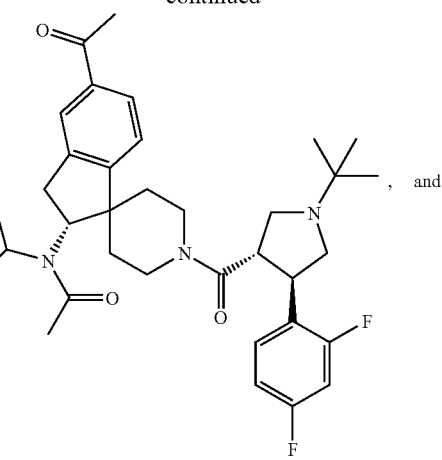
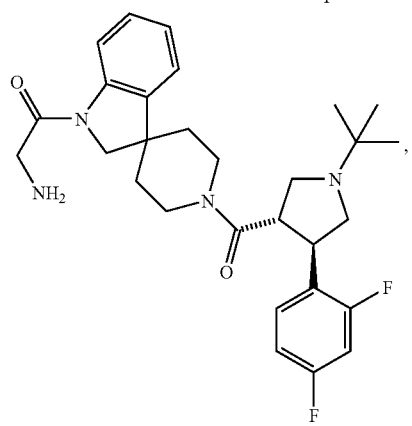
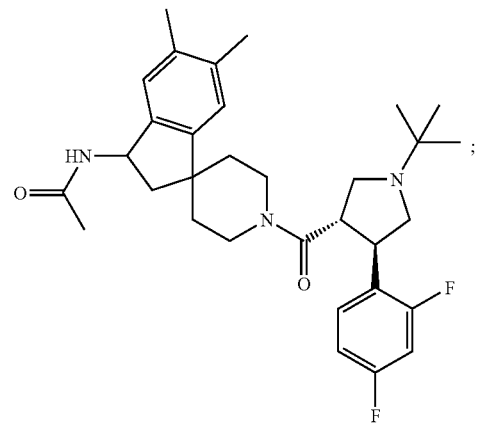
or a pharmaceutically acceptable salt thereof.
Further illustrative of the present invention are the compounds selected from the group consisting of:
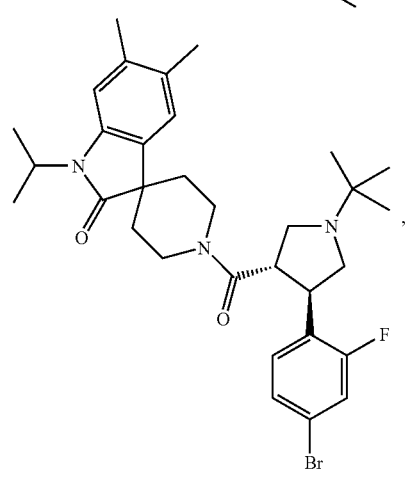
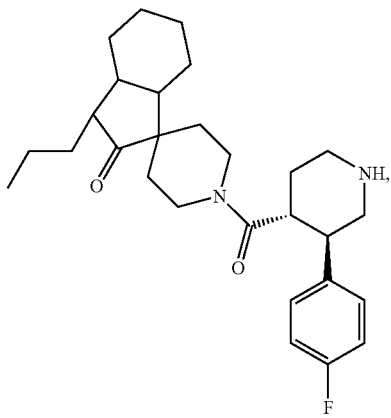

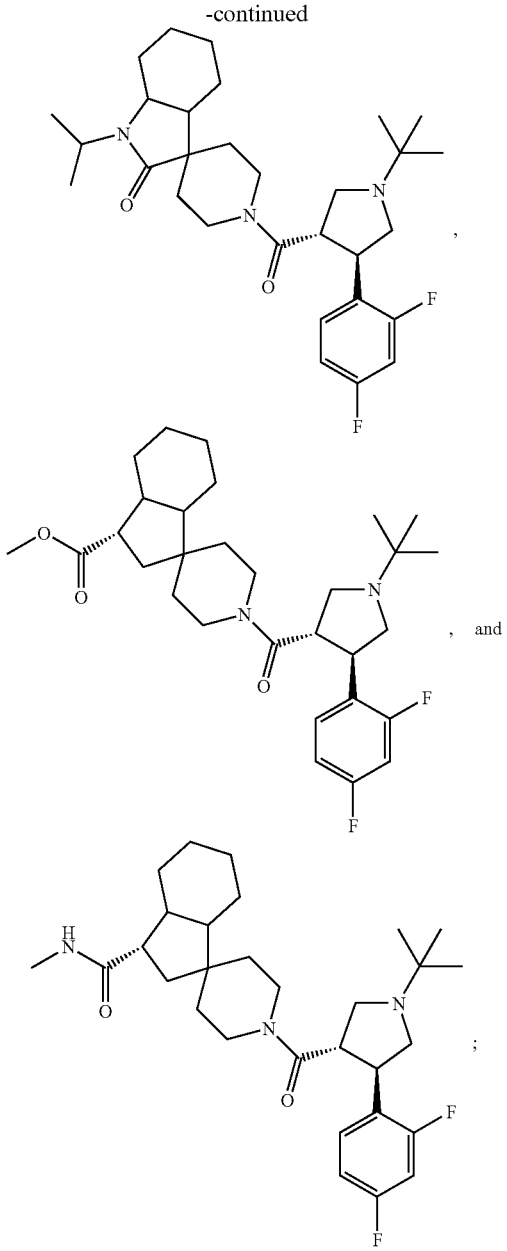

or a pharmaceutically acceptable salt thereof.

The present invention also relates to N-acylated spiropiperidine derivatives useful as melanocortin receptor agonists, in particular, as selective MC-4R agonists. Compounds of the present invention are described by structural formula VI:

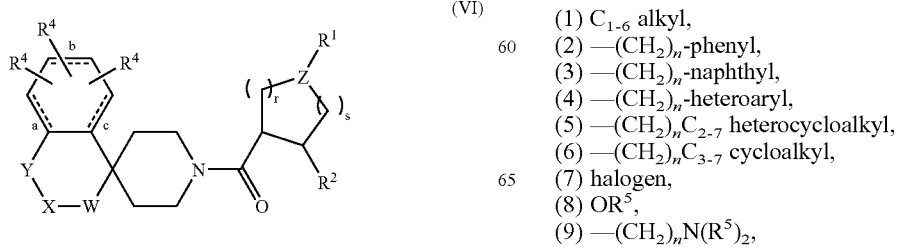

(VI)

or a pharmaceutically acceptable salt thereof; wherein
a, b and c are all single bonds or all double bonds;
W is independently selected from the group consisting of
  (1) C(O),
  (2) N($R^{10}$), and
  (3) C($R^{10}$)$_2$;
X and Y taken together form —C($R^6$)=C($R^6$)—, or
one of X and Y is C($R^6$)$_2$ and the other is selected from the group consisting of
  (1) C($R^6$)$_2$,
  (2) N($R^6$),
  (3) C(O),
  (4) C=N($R^6$)
  (5) oxygen,
  (6) sulfur,
  (7) S(O), and
  (8) S(O)$_2$,
or one of X and Y is N($R^9$) and the other is selected from the group consisting of
  (1) C($R^6$)$_2$,
  (2) C(O),
  (3) C=N($R^6$)
  (4) S(O), and
  (5) S(O)$_2$,
or one of X and Y is C(O) and the other is selected from the group consisting of
  (1) C($R^6$)$_2$,
  (2) N($R^6$),
  (3) oxygen, and
  (4) sulfur;
Z is independently selected from the group consisting of
  (1) CH,
  (2) C($R^1$), and
  (3) N;
$R^1$ is selected from the group consisting of
  (1) hydrogen,
  (2) —(CH$_2$)$_n$—NR$^7$R$^8$,
  (3) amidino,
  (4) C$_{1-4}$ alkyliminoyl,
  (5) C$_{1-10}$ alkyl,
  (6) —(CH$_2$)$_n$—C$_{3-7}$ cycloalkyl,
  (7) —(CH$_2$)$_n$-phenyl,
  (8) —(CH$_2$)$_n$-naphthyl, and
  (9) —(CH$_2$)$_n$-heteroaryl,
wherein phenyl, naphthyl, and heteroaryl are unsubstituted or substituted with one to three groups independently selected from $R^3$, and wherein alkyl and cycloalkyl are unsubstituted or substituted with one to three groups independently selected from $R^3$ and oxo;
$R^2$ is selected from the group consisting of
  (1) phenyl,
  (2) naphthyl, and
  (3) heteroaryl,
wherein phenyl, naphthyl, and heteroaryl are unsubstituted or substituted with one to three groups independently selected from $R^3$;
each $R^3$ is independently selected from the group consisting of
  (1) C$_{1-6}$ alkyl,
  (2) —(CH$_2$)$_n$-phenyl,
  (3) —(CH$_2$)$_n$-naphthyl,
  (4) —(CH$_2$)$_n$-heteroaryl,
  (5) —(CH$_2$)$_n$C$_{2-7}$ heterocycloalkyl,
  (6) —(CH$_2$)$_n$C$_{3-7}$ cycloalkyl,
  (7) halogen,
  (8) OR$^5$,
  (9) —(CH$_2$)$_n$N(R$^5$)$_2$,

(10) —$(CH_2)_nC\equiv N$,
(11) —$(CH_2)_nCO_2R^5$,
(12) $NO_2$,
(13) —$(CH_2)_nNR^5S(O)_pR^5$,
(14) —$(CH_2)_nS(O)_pN(R^5)_2$,
(15) —$(CH_2)_nS(O)_pR^5$,
(16) —$(CH_2)_nNR^5C(O)N(R^5)_2$,
(17) —$(CH_2)_nC(O)N(R^5)_2$,
(18) —$(CH_2)_nNR^5C(O)R^5$,
(19) —$(CH_2)_nNR^5CO_2R^5$,
(20) —$(CH_2)_nNR^5C(O)$-heteroaryl,
(21) —$(CH_2)_nC(O)NR^5N(R^5)_2$,
(22) —$(CH_2)_nC(O)NR^5NR^5C(O)R^5$,
(23) $O(CH_2)_nC(O)N(R^5)_2$,
(24) $CF_3$,
(25) $CH_2CF_3$,
(26) $OCF_3$, and
(27) $OCH_2CF_3$;

wherein phenyl, naphthyl, and heteroaryl are unsubstituted or substituted with one to three substituents independently selected from halogen, hydroxy, $C_{1-4}$ alkyl, trifluoromethyl, and $C_{1-4}$ alkoxy, and wherein alkyl, cycloalkyl, heterocycloalkyl, and ($CH_2$) are unsubstituted or substituted with one to three substituents independently selected from halogen, hydroxy, oxo, $C_{1-4}$ alkyl, trifluoromethyl, and $C_{1-4}$ alkoxy, or wherein two substituents when on the same methylene ($CH_2$) group are taken together with the carbon atom to which they are attached to form a cyclopropyl group;

each $R^4$ is independently selected from the group consisting of
(1) hydrogen,
(2) $C_{1-8}$ alkyl,
(3) —$(CH_2)_n$-phenyl,
(4) —$(CH_2)_n$-naphthyl,
(5) —$(CH_2)_n$-heteroaryl,
(6) —$(CH_2)_nC_{2-7}$ heterocycloalkyl,
(7) —$(CH_2)_nC_{3-7}$ cycloalkyl,
(8) halogen,
(9) $OR^5$,
(10) —$(CH_2)_nN(R^5)_2$,
(11) —$(CH_2)_nC\equiv N$,
(12) —$(CH_2)_nC(O)OR^5$,
(13) —$(CH_2)_nOC(O)R^5$,
(14) $NO_2$,
(15) —$(CH_2)_nNR^5S(O)_pR^5$,
(16) —$(CH_2)_nN(S(O)_pR^5)_2$,
(17) —$(CH_2)_nS(O)_pN(R^5)_2$,
(18) —$(CH_2)_nS(O)_pR^5$,
(19) —$(CH_2)_nNR^5C(O)N(R^5)_2$,
(20) —$(CH_2)_nC(O)N(R^5)_2$,
(21) —$(CH_2)_nNR^5C(O)R^5$,
(22) —$(CH_2)_nNR^5CO_2R^5$,
(23) —$(CH_2)_nNR^5C(O)$-heteroaryl,
(24) —$(CH_2)_nC(O)NR^5N(R^5)_2$,
(25) —$(CH_2)_nC(O)NR^5NR^5C(O)R^5$,
(26) $O(CH_2)_nC(O)N(R^5)_2$,
(27) $CF_3$,
(28) $CH_2CF_3$,
(29) $OCF_3$, and
(30) $OCH_2CF_3$;

wherein phenyl, naphthyl, and heteroaryl are unsubstituted or substituted with one to three substituents independently selected from halogen, hydroxy, $C_{1-4}$ alkyl, trifluoromethyl, and $C_{1-4}$ alkoxy, and wherein alkyl, cycloalkyl, heterocycloalkyl, and ($CH_2$) are unsubstituted or substituted with one to three substituents independently selected from halogen, hydroxy, oxo, $C_{1-4}$ alkyl, trifluoromethyl, and $C_{1-4}$ alkoxy, or wherein two substituents when on the same methylene ($CH_2$) group are taken together with the carbon atom to which they are attached to form a cyclopropyl group;

each $R^5$ is independently selected from the group consisting of
(1) hydrogen,
(2) $C_{1-8}$ alkyl,
(3) —$(CH_2)_nC_{3-7}$ cycloalkyl,
(4) —$(CH_2)_nC_{2-7}$ heterocycloalkyl,
(5) —$(CH_2)_n$-phenyl,
(6) —$(CH_2)_n$-naphthyl,
(7) —$(CH_2)_n$-heteroaryl, and
(8) —$(CH_2)_nC_{3-7}$ bicycloalkyl;

wherein alkyl, phenyl, heteroaryl, heterocycloalkyl, naphthyl, cycloalkyl, bicycloalkyl and ($CH_2$) are unsubstituted or substituted with one to three groups independently selected from halogen, $C_{1-4}$ alkyl, hydroxy, and $C_{1-4}$ alkoxy, or wherein two $R^5$ groups together with the atom to which they are attached form a 4- to 8-membered mono- or bicyclic ring system optionally containing an additional heteroatom selected from O, S, and —$NC_{1-4}$ alkyl;

each $R^6$ is independently selected from the group consisting of
(1) hydrogen,
(2) $C_{1-6}$ alkyl,
(3) —$(CH_2)_nC_{3-7}$ cycloalkyl,
(4) —$(CH_2)_nC_{2-7}$ heterocycloalkyl,
(5) —$(CH_2)_n$-phenyl,
(6) —$(CH_2)_n$-naphthyl,
(7) —$(CH_2)_n$-heteroaryl,
(8) —$(CH_2)_nC(O)R^5$,
(9) —$(CH_2)_nC(O)OR^5$,
(10) —$(CH_2)_nC(OH)R^5$,
(11) —$(CH_2)_nC(O)(CH_2)_n$—$N(R^5)_2$,
(12) —$(CH_2)_nC(O)(CH_2)_n$—$NR^7R^8$,
(13) —$(CH_2)_n$—$OR^5$,
(14) —$(CH_2)_n$—$OC(O)R^5$,
(15) —$(CH_2)_n$—O—$(CH_2)_n$—$N(R^5)_2$,
(16) —$(CH_2)_nCN$,
(17) —$(CH_2)_nN(R^5)_2$,
(18) —$(CH_2)_nN(R^5)C(O)R^5$,
(19) —$(CH_2)_nN(C(O)R^5)_2$,
(20) —$(CH_2)_nN(R^5)C(O)OR^5$,
(21) —$(CH_2)_nN(C(O)OR^5)_2$,
(22) —$(CH_2)_nN(R^5)C(O)(CH_2)_nN(R^5)_2$,
(23) —$(CH_2)_nN(R^5)$—S(O)—$C_{1-8}$ alkyl,
(24) —$(CH_2)_nN(R^5)$—$S(O)_2$—$C_{1-8}$ alkyl,
(25) —$(CH_2)_n$—S—$R^5$,
(26) —$(CH_2)_n$—S(O)—$R^5$, and
(27) —$(CH_2)_n$—$S(O)_2$—$R^5$, wherein phenyl, naphthyl, and heteroaryl are unsubstituted or substituted with one to three groups independently selected from $R^3$, and wherein alkyl, cycloalkyl and heterocycloalkyl are unsubstituted or substituted with one to three groups independently selected from $R^3$ and oxo, and wherein any methylene ($CH_2$) in $R^6$ is unsubstituted or substituted with one to two groups independently selected from halogen, hydroxy, and $C_{1-4}$ alkyl; or wherein two R⁶ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from R³ and oxo;

each R⁷ and R⁸ is independently selected from the group consisting of
(1) hydrogen,
(2) amidino,
(3) $C_{1-4}$ alkyliminoyl,
(4) $C_{1-10}$ alkyl,
(5) —$(CH_2)_n$—$C_{3-7}$ cycloalkyl,
(6) —$(CH_2)_n$-phenyl,
(7) —$(CH_2)_n$-naphthyl, and
(8) —$(CH_2)_n$-heteroaryl,
wherein phenyl, naphthyl, and heteroaryl are unsubstituted or substituted with one to three groups independently selected from R³, and wherein alkyl and cycloalkyl are unsubstituted or substituted with one to three groups independently selected from R³ and oxo;

each R⁹ is independently selected from the group consisting of
(1) hydrogen,
(2) $C_{1-6}$ alkyl,
(3) —$(CH_2)_n C_{3-7}$ cycloalkyl,
(4) —$(CH_2)_n C_{2-7}$ heterocycloalkyl,
(5) —$(CH_2)_n$-phenyl,
(6) —$(CH_2)_n$-naphthyl,
(7) —$(CH_2)_n$-heteroaryl,
(8) —$(CH_2)_n C(O)R^5$,
(9) —$(CH_2)_n C(O)OR^5$,
(10) —$(CH_2)_n C(OH)R^5$,
(11) —$(CH_2)_n C(O)(CH_2)_n$—$N(R^5)_2$,
(12) —$(CH_2)_n C(O)(CH_2)_n$—$NR^7R^8$,
(13) —$(CH_2)_m$—$OR^5$,
(14) —$(CH_2)_m$—$OC(O)R^5$,
(15) —$(CH_2)_m$—O—$(CH_2)_n$—$N(R^5)_2$,
(16) —$(CH_2)_m CN$,
(17) —$(CH_2)_m N(R^5)_2$,
(18) —$(CH_2)_m N(R^5)C(O)R^5$,
(19) —$(CH_2)_m N(C(O)R^5)_2$,
(20) —$(CH_2)_m N(R^5)C(O)OR^5$,
(21) —$(CH_2)_m N(C(O)OR^5)_2$,
(22) —$(CH_2)_m N(R^5)C(O)(CH_2)_n N(R^5)_2$,
(23) —$(CH_2)_m N(R^5)$—S(O)—$C_{1-8}$ alkyl,
(24) —$(CH_2)_m N(R^5)$—$S(O)_2$—$C_{1-8}$ alkyl,
(25) —$(CH_2)_m$—S—$R^5$,
(26) —$(CH_2)_n$—S(O)—$R^5$, and
(27) —$(CH_2)_n$—$S(O)_2$—$R^5$,
wherein phenyl, naphthyl, and heteroaryl are unsubstituted or substituted with one to three groups independently selected from R³, and wherein alkyl, cycloalkyl and heterocycloalkyl are unsubstituted or substituted with one to three groups independently selected from R³ and oxo, and wherein any methylene ($CH_2$) in R⁹ is unsubstituted or substituted with one to two groups independently selected from halogen, hydroxy, and $C_{1-4}$ alkyl; or wherein two R⁹ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from R³ and oxo;

each R¹⁰ is independently selected from the group consisting of
(1) hydrogen,
(2) —$C_{1-6}$ alkyl,
(3) —C(O)—$C_{1-6}$ alkyl, and
(4) —$S(O)_2$—$C_{1-6}$ alkyl;
r is 1 or 2;
s is 1 or 2;
n is 0, 1, 2, or 3;
m is 1, 2, or 3; and
p is 0, 1, or 2.

Illustrative but nonlimiting examples of compounds of the present invention that are useful as melanocortin-4 receptor agonists are the following:

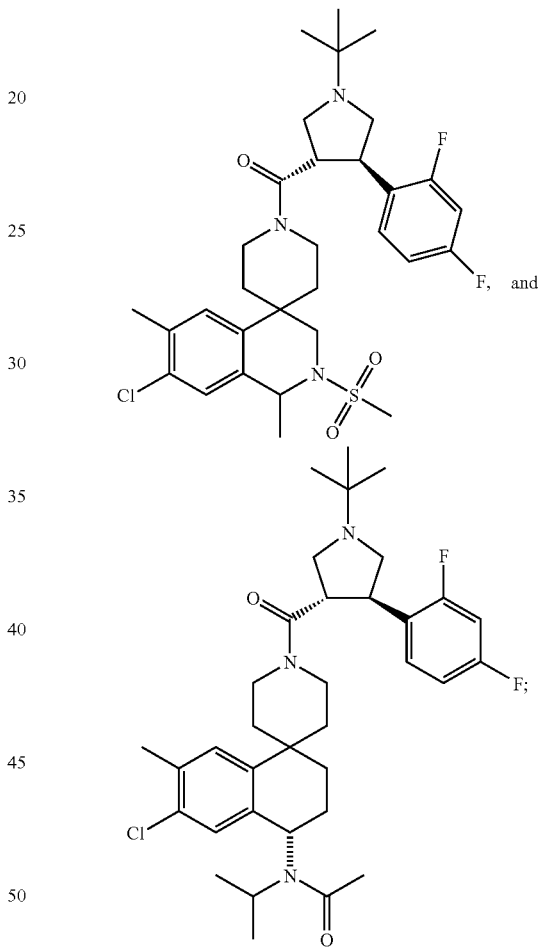

or a pharmaceutically acceptable salt thereof.

The compounds of structural formula I and VI are effective as melanocortin receptor agonists and are particularly effective as selective agonists of MC-4R. They are therefore useful for the treatment and/or prevention of disorders responsive to the activation of MC-4R, such as obesity, diabetes as well as male and/or female sexual dysfunction, in particular, erectile dysfunction, and further in particular, male erectile dysfunction.

Another aspect of the present invention provides a method for the treatment or prevention of obesity or diabetes in a mammal in need thereof which comprises administering to said mammal a therapeutically or prophylactically effective amount of a compound of structural formula I or VI.

Another aspect of the present invention provides a method for the treatment or prevention of male or female sexual dysfunction including erectile dysfunction which comprises administering to a mammal in need of such treatment or prevention a therapeutically or prophylactically effective amount of a compound of structural formula I or formula VI.

Another aspect of the present invention provides a pharmaceutical composition comprising a compound of structural formula I or VI and a pharmaceutically acceptable carrier.

Yet another aspect of the present invention provides a method for the treatment or prevention of male or female sexual dysfunction including erectile dysfunction which comprises administering to a mammal in need of such treatment or prevention a therapeutically or prophylactically effective amount of a compound of structural formula I or formula VI in combination with a therapeutically effective amount of another agent known to be useful for the treatment of these conditions.

Yet another aspect of the present invention provides a method for the treatment or prevention of obesity which comprises administering to a mammal in need of such treatment or prevention a therapeutically or prophylactically effective amount of a compound of structural formula I or formula VI in combination with a therapeutically effective amount of another agent known to be useful for the treatment of this condition.

Yet another aspect of the present invention relates to the use of a compound of formula I or formula VI for the manufacture of a medicament useful for the treatment or prevention, or suppression of a disease mediated by the melanocortin-4 receptor in a mammal in need thereof.

Yet another aspect of the present invention relates to the use of a compound of formula I or formula VI for the manufacture of a medicament useful for the treatment or prevention, or suppression of a disease mediated by the melanocortin-4 receptor, wherein the disease is selected from the group consisting of obesity, diabetes, male sexual dysfunction and female sexual dysfunction in a mammal in need thereof.

Yet another aspect of the present invention relates to the use of a compound of formula I or formula VI for the manufacture of a medicament useful for the treatment or prevention, or suppression of male erectile dysfunction in a mammal in need thereof.

Yet another aspect of the present invention relates to the use of a therapeutically effective amount of a compound of formula I or formula VI, or a pharmaceutically acceptable salt thereof, and a therapeutically effective amount of an agent selected from the group consisting of an insulin sensitizer, an insulin mimetic, a sulfonylurea, an α-glucosidase inhibitor, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a bombesin receptor subtype 3 agonist, and a ghrelin receptor antagonist, or a pharmaceutically acceptable salt thereof, for the manufacture of a medicament useful for the treatment, control, or prevention of diabetes or obesity in a mammal in need of such treatment.

Yet another aspect of the present invention relates to the use of a therapeutically effective amount of a compound of formula I or formula VI, and pharmaceutically acceptable salts and esters thereof, and a therapeutically effective amount of an agent selected from the group consisting of an insulin sensitizer, an insulin mimetic, a sulfonylurea, an α-glucosidase inhibitor, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a bombesin receptor subtype 3 agonist, and a ghrelin receptor antagonist, and pharmaceutically acceptable salts and esters thereof, for the manufacture of a medicament for treatment or prevention of diabetes or obesity which comprises an effective amount of a compound of formula I or formula VI and an effective amount of the agent, together or separately.

Yet another aspect of the present invention relates to the use of a therapeutically effective amount of a compound of formula I or formula VI, or a pharmaceutically acceptable salt thereof, and a therapeutically effective amount of an agent selected from the group consisting of: a type V cyclic-GMP-selective phosphodiesterase inhibitor, an $\alpha_2$-adrenergic receptor antagonist, and a dopaminergic agent, or a pharmaceutically acceptable salt thereof, for the manufacture of a medicament useful for the treatment, control, or prevention of erectile dysfunction in a mammal in need of such treatment.

Yet another aspect of the present invention relates to the use of a therapeutically effective amount of a compound of formula I or formula VI, and pharmaceutically acceptable salts and esters thereof; and a therapeutically effective amount of an agent selected from the group consisting of a type V cyclic-GMP-selective phosphodiesterase inhibitor, an $\alpha_2$-adrenergic receptor antagonist, and a dopaminergic agent, and pharmaceutically acceptable salts and esters thereof; for the manufacture of a medicament for treatment or prevention of erectile dysfunction which comprises an effective amount of a compound of formula I or formula VI and an effective amount of the agent, together or separately.

Melanocortin receptor agonist compounds can be provided in kit. Such a kit typically contains an active compound in dosage forms for administration. A dosage form contains a sufficient amount of active compound such that a beneficial effect can be obtained when administered to a patient during regular intervals, such as 1 to 6 times a day, during the course of 1 or more days. Preferably, a kit contains instructions indicating the use of the dosage form for weight reduction (e.g., to treat obesity or overweight) or sexual dysfunction, and the amount of dosage form to be taken over a specified time period.

Throughout the instant application, the following terms have the indicated meanings:

The term "alkyl", as well as other groups having the prefix "alk", such as alkoxy, alkanoyl, means carbon chains of the designated length which may be in a straight or branched configuration, or combinations thereof. The term alkyl also includes methylene groups which are designated as ($CH_2$) herein. Examples of alkyl groups include methyl, ethyl, n-propyl, isopropyl, n-butyl, 1-methylpropyl, 2-methylpropyl, tert-butyl, n-pentyl, 1-methylbutyl, 2-methylbutyl, 3-methylbutyl, 1,2-dimethylpropyl, 1,1-dimethylpropyl, 2,2-dimethylpropyl, n-hexyl, 1-methylpentyl, 2-methylpentyl, 3-methylpentyl, 4-methylpentyl, 1-ethylbutyl, 2-ethylbutyl, 3-ethylbutyl, 1,1-dimethyl butyl, 1,2-dimethylbutyl, 1,3-dimethylbutyl, 2,2-dimethylbutyl, 2,3-dimethylbutyl, 3,3-dimethyl butyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, 4-ethylpentyl, 1-propylbutyl, 2-propylbutyl, 3-propylbutyl, 1,1-dimethylpentyl, 1,2-dimethylpentyl, 1,3-dimethylpentyl, 1,4-dimethylpentyl, 2,2-dimethylpentyl, 2,3-dimethylpentyl. 2,4-dimethylpentyl, 3,3-dimethylpentyl, 3,4-dimethylpentyl, 4,4-dimethylpentyl, 1-methyl-1-ethylbutyl, 1-methyl-2-ethylbutyl, 2-methyl-2-ethylbutyl, 1-ethyl-2-methylbutyl, 1-ethyl-3-methylbutyl, 1,1-diethylpropyl, n-octyl, n-nonyl, and the like.

The term "halogen" is intended to include the halogen atoms fluorine, chlorine, bromine and iodine.

The term "$C_{1-4}$ alkyliminoyl" means $C_{1-3}$alkylC(=NH)—.

The term "aryl" includes phenyl and naphthyl.

The term "heteroaryl" includes mono- and bicyclic aromatic rings containing from 1 to 4 heteroatoms selected from nitrogen, oxygen and sulfur. Examples thereof include, but are not limited to, pyridinyl, furyl, thienyl, pyrrolyl, oxazolyl, thiazolyl, triazolyl, triazinyl, tetrazolyl, thiadiazolyl, imidazolyl, isoxazolyl, isothiazolyl, oxadiazolyl, pyrazolyl, pyrimidinyl, pyrazinyl, pyridazinyl, quinolyl, isoquinolyl, benzimidazolyl, benzofuryl, benzothienyl, indolyl, benzthiazolyl, benzoxazolyl, and the like. In one embodiment of the present invention, heteroaryl is selected from the group consisting of pyridinyl, furyl, thienyl, pyrrolyl, oxazolyl, thiazolyl, triazolyl, triazinyl, tetrazolyl, thiadiazolyl, imidazolyl, pyrazolyl, isoxazolyl, isothiazolyl, oxathiazolyl, pyrimidinyl, pyrazinyl, pyridazinyl, quinolyl, isoquinolyl, benzimidazolyl, benzofuryl, benzothienyl, indolyl, benzthiazolyl, and benzoxazolyl.

Bicyclic heteroaromatic rings include, but are not limited to, benzothiadiazole, indole, benzothiophene, benzofuran, benzimidazole, benzisoxazole, benzothiazole, quinoline, quinazoline, benzotriazole, benzoxazole, isoquinoline, purine, furopyridine, thienopyridine, benzisodiazole, triazolopyrimidine, and 5,6,7,8-tetrahydroquinoline.

The term "cycloalkyl" includes mono- or bicyclic non-aromatic rings containing only carbon atoms. Examples of cycloalkyl include, but are not limited to, cyclopropyl, cyclobutyl, cyclopentyl, cyclohexyl, cycloheptyl.

The term "heterocycloalkyl" is intended to include non-aromatic heterocycles containing one to four heteroatoms selected from nitrogen, oxygen and sulfur. Substitution on the heterocycloalkyl ring includes substitution on the carbon and/or the nitrogen atoms of the heterocycloalkyl ring. Examples of heterocycloalkyls include, but are not limited to, azetidine, piperidine, morpholine, thiamorpholine, pyrrolidine, imidazolidine, tetrahydrofuran, piperazine, 1-thia-4-aza-cyclohexane.

Certain of the above defined terms may occur more than once in the above formula and upon such occurrence each term shall be defined independently of the other; thus for example, $NR^4R^4$ may represent $NH_2$, $NHCH_3$, $N(CH_3)CH_2CH_3$, and the like.

The term "subject" means a mammal. One embodiment of the term "mammal" is a "human," said human being either male or female. The instant compounds are also useful for treating or preventing obesity and obesity related disorders in cats and dogs. As such, the term "mammal" includes companion animals such as cats and dogs.

The term "mammal in need thereof" refers to a mammal who is in need of treatment or prophylaxis as determined by a researcher, veterinarian, medical doctor or other clinician.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

By a melanocortin receptor "agonist" is meant an endogenous or drug substance or compound that can interact with a melanocortin receptor and initiate a pharmacological response characteristic of the melanocortin receptor. By a melanocortin receptor "antagonist" is meant a drug or a compound that opposes the melanocortin receptor-associated responses normally induced by another bioactive agent. The "agonistic" properties of the compounds of the present invention were measured in the functional assay described below. The functional assay discriminates a melanocortin receptor agonist from a melanocortin receptor antagonist.

By "binding affinity" is meant the ability of a compound/drug to bind to its biological target, in the the present instance, the ability of a compound of structural formula I or formula VI to bind to a melanocortin receptor. Binding affinities for the compounds of the present invention were measured in the binding assay described below and are expressed as $IC_{50}$'s.

"Efficacy" describes the relative intensity with which agonists vary in the response they produce even when they occupy the same number of receptors and with the same affinity. Efficacy is the property that enables drugs to produce responses. Properties of compounds/drugs can be categorized into two groups, those which cause them to associate with the receptors (binding affinity) and those that produce a stimulus (efficacy). The term "efficacy" is used to characterize the level of maximal responses induced by agonists. Not all agonists of a receptor are capable of inducing identical levels of maximal responses. Maximal response depends on the efficiency of receptor coupling, that is, from the cascade of events, which, from the binding of the drug to the receptor, leads to the desired biological effect.

The functional activities expressed as $EC_{50}$'s and the "agonist efficacy" for the compounds of the present invention at a particular concentration were measured in the functional assay described below.

Optical Isomers—Diastereomers—Geometric Isomers—Tautomers

Compounds of structural formula I and formula VI contain one or more asymmetric centers and can thus occur as racemates and racemic mixtures, single enantiomers, diastereomeric mixtures and individual diastereomers. The present invention is meant to comprehend all such isomeric forms of the compounds of structural formula I and formula VI.

Some of the compounds described herein contain olefinic double bonds, and unless specified otherwise, are meant to include both E and Z geometric isomers. For example, the $R^6$ substituent $=N-OR^5$ includes both of the following geometric isomers:

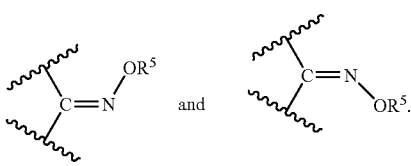

Some of the compounds described herein may exist as tautomers such as keto-enol tautomers. The individual tautomers as well as mixtures thereof are encompassed within the compounds of structural formula I and formula VI.

Compounds of structural formula I and formula VI may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general formula I, IIa, IIb, IIIa, IIIb, IV, V and VI may be obtained by stereospecific synthesis using optically pure starting materials or reagents of known absolute configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Particularly preferred are citric, fumaric, hydrobromic, hydrochloric, maleic, phosphoric, sulfuric, and tartaric acids.

It will be understood that, as used herein, references to the compounds of Formula I and formula VI are meant to also include the pharmaceutically acceptable salts, such as the hydrochloride salts.

Utility

Compounds of formula I and formula VI are melanocortin receptor agonists and as such are useful in the treatment, control or prevention of diseases, disorders or conditions responsive to the activation of one or more of the melanocortin receptors including, but are not limited to, MC-1, MC-2, MC-3, MC-4, or MC-5. Such diseases, disorders or conditions include, but are not limited to, obesity (by reducing appetite, increasing metabolic rate, reducing fat intake or reducing carbohydrate craving), diabetes mellitus (by enhancing glucose tolerance, decreasing insulin resistance), hypertension, hyperlipidemia, osteoarthritis, cancer, gall bladder disease, sleep apnea, depression, anxiety, compulsion, neuroses, insomnia/sleep disorder, substance abuse, pain, male and female sexual dysfunction (including impotence, loss of libido and erectile dysfunction), fever, inflammation, immunemodulation, rheumatoid arthritis, skin tanning, acne and other skin disorders, neuroprotective and cognitive and memory enhancement including the treatment of Alzheimer's disease. Some compounds encompassed by formula I and formula VI show highly selective affinity for the melanocortin-4 receptor (MC-4R) relative to MC-1R, MC-2R, MC-3R, and MC-5R, which makes them especially useful in the prevention and treatment of obesity, as well as male and/or female sexual dysfunction, including erectile dysfunction.

The compositions of the present invention are useful for the treatment or prevention of disorders associated with excessive food intake, such as obesity and obesity-related disorders. The obesity herein may be due to any cause, whether genetic or environmental.

The obesity-related disorders herein are associated with, caused by, or result from obesity. Examples of obesity-related disorders include overeating, binge eating, and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compositions of the present invention are also useful for reducing the risk of secondary outcomes of obesity, such as reducing the risk of left ventricular hypertrophy.

The term "metabolic syndrome", also known as syndrome X, is defined in the Third Report of the National Cholesterol Education Program Expert Panel on Detection, Evaluation and Treatment of High Blood Cholesterol in Adults (ATP-III). E. S. Ford et al., JAMA, vol. 287 (3), Jan. 16, 2002, pp 356-359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III.

The term "diabetes," as used herein, includes both insulin-dependent diabetes mellitus (i.e., IDDM, also known as type I diabetes) and non-insulin-dependent diabetes mellitus (i.e., NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compositions of the present invention are useful for treating both Type I and Type II diabetes. The compositions are especially effective for treating Type II diabetes. The compounds or combinations of the present invention are also useful for treating and/or preventing gestational diabetes mellitus.

Treatment of diabetes mellitus refers to the administration of a compound or combination of the present invention to treat diabetes. One outcome of treatment may be decreasing the glucose level in a subject with elevated glucose levels. Another outcome of treatment may be improving glycemic control. Another outcome of treatment may be decreasing insulin levels in a subject with elevated insulin levels. Another outcome of treatment may be decreasing plasma triglycerides in a subject with elevated plasma triglycerides. Another outcome of treatment may be lowering LDL cholesterol in a subject with high LDL cholesterol levels. Another outcome of treatment may be increasing HDL cholesterol in a subject with low HDL cholesterol levels. Another outcome may be decreasing the LDL/HDL ratio in a subject in need thereof. Another outcome of treatment may be increasing insulin sensivity. Another outcome of treatment may be enhancing glucose tolerance in a subject with glucose intolerance. Another outcome of treatment may be decreasing insulin resistance in a subject with increased insulin resistance or elevated levels of insulin. Another outcome may be decreading triglycerides in a subject with elevated triglycerides. Yet another outcome may be improving LDL cholestrol, non-HDL cholesterol, triglyceride, HDL cholesterol or other lipid analyte profiles.

Prevention of diabetes mellitus refers to the administration of a compound or combination of the present invention to prevent the onset of diabetes in a mammal at risk thereof.

"Obesity" is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes, non-insulin dependent diabetes mellitus—type II (2), impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds or combinations of the present invention to reduce or maintain the body weight of an obese subject. One outcome of treatment may be reducing the body weight of an obese subject relative to that subject's body weight immediately before the administration of the compounds or combinations of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in subjects in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds or combinations of the present invention to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovary disease, cardiovascular diseases, osteoarthritis, dermatological disorders, hypertension, insulin resistance, hypercholesterolemia, hypertriglyceridemia, and cholelithiasis.

"Male sexual dysfunction" includes impotence, loss of libido, and erectile dysfunction.

"Erectile dysfunction" is a disorder involving the failure of a male mammal to achieve erection, ejaculation, or both. Symptoms of erectile dysfunction include an inability to achieve or maintain an erection, ejaculatory failure, premature ejaculation, or inability to achieve an orgasm. An increase in erectile dysfunction and sexual dysfunction can have numerous underlying causes, including but not limited to (1) aging, (b) an underlying physical dysfunction, such as trauma, surgery, and peripheral vascular disease, and (3) side-effects resulting from drug treatment, depression, and other CNS disorders.

Treatment of male sexual dysfunction refers to the administration of a compound or combination of the present invention to treat impotence and/or loss of libido, and/or erectile dysfunction in a male mammal in need thereof. One outcome of treatment may be a decrease in impotence. Another outcome of treatment may be an increase in libido. Yet another outcome of treatment may be a decrese in the magnitude or frequency of erectile dysfunction.

Treatment of male sexual dysfunction refers to the administration of a compound or combination of the present invention to treat one or more of the symptoms of male sexual dysfunction in a male mammal in need thereof. One outcome of treatment may be increasing the ability to achieve an erection. Another outcome of treatment may be increasing the ability to maintain an erection. Another outcome of treatment may be reducing ejaculatory failure. Another outcome of treatment may be decreasing premature ejaculation. Yet another outcome of treatment may be increasing the ability to achieve an orgasm.

Prevention of male sexual dysfunction and male erectile dysfunction refers to the administration of the compounds or combinations of the present invention to prevent the symptoms of sexual dysfunction and erectile dysfunction in a male mammal at risk thereof. "female sexual dysfunction" can be seen as resulting from multiple components including dysfunction in desire, sexual arousal, sexual receptivity, and orgasm related to disturbances in the clitoris, vagina, periurethral glans, and other trigger points of sexual function. In particular, anatomic and functional modification of such trigger points may diminish the orgasmic potential in breast cancer and gynecologic cancer patients. Treatment of female sexual dysfunction with an MC-4 receptor agonist can result in improved blood flow, improved lubrication, improved sensation, facilitation of reaching orgasm, reduction in the refractory period between orgasms, and improvements in arousal and desire. In a broader sense, "female sexual dysfunction" also incorporates sexual pain, premature labor, and dysmenorrhea.

The terms "administration of" and or "administering" a compound should be understood to mean providing a compound of the invention or a prodrug of a compound of the invention to a subject in need of treatment.

The administration of the compounds of the present invention in order to practice the present methods of therapy is carried out by administering a therapeutically effective amount of the compound to a subject in need of such treatment or prophylaxis. The need for a prophylactic administration according to the methods of the present invention is determined via the use of well known risk factors.

The term "therapeutically effective amount" as used herein means the amount of the active compound that will elicit the biological or medical response in a tissue, system, subject, mammal, or human that is being sought by the researcher, veterinarian, medical doctor or other clinician, which includes alleviation of the symptoms of the disorder being treated. The novel methods of treatment of this invention are for disorders known to those skilled in the art.

The term "prophylactically effective amount" as used herein means the amount of the active compound that will elicit the biological or medical response in a tissue, system, subject, mammal, or human that is being sought by the researcher, veterinarian, medical doctor or other clinician, to prevent the onset of the disorder in subjects as risk for obesity or the disorder.

The therapeutically or prophylactically effective amount, or dosage, of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgement.

Administration and Dose Ranges

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I and Formula VI are administered orally or topically.

The effective dosage of active ingredient employed may vary depending on the particular compound employed, the mode of administration, the condition being treated and the severity of the condition being treated. Such dosage may be ascertained readily by a person skilled in the art.

When treating obesity, in conjunction with diabetes and/ or hyperglycemia, or alone, generally satisfactory results are obtained when the compounds of the present invention are administered at a daily dosage of from about 0.001 milligram to about 100 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

When treating diabetes mellitus and/or hyperglycemia, as well as other diseases or disorders for which compounds of formula I and formula VI are useful, generally satisfactory results are obtained when the compounds of the present invention are administered at a daily dosage of from about 0.001 milligram to about 100 milligram per kilogram of animal body weight, preferably given in a single dose or in divided doses two to six times a day, or in sustained release form. In the case of a 70 kg adult human, the total daily dose will generally be from about 0.07 milligrams to about 350 milligrams. This dosage regimen may be adjusted to provide the optimal therapeutic response.

For the treatment of sexual dysfunction compounds of the present invention are given in a dose range of 0.001 milligram to about 100 milligram per kilogram of body weight, preferably as a single dose orally or as a nasal spray.

In the case where an oral composition is employed, a suitable dosage range is, e.g. from about 0.01 mg to about 1500 mg of a compound of Formula I or Formula VI per day, preferably from about 0.1 mg to about 10 mg per day. For oral administration, the compositions are preferably provided in the form of tablets containing from 0.01 to 1,006 mg, preferably 0.01, 0.05, 0.1, 0.5, 1, 2.5, 5, 10, 15, 20, 25, 30, 40, 50, 100, 250, 500, 750, 1000, 1250 or 1500 milligrams of the active ingredient for the symptomatic adjustment of the dosage to the patient to be treated.

For use where a composition for intranasal administration is employed, intranasal formulations for intranasal administration comprising 0.001-10% by weight solutions or suspensions of the compounds of Formula I or Formula VI in an acceptable intranasal formulation may be used.

For use where a composition for intravenous administration is employed, a suitable dosage range is from about 0.001 mg to about 100 mg (preferably from 0.01 mg to about 50 mg, more preferably 0.1 mg to 10 mg) of a compound of Formula I or Formula VI per kg of body weight per day. This dosage regimen may be adjusted to provide the optimal therapeutic response. It may be necessary to use dosages outside these limits in some cases.

For the treatment of diseases of the eye, ophthalmic preparations for ocular administration comprising 0.001-1% by weight solutions or suspensions of the compounds of Formula I or Formula VI in an acceptable ophthalmic formulation may be used.

The magnitude of prophylactic or therapeutic dosage of the compounds of the present invention will, of course, vary depending on the particular compound employed, the mode of administration, the condition being treated and the severity of the condition being treated. It will also vary according to the age, weight and response of the individual patient. Such dosage may be ascertained readily by a person skilled in the art.

Combination Therapy

Compounds of Formula I and Formula VI may be used in combination with other drugs that are used in the treatment/prevention/suppression or amelioration of the diseases or conditions for which compounds of Formula I and Formula VI are useful. Such other drugs may be administered, by a route and in an amount commonly used therefor, contemporaneously or sequentially with a compound of Formula I or Formula VI. When a compound of Formula I or Formula VI is used contemporaneously with one or more other drugs, a pharmaceutical composition containing such other drugs in addition to the compound of Formula I or Formula VI is preferred. Accordingly, the pharmaceutical compositions of the present invention include those that also contain one or more other active ingredients, in addition to a compound of Formula I or Formula VI.

Examples of other active ingredients that may be combined with a compound of Formula I or Formula VI for the treatment or prevention of obesity and/or diabetes, either administered separately or in the same pharmaceutical compositions, include, but are not limited to:

(a) insulin sensitizers including (i) PPARγ antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD), GW-0207, LG-100641, and LY-300512, and the like), and compounds disclosed in WO97/10813, 97/27857, 97/28115, 97/28137, and 97/27847; (ii) biguanides such as metformin and phenformin;

(b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-NH$_2$);

(c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide;

(d) α-glucosidase inhibitors, such as acarbose, adiposine; carniglibose; emiglitate; miglitol; voglibose; pradimicin-Q; salbostatin; CKD-711; MDL-25,637; MDL-73,945; and MOR 14, and the like;

(e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants, such as cholestyramine, colestipol, dialkylaminoalcyl derivatives of a cross-inked dextran; Colestid®; LoCholest®, and the like, (ii) nicotinyl alcohol, nicotinic acid or a salt thereof, (iii) proliferator-activater receptor α agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoA:cholesterol acyltransferase (ACAT)) inhibitors such as avasimibe, and melinamide, (v) antioxidants, such as probucol, (vi) vitamin E, and (vii) thyromimetics;

(f) PPARα agonists such as beclofibrate, benzafibrate, ciprofibrate, clofibrate, etofibrate, fenofibrate, and gemfibrozil; and other fibric acid derivatives, such as Atromid®, Lopid® and Tricor®, and the like, and PPARα agonists as described in WO 97/36579 by Glaxo;

(g) PPARδ agonists, such as those disclosed in WO97/28149; and (h) anti-obesity agents, such as (1) growth hormone secretagogues, growth hormone secretagogue receptor agonists/antagonists, such as NN703, hexarelin, MK-0677, SM-130686, CP-424,391, L-692,429 and L-163,255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid $CB_1$ receptor antagonists or inverse agonists, such as rimonabant (Sanofi Synthelabo), and SR-14778 and SR 141716A (Sanofi Synthelabo), SLV-319 (Solvay), BAY 65-2520 (Bayer), and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, W002/076949, and WO 03/007887; and EPO Application No. EP-658546, EP-656354, EP-576357; (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316, 243, SB 418790, BRL-37344, L-796568, BMS-196085, BRL-35135A, CGP12177A, BTA-243, Trecadrine, Zeneca D7114, SR 59119A, and such as those disclosed in U.S. Pat. No. 5,705,515, and U.S. Pat. No. 5,451,677 and PCT Patent Publications WO94/18161, WO95/29159, WO97/46556, WO98/04526 and WO98/32753, WO 01/74782, and WO 02/32897; (6) pancreatic lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081x, GW-548118x, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,140,354, 6,191,160, 6,313,298, 6,337,332, 6,329,395, 6,326,375, 6,335,345, and 6,340,683, European Patent Nos. EP-01010691, and EP-01044970, and PCT Patent Publication Nos. WO 97/19682, WO 97/20820, WO 97/20821, WO 97/20822, WO 97/20823, WO 98/27063, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/06245, WO 02/04433, and WO 02/51809, and Japanese Patent Application No. JP 13226269; (11) melanin-concentrating hormone 2 receptor (MCH2R) agonist/antagonists; (12) orexin-1 receptor antagonists, such as SB-334867-A, and those disclosed in PCT Patent Application Nos. WO 01/96302, WO 01/68609, WO 02/51232, and WO 02/51838; (13) serotonin reuptake inhibitors such as fluoxetine, paroxetine, and sertraline, and those disclosed in U.S. Pat. No. 6,365,633, and PCT Patent Application Nos. WO 01/27060 and WO 01/162341; (14) melanocortin agonists, such as Melanotan II or those described in WO 99/64002 and WO 00/74679; (15) other Mc4r (melanocortin 4 receptor) agonists, such as CHIR86036 (Chiron), ME-10142, and ME-10145 (Melacure), and those disclosed in PCT Application Nos. WO 01/991752, WO 01/74844, WO 02/12166, WO 02/11715, and WO 02/12178; (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-A (cholecystokinin-A) agonists, such as AR-R 15849, GI 181771, JMV-180, A-71378, A-71623 and SR146131, and those described in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-1H-imidazol-4-yl)propyl N-(4-pentenyl)carbamate, clobenpropit, iodophenpropit, imoproxifan, GT2394 (Gliatech), and those described and disclosed in PCT Application No. WO 02/15905, and O-[3-1H-imidazol-4-yl)propanol]-carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)); (25) β-hydroxy steroid dehydrogenase-1 inhibitors (β-HSD-1); 26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives, such as those disclosed in U.S. Pat. Nos. 5,552,524, 5,552,523, 5,552,522, 5,521,283, and PCT International Publication Nos. WO 96/23513, WO 96/23514, WO 96/23515, WO 96/23516, WO 96/23517, WO 96/23518, WO 96/23519, and WO 96/23520; (32) BRS3 (bombesin receptor subtype 3) agonists; (33) CNTF (Ciliary neurotrophic factors), such as GI-181771 (Glaxo-SmithKline), SR146131 (Sanofi Synthelabo), but-abindide, PD170,292, and PD 149164 (Pfizer); (34) CNTF derivatives, such as axokine (Regeneron), and those disclosed in PCI Application Nos. WO 94/09134, WO 98/22128, and WO 99/43813; (35) monoamine reuptake inhibitors, such as those disclosed in PCT Application Nos. WO 01/27068, and WO 01/62341; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TT-NPB), retinoic acid, and those disclosed in PCT Patent Application No. WO 99/00123; (37) thyroid hormone β agonists, such as KB-2611 (KaroBioBMS), and those disclosed in PCT Application No. WO 02/15845, and Japanese Patent Application No. JP 2000256190; (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide; NVP-DPP728; P32/98; and LAF 237, P 3298, TSL 225, valine pyrrolidide, TMC-2A/2B/2C, CD-26 inhibitors, FE 999011, P9310/K364, VIP 0177, DPP4, SDZ 274-444; and the compounds disclosed in WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); and WO 03/000181 (3 Jan. 2003); (45) fatty acid transporter inhibitors; (46) dicarboxylate transporter inhibitors; (47) glucose transporter inhibitors; (48) phosphate transporter inhibitors; (49) Metformin (Glucophage®); and (50) Topiramate (Topimax®); and (50) peptide YY, PYY 3-36, peptide YY analogs, and PYY agonists such as those disclosed in WO 03/026591, WO 03/057235, and WO 03/027637; and (51) cyclo-oxygenase-2 inhibitors such as rofecoxib, celecoxib, and arcoxia.

Examples of other anti-obesity agents that can be employed in combination with a compound of Formula I and Formula VI are disclosed in "Patent focus on new anti-obesity agents," *Exp. Opin. Ther. Patents,* 10: 819-831 (2000); "Novel anti-obesity drugs," *Exp. Opin. Invest. Drugs,* 9: 1317-1326 (2000); and "Recent advances in feeding suppressing agents: potential therapeutic strategy for the treatment of obesity, *Exp. Opin. Ther. Patents,* 11: 1677-1692 (2001). The role of neuropeptide Y in obesity is discussed in *Exp. Opin. Invest. Drugs,* 9: 1327-1346 (2000).

Cannabinoid receptor ligands are discussed in *Exp. Opin. Invest. Drugs*, 9: 1553-1571 (2000).

Examples of other active ingredients that may be combined with a compound of Formula I or Formula VI for the treatment or prevention of male or female sexual dysfunction, in particular, male erectile dysfunction, either administered separately or in the same pharmaceutical compositions, include, but are not limited to (a) type V cyclic-GMP-specific phosphodiesterase (PDE-V) inhibitors, including sildenafil and (6R,12aR)-2,3,6,7,12,12a-hexahydro-2-methyl-6-3,4-methylenedioxyphenyl)-pyrazino[2',1':6,1]pyrido[3,4-b]indole-1,4-dione (IC-351); (b) alpha-adrenergic receptor antagonists, including phentolamine and yohimbine or pharmaceutically acceptable salts thereof; (c) dopamine receptor agonists, such as apomorphine or pharmaceutically acceptable salts thereof; and (d) nitric oxide (NO) donors.

The instant invention also includes administration of a single pharmaceutical dosage formulation which contains both the MC-4R agonist in combination with a second active ingredient, as well as administration of each active agent in its own separate pharmaceutical dosage formulation. Where separate dosage formulations are used, the individual components of the composition can be administered at essentially the same time, i.e., concurrently, or at separately staggered times, i.e. sequentially prior to or subsequent to the administration of the other component of the composition. The instant invention is therefore to be understood to include all such regimes of simultaneous or alternating treatment, and the terms "administration" and "administering" are to be interpreted accordingly. Administration in these various ways are suitable for the present compositions as long as the beneficial pharmaceutical effect of the combination of the MC-4R agonist and the second active ingredient is realized by the patient at substantially the same time. Such beneficial effect is preferably achieved when the target blood level concentrations of each active ingredient are maintained at substantially the same time. It is preferred that the combination of the MC-4R agonist and the second active ingredient be co-administered concurrently on a once-a-day dosing schedule; however, varying dosing schedules, such as the MC-4R agonist once a day and the second active ingredient once, twice or more times per day, is also encompassed herein. A single oral dosage formulation comprised of both a MC-4R agonist and a second active ingredient is preferred. A single dosage formulation will provide convenience for the patient, which is an important consideration especially for patients with diabetes or obese patients who may be in need of multiple medications.

The compounds in the combinations of the present invention may be administered separately, therefore the invention also relates to combining separate pharmaceutical compositions into a kit form. The kit, according to this invention, comprises two separate pharmaceutical compositions: a first unit dosage form comprising a prophylactically or therapeutically effective amount of the melanocortin-4 receptor agonist, or a pharmaceutically acceptable salt or ester thereof, and a pharmaceutically acceptable carrier or diluent in a first unit dosage form, and a second unit dosage form comprising a prophylactically or therapeutically effective amount of the second active ingredient or drug, or a pharmaceutically acceptable salt or ester thereof, and a pharmaceutically acceptable carrier or diluent in a second unit dosage form.

In one embodiment, the kit further comprises a container. Such kits are especially suited for the delivery of solid oral forms such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days or time in the treatment schedule in which the dosages can be administered.

Pharmaceutical Compositions

Another aspect of the present invention provides pharmaceutical compositions which comprises a compound of Formula I, or Formula VI, and a pharmaceutically acceptable carrier. The pharmaceutical compositions of the present invention comprise a compound of Formula I or Formula VI as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I and Formula VI can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the typical oral dosage unit form, in which case solid pharmaceutical carriers are typically employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I and formula VI may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Preparation of Compounds of the Invention

The compounds of structural formula I and formula VI of the present invention can be prepared according to the procedures of the following Schemes and Examples, using appropriate materials and are further exemplified by the following specific examples. Moreover, by utilizing the procedures described in detail in PCT International Application Publications WO 02/068387 (6 Sep. 2002) and WO 02/068388 (6 Sep. 2002), in conjunction with the disclosure contained herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogencarbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. CBZ and BOC are commonly used protecting groups in organic synthesis, and their removal conditions are known to those skilled in the art. For example, CBZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of CBZ groups can also be achieved by treatment with a solution of hydrogen bromide in acetic acid or by treatment with a mixture of TFA and dimethylsulfide. Removal of BOC protecting groups is carried out with a strong acid, such as trifluoroacetic acid, hydrochloric acid, or hydrogen chloride gas, in a solvent such as methylene chloride, methanol, or ethyl acetate.

Abbreviations Used in the Description of the Preparation of the Compounds of the Present Invention:

BOC (Boc) is t-butyloxycarbonyl, BOP is benzotriazol-1-yloxytris(dimethylamino)-phosphonium hexafluorophosphate, Bn is benzyl, Bu is butyl, calc. or calc'd is Calculated, celite is Celite™ diatomaceous earth, CBZ (Cbz) is benzyloxycarbonyl, c-hex is cyclohexyl, c-pen is cyclopentyl, c-pro is cyclopropyl, DEAD is diethyl azodicarboxylate, DIEA is diisopropyl-ethylamine, DMAP is 4-dimethylaminopyridine, DMF is N,N-dimethylformamide, dppf is 1,1'-Bis(diphenylphosphino)ferrocene, EDC is 1-(3-dimethylaminopropyl)3-ethylcarbodiimide HCl, eq is equivalent(s), ES-MS is electron spray ion-mass spectroscopy, Et is ethyl, EtOAc is ethyl acetate, h or hr is hour(s), HATU is O-(7-azabenzotriazol-1-yl)-1,1,3,3-tetramethyluronium hexafluorophosphate, HOAt is 1-hydroxy-7-azabenzotriazole, HOBt is 1-hydroxybenzotriazole hydrate, HPLC is high performance liquid chromatography, LC-MS or LC-MASS is liquid chromatography mass spectrum, LDA is lithium diisopropylamide, MC-xR is melanocortin receptor (x being a number), Me is methyl, MF is molecular formula, MS is mass spectrum, Ms is methane sulfonyl, NMM is N-Methylmorpholine, NMO is N-Methylmorpholine-N-oxide, OTf is trifluoromethanesulfonyl, Ph is phenyl, Phe is phenyl alanine, Pr is propyl, iPr is isopropyl, prep. is prepared, PyBrop is bromo-tris-pyrrolidino-phosphonium hexafluorophosphate, r.t. or rt is room temperature, Tf is triflate or trifluoromethanesulfonate, TFA is trifluoroacetic acid, THF is tetrahydrofuran, and TLC is thin-layer chromatography.

Reaction Schemes A-U illustrate methods employed in the synthesis of the compounds of the present invention of structural formula I. All substituents are as defined above unless indicated otherwise.

Reaction Scheme A illustrates a key step in the synthesis of the novel compounds of structural formula I of the present invention. As shown in reaction Scheme A, the reaction of a piperidine derivative of type 1 with a carboxylic acid derivative of formula 2 affords a title compound of structural formula I. The amide bond coupling reaction illustrated in reaction Scheme A is conducted in an appropriate inert solvent such as dimethylformamide (DMF), methylene chloride or the like and may be performed with a variety of reagents suitable for amide coupling reactions such as O-(7-azabenzotriazol-1-yl)-1,1,3,3-tetramethyluronium hexafluorophosphate (HATU), 1-(3-methylaminopropyl)-3-ethylcarbodiimide hydrochloride (EDC) or benzotriazol-1-yloxytripyrrolidinephosphonium hexafluorophosphate (PyBOP). Preferred conditions for the amide bond coupling reaction shown in reaction Scheme A are known to those skilled in organic synthesis. Such modifications may include, but are not limited to, the use of basic reagents such as triethylamine (TEA), N,N-diisopropylethylamine (DIPEA), or N-methylmorpholine (NMM), or the addition of an additive such as 1-hydroxy-7-azabenzotriazole (HOAt) or 1-hydroxybenzotriazole (HOBt). Alternatively, 4-substituted piperidines of formula A-1 may be treated with an active ester or acid chloride derived from carboxylic acid A-2 which also affords compounds of structural formula I. The amide bond coupling shown in reaction Scheme A is usually conducted at a temperature between 0° C. and room temperature, occasionally at elevated temperatures, and the coupling reaction is typically conducted for periods of 1 to 24 hours.

erocyclic compound of structural formula I (Z=N, $R^1$=H) may then be subjected to one of several alkylation strategies known in organic chemistry to add another $R^1$ group. For instance, compounds (I) (Z=N, $R^1$=H) may be utilized in a reductive amination reaction with a suitable carbonyl containing reagent 3. The reductive amination is achieved by initial formation of an imine between the amine of formula I (Z=N, $R^1$=H) and either an aldehyde or ketone of formula 3. The intermediate imine is then treated with a reducing agent capable of reducing carbon-nitrogen double bonds such as sodium cyanoborohydride or sodium triacetoxyborohydride and an alkylated product of structural formula I is produced. Alternatively, a heterocyclic compound of structural formula (I) (Z=N, $R^1$=H) may be directly alkylated using an alkylating agent such as 4 in a polar aprotic solvent such as DMF. In this reaction, the substituent leaving group, LG, of compound 4 is a leaving group such as a halide, mesylate or triflate, and the product is the compound of structural formula I (Z=N) bearing the $R^1$ substituent.

Scheme A

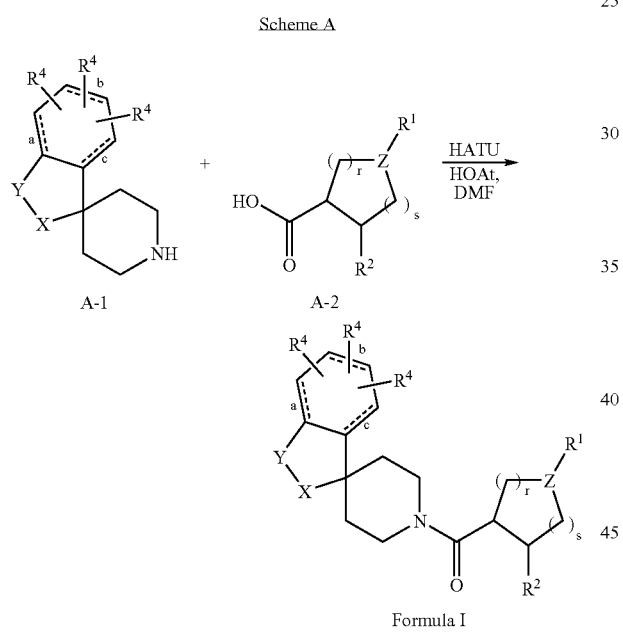

If it is desired to produce a compound of structural formula I wherein Z is a nitrogen and $R^1$ is a hydrogen, the N-BOC protected analogs of structural formula I may be used in the synthesis and deprotected under acidic conditions, for instance using trifluoroacetic acid in a solvent like methylene chloride or hydrogen chloride in a solvent such as ethyl acetate at a temperature between 0° C. and room temperature.

When it is desired to prepare compounds of structural formula I wherein Z is a nitrogen and $R^1$ is not a hydrogen, the compounds of general formula I (Z=N, $R^1$=H) may be further modified using the methodology described below in reaction Scheme B. For example, the N-BOC protected compound of structural formula I can be deprotected under acidic conditions for instance by treatment with hydrogen chloride in ethyl acetate or using trifluoroacetic acid in dichloromethane as previously described. The resulting het- Scheme B

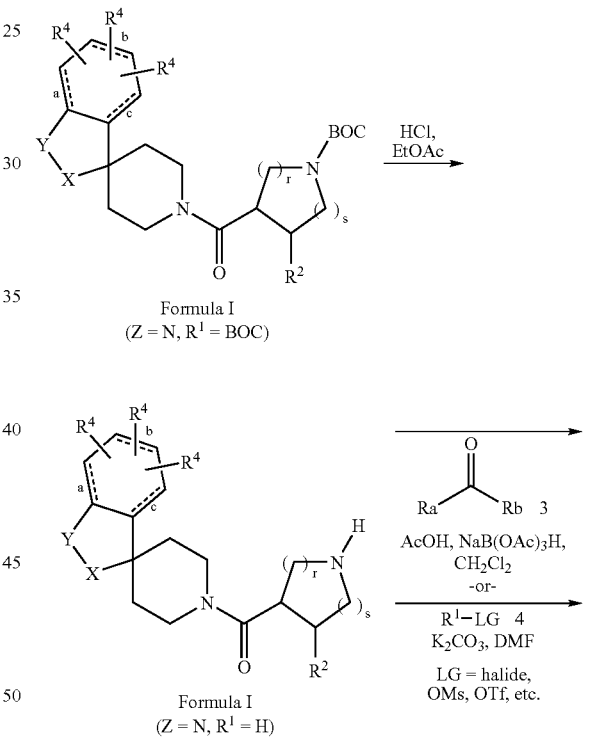

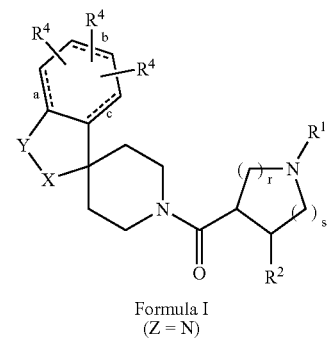

Reaction Schemes C-O illustrate methods for the synthesis of the carboxylic acids of general formula 2 that are utilized in the amide bond coupling reaction shown in reaction Scheme A. These schemes also feature methods for modification or elaboration of compounds of general formula I. Reaction Schemes P-U illustrate additional methods for the synthesis of 4,4-disubstituted piperidines of general formula 1 that are used in the amide bond coupling reaction, and also feature methods for elaboration of compounds of general formula I.

Reaction Scheme C illustrates a preferred method for the synthesis of compounds of general formula 2 wherein Z is a nitrogen, r is 2 and s is 1 such that the resulting heterocycle is a 3-aryl-piperidine carboxylic acid derivative 12. The synthesis of 12 begins with a commercially available β-keto ester such as 5. Generally a protecting group interchange of an N-BOC group for the N-benzyl group is performed initially. Thus a β-keto ester of formula 5 is subjected to debenzylation by hydrogenolysis using a palladium-on-carbon catalyst in a solvent system such as 1:1 ethanol-water under a hydrogen atmosphere. The resulting piperidone 6 is then protected as its tert-butyl carbamate using BOC anhydride in the presence of a base and a suitable solvent. For example, this can be accomplished in a two phase mixture of chloroform and aqueous sodium bicarbonate as shown. Incorporation of the 3-aryl substituent is then performed in two steps. First, the β-keto ester group is converted to the corresponding vinyl triflate 8 using trifluoromethanesulfonic anhydride and an organic base like N,N-diisopropylethylamine in an aprotic solvent such as methylene chloride. The resulting vinyl triflate 8 is then subjected to a palladium-catalyzed cross-coupling reaction with an aryl boronic acid (2) using a palladium (II) catalyst such as [1,1'-bis(diphenylphosphino)-ferrocene]dichloropalladium(II). Preferred conditions for this reaction are the use of a toluene-ethanol-aqueous sodium carbonate solvent system at an elevated temperature, for instance 50-100° C., for a period of 2-24 hours. The resulting aryl-substituted tetrahydropyridine derivative 10 can be reduced to a piperidine such as 11 using a variety of known techniques and the method chosen will determine the stereochemical outcome of the product. For instance, hydrogenation of 10 with a palladium-on-carbon catalyst in a solvent such as ethanol affords cis-3,4-disubstituted piperidines of general formula 11. Alternatively, a dissolving metal reduction using a metal, such as magnesium in methanol, reduces the double bond of 10 and produces a mixture of both cis and trans 3,4-disubstituted piperidines of formula 11. The resulting mixture of cis and trans diastereoisomers may be separated chromatographically or it may be subsequently epimerized to afford the pure trans isomer of 11 by treating the mixture with a base like sodium methoxide in methanol. Finally, hydrolysis of either the cis or trans 3-aryl-4-piperidine carboxylic ester 11 affords either a cis or trans 3-aryl-4-piperidine carboxylic acid of general formula 1, corresponding to an acid of general formula 2 wherein r is 2 and s is 1. The cis or trans carboxylic acids of general formula 12 are produced as racemates and either may be resolved to afford enantiomerically pure compounds by methods known in organic synthesis. Preferred methods include resolution by crystallization of diastereoisomeric salts derived from acids 12 and a chiral amine base or the use of chiral stationary phase liquid chromatography columns. Alternatively, the cis or trans carboxylic esters 11 can also be resolved by the use of chiral stationary phase liquid chromatography columns.

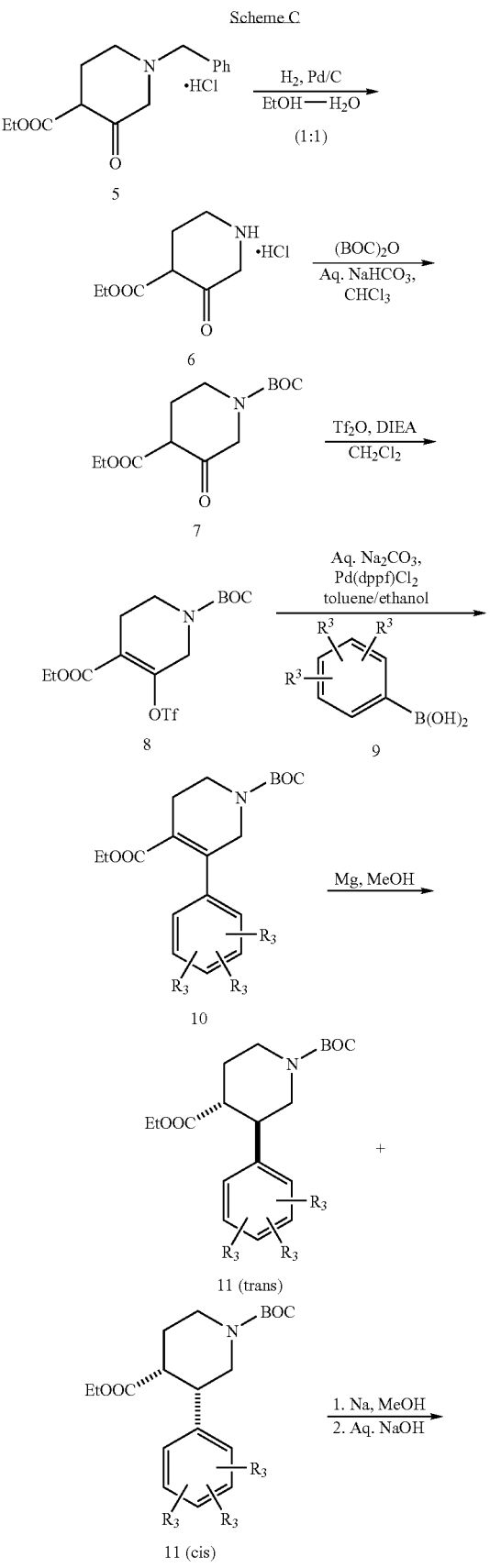

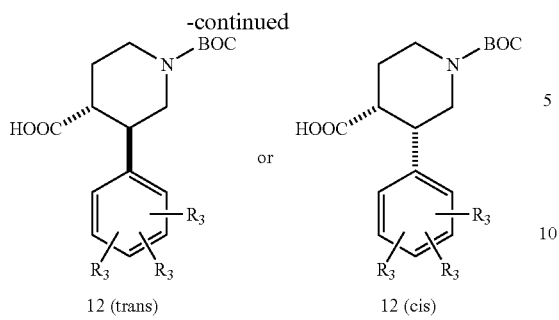

12 (trans) or 12 (cis)

Reaction Scheme D illustrates a preferred method for the synthesis of compounds of general formula 2 wherein Z is a nitrogen, r is 1 and s is 2, such that the resulting heterocycle is a 4-aryl-3-piperidine-carboxylic acid derivative 19. The synthesis of 19 is similar to the synthesis shown in reaction Scheme C, and may begin with either of the commercially available β-keto esters 13 or 14. Conversion of 13 or 14 to the N-BOC-protected piperidine 15 is performed as shown and the resulting β-keto ester is subjected to the two-step arylation protocol previously described in Scheme C to yield 17. Reduction of the double bond of 17 using conditions appropriate for obtaining either cis or trans 18 is followed by ester hydrolysis which affords either a cis or trans 4-aryl-3-piperidine-carboxylic acid of general formula 19 which corresponds to an acid of general formula 2 wherein Z is a nitrogen, r is 1 and s is 2. The cis or trans carboxylic acids of general formula 19 are produced as racemates and either may be resolved to afford enantiomerically pure compounds by methods known in organic synthesis. Preferred methods include resolution by crystallization of diastereoisomeric salts derived from the acids 19 and a chiral amine base or by the use of chiral stationary phase liquid chromatography columns. As before, the cis or trans carboxylic esters 18 can also be resolved by the use of chiral stationary phase liquid chromatography columns.

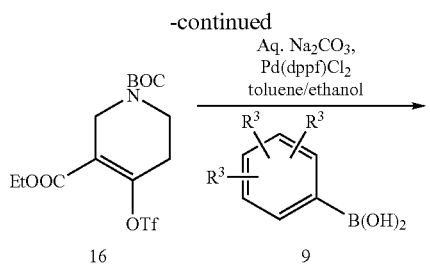

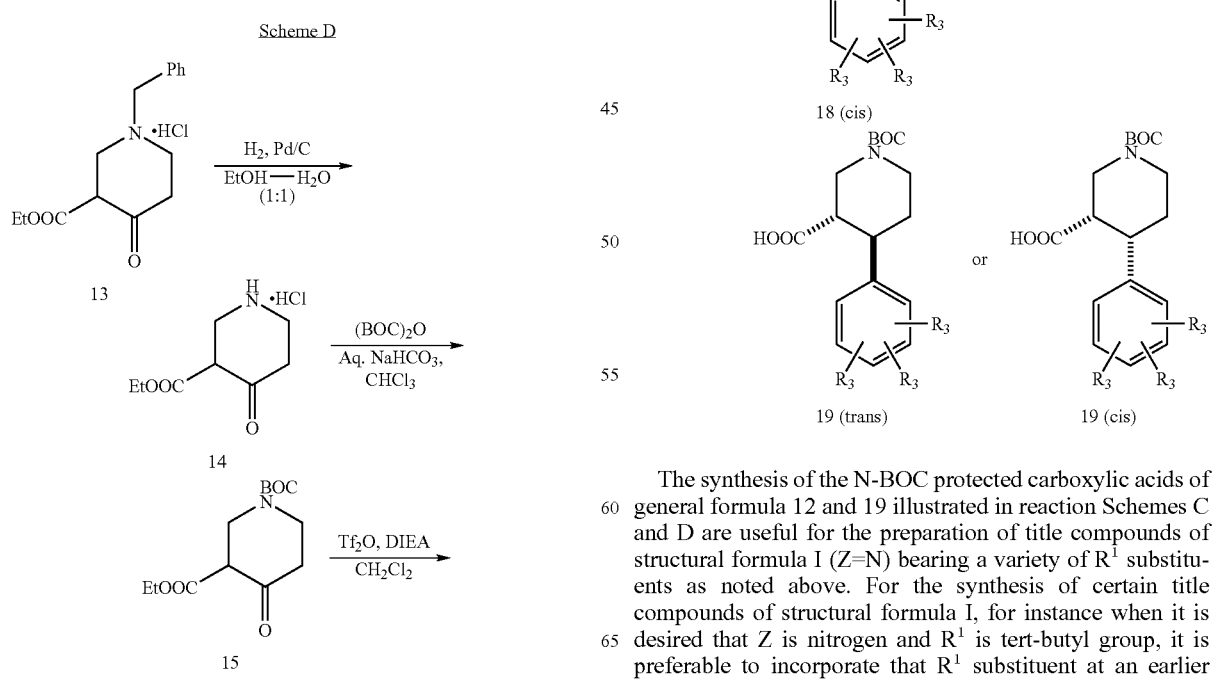

The synthesis of the N-BOC protected carboxylic acids of general formula 12 and 19 illustrated in reaction Schemes C and D are useful for the preparation of title compounds of structural formula I (Z=N) bearing a variety of $R^1$ substituents as noted above. For the synthesis of certain title compounds of structural formula I, for instance when it is desired that Z is nitrogen and $R^1$ is tert-butyl group, it is preferable to incorporate that $R^1$ substituent at an earlier stage of the synthesis. The synthesis of a 1-substituted-3- ketopiperidine-4-carboxylic ester (23) is shown in reaction Scheme E. A primary amine 20 bearing a desired $R^1$ substituent like a tert-butyl group is reacted with ethyl 4-bromobutyrate at elevated temperature in the absence of a solvent to afford the N-substituted ethyl 4-aminobutyrate 21. The amino ester 21 is then alkylated a second time with ethyl bromoacetate in a high boiling inert solvent such as toluene and in the presence of a base such as powdered potassium carbonate. The resulting aminodiester of general formula 22 is then cyclized using an intramolecular Dieckmann reaction to afford a piperidine such as 23. The Dieckmann reaction is performed using a strong base such as potassium tert-butoxide or the like, in an aprotic solvent such as THF at temperatures between room temperature and the boiling point of the solvent. The resulting 1-substituted-3-ketopiperidine-4-carboxylic ester 23 corresponds to a compound of general formula 7 shown in reaction Scheme C, where the BOC group is replaced with the desired $R^1$ substituent. The compounds of general formula 23 may then be converted to compounds of general formula 2 (Z=N) where the $R^1$ substituent replaces the BOC group using the reaction sequence illustrated in reaction Scheme C.

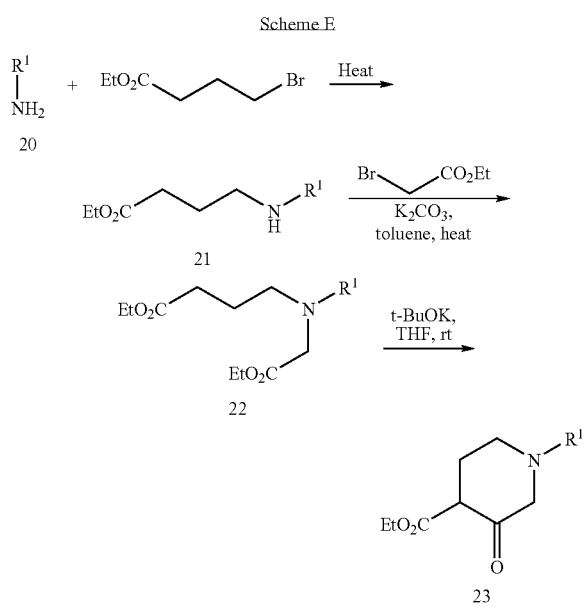

When it is desirable to synthesize a compound of general formula 19 wherein the BOC group is replaced with a substituent group $R^1$, a reaction sequence similar to the one illustrated in reaction Scheme D may be employed starting with a compound of general formula 15, which may be synthesized as shown in reaction Scheme F. An amine 20 bearing the desired $R^1$ substituent is first subjected to a Michael addition with excess ethyl acrylate in the presence of a solvent such as THF or ethanol. The resulting diester 24 is then converted to a 1-substituted-4-ketopiperidine-3-carboxylic ester 25 using an intramolecular Dieckmann reaction under conditions similar to those illustrated in reaction Scheme E. The substituted piperidine 25 corresponds to a compound of general formula 15 shown in reaction Scheme D, wherein the BOC group is replaced with the desired $R^1$ substituent. The compounds of general formula 25 may then be converted to compounds of general formula 2 where the $R^1$ substituent replaces the BOC group using the methodology illustrated in reaction Scheme D.

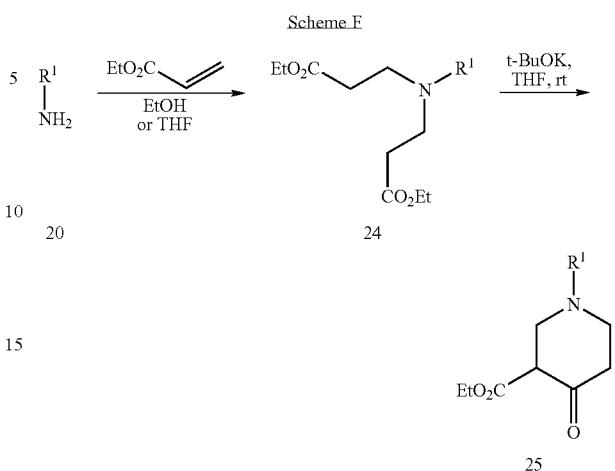

Reaction Scheme G illustrates a strategy for the synthesis of compounds of general formula 2 (Z=N) wherein the values of r and s are selected such that the resulting heterocycle is a 3-aryl-4-pyrrolidine carboxylic acid derivative (31). The preferred method for the synthesis of compounds of general formula 31 involves the azomethine ylid 3+2 cycloaddition reaction of an azomethine ylid precursor of general formula 27 and a substituted cinnamic ester 26. The azomethine cycloaddition reaction of 26 and 27 affords the 3,4-disubstituted pyrrolidine 28, and the stereochemical relationship of the substituents on the newly formed pyrrolidine ring is determined by the stereochemistry of the double bond in the cinnamate ester 26. Thus the trans ester 26 affords a trans 3,4-disubstituted pyrrolidine of formula 28. The corresponding cis cinnamate ester affords a cis 3,4-disubstituted pyrrolidine of general formula 28. Cis or trans 3-arylpyrrolidine-4-carboxylic esters of general formula 28 may be resolved to afford enantiomerically pure compounds using a method such as resolution by crystallization of the diastereoisomeric salts derived from 28 and a chiral carboxylic acid, or directly by the use of chiral stationary phase liquid chromatography columns. Reaction Scheme G illustrates the case where a trans cinnamic ester 26 is converted to a trans 3,4-disubstituted pyrrolidine 28 and its subsequent resolution affords the enantiomerically pure trans pyrrolidine esters 29 and 30. Finally, the esters of general formula 28 (or their pure enantiomers 29 and 30) are hydrolyzed to the corresponding amino acid hydrochlorides of general formula 31 as shown at the bottom of reaction Scheme G.

Amino acids of general formula 31 are zwitterionic. Therefore it is in some cases difficult to achieve efficient separation and purification of these compounds from aqueous reactions or workups. In these cases it is preferred to effect the hydrolysis using a reagent such potassium trimethylsilanolate in diethyl ether. Under these conditions the potassium salt of the carboxylic acid is produced which affords an easily isolated precipitate in ether. The resulting salt is then converted to the corresponding amino acid hydrochloride by treatment with excess hydrogen chloride in a suitable solvent such as ethyl acetate. Alternatively, esters such as 28 may be converted directly to the amino acid hydrochlorides 31 under acidic hydrolysis conditions. The hydrolysis of the ester 28 is achieved by prolonged reaction with concentrated hydrochloric acid at an elevated temperature. For example, this reaction may be conducted in 8 M hydrochloric acid at reflux overnight. The reaction mixture is then cooled and evaporated in vacuo to afford the amino acid hydrochloride 31. The amino acid hydrochlorides of general formula 31 correspond to an amino acid hydrochloride of general formula 2 (Z=N) wherein both r and s are 1 and may be employed directly in the amide bond coupling step illustrated in reaction Scheme A to produce the compounds of the present invention of structural formula I.

Another preferred method for the synthesis of enantiomerically pure 3-arylpyrrolidine-4-carboxylic acid derivatives is illustrated in reaction Scheme H. In this synthetic method, cinnamyl oxazolidinones of general formula 34 are readily prepared from cinnamic acids and (S)-(−)-4-benzyl-2-oxazolidinone using published methodology (Ho, G.-J.; Mathre, D. J. *J. Org. Chem.* 1995, 60, 2271 and references cited therein). The acylation of chiral auxiliary 33 with cinnamic acids of formula 32 is performed by initial activation of the acid to afford a mixed anhydride. Typically acids of general formula 32 are reacted with an acid chloride such as pivaloyl chloride in the presence of a base such as triethylamine and in a suitable aprotic solvent such as THF. The intermediate cinnamyl-pivaloyl anhydride is converted to the product 34 by reaction with the oxazolidinone 33 in the presence of lithium chloride, an amine base such as triethylamine and in a solvent such as THF, and the reaction is conducted at temperatures between −20° C. and room temperature for periods of 1-24 hours. Alternatively, the oxazolidinone 33 may be deprotonated with a strong base such as n-butyllithium in THF at low temperatures such as −78° C. and then reacted with a mixed anhydride obtained from acid 32 and an acid chloride like pivaloyl chloride as noted above. The cinnamyl oxazolidinone of general formula 34, which is produced by either of these methods, is then reacted with the azomethine ylid precursor 27 in a manner similar to that described in reaction Scheme G, and the products of the reaction are the substituted pyrrolidines of general formula 35, which may be separated into pyrrolidines of general formula 36 and 37 as shown. The products 36 and 37 are diastereoisomers of each other and may therefore be separated by standard methods such as recrystallization or by liquid chromatography on a stationary phase such as silica gel. As discussed above, if the trans isomer of the cinnamic acid of general formula 32 is employed in the first step of reaction Scheme H, then a trans isomer of the substituted cinnamyl oxazolidinone 34 is produced. If such a trans cinnamyl oxazolidinone is then subjected to the azomethine ylid cycloaddition with an azomethine ylid precursor of formula 27, the products are the diastereoisomeric trans-disubstituted pyrrolidines related to 36 and 37.

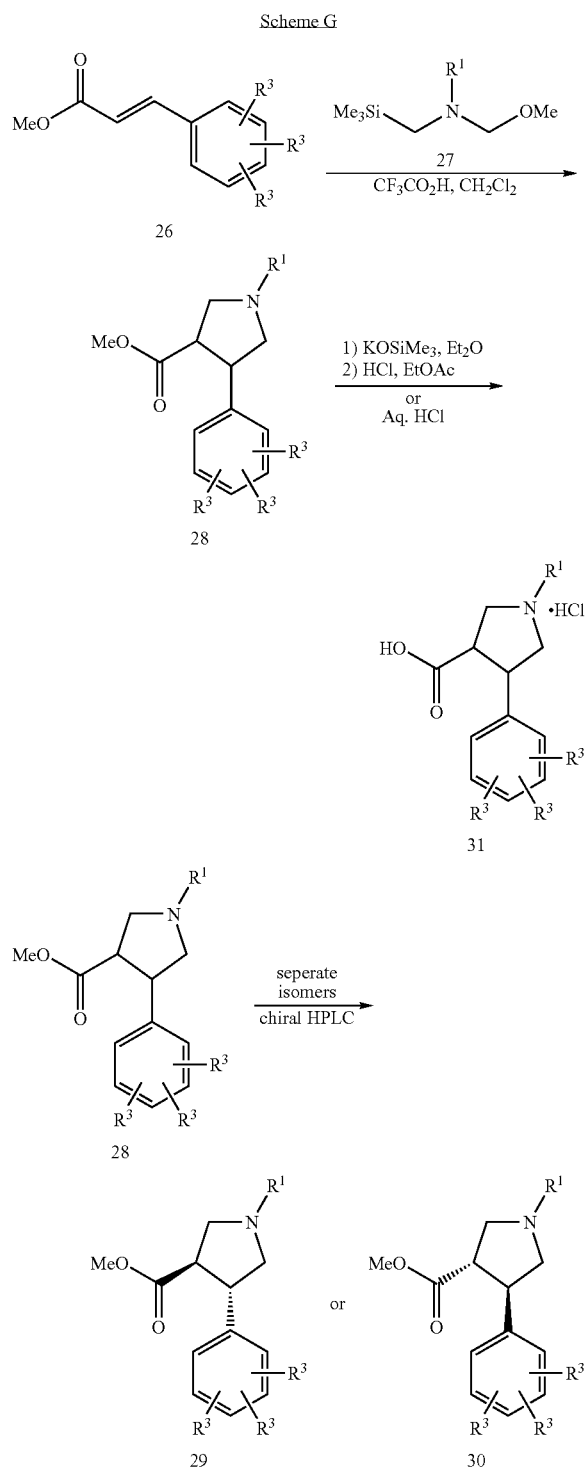

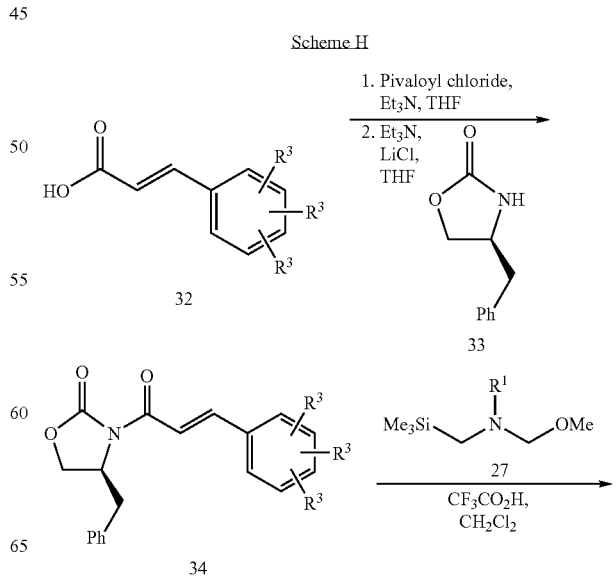

-continued

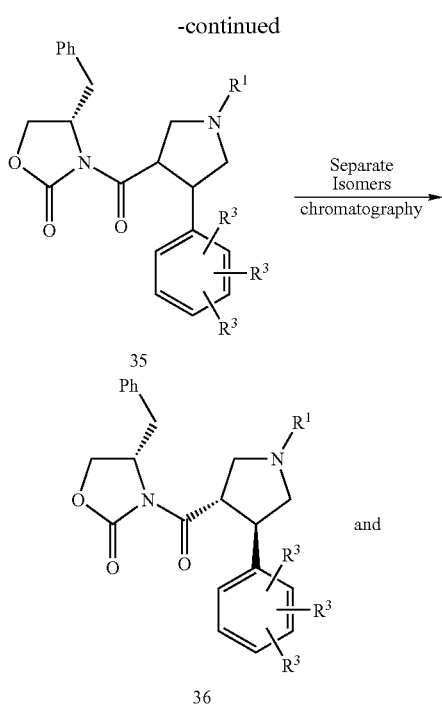

The azomethine ylid cycloaddition reactions shown in reaction Schemes G and H are generally conducted with the commercially available azomethine ylid precursor N-(methoxymethyl)-N-(trimethylsilylmethyl)-benzylamine (27, $R^1$=—$CH_2Ph$). When the $R^1$ substituent in the title compounds of structural formula I is chosen to be a group other than benzyl, it is generally preferable to remove the benzyl group from the substituted pyrrolidine compound at this point, and replace it with a more readily removed protecting group such as an N-BOC group. Reaction Scheme I illustrates this process with a generalized 3,4-disubstituted pyrrolidine of formula 35. The preferred method for removal of the N-benzyl group from compounds of general formula 35 will depend upon the identity of the $R^3$ substituents. If these substituents are unaffected by hydrogenation conditions, then the N-benzyl group may be removed by hydrogenolysis using a palladium-on-carbon catalyst in a solvent such as ethanol and in the presence of hydrogen gas or a hydrogen donor such as formic acid. Occasionally it may be preferred that one of the substituents $R^3$ be a halogen or another substituent defined above which would be reactive under hydrogenation conditions. In these cases, the compound of general formula 35 is reacted with 1-chloroethyl chloroformate in an inert solvent such as toluene at temperatures between room temperature and 110° C. (Olafson, R. A. et al.

*J. Org. Chem.* 1984, 49, 2081). The toluene is then removed, and the residue is heated in methanol for a period of 15-60 minutes, and the product is the debenzylated pyrrolidine of general formula 38. The resulting pyrrolidine 38 is then protected as its tert-butyl carbamate (39) using BOC anhydride in the presence of a base and a suitable solvent. For example, this can be accomplished in a two phase mixture of chloroform and aqueous sodium bicarbonate as shown in reaction Scheme I.

The oxazolidinone chiral auxilliary is next hydrolyzed from the pyrrolidines of general formula 39 as shown at the bottom of reaction Scheme I. The hydrolysis reaction is accomplished using lithium hydroperoxide generated in situ from lithium hydroxide and 30% aqueous hydrogen peroxide. The reaction is typically conducted in a solvent system such as aqueous THF, and the reaction is performed at temperatures between 0° C. and room temperature for a period of 1-6 hours. The resulting carboxylic acids of general formula 40 correspond to carboxylic acids of general formula 2 wherein Z is nitrogen, and both r and s are 1. Using the methodology presented in reaction Scheme A, the compounds of general formula 40 may then be converted to the compounds of the present invention of structural formula I (Z=N).

Scheme I

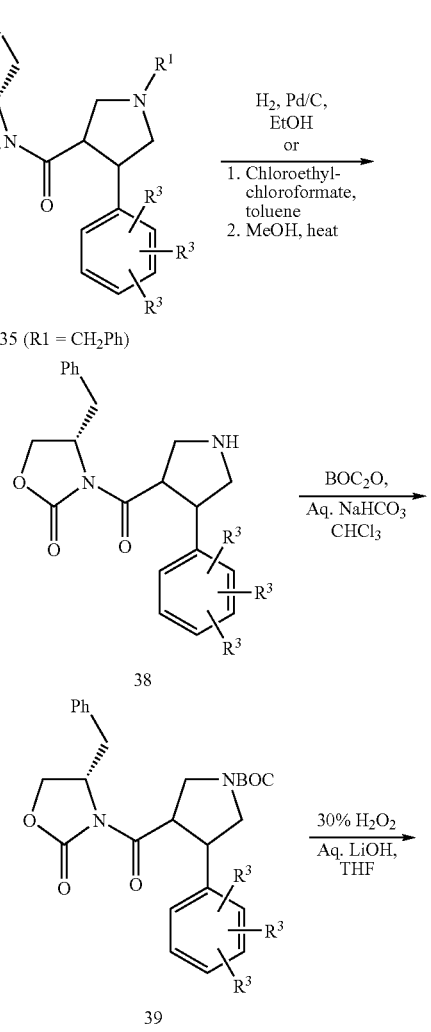

-continued

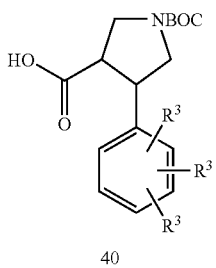

40

As noted previously in the discussions of reaction Schemes E and F, it may occasionally be preferable to incorporate the $R^1$ substituent into the substituted pyrrolidine of general formula 40 at an earlier stage of the synthesis, for instance when it is desired that $R^1$ be a tert-butyl group. In such cases, it is possible to utilize an azomethine ylid precursor (27) bearing the desired $R^1$ substituent in the cycloaddition reactions illustrated in reaction Schemes G and H. Reaction Scheme J illustrates the preparation of azomethine precursors of formula 27 starting with amines of general formula 20. Reaction of the amine of formula 20 with chloromethyltrimethylsilane at high temperature and in the absence of solvent affords the N-trimethylsilylmethyl-substituted amine of general formula 41. Subsequent reaction of 41 with aqueous formaldehyde in the presence of methanol and a base such as potassium carbonate then affords the generalized ylid precursor 27 which can be utilized in the cycloaddition reactions discussed above.

Scheme J

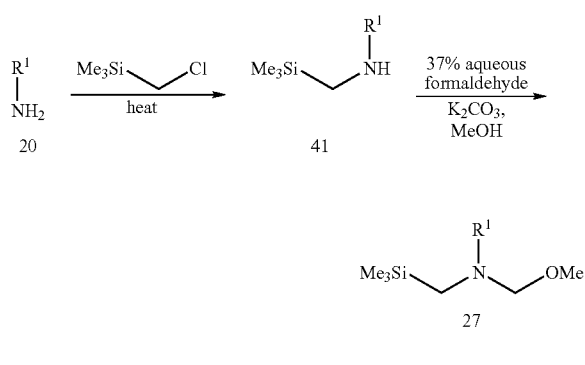

Reaction Schemes K and L illustrate the synthesis of the novel compounds of structural formula I (Z=C) when it is preferred to effect the amide bond coupling step prior to incorporation of the basic substituent $R^1$ as mentioned above. Reaction Scheme K illustrates a preferred method for the synthesis of compounds of structural formula I which employs a piperidine of general formula 1 and a cycloalkanone carboxylic acid of general formula 42 as the partners in the amide bond coupling step. The piperidine of formula 1 and the carboxylic acid of formula 42 are first coupled to afford an amide of general formula 43 using the reagents and conditions described for the generalized amide coupling shown in reaction Scheme A. The $R^1$ substituent ($R^1$=$NR^7R^8$) may then be incorporated at the position of the carbonyl group by performing a reductive amination reaction with an amine of general formula 44. Typical conditions for effecting such a reductive amination include preforming an imine 45 from ketone 43 and amine 44 followed by reduction of the intermediate imine with reducing agents such as sodium borohydride, sodium cyanoborohydride or sodium triacetoxyborohydride. Formation of the intermediate imine 45 derived from piperidine 1 and acid 42 may occur spontaneously in solution or it may be promoted with agents such as titanium (IV) isopropoxide in a solvent such as methanol or with anhydrous magnesium sulfate in chloroform. The formation of the imine 45 is generally performed at temperatures between 0° C. and the reflux temperature of the solvent, frequently at room temperature. The imine formation step is generally allowed to proceed to completion over a period of several hours to 1 day prior to the reduction step which minimizes the formation of secondary alcohols formed by simple reduction of the keto group in compounds of general formula 43. The intermediate imine 45 may in some cases be isolated and purified, however it is generally preferred to use it directly in the reduction step. The reduction of the imine 45 is typically conducted in an alcoholic solvent such as methanol or ethanol at temperatures between 0° C. and room temperature, and the reduction is generally completed in periods of several hours or less.

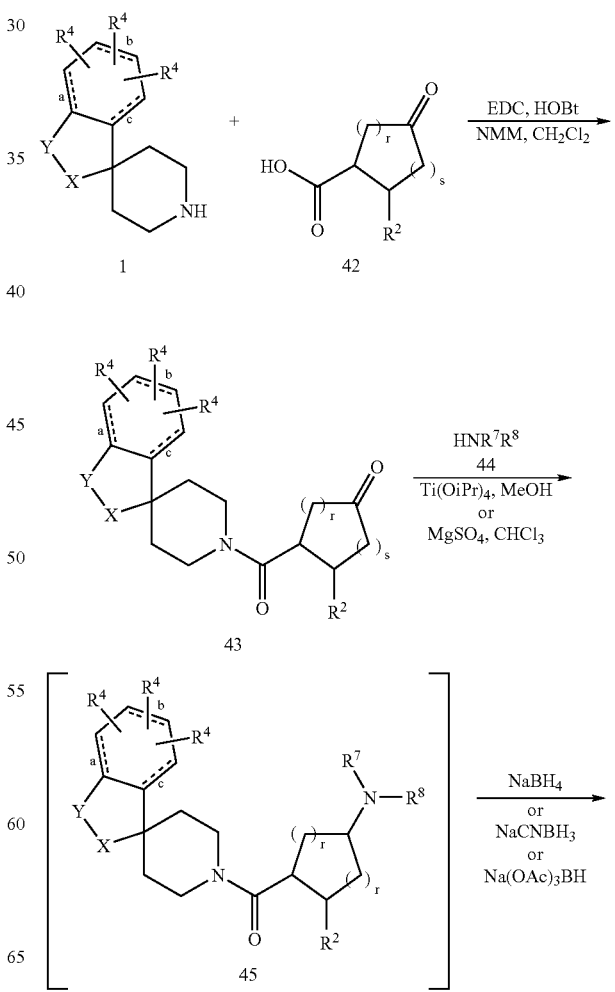

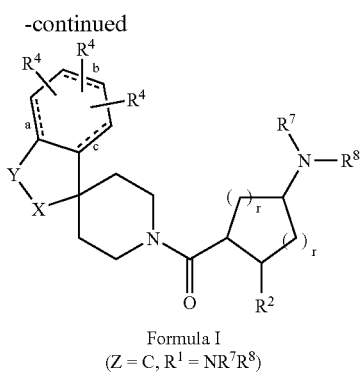

Formula I
(Z = C, R¹ = NR⁷R⁸)

Reaction Scheme L illustrates a preferred method for the synthesis of compounds of structural formula I (Z=C) which employs a piperidine of general formula 1 and a hydroxyl-substituted cycloalkyl carboxylic acid of general formula 46 as the partners in the amide bond coupling step. The amide bond coupling step between piperidine 1 and carboxylic acid 46 is performed first, typically using a carbodiimide reagent like EDC to promote the coupling as described above or by any of the other methods described in the discussion for reaction Scheme A. The hydroxyl-substituted amide 47 which is produced is then further synthetically modified to incorporate the R¹ substituent present in the title compounds of structural formula I (Z=C). A variety of methods known to those skilled in organic synthesis may be used to incorporate the R¹ substituent. For instance, the hydroxyl group of compounds of general formula 47 may be oxidized using a variety of methods to afford carbonyl compounds of general formula 43. The resulting ketoamides of general formula 43 may then be converted to the title compounds of structural formula I (Z=C) using the reductive amination method described in reaction Scheme K.

Occasionally, it may be preferable to utilize hydroxyl-substituted compounds of general formula 47 in a Fukuyama-Mitsunobu reaction (Fukuyama, T.; Cheung, M.; Jow, C.-K.; Hidai, Y.; Kan, T. *Tetrahedron Lett.* 1997, 33, 5831-4) sequence as shown in reaction Scheme L. In this method for the synthesis of the novel title compounds of structural formula I (Z=C), the intermediate hydroxyl-substituted cycloalkylamide 47 is reacted with a 2,4-dinitrobenzene-sulfonamide of general formula 48 in the presence of triphenylphosphine and an azodicarboxylate reagent such as DEAD. The reaction is performed in a suitable aprotic solvent such as benzene, toluene or tetrahydrofuran, typically at room temperature, and the reaction is generally complete in 0.5-3 hours. The product of this reaction is the secondary 2,4-dinitrobenzenesulfonamide of general formula 49, which may then be readily converted to a title compound of structural formula I (Z=C) wherein R⁸=H. The deprotection of the sulfonamide group is accomplished by reaction of 49 with either a base like n-propylamine in a solvent like methylene chloride or by reaction of 49 with a nucleophilic reagent such as mercaptoacetic acid with triethylamine in methylene chloride. In either case the reaction is typically conducted at room temperature, for periods of 5 minutes to one hour. An advantage of the Fukuyama-Mitsunobu reaction sequence is that the stereochemistry of the carbon atom undergoing substitution is cleanly inverted. Thus if the hydroxyl-substituted cycloalkylamide 47 is a single diastereoisomer, then the product 49 will be a single diastereoisomer also. This is in contrast to the reductive amination strategy discussed in reaction Scheme K which generally affords a mixture of epimeric products.

The secondary amine of formula I (Z=C, R¹=N(H)R⁷) shown in reaction Scheme L may then be further synthetically modified using a variety of methods known in organic synthesis to incorporate other embodiments of the R⁸ substituent. For instance, a compound of structural formula I (Z=C) where R⁸=H may be subjected to a reductive amination reaction with an appropriate aldehyde or ketone using the conditions described in reaction Scheme K. Alternatively, a compound of structural formula I (Z=C) where R⁸=H may be directly alkylated with an appropriate alkylating agent using the conditions described in reaction Scheme B.

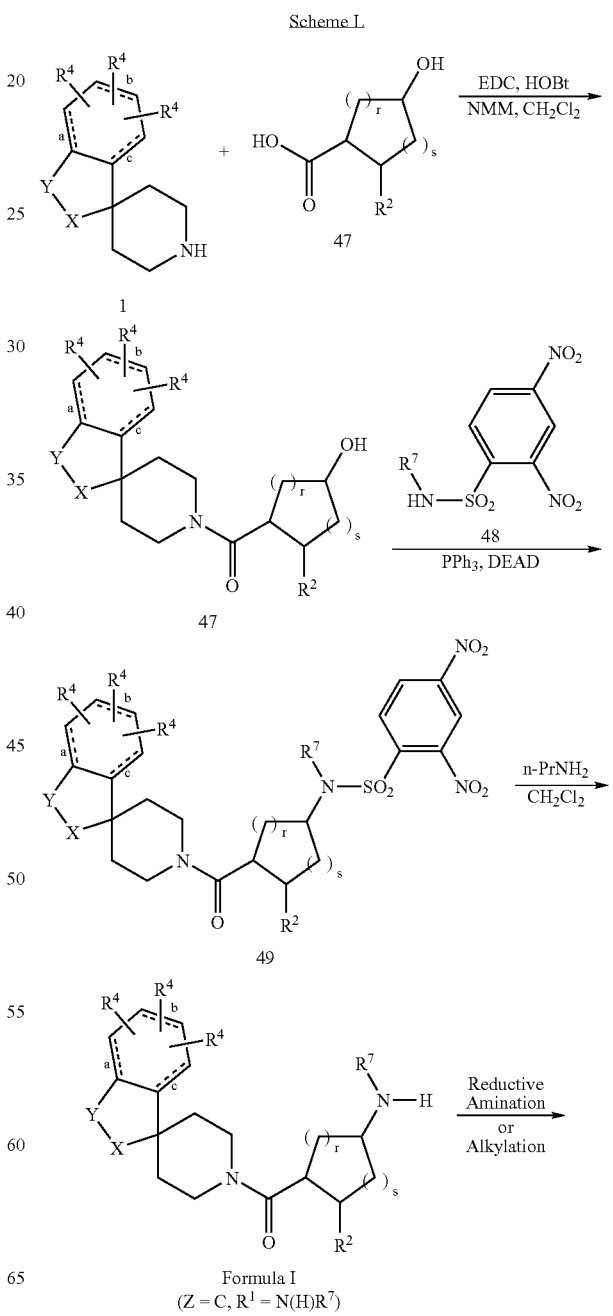

Scheme L

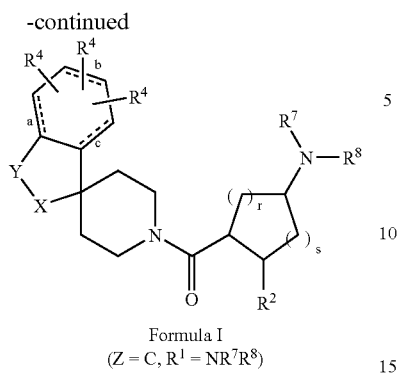

Formula I
(Z = C, R¹ = NR⁷R⁸)

Reaction Scheme M illustrates a preferred method for the synthesis of the cycloalkyl carboxylic acids of general formula 42 when the values of r and s are selected such that the resulting carbocyclic ring is a six-membered ring. In this method a Diels-Alder reaction between an α,β-unsaturated ester of general formula 50 and 2-trimethylsilyloxybutadiene (51) affords a mixture of the two regioisomeric silylenolethers 52 and 53. The silylenolethers 52 and 53 are generally subjected to an hydrolysis reaction using hydrochloric acid in a solvent such as methanol and the two regioisomeric ketones 54 and 55 are then separated by conventional chromatographic methods. The olefin geometry of the starting α,β-unsaturated ester of general formula 50 determines the relative stereochemistry of the two substituents on the six-membered ring. Thus a trans α,β-unsaturated ester 50 affords the trans-disubstituted products 52 and 53 as shown, whereas the corresponding cis isomer of compounds of general formula 50 will afford the corresponding cis isomers of 52 and 53. Once the regioisomeric cyclohexanones of general formulae 54 and 55 are separated, they may then be individually hydrolyzed. For instance, hydrolysis using lithium hydroxide in refluxing tetrahydrofuran, affords the carboxylic acids of general formula 42 (r=2, s=1) and 42 (r=1, s=2). The acids of general formula 42 are finally converted to the novel title compounds of structural formula I (Z=C) using the methodology described above in reaction Schemes K and L.

Scheme M

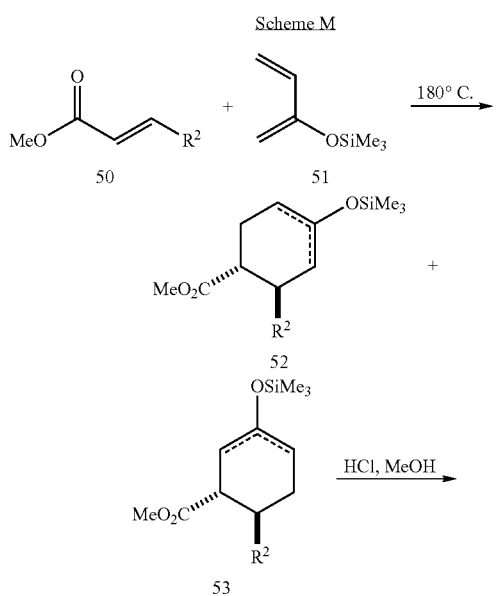

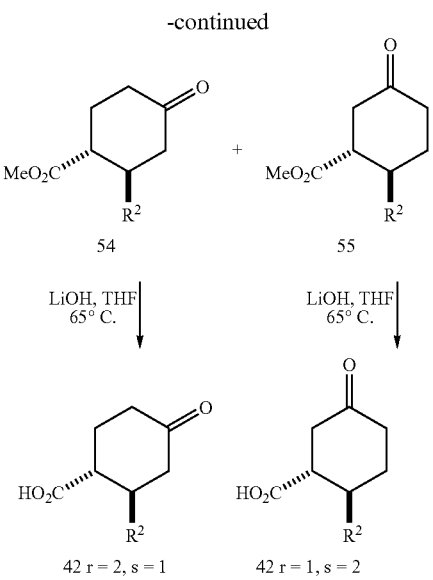

Reaction Scheme N illustrates a preferred method for the synthesis of the cycloalkyl carboxylic acids of general formula 42 when the values of r and s are selected such that the resulting carbocyclic ring is a five-membered ring. In this method an α,β-unsaturated ester of general formula 50 is subjected to a trimethylenemethane cycloaddition reaction (Trost, B. M.; Chan, D. M. T. *J. Am. Chem. Soc.* 1979, 101, 6429) to afford a cyclopentane derivative of general formula 57. The cycloaddition is performed by reacting the α,β-unsaturated ester of general formula 50 with 2-[(trimethylsilyl)methyl]-2-propen-1-yl acetate (56) in the presence of a palladium(0) catalyst in a solvent such as tetrahydrofuran. A preferred palladium(0) catalyst for the cycloaddition may be generated by mixing palladium acetate and triisopropyl phosphite in the reaction mixture. The cycloaddition reaction is typically conducted at the reflux temperature of the solvent, for instance 65° C., and the reaction is usually completed in periods of 2-8 hours. The olefin geometry of the starting α,β-unsaturated ester of general formula 50 determines the relative stereochemistry of the two substituents on the five-membered ring. Thus a trans α,β-unsaturated ester 50 affords the trans-disubstituted product 57 as shown, whereas the corresponding cis isomer of compounds of general formula 50 affords the corresponding cis-disubstituted isomer of 57. The exocyclic olefin present in compounds of general formula 57 is next oxidatively removed to afford a cyclopentanone derivative of general formula 58. A preferred method for the oxidative cleavage reaction is the two step process shown in reaction Scheme N. The methylene cyclopentane derivative of formula 57 is first oxidized to a 1,2-diol derivative using catalytic osmium tetraoxide in the presence of a stoichiometric reoxidant such as N-methylmorpholine-N-oxide and a solvent system such as acetone-water. The intermediate 1,2-diol which forms is generally not isolated, but is in turn subjected to cleavage with sodium periodate in a solvent system like methanol-water to afford ketones of general formula 58. Both steps in the oxidative cleavage sequence are generally completed during periods of several minutes to a few hours and the reaction steps are typically conducted at low temperatures, for instance between 0° C. and room temperature. Alternatively, the oxidative cleavage of olefins of general formula 57 may be accomplished using ozone, or by other methods known in organic synthesis. The cyclopentanones of general formula 58 may then be hydrolyzed, for instance using sodium hydroxide in methanol, to afford the carboxylic acids of general formula 42 (r=1, s=1). The acids of general formula 42 are finally converted to the novel title compounds of structural formula I (Z=C) using the methodology described above in reaction Schemes K and L.

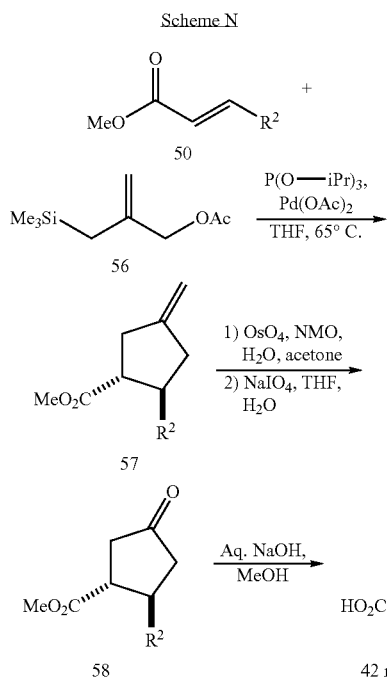

Enantiomerically pure compounds may be prepared from starting materials bearing a suitable covalently attached chiral auxiliary group using synthetic transformations similar to those outlined above. Reaction Scheme O illustrates the use of a covalently attached chiral oxazolidinone auxiliary for the preparation of enantiomerically pure cyclopentanones of general formula 58. In this method of preparation, an α,β-unsaturated acyloxazolidone of general formula 34, synthesized as shown in Scheme H, is subjected to the trimethylenemethane cycloaddition reaction with compound 56 as described above in reaction Scheme N. The α,β-unsaturated acyloxazolidones of general formula 59 are readily prepared according to the methods described in the discussion for reaction Scheme H. The compounds of general formula 34 undergo the trimethylenemethane cycloaddition under the same conditions as compounds of general formula 50 (Scheme N) and the products are the diastereoisomeric cyclopentanes 59 and 60. Compounds of general formulae 59 and 60 are readily separated from each other by conventional chromatographic methods or by recrystallization, and may then be converted to the compounds of general formula 58 individually. This process is illustrated at the bottom of reaction Scheme O for the case of the cyclopentane with the absolute stereochemistry shown in formula 59. The enantiomerically pure compounds of general formula 59 are first hydrolyzed to afford intermediate carboxylic acids and (S)-(–)-4-benzyl-2-oxazolidinone using a reagent such as lithium hydroperoxide, typically generated in situ, in a suitable solvent system such as aqueous tetrahydrofuran. The carboxylic acid formed is generally then converted to a methyl ester 61 using diazomethane, trimethylsilyldiazomethane or any of the esterification methods commonly employed in organic synthesis. The olefin present in the esters of general formula 61 is then subjected to the oxidative cleavage method presented in the discussion of reaction Scheme N to afford enantiomerically pure compounds of general formula 58. The cyclopentanones of general formula 58 may then be hydrolyzed, for instance using sodium hydroxide in methanol, to afford the carboxylic acids of general formula 42 (r=1, s=1). The acids of general formula 42 are finally converted to the novel title compounds of structural formula I (Z=C) using the methodology described above in reaction Schemes K and L.

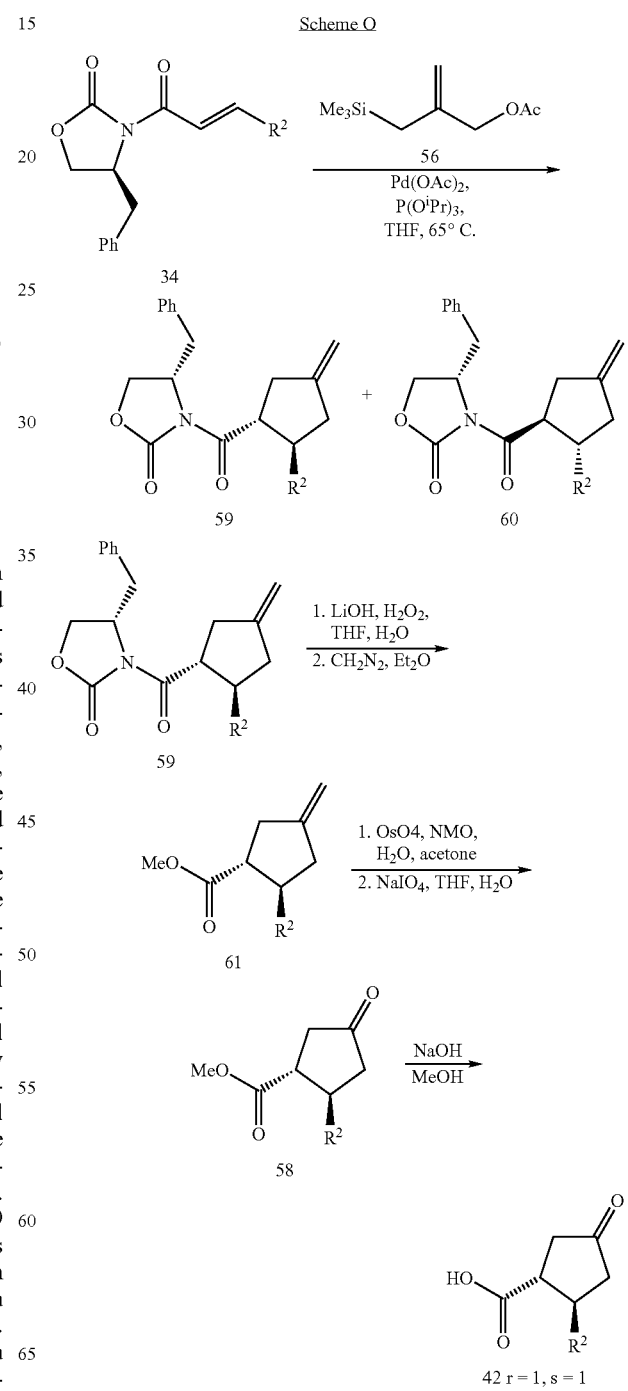

When it is desired to prepare individual enantiomers of the novel title compounds of structural formula I, it is possible to perform a resolution of the compounds of structural formula I using one of the methods known in the art of organic synthesis. For instance, enantiomerically pure compounds (I) may be prepared by crystallization of diastereoisomeric salts formed from the racemic compounds of structural formula I and an optically active carboxylic acid. The two diastereoisomeric salts are separated from each other by fractional crystallization, then the enantiomerically pure compounds of structural formula I are regenerated by treatment of the purified salts with a base. Alternatively, racemic compounds of structural formula I may be resolved by preparative HPLC using commercially available chiral stationary phase columns. Another strategy for the preparation of enantiomerically pure compounds of structural formula I involves preparing enantiomerically pure compounds of general formula 2 prior to their use in the amide bond forming reaction outlined in reaction Scheme A. Racemic compounds of general formula 2, or intermediates used to prepare compounds of formula 2 as described in the previous reaction Schemes (i.e. acids 12, 19, 31, 42 and 46, or esters 11, 18, 28, 54, 55 and 58) may also be resolved using the classical methods previously discussed.

Preparation of 4,4-Disubstituted Piperidine Intermediates

Scheme P discloses examples of 4,4-disubstituted piperidine intermediates of general formula 1 used as indicated in the examples of the present invention (3-1, 4-1, and 9-1). The 4,4-disubstituted piperidine intermediates of general formula P-1, P-2 and P-3 in Scheme P, which may be employed to synthesize the compounds of this invention, may be prepared according to the methods disclosed in U.S. Pat. No. 5,804,578 (Sep. 8, 1998), U.S. Pat. No. 5,578,593 (Nov. 26, 1996), U.S. Pat. No. 6,472,398 (Oct. 29, 2002), U.S. Pat. No. 6,294,534 (Sep. 25, 2001), WO 01/70337, and WO 99/64002.

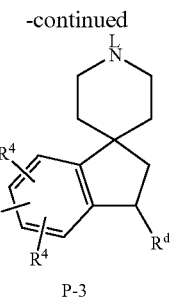

P-3

L is H or a protecting group D is O, S, NR, NH, NS(O)$_2$R, S(O), or S(O)$_2$, or CH(R$^7$)
R$^7$ is (CH$_2$)$_n$aryl, —C(O)R$^2$, —SO$_2$R$^2$, —C(O)NR$^2$)$_2$, —CO$_2$R$^2$, —SO$_2$NR$^2$, or as defined in U.S. Pat. No. 5,804,578

R$^2$ is as defined in U.S. Pat. No. 5,804,578
R$^d$ is (CH$_2$)$_n$CO$_2$H, (CH$_2$)$_n$CO$_2$Me, —CON(R$^2$)$_2$, —OTs, —OTf, CN, —SMe, tetrazole, pyridine, —Sn(Me)$_3$ or as defined in U.S. Pat. No. 5,804,578

Reaction Scheme Q illustrates a preferred method for the synthesis of a compound of general formula 1 (X=C, Y=CHN(H)CBZ). In this method, a carboxylic acid such as 62 is subjected to the Curtius reaction to afford a product of general formula 63. The reaction is performed by reacting acid 62 with diphenylphosphoryl azide in the presence of a tertiary amine such as triethylamine or diisopropylamine in a solvent such as toluene. The rearrangment is typically conducted at the reflux temperature of the solvent, for instance 110° C., and the rearrangement is usually completed in periods of 1-5 hours. The intermediate isocyanate which forms is generally not isolated, but is in turn subjected to in-situ reaction with a suitable alcohol such as benzyl alcohol to afford a product of general formula 63. The N-BOC group can be removed by any of the known methods such as treatment with a protic acid such as hydrogen chloride in an inert organic solvent such as ethyl acetate or trifluoroacetic acid in methylene chloride. The product amine 64 can be used as a coupling partner in reaction Scheme A.

Scheme P

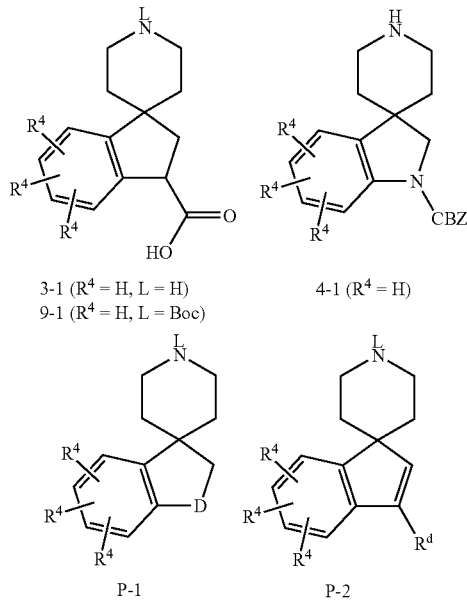

Scheme Q

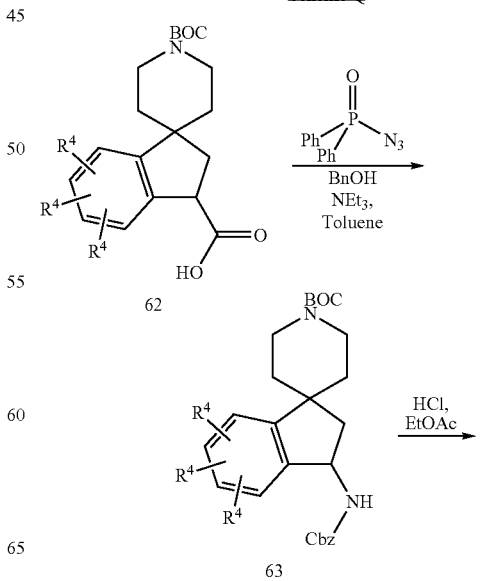

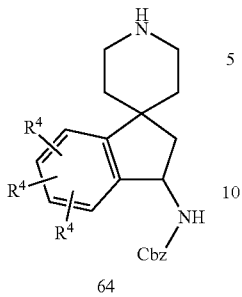

64

Reaction Scheme R illustrates general methods for the elaboration of the Y substituent following assembly of compounds of structural formula I (X=C, Y=CHCO$_2$Me) as described in reaction Scheme A. For example, conversion of the methyl ester to the carboxylic acid of structural formula I (X=C, Y=CHCO$_2$H) can be affected by dealaylation using potassium trimethylsilanolate at room temperature in an inert organic solvent such as tetrahydrofuran for a period of about one to about 24 hours to provide, after acidification, the corresponding carboxylic acid. In certain cases, a base-catalyzed hydrolysis known to those skilled in the art may be used to effect this same transformation. The acid may be reacted further to form an amide by treatment with a primary or secondary amine under a variety of amide coupling protocols such as those described in Scheme A to provide a compound of structural formula I (X=C, Y=CHCONR$^7$R$^8$).

Scheme R

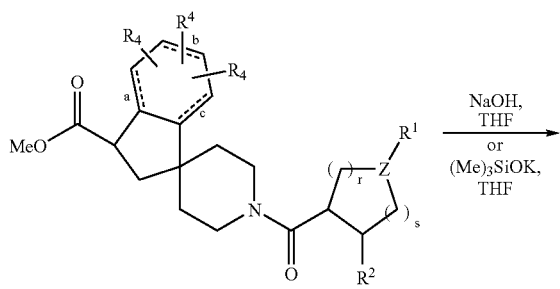

Formula I
(X = C, Y = CHCO$_2$Me)

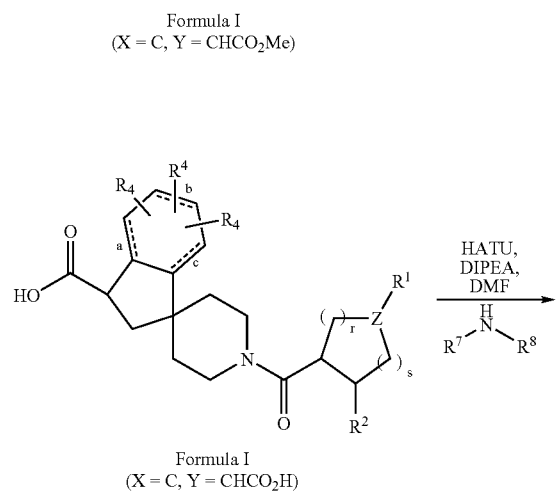

Formula I
(X = C, Y = CHCO$_2$H)

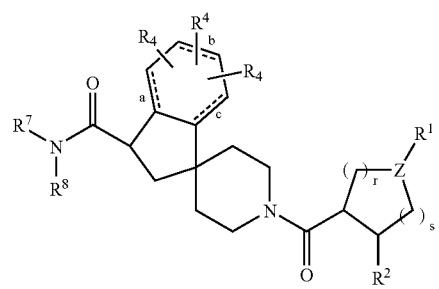

Formula I
(X = C, Y = CHCONR$^7$R$^8$)

Reaction Scheme S illustrates general methods for the elaboration of the Y substituent following assembly of compounds of structural formula I (X=C, Y=N(H)CBZ or CHN(H)CBZ) as described in reaction Scheme A. The N-CBZ protected compound of structural formula I (X=C, Y=N(H)CBZ or CHN(H)CBZ) is first deprotected by hydrogenolysis using a palladium-on-carbon catalyst in a solvent system such as methanol, ethanol, acetic acid or mixtures thereof under a hydrogen atmosphere. The resulting compound of structural formula I (X=C, Y=NH or CHNH$_2$) may then be subject to one of several acylation methods known in organic chemistry. For instance, a compound of structural formula I (X=C, Y=NH or CHNH$_2$) can be reacted with a carboxylic acid 65 under a variety of amide coupling protocols such as those described in the discussion for Scheme A to provide a product of structural formula I (X=C, Y=NC(O)R or CHNHC(O)R). Alternatively, a compound of structural formula I (X=C, Y=NH or CHNH$_2$) may be acylated using an acid chloride derivative 66. The acylation reaction is typically conducted in the presence of a tertiary amine such as triethylamine, N,N-diisopropylethylamine or N-methylmorpholine in an aprotic solvent such as methylene chloride or DMF to afford a product of structural formula I (X=C, Y=NC(O)R or CHNHC(O)R) as shown in Scheme S.

Scheme S

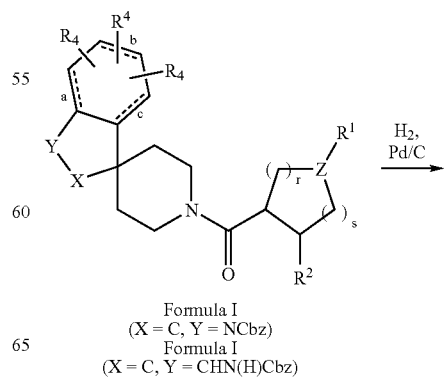

Formula I
(X = C, Y = NCbz)
Formula I
(X = C, Y = CHN(H)Cbz)

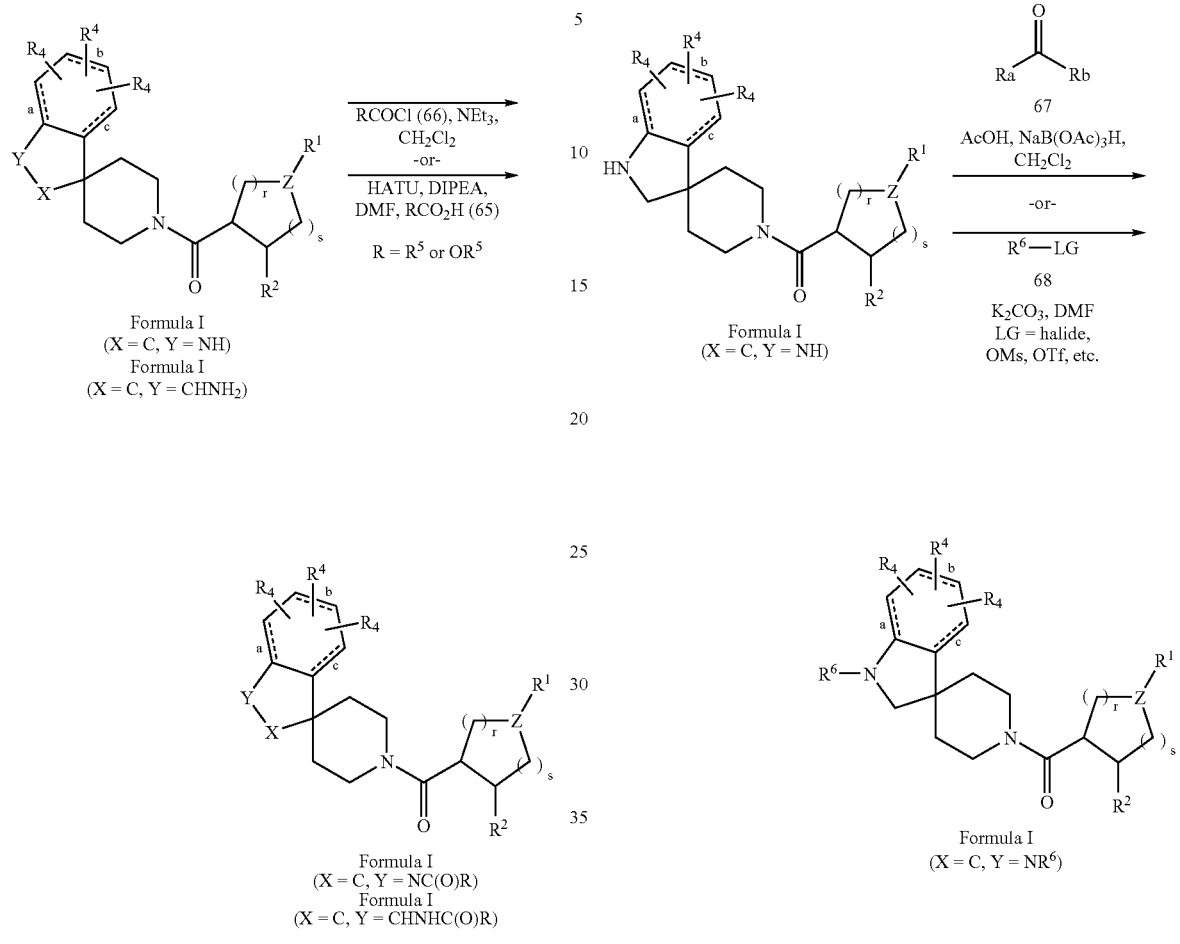

Reaction Scheme T illustrates general methods for the elaboration of the Y substituent following assembly of compounds of structural formula I (X=C, Y=NH) as described in the preceeding reaction Scheme S. For example, a compound of structural formula I (X=C, Y=NH) may be subjected to one of several alkylation strategies known in organic chemistry. For instance, compound (I) (X=C, Y=NH) may be utilized in a reductive amination reaction with a suitable carbonyl containing partner (67). The reductive amination is achieved by initial formation of an imine between the amine of formula I (X=C, Y=NH) and either an aldehyde or ketone of formula 67. The intermediate imine is then treated with a reducing agent capable of reducing carbon-nitrogen double bonds such as sodium cyanoborohydride or sodium triacetoxyborohydride and an alkylated product of structural formula I (X=C, Y=NR) is produced. Alternatively, a compound of structural formula (I) (X=C, Y=NH) may be directly alkylated using an alkylating agent such as 68 in a polar aprotic solvent such as DMF. In this reaction, the substituent leaving group, LG, of compound 68 is a leaving group such as a halide, mesylate or triflate and the product is the compound of structural formula I (X=C, Y=NR$^6$).

In a similar manner to the conditions described in reaction Scheme T, compounds of structural formula I (X=C, Y=CHNH$_2$) can be elaborated to products of structural formula I (X=C, Y=CHN(H)R), and can be further elaborated to products of structural formula I (X=C, Y=CN(R)$_2$), as shown in Scheme U.

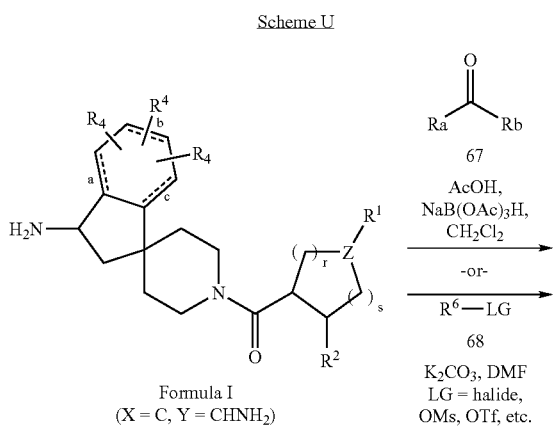

-continued

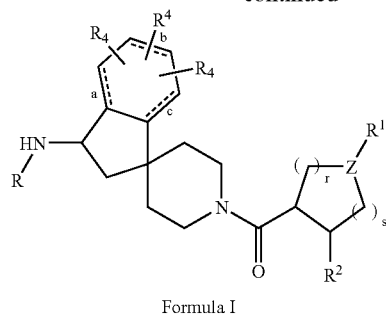

Formula I
(X = C, Y = CHN(H)R -
wherein N(H)R = R⁶)

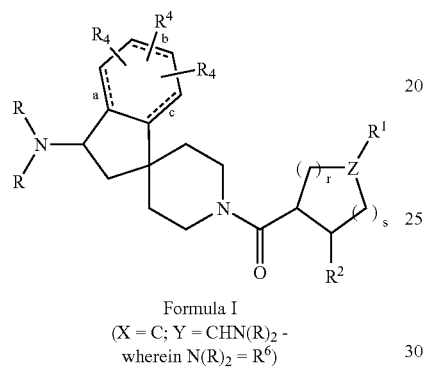

Formula I
(X = C; Y = CHN(R)₂ -
wherein N(R)₂ = R⁶)

Reaction Scheme V illustrates a general method for reducing the aryl ring of compounds of general formula V-1 to provide the cyclohexyl compounds of general formula V-2. The aryl ring of a compound of formula V-1 may be reduced by hydrogenation in the presence of a platinum (IV) oxide catalyst in a solvent such as glacial acetic acid at an elevated pressure, such as 45 psi of hydrogen gas.

Scheme V

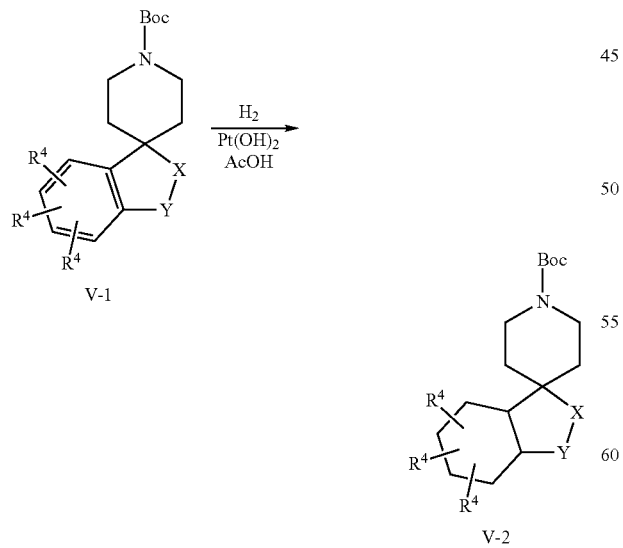

The following examples are provided to illustrate the invention and are not to be construed as limiting the scope of the invention in any manner. Pyrrolidine acid intermediate 1-4 was prepared as described below following the general procedures described in Schemes J and G.

Preparation of Intermediate (1-4)

(3S,4R)-1-tert-butyl-4-(2,4-difluorophenyl)pyrrolidine-3-carboxylic acid

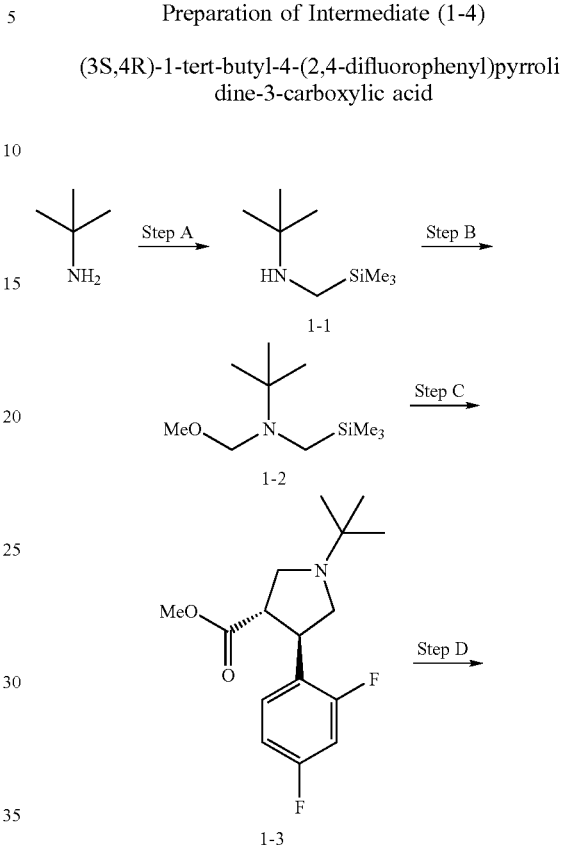

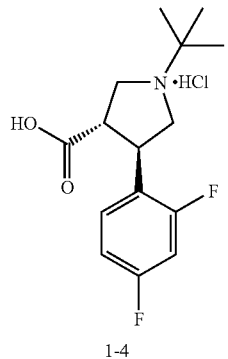

1-4

Step A: Preparation of N-tert-butyl-N-(trimethylsilylmethyl) amine (1-1)

A mixture of tert-butylamine (18.0 mL, 171 mmol) and (chloromethyl)trimethylsilane (7.00 g, 57.1 mmol) was heated in a thick-walled glass tube at 200° C. overnight After cooling to ambient temperature, the reaction mixture was poured into 1 N NaOH and extracted three times with diethyl ether. The combined organic extracts were washed with brine, dried (MgSO₄), and the volatiles evaporated in vacuo. Distillation (atmospheric pressure; ~135° C.) of the residual liquid gave the title compound 1-1 as a colorless liquid.

Step B: Preparation of N-tert-butyl-N-(methoxymethyl)-N-(trimethylsilylmethyl)amine (1-2)

N-tert-Butyl-N-(trimethylsilylmethyl)amine 1-1 (8.47 g, 53.1 mmol) was added dropwise, over approximately 30 min, via a pressure equalizing addition funnel to a stirred solution of aqueous formaldehyde (5.98 mL of a 37 wt. % solution in water, 79.7 mmol) at 0° C. After 45 min, methanol (6.45 mL, 159.3 mmol) was added and the resulting solution was saturated with potassium carbonate. After stirring vigorously for approximately 5 h, the aqueous phase was removed. The organic phase was saturated with potassium carbonate and stirred overnight. The reaction mixture was poured into water and extracted three times with diethyl ether. The combined organic extracts were washed with brine, dried (MgSO$_4$) and the volatiles evaporated in vacuo. Distillation (high vacuum; ~70° C.) of the residual liquid afforded the title compound 1-2 as a colorless liquid.

Step C: Preparation of methyl (3R,4S)-1-tert-butyl-4-(2,4-difluorophenyl)pyrrolidine-3-carboxylate and methyl (3S,4R)-1-tert-butyl-4-(2,4-difluorophenyl)pyrrolidine-3-carboxylate (1-3)

Trifluoroacetic acid (116 μL, 1.51 mmol) was added to a solution of compound 1-2 (3.07 g, 15.1 mmol) and methyl (2E)-3-(2,4-difluorophenyl)prop-2-enoate (2.99 g, 15.1 mmol) in methylene chloride (60 mL) at ambient temperature. After 18 h, the reaction mixture was poured into saturated aqueous sodium bicarbonate and extracted three times with methlene chloride. The combined organic extracs were washed with brine, dried (Na$_2$SO$_4$) and concentrated in vacuo. Purification of the residue by normal phase medium pressure liquid chromatography on silica gel (gradient elution; 0-9% methanol (containing 10% v/v ammonium hydroxide)/methylene chloride as eluent) gave the title compound 1-3 as a racemic mixture. The racemic titled compound was resolved into its enantiomeric components using preparative chiral high pressure liquid chromatography on CHIRALPAK AD Phase (5% isopropanol/heptanes as eluent) to give in order of elution: methyl (3S,4R)-1-tert-butyl-4-(2,4-difluorophenyl)pyrrolidine-3-carboxylate enantiomer as a colorless oil followed by the methyl (3R,4S)-1-tert-butyl-4-(2,4-difluorophenyl)pyrrolidine-3-carboxylate enantiomer 1-3 as a colorless oil.

Step D: Preparation of (3S,4R)-1-tert-butyl-4-(2,4-difluorophenyl)pyrrolidine-3-carboxylic acid hydrochloride salt (1-4)

A mixture of the methyl (3S,4R)-1-tert-butyl-4-(2,4-difluorophenyl)pyrrolidine-3-carboxylate enantiomer 1-3 (1.37 g, 4.61 mmol) and potassium trimethylsilanolate (0.68 g, 5.30 mmol) in diethyl ether (23 mL) was stirred at room temperature overnight. A saturated solution of hydrogen chloride in ethyl acetate was then added, the volatiles were evaporated to give 1-4, which was used without further purification in the preparation of Examples detailed below.

Alternatively, (3S,4R)-1-tert-butyl-4-(2,4-difluorophenyl)pyrrolidine-3-carboxylic acid (1-4 may be prepared according to the procedure of Scheme W:

Scheme W

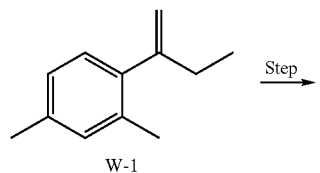

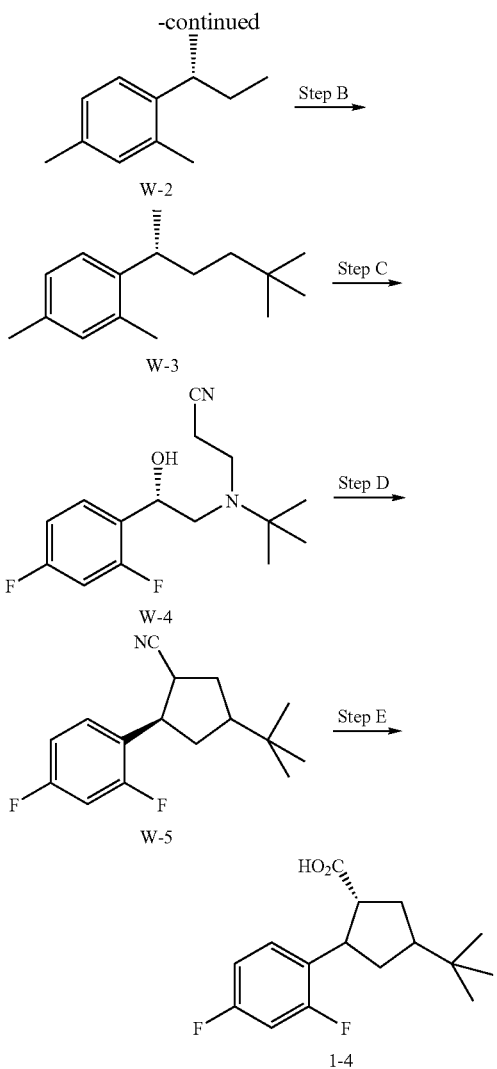

Step A: A solution of (S)-2-methyl-CBS-oxazaborolidine (131 mL, 1 M in toluene), borane-N,N-diethylaniline (46.36 L) in MTBE (10 L) was heated to 38-42° C., then a solution of 2-chloro-2',4'-difluoro-acetophenone W-1 (4891 g) in MTBE (16 L) was added over 10 hr. The homogeneous solution was stirred at 40° C. for one hour, then allowed to cooled to 18° C. and stirred overnight. Methanol (2.3 L) was added over 60 min, while maintaining the temperature at <20° C. with cooling. The reaction mixture was stirred 30 min, then 5.0 N aq HCl (10 L) was added over 30 min, while maintaining the temperature at 22-25° C. with cooling. After stirring 30 min, the phases were separated, and the organic phase was washed with saturated aqueous NaCl, then concentrated in vacuo to obtain a solution of compound W-2.

Step B: Compound W-2 in the MTBE solution from Step A (5040 g, 98 wt %, 25.67 mol) was diluted with methanol (5 L), then tert-butylamine (25 L) was added. The mixture was cooled to 25° C., solid NaOH pellets (1048 g) were added, and the resulting reaction mixture was stirred and warmed to reflux. After 12-20 hr at reflux, the mixture was concentrated in vacuo to ⅓ volume, then water (5 L) and MTBE (20 L) were added. The phases were separated and the aqueous phase was re-extracted with MTBE (2×2 L). The combined extracts were washed with saturated aqueous NaCl (1 L), and then concentrated in vacuo. Heptane (40 L) was added and the concentration was continued to bring the volume to 20 L. The mixture was heated to ~90° C. to dissolve all solids, then allowed to cool to 22° C. to crystallize over 4 hr. The mixture was cooled to 0° C., stirred 12-15 hr, then filtered. The resulting filtrate was washed with cold heptane (2×5 L), then dried in vacuo at 35° C. to obtain compound W-3.

Step C: A mixture of compound W-3 (5.205 kg, 99.9%, 22.68 mol) and acrylonitrile (26.9 L, 408 mol) was heated to reflux (~77° C.) under nitrogen atmosphere. After heating for 20 h (~90% conversion), one equivalent each of ethanol (1.32 L, 22.68 mol) and formamide (0.9 L, 22.68 mol) was added and heating was continued for 12 h. After cooling to 22° C., the solution was concentrated to 12 L by distillation (80-90 torr at 20-22° C. pot temperature), and the resulting residue was diluted with isopropyl acetate (22 L) and re-concentrated (55-75 torr and 22-27° C. pot temperature). This was repeated. Then the residue was diluted with isopropyl acetate to a total volume of 34 L, and the supernatant was filtered using a 10-15 μm porosity filter. The filter cake was washed with isopropyl acetate, and the filtrate was diluted with a total of 24 L of isopropyl acetate. The combined filtrate (~54 L) was washed with a solution made up of water (31.2 L), acetic acid (52 mL, 4 mol %), and saturated brine (3.1 L), followed by a 12% aqueous NaCl wash (2×34 L). The organic layer was concentrated (15-45 torr and 5-29° C.) to ~15 L volume and flushed with 5×6 L n-heptane, during which time product crystallized. The slurry was diluted with n-heptane to a volume of 23 L and stirred at 0-5° C. for 1-3 days until a concentration of 10 g/18 L is achieved, then filtered and washed with cold (5° C.) n-heptane (14 L). The wet cake was dried in vacuo at 20° C. with a nitrogen sweep to afford compound W-4.

Step D: A solution of compound W-4 (5.73 kg, 99.9%, 20.28 mol) in dry THF (31.3 L) was cooled to −20° C., then chloro diethylphosphate (3.79 kg, 21.29 mol) was added. LiHMDS (1.35 M in THF solution; 31.5 L, 42.58 mol) was slowly added over 1.5 h while maintaining the reaction temperature at −15° C. After stirring at −15° C. for 2 h, the reaction mixture was quenched with water (50.6 L) at <15° C. and extracted with n-heptane (40.5 L) at 20° C. The organic layer was washed with 10% aq NaCl solution (52 L), and extracted with 3 N HCl solution (40.6 L, 121.8 mol) with cooling to keep the temperature <35° C. The aqueous layer (58 L) was adjusted to pH 11-12 with 50% aq NaOH (6.13 L, 116.1 mol) and extracted with n-heptane (54 L). The organic phase was washed once with 10% aq NaCl solution (26 L) and the resulting heptane solution containing compound W-5 was used in Step E.

Step E: The solution of compound W-5 (4.88 kg, 18.46 mol) in n-heptane (~65 L total) from the Step D was solvent-switched to ethanol (~20.6 L total). To this solution was added 50% aq NaOH (2.7 L, 51.15 mol) over 2 min with stirring. Upon addition of the NaOH, the temperature of the mixture rose from 16 to 34° C. The mixture was then heated to reflux (78-80° C.) under nitrogen for 5-6 h. After cooling to 20° C., the solution was diluted with ethanol (25.4 L) and methanol (40.6 L). The solution was then cooled to 12° C.; the pH was adjusted to apparent pH 6.8 with 96% $H_2SO_4$ (1.42 L, 25.6 mol), while maintaining the temperature at ~20° C. The sodium sulfate slurry was filtered through a bed of Solka-Floc® (5 kg) and anhydrous powder $Na_2SO_4$ (4 kg), and washed with 1:1 EtOH:MeOH (20 L). The filtrate was filtered, concentrated and solvent-switched to a 2-propanol solution (~15 L volume). The resulting slurry was heated at reflux (~80° C.) for 2 h, then cooled to 16° C.

MTBE (30.4 L, 3 vol relative to IPA) was added to the mixture over 5 h. After stirring at 16-17° C. for 3 days, the resulting slurry was filtered and washed with 12 L 1:3 IPA:MTBE. The solids were dried in vacuo (150 torr) at 50° C. with a nitrogen sweep to give compound 1-4.

SCHEME 1

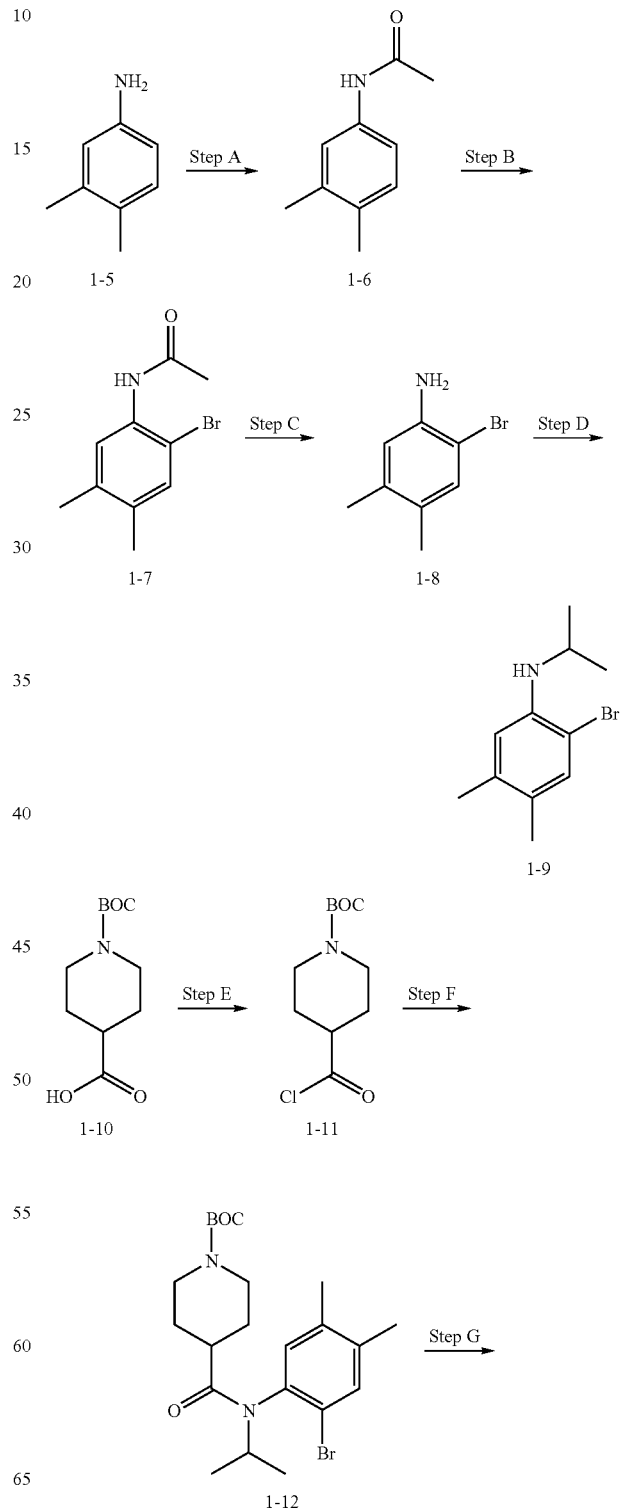

-continued

Step H

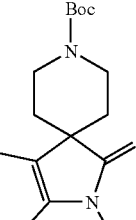

1-13

1-4

1-14

EXAMPLE 1

Preparation of (1-14)

Step A: Preparation of N-(3,4-dimethylphenyl)acetamide (1-6)

Acetic anhydride (38.9 mL, 412 mmol) was added to a stirred solution of 3,4-dimethylaniline 1-5 (10.0 g, 82.5 mmol) in pyridine (150 mL) at ambient temperature. After stirring at approximately 60° C. for 2 h, the volatiles were removed in vacuo, and the residue was partitioned between diethyl ether and aqueous 1 N hydrochloric acid. The organic phase was separated and washed with saturated aqueous sodium bicarbonate, brine, dried (sodium sulfate) and concentrated in vacuo to afford 1-6 as a white crystalline solid.

Step B: Preparation of N-(2-bromo-4,5-dimethylphenyl)acetamide (1-7)

Bromine (5.08 mL, 99.1 mmol) was added over 1 h to a stirred solution of N-(3,4-dimethylphenyl)acetamide 1-6 (13.5 g, 82.6 mmol) in acetic acid (200 mL) at approximately 15° C. After 15 minutes, water (400 mL) was added until no further precipitation was observed. The resultant solid was filtered, washed with water (until white) and dried in vacuo to afford 1-7 as a white crystalline solid.

Step C: Preparation of 2-bromo-4,5-dimethylaniline (1-8)

Potassium hydroxide (15.9 g, 284 mmol) was added to a stirred solution of N-2-bromo-4,5-dimethylphenyl)acetamide (1-7) (17.2 g, 71.0 mmol) in methanol (350 mL) at ambient temperature. After stirring at approximately 80° C. for 18 h, the reaction mixture was cooled and the organic volatiles removed in vacuo. The remaining aqueous phase was diluted with additional water (65 mL) and the resultant solid product was filtered, washed with water and dried in vacuo to afford 1-8 as a white solid.

Step D: Preparation of 2-bromo-N-isopropyl-4,5-dimethylaniline (1-9)

A solution of acetone (5.60 mL, 76.3 mmol) and aqueous 4 M sulfuric acid (5.20 mL, 20.8 mmol) in tetrahydrofuran (15 mL) was added dropwise to a stirred solution of 2-bromo-4,5-dimethylaniline 1-8 (13.9 g, 69.3 mmol) in tetrahydrofuran (40 mL) at approximately 0° C. Sodium borohydride (2.62 g, 69.3 mmol) was added cautiously and the resulting mixture allowed to warm to ambient temperature. After 30 min, the reaction was quenched by the careful sequential addition of water (25 mL) and sodium hydroxide pellets (until strongly alkaline). The reaction mixture was extracted with tert-butyl methyl ether (150 mL) and the organic phase was washed with brine, dried (sodium sulfate) and concentrated in vacuo to give a crude residue. Purification of the crude residue by flash chromatography over silica gel (gradient elution; 0%-20% ethyl acetate/hexanes as eluent) afforded 1-9 as a clear, pale orange oil.

Step E: Preparation of tert-butyl 4-(chlorocarbonyl)piperidine-1-carboxylate (1-11)

Oxalyl chloride (32.7 mL of a 2 M solution in methylene chloride, 65.4 mmol) followed by N,N-dimethylformamide (0.5 mL) were added to a stirred solution of 1-tert-butoxycarbonyl)piperidine-4-carboxylic acid 1-10 (10.0 g, 43.6 mmol) in methylene chloride (150 mL) at approximately 0° C. After 1 h, the volatiles were removed in vacuo, azeotroping twice with toluene to afford 1-11 as an orange oil. Compound 1-11 was dissolved in methylene chloride to generate 43.6 mL of a 1M solution and used as such in the subsequent reaction.

Step F: Preparation of tert-butyl 4-{[(2-bromo-4,5-dimethylphenyl)(isopropyl)-amino]carbonyl}piperidine-1-carboxylate (1-12)

N,N-dimethylaniline (7.12 mL, 56.2 mmol) followed by tert-butyl 4-(chlorocarbonyl)piperidine-1-carboxylate 1-11 (42.1 mL of a 1 M solution in methylene chloride, 42.1 mmol) were added to a neat stirred mixture of 2-bromo-N-isopropyl-4,5-dimethylaniline 1-9 (6.80 g, 28.1 mmol) and N,N-dimethylamino-pyridine (172 mg, 1.40 mmol) at approximately 0° C. The resulting mixture was heated to reflux for 30 min, cooled to ambient temperature and partitioned between diethyl ether and aqueous 1 N hydrochloric acid. The organic phase was separated and washed successively with aqueous 1 N hydrochloric acid, saturated aqueous sodium bicarbonate, brine, dried (sodium sulfate) and concentrated in vacuo to give a crude residue. Purification of the crude residue by flash chromatography over silica gel (gradient elution; 0%-40% ethyl acetate/hexanes as eluent) afforded 1-12 as a white solid.

Step G: Preparation of (1-13)

A stirred mixture of tert-butyl 4-{[(2-bromo-4,5-dimethylphenyl)(isopropyl)amino]carbonyl}piperidine-1-carboxylate 1-12 (3 g, 6.52 mmol), bis(dibenzylideneacetone)palladium (187 mg, 0.326 mmol), racemic 2,2'-bis (diphenylphosphino)-1,1'-binaphthyl (309 mg, 0.496 mmol) and sodium tert-butoxide (954 mg, 9.93 mmol) in dioxane (100 mL) was heated at approximately 100° C. for 18 h. The reaction mixture was poured into aqueous 2 N hydrochloric acid and extracted three times with diethyl ether. The combined ethereal extracts were washed with brine, dried (sodium sulfate) and concentrated in vacuo to give a crude residue. Purification of the crude residue by flash chroma- Step H: Preparation of (1-14)

Hydrogen chloride (4 mL of a 4 M solution in dioxane, 4 mmol) was added to a stirred solution of 1-13 (128 mg, 0.344 mmol) in methylene chloride (2 mL) at ambient temperature. After 1 h, the reaction mixture was evaporated to dryness in vacuo and re-dissolved in methylene chloride (5 mL). (3S,4R)-1-tert-butyl-4-(2,4-difluorophenyl)pyrrolidine-3-carboxylic acid hydrochloride 1-4 (100 mg, 0.313 mmol), 1-hydroxybenzotriazole hydrate (57.0 mg, 0.375 mmol), 1-[3-(dimethylamino)propyl]-3-ethylcarbodiimide hydrochloride (72.0 mg, 0.375 mmol) and 4-methylmorpholine (0.155 mL, 1.42 mmol) were added successively. After aging at room temperature for 18 h, the reaction mixture was diluted with ethyl acetate and washed successively with saturated aqueous sodium bicarbonate, brine, dried (sodium sulfate) and concentrated in vacuo to give a crude residue. Purification of the crude residue by flash chromatography over silica gel (gradient elution; 0%-20% methanol/methylene chloride as eluent) afforded a white solid, which was dissolved in the minimum amount of methylene chloride and acidified with hydrogen chloride (1M solution in diethyl ether). The volatiles were removed in vacuo to afford 1-14 as a white solid (m/z (ES) 538 (MH+)).

Following procedures similar to that described above for Example 1, the following compounds were prepared:

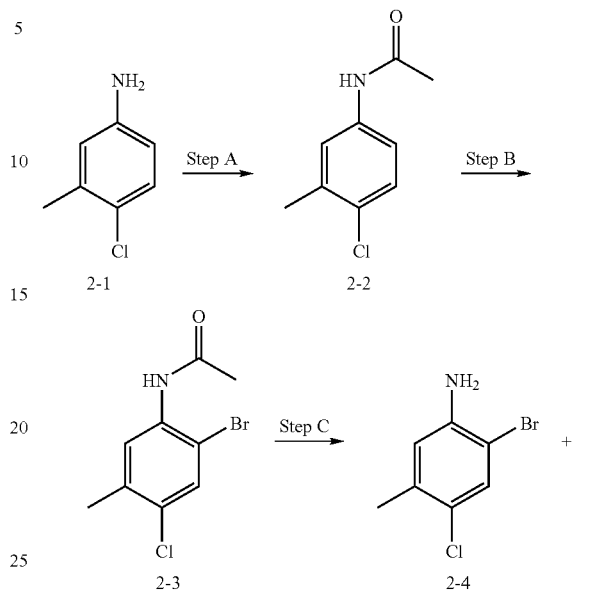

Scheme 2

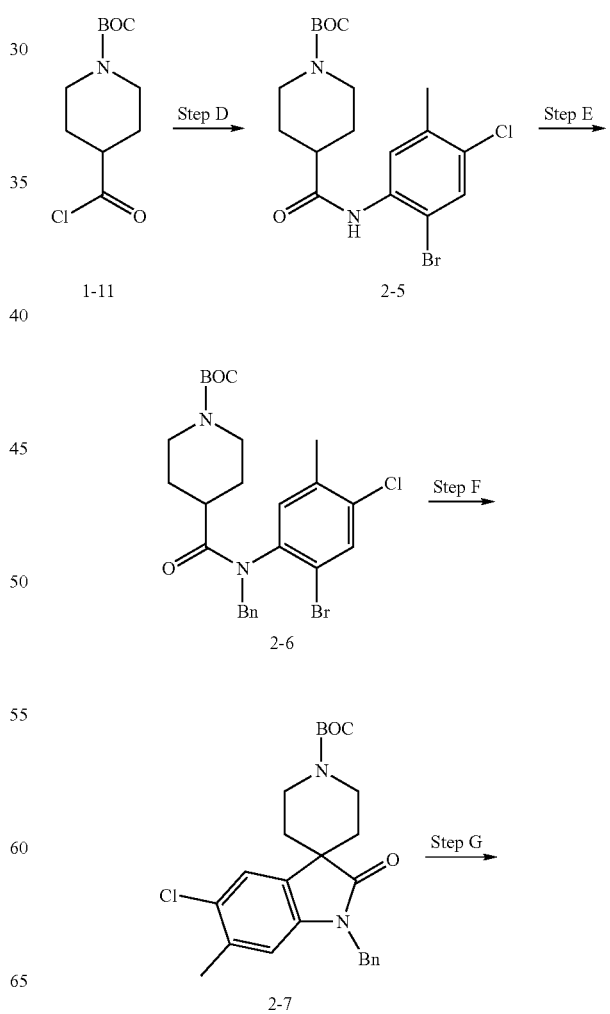

| Ex. # | R$^{4a}$ | R$^{4b}$ | Parent Ion m/z (M + H) |
|---|---|---|---|
| 2 | Cl | H | 544 |
| 3 | H | Cl | 544 |
| 4 | Me | H | 524 |
| 5 | H | Me | 524 |
| 6 | Cl | Me | 558 |
| 7 | Me | Cl | 558 |
| 8 | H | H | 510 |
| 9 | F | H | 528 |
| 10 | NH$_2$ | H | 525 |
| 11 | H | NH$_2$ | 525 |
| 12 | H | F | 528 |
| 13 | H | CN | 535 |
| 14 | H | Br | 590 |
| 15 | H | I | 636 |
| 16 | Me | NH$_2$ | 539 |
| 17 | NH$_2$ | Me | 539 |
| 18 | H | OH | 526 |
| 19 | H | NMe$_2$ | 553 |
| 20 | H | OMe | 540 |

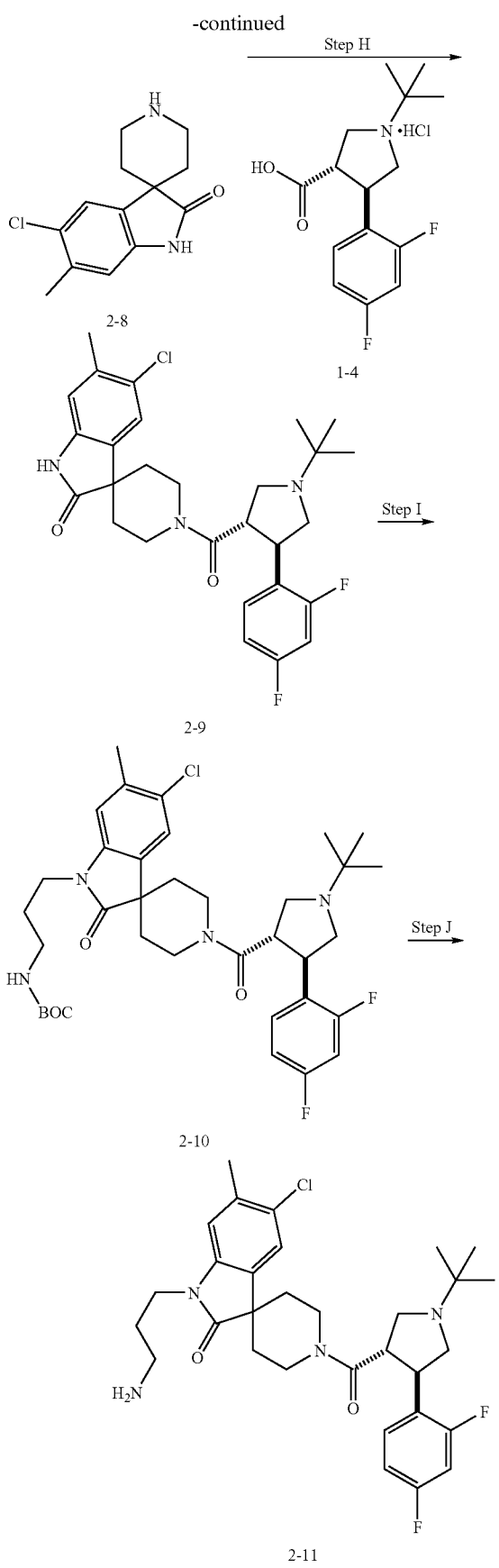

EXAMPLE 21

Preparation of (2-11)

Steps A-D: Preparation of tert-butyl 4-{[(2-bromo-4-chloro-5-methylphenyl)amino]carbonyl}piperidine-1-carboxylate (2-5)

Tert-butyl 4-{[(2-bromo-4-chloro-5-methylphenyl)amino]carbonyl}-piperidine-1-carboxylate 2-5 was prepared from 4-chloro-3-methylaniline 2-1 following a similar procedure to that described for 4-{[(2-bromo-4,5 dimethylphenyl)(isopropyl)amino]carbonyl}piperidine-1-carboxylate 1-12.

Step E: Preparation of tert-butyl 4-{[benzyl(2-bromo-4-chloro-5-methylphenyl)amino]carbonyl}piperidine-1-carboxylate (2-6)

Sodium hydride (193 mg, 8.06 mmol) was added to a stirred solution of tert-butyl 4-{[(2-bromo-4-chloro-5-methylphenyl)amino]carbonyl}piperidine-1-carboxylate 2-5 (2.90 g, 6.72 mmol) in N,N-dimethylformamide (40 mL) at approximately 0° C. The reaction mixture was warmed to ambient temperature and aged for 30 min. Benzyl bromide (1.20 mL, 10.1 mmol) was added and after 1 h, the reaction mixture was poured into aqueous 2 N hydrochloric acid and extracted with diethyl ether. The organic phase was washed with saturated aqueous sodium bicarbonate, brine, dried (sodium sulfate) and concentrated in vacuo to give a crude residue. Purification of the crude residue by flash chromatography over silica gel (gradient elution; 0%-20% acetone/methylene chloride as eluent) afforded 2-6 as a white solid.

Step F: Preparation (2-7)

Compound 2-7 was prepared from tert-butyl 4-{[benzyl (2-bromo-4-chloro-5-methylphenyl)amino] carbonyl}piperidine-1-carboxylate 2-6 following a similar procedure to that described for 1-13.

Step G: Preparation of (2-8)

A solution of 2-7 (1.18 g, 2.68 mmol) and anisole (1.45 mL, 13.4 mmol) in trifluoroacetic acid/concentrated sulfuric acid (20:1, 157.5 mL) was heated in a pressure tube at approximately 110° C. for 18 h. After cooling to ambient temperature, the volatiles were removed in vacuo. The residue was neutralized with aqueous 2.5 N sodium hydroxide and extracted with ethyl acetate. The organic phase was washed with brine, dried (sodium sulfate) and concentrated in vacuo to afford 2-8 as an orange gum.

Step H: Preparation (2-9)

Compound 2-9 was prepared from 2-8 following a similar procedure to that described for 1-14.

Step I: Preparation of (2-10)

Sodium hydride (4.00 mg, 0.174 mmol) was added to a stirred solution of 2-9 (60.0 mg, 0.116 mmol) in N,N-dimethylformamide (1 mL) at approximately 0° C. After 15 min, tert-butyl 2-bromopropylcarbamate (83.0 mg, 0.349 mmol) was added and the resulting mixture was aged at ambient temperature for 1 h. The reaction mixture was poured into saturated aqueous sodium bicarbonate and extracted with ethyl acetate. The organic phase was washed with brine, dried (sodium sulfate) and concentrated in vacuo. Purification of the crude residue by flash chromatography over silica gel (gradient elution; 60%-100% acetone/methylene chloride afforded 2-10 as a white solid.

Step J: Preparation of (2-11)

Hydrogen chloride (1 mL of a 4M in dioxane, 1 mmol) was added to a stirred solution of 2-10 (30 mg, 45 μmol) in methylene chloride (0.5 mL) at ambient temperature. After 1 h, the volatiles were removed in vacuo and the residue was triturated with diethyl ether/hexanes to afford 2-11 as a white powder (m/z (ES) 574 (MH+)).

Following procedures similar to that described above for Example 21, the following compounds were prepared:

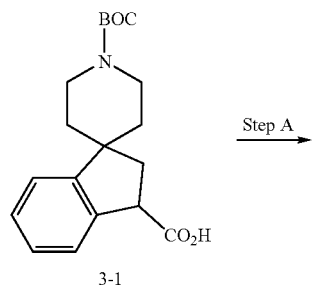

| Ex. # | $R^6$ | Parent Ion m/z (M + H) |
|---|---|---|
| 22 | —CH$_2$CH$_2$NH$_2$ | 559 |
| 23 | —CH$_2$CH$_2$NHBoc | 516* |
| 24 | —CH$_2$CH$_2$NMe$_2$ | 587 |
| 25 | —(CH$_2$)$_3$NHC(O)Me | 573 |
| 26 | —CH$_2$CH$_2$CH$_2$NHBoc | 673 |
| 27 | —CH(Me)CN | 569 |
| 28 | —CH(Me)CO$_2$tBu | 644 |
| 29 | —CH(Me)CO$_2$H | 588 |
| 30 | —CH(Me)CH$_2$Me | 572 |
| 31 | —CH(Me)Ph | 620 |
| 32 | —CH$_2$Ph | 572 |
| 33 | H | 516 |

*(M − $^t$Bu + H)

SCHEME 3

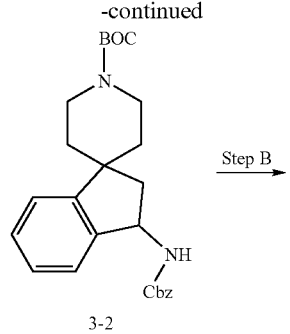

3-2

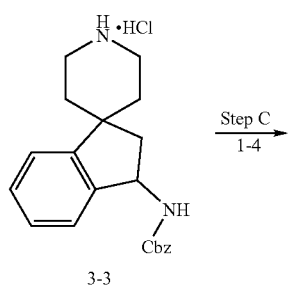

3-3

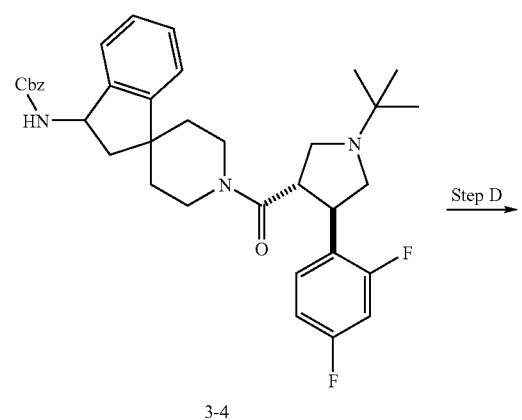

3-4

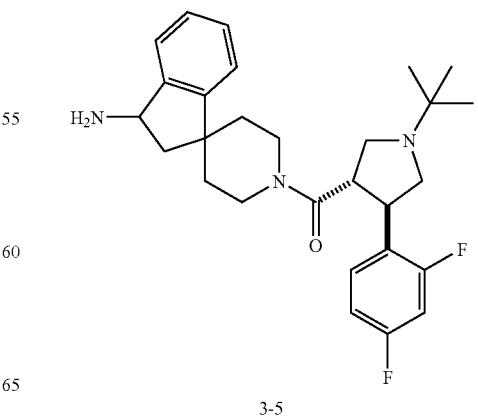

3-5

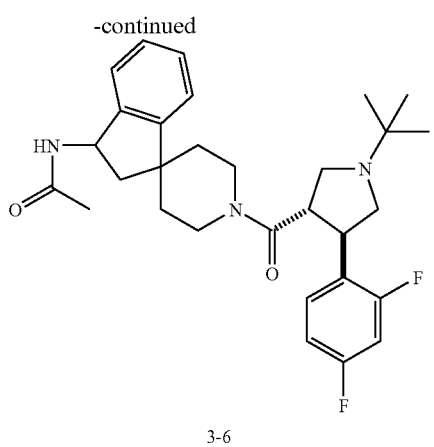

3-6

EXAMPLE 34

Preparation of (3-6)

Step A: Preparation of (3-2)

Diphenylphosphoryl azide (1.95 mL, 9.05 mmol) was added to a stirred solution of compound 3-1 (2.50 g, 7.54 mmol) and triethylamine (1.47 mL, 10.5 mmol) in toluene (35 mL) at ambient temperature. The resulting mixture was stirred at approximately 85° C. for 4 h and then cooled to room temperature. Benzyl alcohol (0.94 mL, 9.08 mmol) was added and the resulting solution was aged at ambient temperature for 18 h. The reaction mixture was poured into aqueous 1 N hydrochloric acid and extracted three times with ethyl acetate. The combined organic extracts were washed with water, brine, dried (magnesium sulfate) and concentrated in vacuo. Purification of the crude residue by flash chromatography over silica gel (gradient elution; 0%-40% ethyl acetate/hexanes as eluent) afforded compound 3-2 as a colorless oil.

Step B: Preparation of (3-3)

A saturated solution of hydrogen chloride in ethyl acetate (20 mL) was added to a stirred solution of compound 3-2 (2.69 g, 6.17 mmol) in methylene chloride (20 mL) at approximately 0° C. After 2 h, the volatiles were evaporated in vacuo, and the crude residue was triturated twice with dry diethyl ether to give compound 3-3 as a colorless solid.

Step C: Preparation of (3-4)

N,N-Diisopropylethylamine (1.09 mL, 6.26 mmol) was added to a stirred solution of (3S,4R)-1-tert-butyl-4-(2,4-difluorophenyl)pyrrolidine-3-carboxylic acid hydrochloride 1-4 (0.671 g, 2.09 mmol), compound 3-3 (0.705 g, 2.09 mmol) and O-(7-azabenzotriazol-1-yl)-1,1,3,3-tetramethyluronium hexafluorophosphate (0.954 g, 2.51 mmol) in N,N-dimethylformamide (10 mL) at ambient temperature. After 18 h, the reaction mixture was poured into water and extracted three times with ethyl acetate. The combined organic extracts were washed with water, brine, dried (sodium sulfate) and concentrated in vacuo. Purification of the crude residue by flash chromatography over silica gel (gradient elution; 0%-9% methanol (containing 10% v/v ammonium hydroxide)/methylene chloride as eluent) furnished compound 3-4 as a colorless foam.

Step D: Preparation of (3-5)

A mixture of compound 3-4 (2.09 mmol) and palladium (II) hydroxide (0.126 g) in ethanol/glacial acetic acid (1:1, 8 mL) was hydrogenated at atmospheric pressure for 18 h. The resulting mixture was filtered through a short column of celite®, eluting copiously with ethanol. The filtrate was evaporated and the residue was partitioned between methylene chloride and saturated aqueous sodium bicarbonate. The organic phase was separated and the aqueous phase was re-extracted twice with methylene chloride. The combined organic extracts were washed with water, brine, dried (sodium sulfate) and concentrated in vacuo. Purification of the crude residue by flash chromatography over silica gel (gradient elution; 0%-9% methanol (containing 10% v/v ammonium hydroxide)/methylene chloride as eluent) furnished compound 3-5 as a colorless foam.

Step E: Preparation of (3-6)

Acetyl chloride (11.4 µL, 160 µmol) was added to a stirred solution of compound 3-5 (50.0 mg, 107 µmol) and triethylamine (44.7 µL, 321 µmol) in methylene chloride at approximately 0° C. The resulting mixture was allowed to warm to ambient temperature and aged for 18 h. The reaction mixture was poured into water and extracted three times with methylene chloride. The combined organic extracts were washed with water, brine, dried (sodium sulfate) and concentrated in vacuo. Purification of the crude residue by preparative reversed phase high performance liquid chromatography on YMC Pack Pro C18 phase (gradient elution; 0%-100% acetonitrile/water as eluent, 0.1% TFA modifier) followed by lyophilization gave compound 3-6 as a colorless flocculent solid (m/z (ES) 510 ((MH+)).

Following procedures similar to that described above for Example 34, the following compounds were prepared:

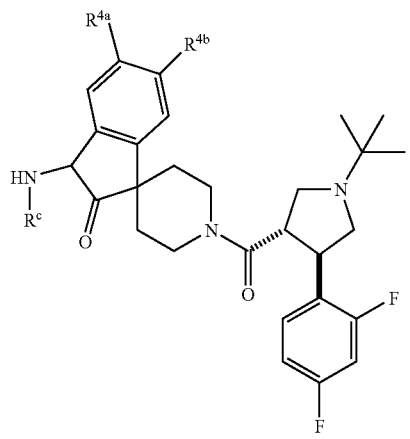

| Ex. # | $R^{4a}$ | $R^{4b}$ | $R^c$ | Parent Ion m/z (M + H) |
|---|---|---|---|---|
| 35 | Me | Me | —C(O)Me | 538 |
| 36 | H | H | —C(O)CH₂Me | 524 |

-continued
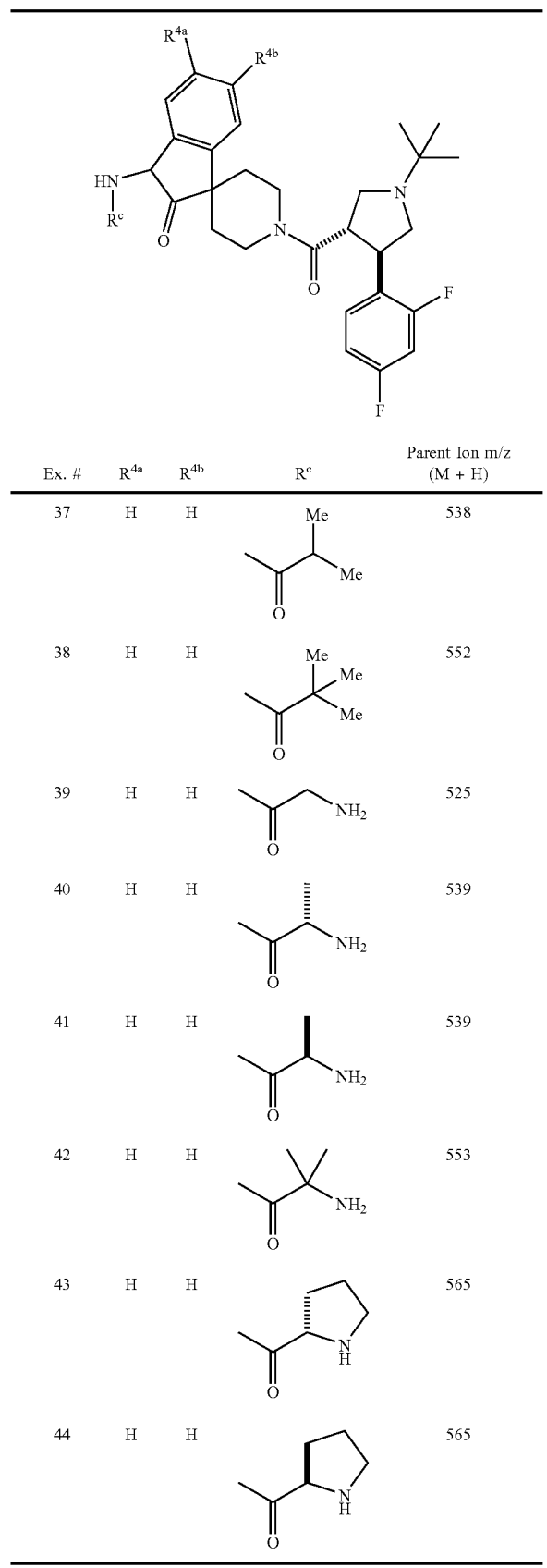
| Ex. # | R4a | R4b | Rc | Parent Ion m/z (M + H) |
|---|---|---|---|---|
| 37 | H | H | (CH3)2CH-C(O)- with Me,Me | 538 |
| 38 | H | H | (CH3)3C-C(O)- | 552 |
| 39 | H | H | H2N-CH2-C(O)- | 525 |
| 40 | H | H | CH3-CH(NH2)-C(O)- | 539 |
| 41 | H | H | CH3-CH(NH2)-C(O)- | 539 |
| 42 | H | H | (CH3)2C(NH2)-C(O)- | 553 |
| 43 | H | H | prolyl | 565 |
| 44 | H | H | prolyl | 565 |
SCHEME 4
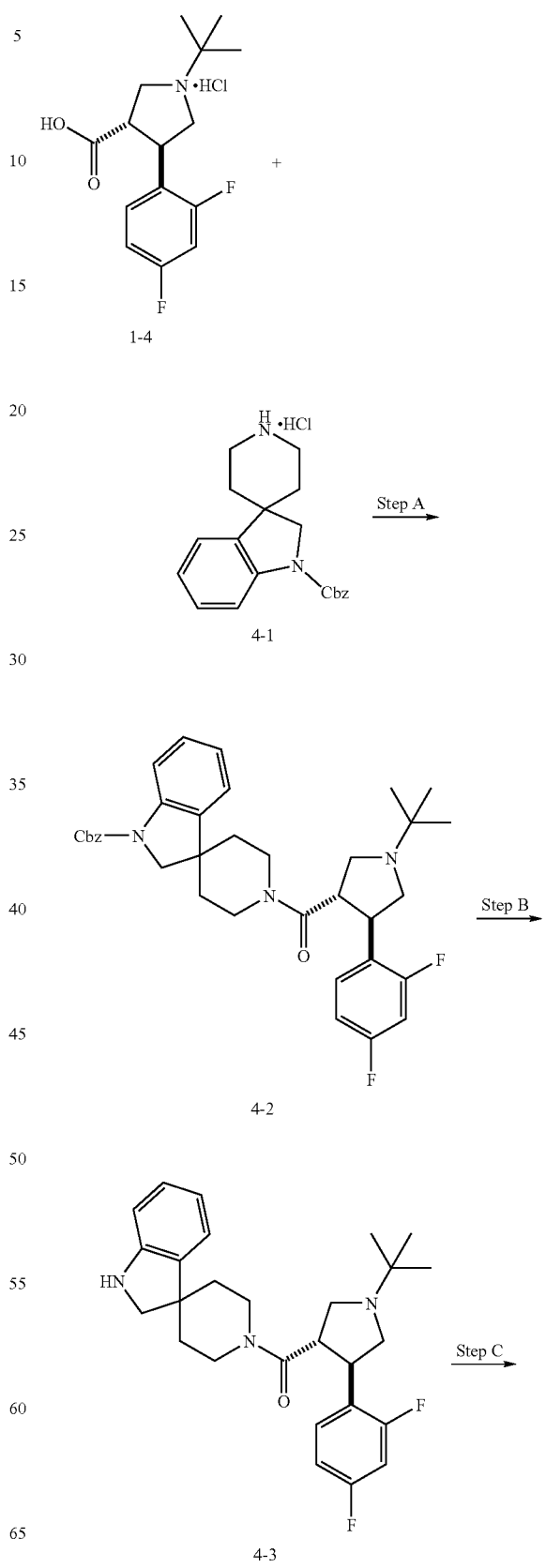

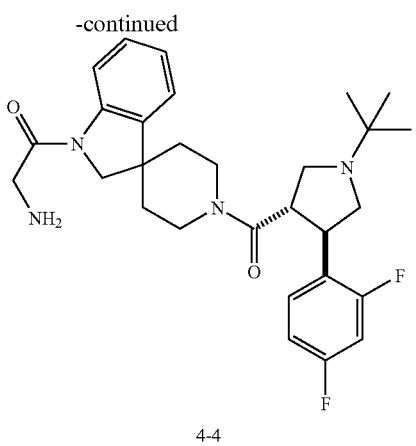

4-4

EXAMPLE 45

Preparation of (4-4)

Step A: Preparation of (4-2)

N,N-Diisopropylethylamine (1.50 mL, 8.61 mmol) was added to a stirred solution of (3S,4R)-1-tert-butyl-4-(2,4-difluorophenyl)pyrrolidine-3-carboxylic acid hydrochloride 1-4 (0.921 g, 2.87 mmol), compound 4-1 (1.03 g, 2.87 mmol) and O-(7-azabenzotriazol-1-yl)-1,1,3,3-tetramethyluronium hexafluorophosphate (1.31 g, 3.45 mmol) in N,N-dimethylformamide (15 mL) at ambient temperature. After 18 h, the reaction mixture was poured into water and extracted three times with ethyl acetate. The combined organic extracts were washed with water, brine, dried (sodium sulfate) and concentrated in vacuo. Purification of the crude residue by flash chromatography over silica gel (gradient elution; 0%-9% methanol (containing 10% v/v ammonium hydroxide)/methylene chloride as eluent) furnished compound 4-2 as a colorless foam.

Step B: Preparation of (4-3)

A mixture of compound 4-2 (2.87 mmol) and palladium (II) hydroxide (0.169 g) in ethanol/glacial acetic acid (1:1, 10 mL) was hydrogenated at atmospheric pressure for 18 h. The resulting mixture was filtered through a short column of celite®, eluting copiously with ethanol. The filtrate was evaporated and the residue was partitioned between methylene chloride and saturated aqueous sodium bicarbonate. The organic phase was separated and the aqueous phase was reextracted twice with methylene chloride. The combined organic extracts were washed with water, brine, dried (sodium sulfate) and concentrated in vacuo. Purification of the crude residue by flash chromatography over silica gel (gradient elution; 0%-9% methanol (containing 10% v/v ammonium hydroxide)/methylene chloride as eluent) furnished compound 4-3 as a colorless foam.

Step C: Preparation of (4-4)

N,N-Diisopropylethylamine (27.9 μL, 160 μmol) was added to a stirred solution of N-Boc-Glycine (11.3 mg, 64.5 μmol), compound 4-3 (24.2 mg, 53.4 μmol) and O-(7-azabenzotriazol-1-yl)-1,1,3,3-tetramethyluronium hexafluorophosphate (30.5 mg, 80.2 μmol) in N,N-dimethylformamide (0.75 mL) at ambient temperature. After 18 h, the reaction mixture was poured into water and extracted three times with methylene chloride. The combined organic extracts were dried (sodium sulfate) and concentrated in vacuo. The crude residue was dissolved in methylene chloride (1 mL) to which a saturated solution of hydrogen chloride in ethyl acetate (1 mL) was added. After 1.5 h, the volatiles were removed in vacuo and the crude residue was purified by preparative reversed phase high performance liquid chromatography on YMC Pack Pro C18 phase (gradient elution; 0%-100% acetonitrile/water as eluent, 0.1% TFA modifier). Lyophilization of the purified fractions gave compound 4-4 as a colorless flocculent solid (m/z (ES) 511 (MH+)).

Following procedures similar to that described above for Example 45, the following compounds were prepared:

| Ex. # | $R^{4a}$ | $R^{4b}$ | $R^6$ | Parent Ion m/z (M + H) |
|---|---|---|---|---|
| 46 | H | H | acetyl (C(O)Me) | 496 |
| 47 | H | H | C(O)CH(NH₂)CH₃ (stereo) | 525 |
| 48 | H | H | C(O)CH(NH₂)CH₃ (stereo) | 525 |
| 49 | H | H | prolinyl C(O) (stereo) | 551 |
| 50 | H | H | prolinyl C(O) (stereo) | 551 |

Scheme 5

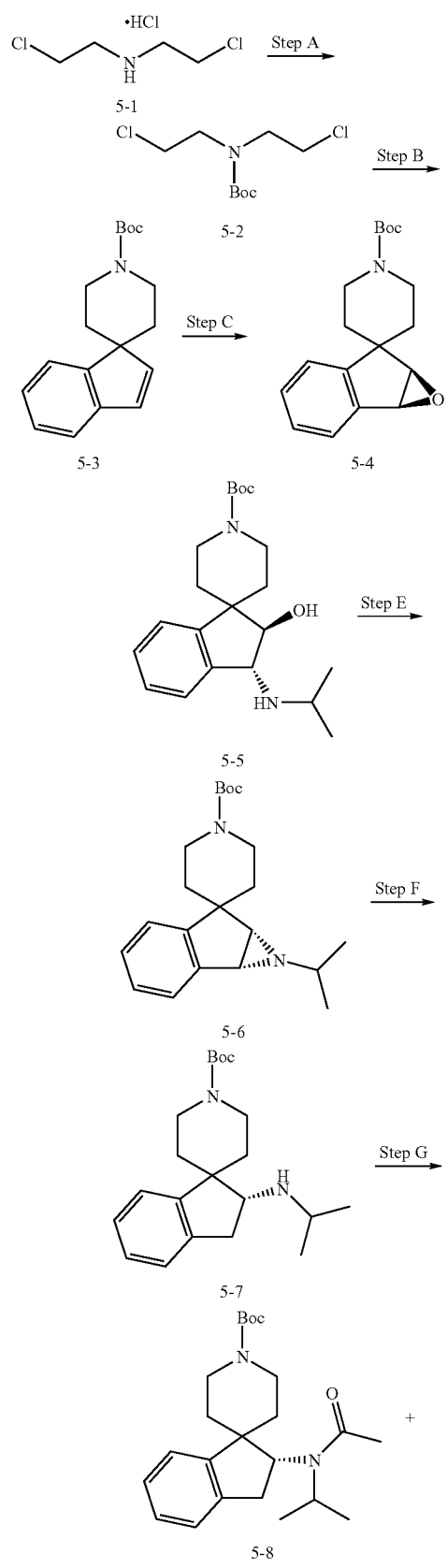

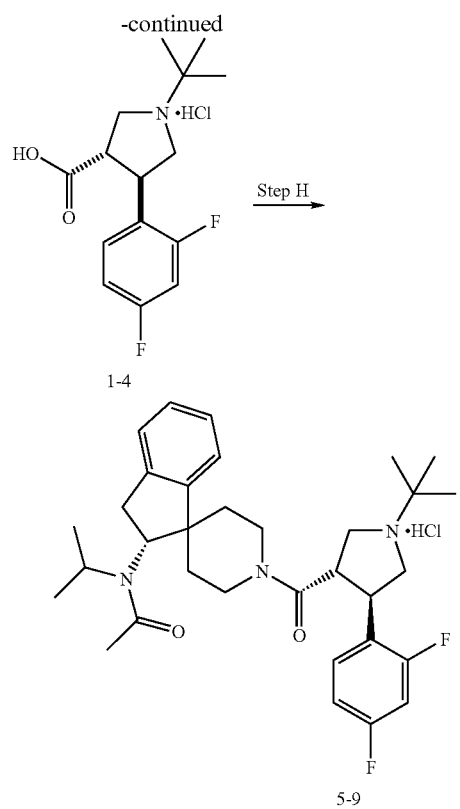

EXAMPLE 51

Preparation of (5-9)

Step A: Preparation of tert-butyl bis(2-chloroethyl)carbamate (5-2)

Over a period of 3 h, triethylamine (1000 mL) was added to a solution of di-tert-butyl dicarbonate (1121 g, 5.2 mol) and N,N-bis(2-chloroethyl)amine hydrochloride 5-1 (1.00 kg, 5.64 mol) in methylene chloride (3600 mL) at ambient temperature. After stirring at ambient temperature for 18 h, the reaction mixture was filtered, rinsing the cake with methylene chloride. The filtrate was washed with water, brine, dried (magnesium sulfate), filtered through sodium sulfate and concentrated in vacuo. Purification of the crude residue by flash chromatography over silica gel (10% ethyl acetate/hexanes as eluent) afforded compound 5-2 as a pale yellow oil.

Step B: Preparation of (5-3)

n-Butyllithium (1785 mL of a 2.5 M solution in hexanes, 4.46 mol) was added over 2 h to a stirred solution of indene (568 g, 4.90 mmol) in tetrahydrofuran (3572 mL) at approximately 0° C. Lithium bis(trimethylsilyl)amide (5768 mL of a 1.0 M solution in tetrahydrofuran, 5.77 mol) was added over a period of 2.5 h (maintaining the reaction temperature below approximately 5° C.). A solution of tert-butyl bis(2-chloroethyl)carbamate 5-2 (1244.5 g, 5.16 mol) in tetrahydrofuran (3572 mL) was then added over a period of 2.5 h (again maintaining the reaction temperature below approximately 5° C.). The resultant solution was allowed to warm slowly to ambient temperature over 18 h. The reaction mixture was poured into water and extracted with isopropyl acetate. The organic phase was treated with Darco® charcoal (365 g), magnesium sulfate (365 g) and silica gel (183 g) and stirred for 1 h. The solution was filtered and concentrated in vacuo to give a crude residue, which was recrystallized from hexane to afford compound 5-3 as white crystals.

Step C: Preparation of (5-4)

(S,S)-(+)-N,N'-Bis(3,5-Di-tert-butylsalicylidene)-1,2-cyclohexane diamino-manganese (III) chloride (110 mg, 0.175 mmol) was added to a stirred solution of compound 5-3 (11.0 g, 3.50 mmol) in methylene chloride (30.0 mL) at ambient temperature followed by 4-phenylpyridine N-oxide (180 mg, 1.05 mmol). After stirring at ambient temperature for 10 min, sodium hypochlorite (7.01 mL of a 1.0 M aqueous solution, 7.01 mmol) was added. After a further 2 h, the reaction mixture was diluted with water and extracted with ethyl acetate. The organic phase was washed with brine, dried (sodium sulfate) and concentrated in vacuo.

Purification of the crude residue by flash chromatography over silica gel (gradient elution; 0%-20% ethyl acetate/hexanes as eluent) afforded 5-4 as a white solid.

Step D: Preparation of (5-5)

A solution of compound 5-4 (1.43 g, 4.75 mmol) in isopropylamine (30 mL) was heated in a sealed tube at approximately 60° C. for 18 h. The reaction mixture was cooled and concentrated in vacuo. Purification of the crude residue by flash chromatography over silica gel (gradient elution; 20%-60% ethyl acetate/hexanes as eluent) afforded compound 5-5 as a white solid.

Step E: Preparation of (5-6)

Triethylamine (1.00 mL, 7.12 mmol) followed by methanesulfonyl chloride (0.440 mL, 5.69 mmol) was added to a stirred solution of compound 5-5 (1.71 g, 4.74 mmol) in dichloroethane (30 mL) at approximately 0° C. After stirring at approximately 60° C. for 2 h, the reaction mixture was cooled, poured into saturated aqueous sodium bicarbonate and extracted with ethyl acetate. The organic phase was washed with brine, dried (sodium sulfate) and concentrated in vacuo to give a crude residue, which was purified by flash chromatography over silica gel (gradient elution; 0%-25% acetone/methylene chloride as eluent) to afford compound 5-6 as a white solid.

Step F: Preparation of (5-7)

A mixture of compound 5-6 (1.00 g, 2.92 mmol), palladium (II) hydroxide (0.205 g) and glacial acetic acid (0.167 mL, 2.92 mmol) in ethanol (30 mL) was hydrogenated at 50 psi for 18 h. The resulting mixture was filtered through a short column of celite®, eluting with ethanol. The filtrate was evaporated in vacuo. The crude residue was purified by flash chromatography over silica gel (gradient elution; 0%-35% acetone/methylene chloride as eluent) furnished compound 5-7 as a white solid.

Step G: Preparation of (5-8)

Acetic anhydride (0.134 mL, 1.42 mmol) was added to a stirred solution of compound 5-7 (50.0 mg, 0.142 mmol) in pyridine (2 mL) at ambient temperature. After stirring at approximately 100° C. for 18 h, the reaction mixture was cooled and concentrated in vacuo. Purification of the crude residue by flash chromatography over silica gel (gradient elution; 0%-40% ethyl acetate/hexanes as eluent) afforded compound 5-8 as an off-white solid.

Step H: Preparation of (5-9)

Hydrogen chloride (2.5 mL of a 4 M solution in dioxane, 10 mmol) was added to a stirred solution of compound 5-8 (71.1 mg, 0.180 mmol) in methylene chloride (2 mL) at ambient temperature. After 1 h, the reaction mixture was evaporated to dryness in vacuo and re-dissolved in methylene chloride (5 mL). (3S,4R)-1-tert-butyl-3-carboxy-4-(2,4-difluorophenyl)pyrrolidinium chloride 1-4 (58.5 mg, 0.180 mmol), 1-hydroxybenzotriazole hydrate (27.2 mg, 0.200 mmol), 1-[3-(dimethylamino)-propyl]-3-ethylcarbodiimide hydrochloride (38.5 mg, 0.200 mmol) and 4-methyl-morpholine (0.090 mL, 0.820 mmol) were added successively. After aging at room temperature for 18 h, the reaction mixture was diluted with ethyl acetate and washed successively with saturated aqueous sodium bicarbonate, brine, dried (sodium sulfate) and concentrated in vacuo. Purification of the crude residue by flash chromatography over silica gel (gradient elution; 0%-20% methanol/methylene chloride as eluent) afforded a white solid, which was dissolved in the minimum amount of methylene chloride and acidified with hydrogen chloride (1M solution in diethyl ether). The volatiles were removed in vacuo to afford compound 5-9 as a white solid (m/z (ES) 552 (MH+)).

EXAMPLE 52

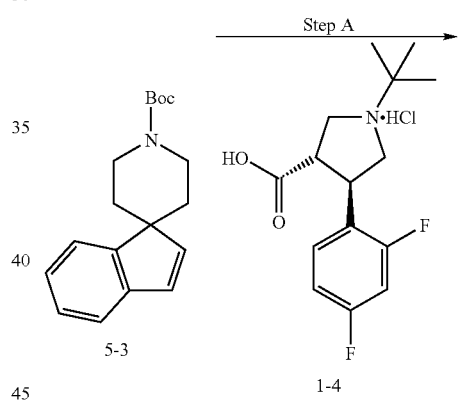

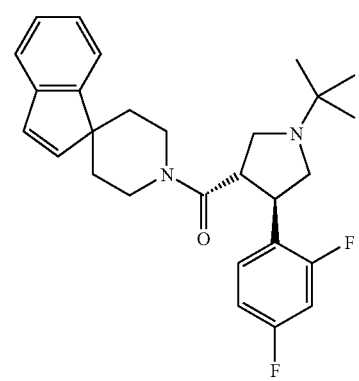

Compound 52 was prepared from 5-3 following a similar procedure to that described for 5-9 (m/z (ES) 451 (MH$^+$)).

EXAMPLE 53

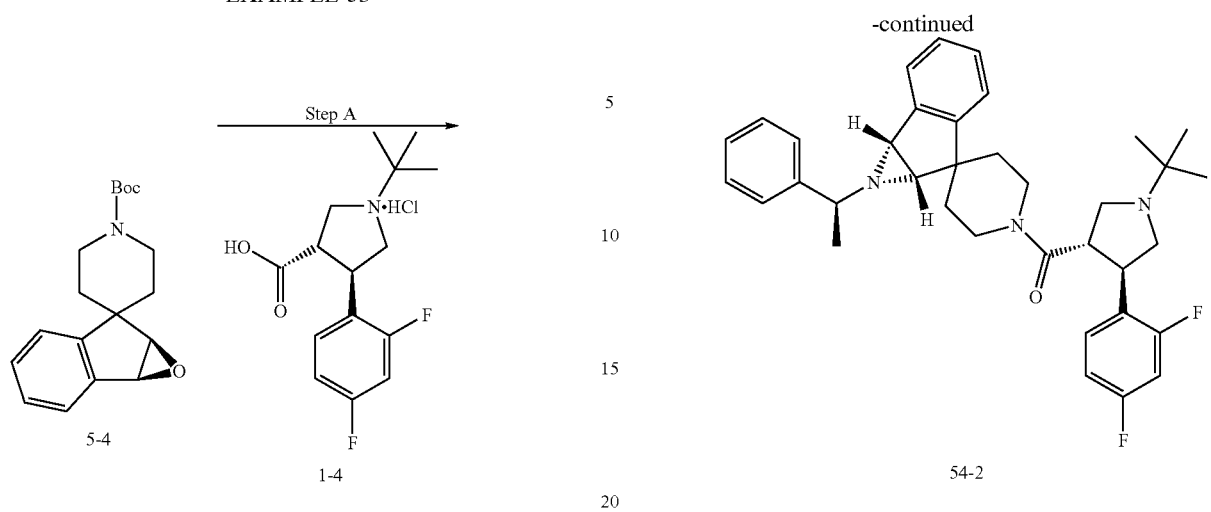

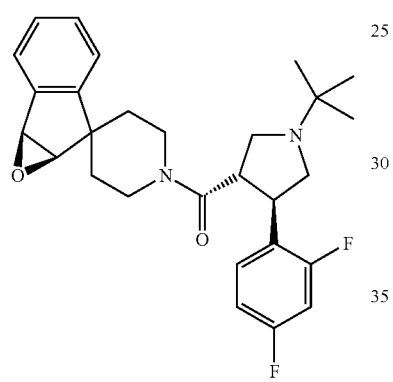

Compound 53 was prepared from 5-4 following a similar procedure to that described for 5-9 (m/z (ES) 467 (MH+)).

EXAMPLE 54

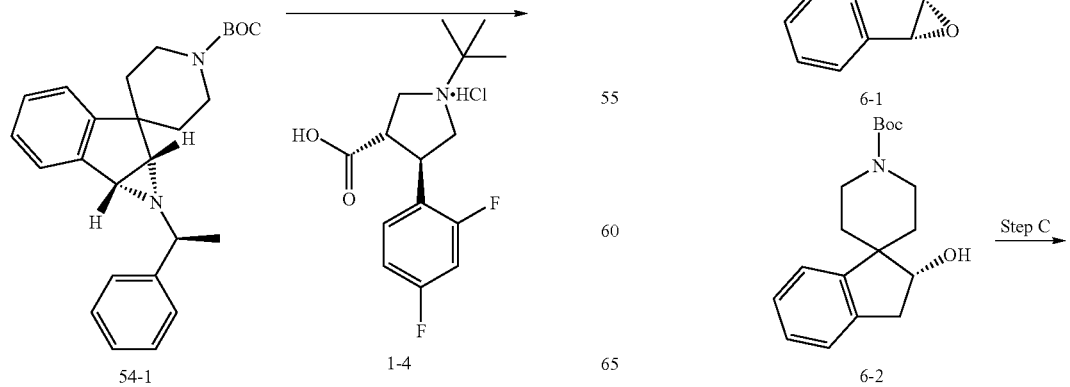

Step A: Preparation of (54-1)

Compound 54-1 was prepared from 5-4 following a similar procedure to that described for the preparation of compound 5-6 and substituting methyl benzyl amine in the place of isopropyl amine for the procedure described for the synthesis of compound 5-5.

Step B: Preparation of (5-9)

Compound 54-2 was prepared from 54-1 following a similar procedure to that described for 5-9 (m/z (ES) 570 (MH+)).

Step D: Preparation of (6-4)

Compound 6-4 was prepared from compound 6-3 following a similar procedure to that described for 5-9 (m/z (ES) 511 (MH+)).

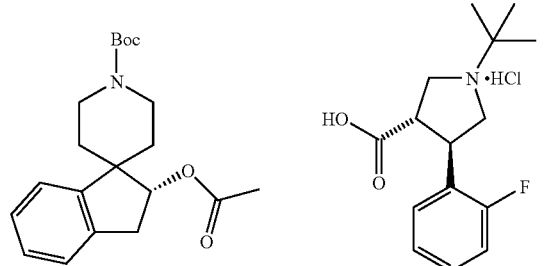

6-3        1-4

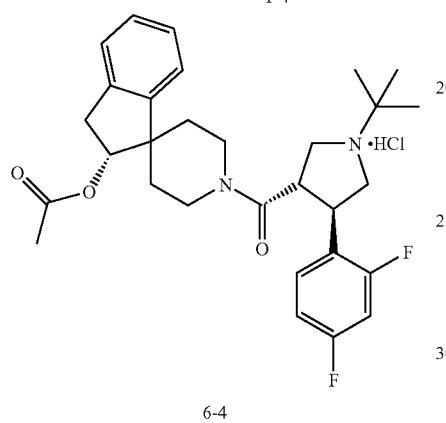

6-4

EXAMPLE 55

Preparation of (6-4)

Step A: Preparation of (6-1)

Compound 6-1 was prepared from 5-3 following a similar procedure to that described for 5-4.

Step B: Preparation of (6-2)

Ammonium formate (1.60 g, 25.4 mmol) was added to a stirred solution of compound 6-1 (385 mg, 1.28 mmol) and 5% palladium on activated carbon (45 mg) at ambient temperature. After stirring at approximately 80° C. for 1 h, the reaction was cooled, filtered through a short column of celite®, eluting with dioxane. The filtrate was washed with brine, dried (sodium sulfate) and concentrated in vacuo. The crude residue was purified by flash chromatography over silica gel (20% ethyl acetate/hexanes as eluent) furnished 6-2 as a white solid.

Step C: Preparation of (6-3)

Triethylamine (0.100 mL, 0.717 mmol) followed by acetyl chloride (0.0185 mL, 0.260 mmol) was added to a stirred solution of compound 6-2 (120 mg, 0.260 mmol) in methylene chloride (5 mL) at approximately 0° C. After stirring at ambient temperature for 18 h, the reaction mixture was diluted with methylene chloride and washed successively with saturated aqueous sodium bicarbonate, brine, dried (sodium sulfate) and concentrated in vacuo. Purification of the crude residue by flash chromatography over silica gel (20% ethyl acetate/hexanes as eluent) furnished 6-3 as a white solid.

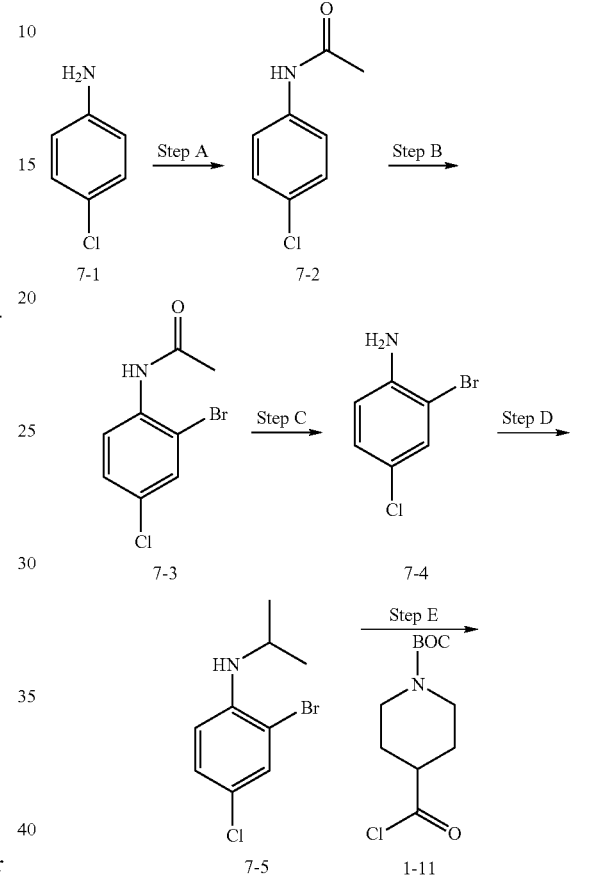

Scheme 7

-continued

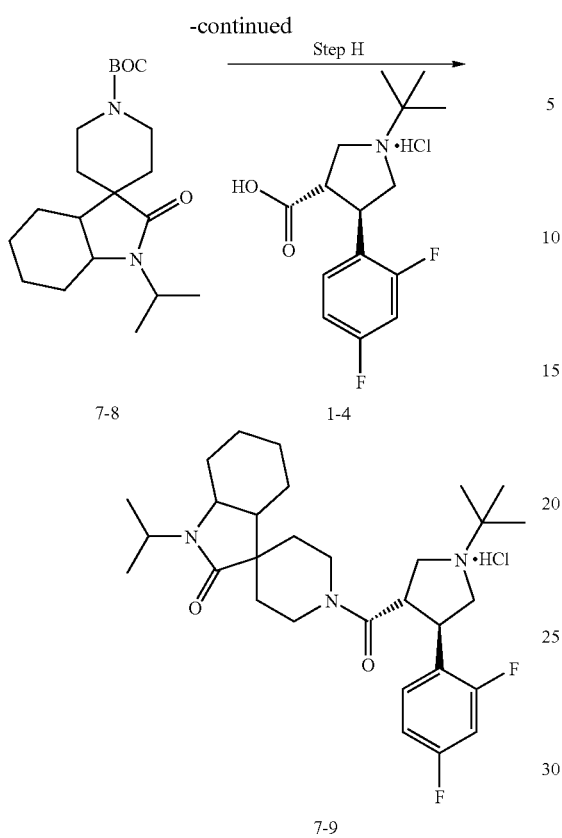

7-8      1-4

7-9

EXAMPLE 56

Steps A-F: Preparation of (7-7)

Compound 7-7 was prepared from compound 7-1 following a similar procedure to that described for compound 1-13.

Step G: Preparation of (7-8)

A mixture of compound 7-7 (500 mg, 1.32 mmol), platinum (IV) oxide (300 mg) in glacial acetic acid (10 mL) was hydrogenated at 45 psi for 20 h. The resulting mixture was filtered through a short column of celite®, eluting with ethanol. The filtrate was evaporated in vacuo. The crude residue was purified by flash chromatography over silica gel (gradient elution; 0%-20% acetone/methylene chloride as eluent) furnished compound 7-8 as a white foam.

Step H: Preparation (7-9)

Compound 7-9 was prepared from compound 7-8 following a similar procedure to that described for 1-14 (m/z (ES) 516 (MH+)).

Scheme 8

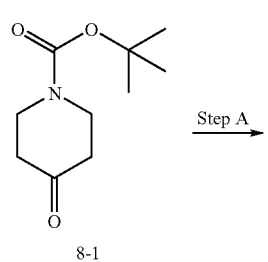

8-1

-continued

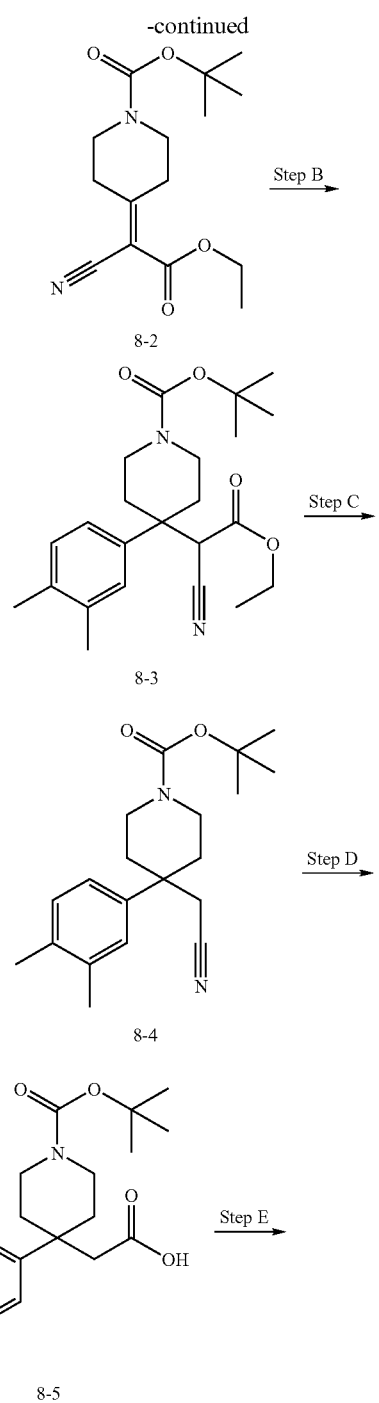

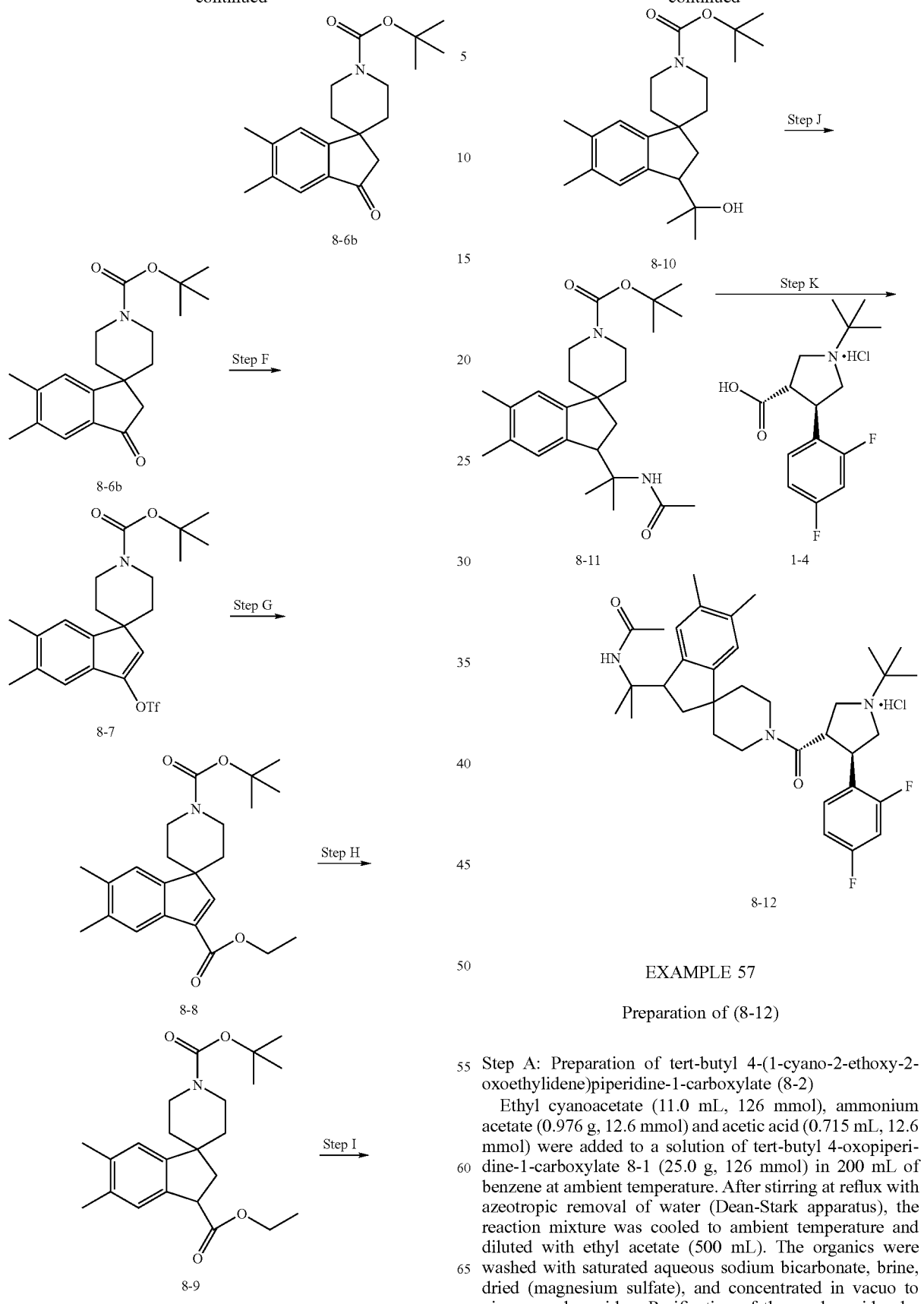

EXAMPLE 57

Preparation of (8-12)

Step A: Preparation of tert-butyl 4-(1-cyano-2-ethoxy-2-oxoethylidene)piperidine-1-carboxylate (8-2)

Ethyl cyanoacetate (11.0 mL, 126 mmol), ammonium acetate (0.976 g, 12.6 mmol) and acetic acid (0.715 mL, 12.6 mmol) were added to a solution of tert-butyl 4-oxopiperidine-1-carboxylate 8-1 (25.0 g, 126 mmol) in 200 mL of benzene at ambient temperature. After stirring at reflux with azeotropic removal of water (Dean-Stark apparatus), the reaction mixture was cooled to ambient temperature and diluted with ethyl acetate (500 mL). The organics were washed with saturated aqueous sodium bicarbonate, brine, dried (magnesium sulfate), and concentrated in vacuo to give a crude residue. Purification of the crude residue by recrystallization from 10% ethyl acetate/hexanes afforded 8-2 as a white crystalline solid.

Step B: Preparation of tert-butyl 4-(1-cyano-2-ethoxy-2-oxoethyl)-4-(3,4-dimethylphenyl)piperidine-1-carboxylate (8-3)

3,4-Dimethylmagnesium bromide (250 mL of a 0.5 M solution in tetrahydrofuran, 125 mmol, Rieke Metals, Inc., 3045) was added to a suspension of copper (I) cyanide (5.48 g, 61.2 mmol) in anhydrous tetrahydrofuran (400 mL) under nitrogen at approximately −50° C. After stirring at approximately −50° C. for 10 minutes, the reaction mixture was allowed to warm to ambient temperature over 1 h then recooled to approximately −50° C. A solution of tert-butyl 4-(1-cyano-2-ethoxy-2-oxoethylidene)piperidine-1-carboxylate 8-2 (15.0 g, 51.0 mmol) in tetrahydrofuran (50 mL) was added. After stirring at −50° C. for 3 h, the reaction mixture was warmed to 0° C. and quenched with saturated aqueous ammonium chloride. The mixture was extracted with ethyl acetate and the organic layer was washed with brine, dried (magnesium sulfate) and concentrated in vacuo to give compound 8-3 as light yellow oil.

Step C: Preparation of tert-butyl 4-(cyanomethyl)-4-3,4-dimethylphenyl)piperidine-1-carboxylate (8-4)

Lithium chloride (2.96 g, 69.8 mmol) and water (5.0 mL) were added to a solution of tert-butyl 4-(1-cyano-2-ethoxy-2-oxoethyl)-4-(3,4-dimethylphenyl)piperidine-1-carboxylate 8-3 (20.0 g, 49.9 mmol) in dimethyl sulfoxide (200 mL). The reaction mixture was heated to 160° C. and stirred at approximately 160° C. for 3 hours. The reaction mixture was then cooled to ambient temperature, quenched with cold water (800 mL) and extracted with ethyl ether (4×500 mL). The ether layer was dried (magnesium sulfate) and concentrated in vacuo to give a crude residue. Purification of the crude residue by flash chromatography over silica gel (gradient elution; 20%-40% ethyl acetate/hexanes as eluent) afforded compound 8-4 as a white solid.

Step D: Preparation of [1-(tert-butoxycarbonyl)-4-(3,4-dimethylphenyl)piperidin-4-yl]acetic acid (8-5)

Water (50 mL) and potassium hydroxide (11.9 g, 213 mmol) were added to a solution of tert-butyl 4-(cyanomethyl)-4-(3,4-dimethylphenyl)piperidine-1-carboxylate 8-4 (14.0 g, 42.6 mmol) in ethanol (200 mL). The reaction was heated at approximately 90° C. until complete conversion of starting material (as monitored by high-pressure liquid chromatography). The reaction mixture was then cooled to ambient temperature, quenched with ice cold 1 N aqueous hydrochloric acid (500 mL) and extracted with ethyl acetate (3×500 mL). The organic phase was washed with brine, dried (magnesium sulfate) and concentrated in vacuo to give a crude residue. Purification of the crude residue by flash chromatography over silica gel (gradient elution; 20%-40% ethyl acetate/hexanes as eluent) afforded compound 8-5 as a white solid.

Step E: Preparation of (8-6a) and (8-6b)

Oxalyl chloride (20.6 mL of a 2.0 M solution in dichloromethane, 41.2 mmol) followed by N,N-dimethylformamide (0.5 mL) were slowly added to a stirred solution of [1-(tert-butoxycarbonyl)-4-(3,4-dimethylphenyl)piperidin-4-yl]acetic acid 8-5 (13.0 g, 37.4 mmol) in dichloromethane (250 mL) at approximately 0° C. After stirring at 0° C. for 30 minutes, then at ambient temperature for approximately 1 h; after the bubbling ceased, the volatiles were removed in vacuo and nitromethane (500 ml) was added. Aluminum chloride (12.5 g, 93.5 mmol) was added portionwise to the resulting suspension, under nitrogen, at approximately 0° C. After stirring at 0° C. for 30 minutes, the reaction mixture was poured into 200 g of ice containing 600 mL of 1 N aqueous sodium hydroxide. The solids were filtered and the filtrate was extracted with ethyl acetate (3×500 mL). The organic layer was washed with brine, dried (sodium sulfate), and concentrated in vacuo to a volume of approximately 500 mL. Triethylamine (10 mL) and di(tert-butyl) dicarbonate (9.80 g, 44.9 mmol) were added to the resulting solution. After stirring at ambient temperature overnight the reaction mixture was concentrated in vacuo to give a crude residue. Purification of the crude residue by flash chromatography over silica gel (20% ethyl acetate/hexanes as eluent) afforded compounds 8-6a and 8-6b as white solids.

Step F: Preparation of (8-7)

Potassium bis(trimethylsilyl)amide (23.3 mL, 11.7 mmol, 0.5 mL in toluene) was slowly added to a solution of compound 8-6b (3.20 g, 9.71 mmol) in anhydrous tetrahydrofuran (60 mL) at approximately 0° C. After stirring for 1 h, a solution of N-phenyl-trifluoromethanesulfonamide (4.16 g, 11.7 mmol) in anhydrous tetrahydrofuran (40 mL) was added, and the reaction mixture was slowly warmed to ambient temperature. Upon completion, water was added and the mixture was extracted with ethyl acetate (3×150 mL). The organic layer was washed with brine, dried (sodium sulfate) and concentrated in vacuo to give a crude residue. Purification of the crude residue by flash chromatography over silica gel (gradient elution; 0%-10% ethyl acetate/hexanes as eluent) afforded compound 8-7 as a white solid.

Step G: Preparation of (8-8)

A mixture of compound 8-7 (3.70 g, 8.02 mmol), triethylamine (2.24 mL, 16.0 mmol), triphenylphosphine (0.126 g, 0.481 mmol), and palladium acetate (54 mg, 0.241 mmol) in ethanol (15 mL) and N,N-dimethylformamide (30 mL) was purged for 10 minutes with carbon monoxide. After stirring under an atmosphere of carbon monoxide for 24 hours, the volatiles were removed in vacuo and the reaction mixture was diluted with water and extracted with ethyl acetate. The organic phase was washed with 1 N aqueous hydrochloric acid, water, brine, dried (magnesium sulfate) and concentrated in vacuo to give a crude residue. Purification of the crude residue by flash chromatography over silica gel (gradient elution; 0%-10% ethyl acetate/hexanes as eluent) afforded compound 8-8 as a white solid.

Step H: Preparation of (8-9)

A mixture of compound 8-8 (2.00 g, 5.19 mmol) and 10% Pd on carbon (552 mg, 0.519 mmol) in ethanol (100 mL) was hydrogenated at 50 psi for 20 h. The resulting mixture was filtered through a short column of celite®, eluting with ethanol. The filtrate was evaporated in vacuo to give compound 8-9 as a white solid.

Step I: Preparation of (8-10)

Methyllithium (20.0 mL of a 1.4 N solution in tetrahydrofuran, 28.0 mmol) was added to a solution of compound 8-9 (1.10 g, 2.84 mmol) in anhydrous tetrahydrofuran (100.0 mL) at approximately −78° C. After stirring at −78° C. for 1 h the reaction mixture was quenched with hydrogen chloride (4.0 M solution in dioxane) at −78° C. The reaction was concentrated in vacuo to give a crude residue. Diethyl ether was added, the solution was filtered and the filtrate was concentrated in vacuo to give compound 8-10 as a white solid.

Step J: Preparation of (8-11)

Concentrated sulfuric acid (1.10 mL, 20.5 mmol) in acetonitrile (10 mL) was added to a solution of compound 8-10 (0.640 g, 1.71 mmol) in acetonitrile (40 mL) at ambient temperature. After stirring at approximately 60° C. for 4 h, the reaction mixture was quenched with 1 N aqueous sodium hydroxide and extracted with ethyl acetate (3×150 mL). The combined organic layers were dried (magnesium sulfate) and concentrated in vacuo to give a crude residue. Purification of the crude residue by high-pressure liquid chromatography (gradient elution; 15%-95% acetonitrile/water as eluent) afforded compound 8-11 as a white solid.

Step K: Preparation of (8-12)

Compound 8-11 (0.110 g, 0.385 mmol), O-(7-azabenzotriazol-1-yl)-N,N,N',N',-tetramethyluronium hexafluorophosphat (HATU, 0.175 g, 0.461 mmol), 1-hydroxyl-7-azabenzotriazole (HOAT, 0.063 g, 0.461 mmol) and 4-methylmorpholine (0.194 g, 1.92 mmol) were added to a solution of compound 1-4 (0.120 g, 0.422 mmol) in dichloromethane (10.0 mL). After stirring at ambient temperature overnight the volatiles were removed in vacuo to give a crude residue. Purification of the crude residue by preparative thin-layer chromatography (10% triethylamine/ethyl acetate as eluent) afforded compound 8-12 as a white solid. The diastereomers were separated by high-pressure liquid chromatography with ChiralPak AD column (10% isopropanol in heptane as eluent), (m/z (ES) 580 (MH+)).

Following procedures similar to that described above for Example 57, followed by the separation of the resulting diastereomers using high-pressure liquid chromatography (ChiralPak, 10% isopropanol/heptane), the following compounds were prepared:

| Ex. # | $R^{4a}$ | $R^{4b}$ | *chiral center | Parent Ion m/z (M + H) |
|---|---|---|---|---|
| 58 | Me | Me | R | 580 |
| 59 | Me | Me | S | 580 |
| 60 | H  | H  | R | 552 |
| 61 | H  | H  | S | 552 |

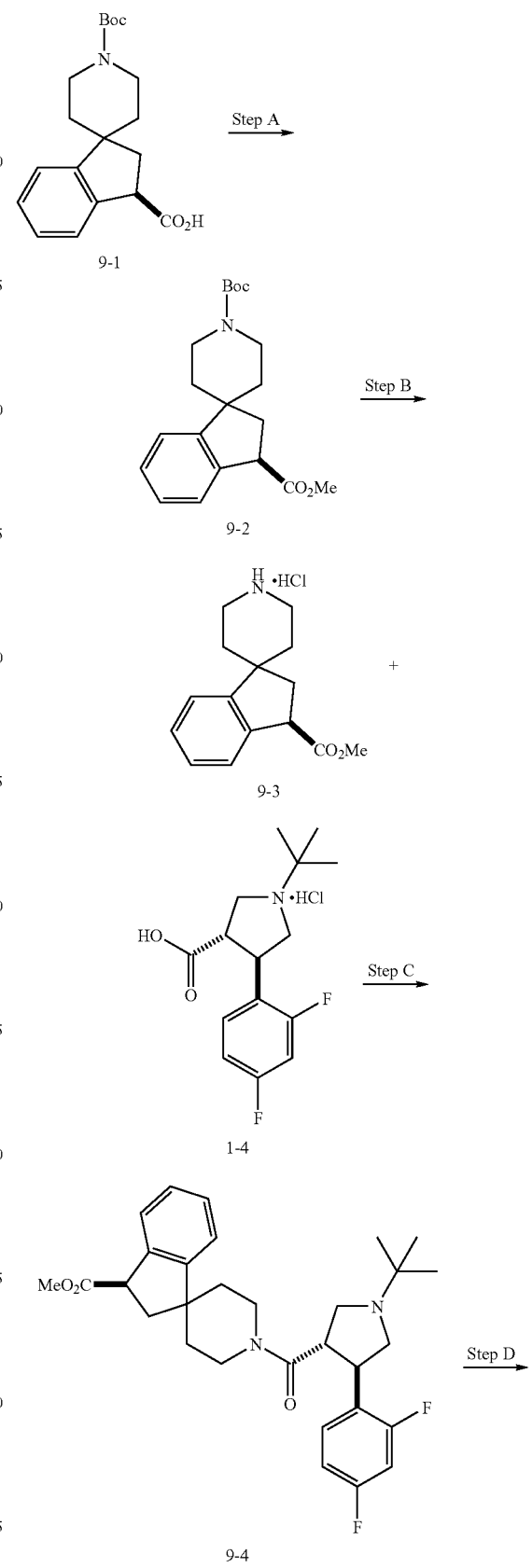

Scheme 9

-continued

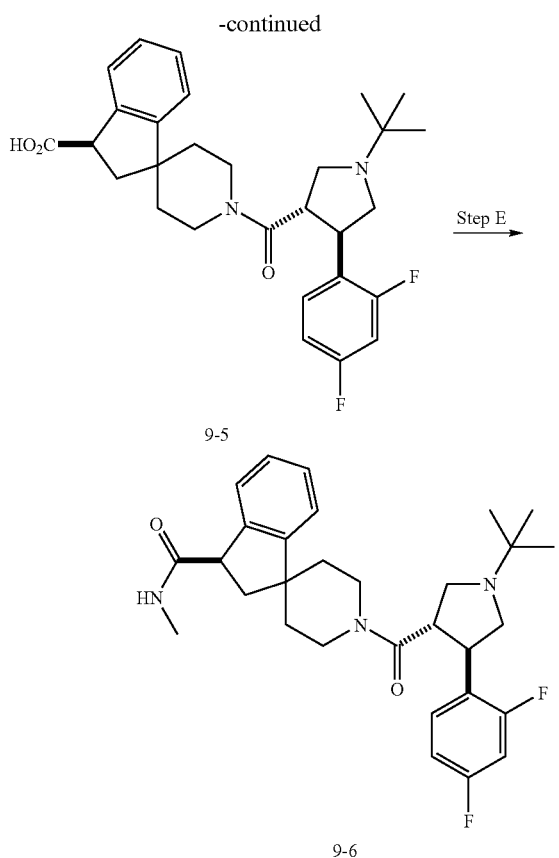

9-5

9-6

EXAMPLE 62

Preparation of (9-6)

Step A: Preparation of (9-2)

A freshly prepared ethereal solution of diazomethane (excess) was added to a stirred solution of compound 9-1 (0.200 g, 0.604 mmol) in diethyl ether (3 mL) at room temperature. After approximately 30 min, the volatiles were evaporated to give crude 9-2 as a colorless foam.

Step B: Preparation of (9-3)

A saturated solution of hydrogen chloride in ethyl acetate (~5 mL) was added to a stirred solution of compound 9-2 (0.604 mmol) in methylene chloride (5 mL) at approximately 0° C. After 1 h, the volatiles were evaporated in vacuo, and the crude residue was triturated twice with dry diethyl ether to give 9-3 as a colorless solid (m/z (ES) 246 (MH+)).

Step C: Preparation of (94)

N,N-Diisopropylethylamine (0.316 mL, 1.81 mmol) was added to a stirred solution of (3S,4R)-1-tert-butyl-4-(2,4-difluorophenyl)pyrrolidine-3-carboxylic acid hydrochloride 1-4 (0.193 g, 0.604 mmol), compound 9-3 (0.604 mmol) and O-(7-azabenzotriazol-1-yl)-1,1,3,3-tetramethyluronium hexafluorophosphate (0.344 g, 0.906 mmol) in N,N-dimethylformamide (6 mL) at ambient temperature. After 18 h, the reaction mixture was poured into saturated aqueous sodium bicarbonate and extracted three times with methylene chloride. The combined organic extracts were washed with water, brine, dried (sodium sulfate) and concentrated in vacuo. Purification of the crude residue by flash chromatography over silica gel (gradient elution; 0%-9% methanol (containing 10% v/v ammonium hydroxide)/methylene chloride as eluent) furnished 9-4 as a very pale yellow foam (m/z (ES) 511 (MH+)).

Step D: Preparation of (9-5)

Potassium trimethylsilanolate (25.1 mg, 0.196 mmol) was added to a stirred solution of compound 9-4 (50.0 mg, 0.0979 mmol) in tetrahydrofuran (1 mL) at room temperature. After approximately 15 h, the volatiles were evaporated in vacuo and the crude residue was treated with a saturated solution of hydrogen chloride in ethyl acetate (excess). After approximately 5 min, the reaction mixture was concentrated under reduced pressure and the crude residue triturated twice with dry diethyl ether to give 9-5 as an amorphous white solid (m/z (ES) 497 (MH+)).

Step E: Preparation of (9-6)

N-Methylmorpholine (75.3 µL, 685 µmol) was added to a stirred mixture of compound 9-5 (97.9 µmmol), methylamine hydrochloride (33.1 mg, 0.490 mmol), 1-ethyl-3-(3-dimethylaminopropyl)carbodiimide hydrochloride (22.5 mg, 0.118 mmol) and 1-hydroxybenzotriazole (36.7 mg, 0.272 mmol) in methylene chloride (10 mL) at 0° C. After 18 h, the reaction mixture was poured into saturated aqueous sodium bicarbonate and extracted three times with methylene chloride. The combined organic extracts were washed with water, brine, dried (sodium sulfate) and concentrated in vacuo. Purification of the crude residue by preparative reversed phase HPLC on YMC Pack Pro C18 phase (gradient elution; 0%-100% acetonitrile/water as eluent, 0.1% TFA modifier) furnished 96 as a colorless buff solid (m/z (ES) 510 (MH+)).

Following procedures similar to that described above for Example 62, the following compounds were prepared:

| Ex. # | $R^{4a}$ | $R^{4b}$ | $R^6$ | Parent Ion m/z (M + H) |
|---|---|---|---|---|
| 63 | H | H | MeO-C(O)- | 511 |

-continued
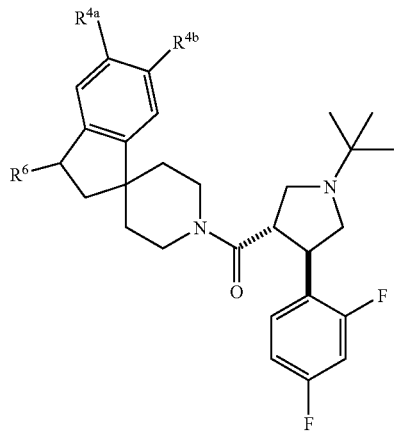
| Ex. # | R⁴ᵃ | R⁴ᵇ | R⁶ | Parent Ion m/z (M + H) |
|---|---|---|---|---|
| 64 | H | H | 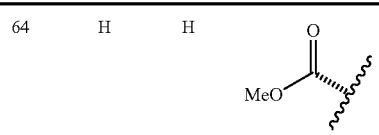 | 511 |
| 65 | Me | Me | 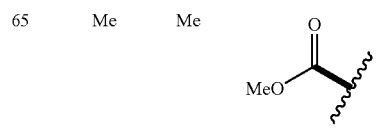 | 539 |
| 66 | Me | Me | 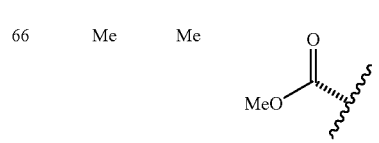 | 539 |
| 67 | H | H | 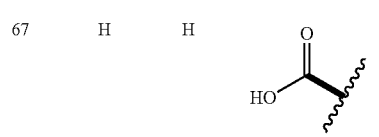 | 497 |
| 68 | H | H | 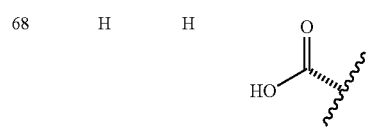 | 497 |
| 69 | H | H | 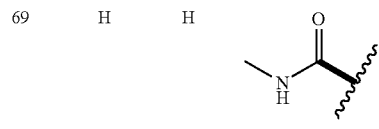 | 510 |
| 70 | H | H | 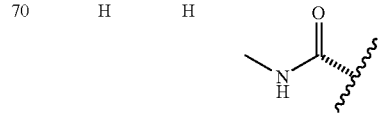 | 510 |
| 71 | H | H | 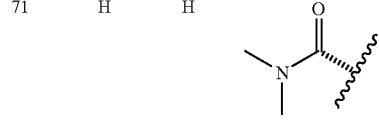 | 524 |
-continued
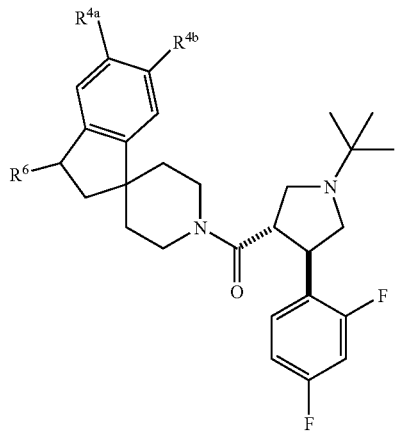
| Ex. # | R⁴ᵃ | R⁴ᵇ | R⁶ | Parent Ion m/z (M + H) |
|---|---|---|---|---|
| 72 | H | H | 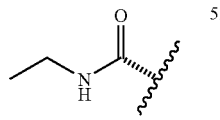 | 524 |
| 73 | H | H | 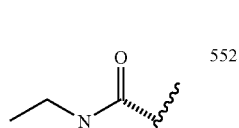 | 552 |
| 74 | H | H | 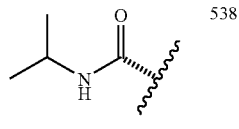 | 538 |
| 75 | H | H | 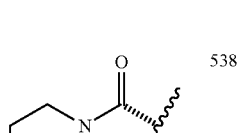 | 538 |
| 76 | H | H | 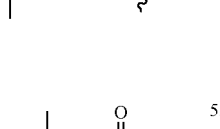 | 552 |
| 77 | H | H | 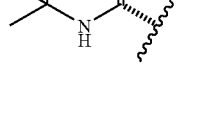 | 536 |

Scheme 10

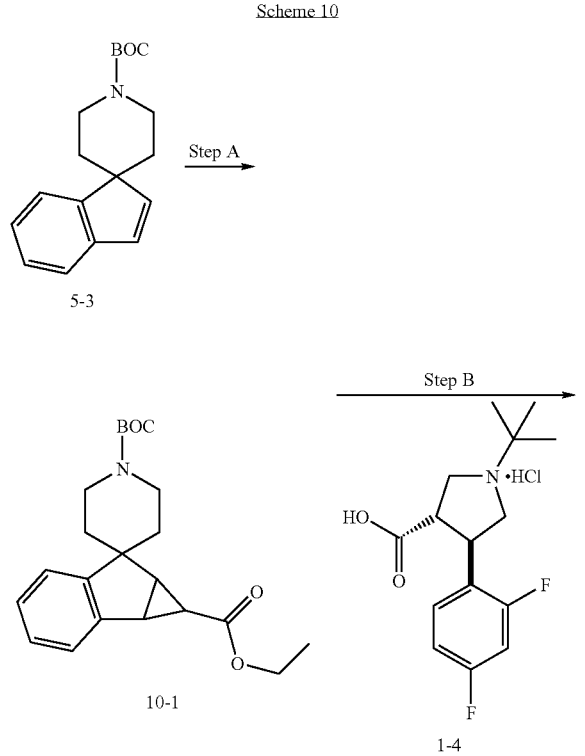

tography over silica gel (gradient elution; 0%-20% ethyl acetate/hexanes as eluent) afforded 10-1 as a white foam.

Step B: Preparation of (10-2)

Compound 10-2 was prepared from 10-1 following a similar procedure to that described for 1-14 (m/z (ES) 537 (MH$^+$)).

Scheme 11

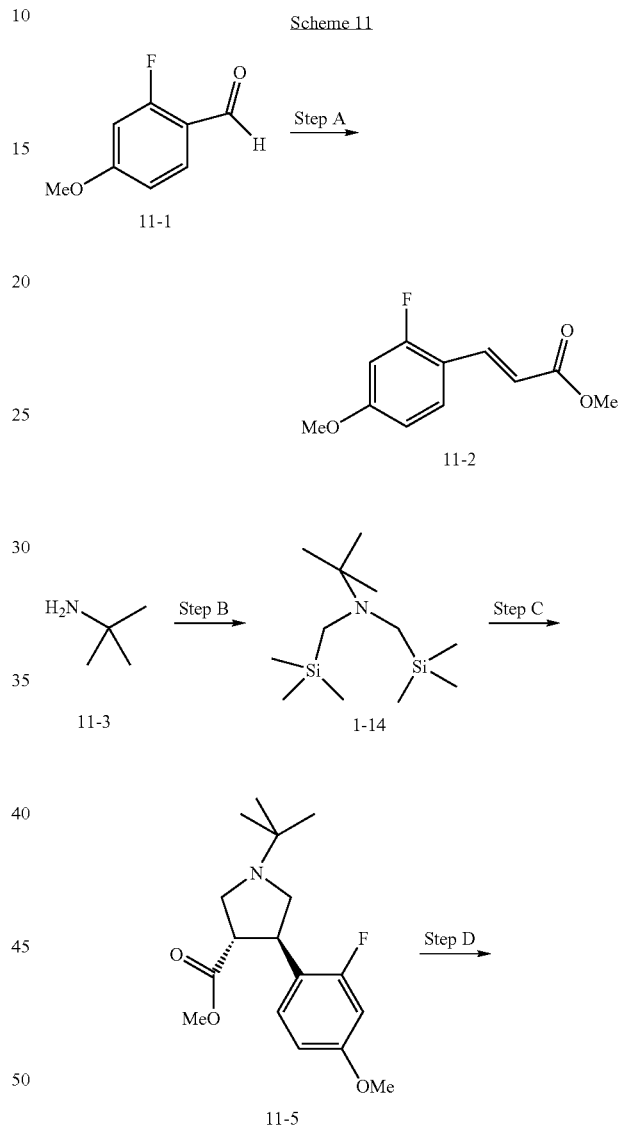

EXAMPLE 78

Preparation of (10-2)

Step A: Preparation of (10-1)

Rhodium acetate (75.0 mg, 0.175 mmol) and ethyl diazoacetate (0.203 mL, 1.93 mmol) were added to a stirred solution of compound 5-3 (500 mg, 1.75 mmol) in dichloroethane at approximately 0° C. After stirring at ambient temperature for 18 h, then at approximately 80° C. for 20 h, the volatiles were removed in vacuo, and the residue was partitioned between diethyl ether and aqueous 1 N hydrochloric acid. The organic phase was separated and washed with saturated aqueous sodium bicarbonate, brine, dried (sodium sulfate) and concentrated in vacuo to give a crude residue. Purification of the crude residue by flash chroma-

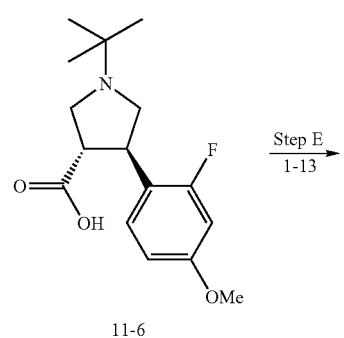

-continued

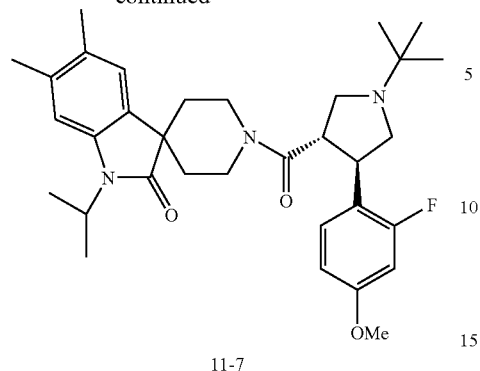

11-7

EXAMPLE 79

Preparation of (11-7)

Step A: Preparation of (11-2)

A solution of 2-fluoro-4-methoxybenzaldehyde 11-1 (2.43 g, 15.8 mmol, Aldrich) in THF (100 ml) was cooled it to 0° C., followed by the addition of methyl(triphenyl)phosphoranylidene (5.88 g). The mixture was stirred at room temperature overnight, then concentrated in vacuo to give a crude residue, which was purified by flash chromatography to give compound 11-2.

Step B: Preparation of (11-3)

To a solution of compound 11-2 (10 ml, 94 mmol) and iodomethyltrimethyl silane (28 ml, 189 mmol) in acetonitrile (30 ml) was added potassium carbonate (26 g, 189 mmol). The reaction mixture was stirred in a sealed reaction vessel at 80° C. for three days, followed by the addition of saturated sodium bicarbonate (100 ml) and extraction with ether. The combined ether layers were dried (sodium sulfate), and concentrated in vacuo to give the desired compound 11-3.

Step C: Preparation of (11-4)

To a solution of compounds 11-3 (525 mg) and 11-2 (1.0 g) in dry acetonitrile (10 ml) was added AgF (1.27 g). The mixture was stirred at room temperature overnight, filtered, and the resulting filtrate was concentrated in vacuo to give a crude residue. Purification of the crude residue by flash chromatography (20% EtOAc to 70% EtOAc in hexane) afforded compound 11-4 as a clear oil.

Step D: Preparation of (11-5)

To a solution of compound 11-4 (135 mg) in concentrated HCl (2.5 ml) was added water (7.5 ml). The reaction mixture was stirred at about 84° C. overnight and concentrated in vacuo to give compound 11-5.

Step E: Preparation of (11-6)

To a solution of compound 11-6 (40 mg) and compound 1-13 (37.1 mg) in methylene chloride (2 ml) was added diisopropylamine (83.6 µL), HOAt (16.3 mg), and HATU (54.7 mg). The mixture was stirred at room temperature overnight, then concentrated in vacuo to give a crude residue, which was purified by preparative TLC (10% MeOH in methylene chloride) to afford compound 11-7 as a mixture of diastereomers. The mixture of diastereomers of compound 11-7 was separated into it's individual diastereomers bu chiral HPLC (chiral OD column, 5% isopropyl alcohol in heptane) (m/z (ES) 550 (MH+)).

Scheme 12

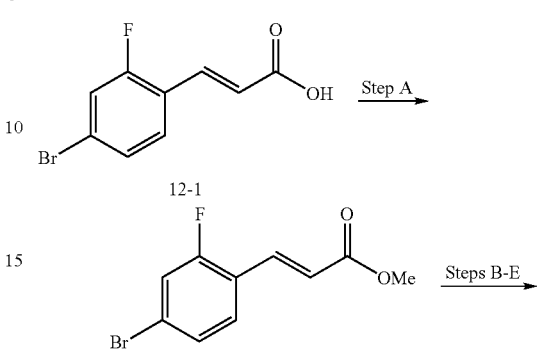

EXAMPLE 80

Preparation of (12-3)

Step A: Preparation of (12-2)

Thionyl chloride (5.9 ml) was added dropwise to 100 ml of methanol, followed by the addition of 4-bromo-2-fluorocinnamic acid 12-1 (4.0 g, Aldrich). The mixture was refluxed for 2 hours, then concentrated in vacuo to give compound 12-2.

Steps B-E: Preparation of (12-3)

Compound 12-3 was prepared from 12-2 following a similar procedure to that described for 11-7 (m/z (ES) 599 (MH+)).

Scheme 13

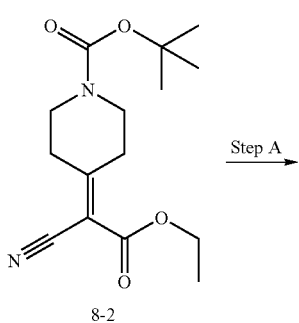

8-2

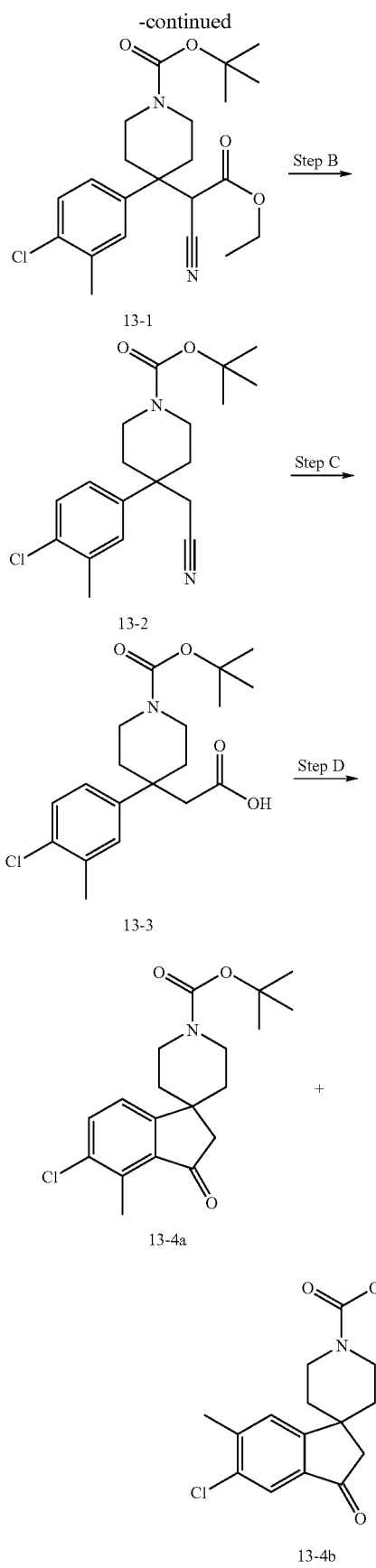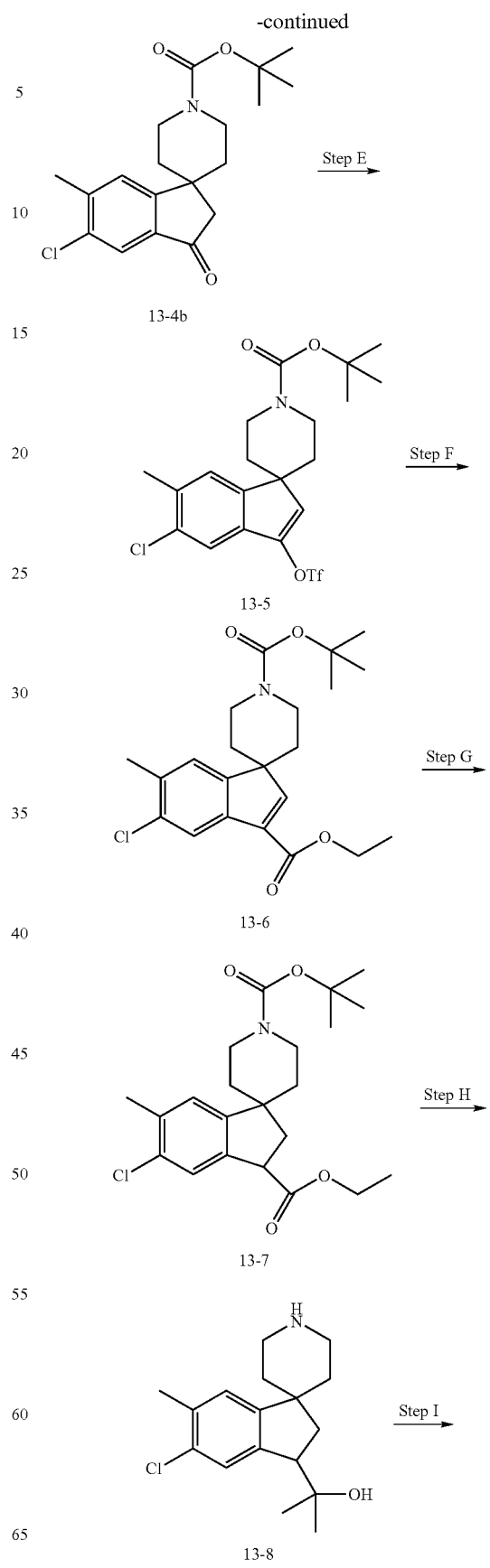

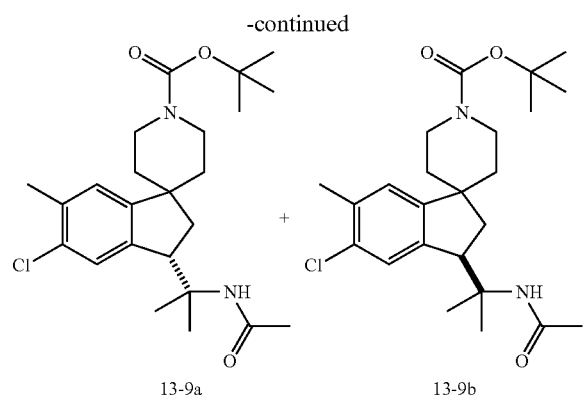

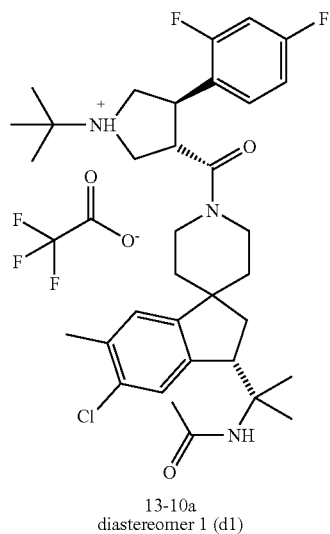

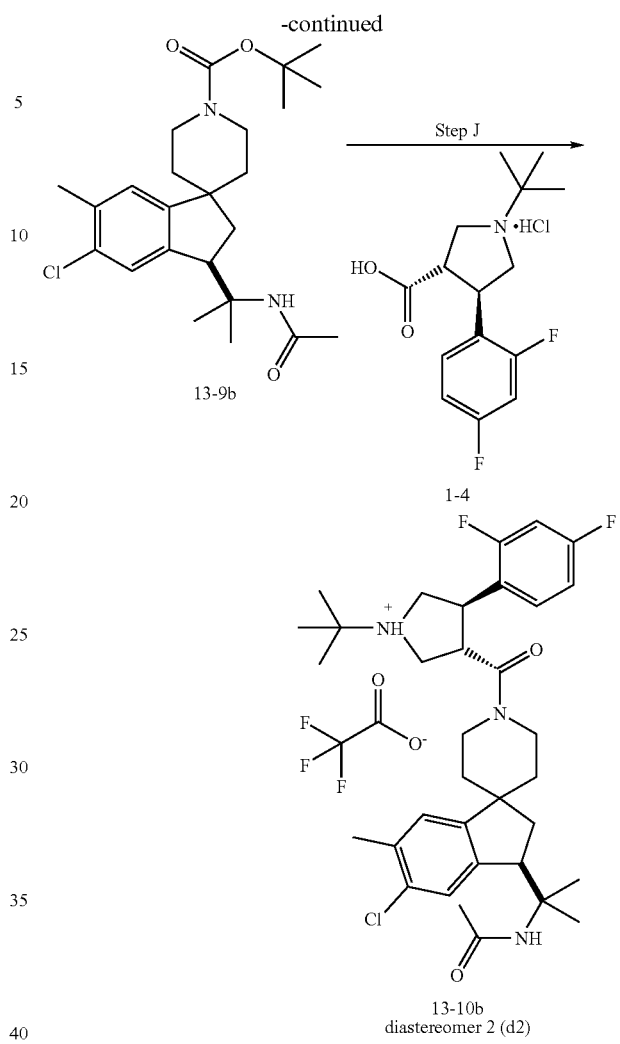

EXAMPLE 81

Preparation of (13-10a) and (13-10b)

Step A: Preparation of (13-1)

Copper (I) cyanide (24.34 g, 272 mmol) was added to a solution of 4-chlorophenylmagnesium bromide (1087 mL of a 1M solution in tetrahhydrofuran, 543 mmol) in tetrahydrofuran (100 mL) at approximately −50° C. After stirring at approximately −50° C. for 10 min, the reaction mixture was allowed to warm to ambient temperature and stirred for a further 45 min. Reaction mixture was recooled to approximately −50° C. and a solution of 8-2 in tetrahydrofuran (150 mL) was added via an addition funnel over about 20 min. The resulting solution was allowed to warm slowly to approximately −10° C. over 3 hr. The reaction was quenched with saturated aqueous ammonium chloride (200 mL) and water (200 mL). The emulsion was poured into ethyl acetate (200 mL). The aqueous phase was extracted with ethyl actetate. The combined organics were washed with water and brine, dried (sodium sulfate) and concentrated in vacuo to give compound 13-1 which was used without further purification (m/z (ES) 421 (MH+)).

Step B: Preparation of (13-2)

Lithium chloride (8.06 g, 190.2 mmol) followed by water (12.24 mL, 679.4 mmol) were added to a solution of 13-1 (57.2 g, 135.9 mmol) in dimethylsulfoxide (300 mL). After stirring at approximately 160° C. for 2 h, the reaction mixture was cooled to ambient temperature, quenched with cold water (400 mL) and extracted with ethyl ether (4×275 mL). The combined organic extracts were dried (magnesium sulfate) and concentrated in vacuo to give compound 13-2 which was used without further purification (m/z (ES) 349 (MH+)).

Step C: Preparation of (13-3)

Potassium hydroxide (152.5 g, 717 mmol) was added to a solution of compound 13-2 (47.4 g, 135 mmol) in ethanol (600 mL) and water (150 mL). After stirring the reaction mixture at approximately 90° C. for 3 days, voaltiles were removed in vacuo, ice/water was added to the residue and it was cooled (ice bath), neutralized with a mixture of concentrated hydrochloric acid (about 210 mL)/ice and extracted with ethyl acetate. The combined organic extracts were washed with brine, dried (sodium sulfate) and concentrated in vacuo to give a crude residue. Purification of the crude residue by flash chromatography over silica gel (gradient elution; 0%-40% acetone/methylene chloride as eluent) afforded compound 13-3 as a white solid (m/z (ES) 368 (MH+)).

Step D: Preparation of (13-4a) and (13-4b)

Oxalyl chloride (6.75 mL, 77.4 mmol) followed by N,N-dimethylformamide (0.06 mL) were added to a stirred solution of compound 13-3 (14.4 g, 39.14 mmol) in dichloromethane (115 mL) at approximately 0° C. under a drying tube. After stirring at 0° C. for 30 min then at ambient temperature for 1.5 h, the drying tube was removed, and hydrogen chloride (40 mL of a 4.0M solution in 1,4-dioxanes) was added. After stirring at ambient temperature for 90 minutes, the volatiles were removed in vacuo and the mixture was placed on an oil pump for 30 minutes. The resulting solid was treated with dichloromethane (115 mL). Aluminum chloride (13.1 g, 98.2 mmol) was added to the resulting suspension at approximately 0° C. After stirring at 0° C. for 30 minutes, the reaction mixture was warmed to room temperature and stirred for 75 minutes. Then the reaction mixture was poured into aqueous sodium hydroxide solution (5 M, 50 mL) containing ice. 1,4-Dioxanes (150 mL) followed by di-tert-butyl dicarbonate (12.8 g, 58.6 mmol) were added to the resulting mixture. After stirring at ambient temperature overnight the reaction mixture was concentrated in vacuo to give a crude residue. The residue was diluted with aqueous sodium hydroxide solution (5 M, 50 mL) and extracted with dichloromethane. The organic phase was dried (sodium sulfate) and concentrated to give a residue. Purification of the crude residue by flash chromatography over silica gel (20% ethyl acetate/hexanes as eluent) afforded compounds 13-4a and 13-4b as white solids.

Step E: Preparation of (13-5)

Potassium bis(trimethylsilyl)amide (12.7 mL, 6.35 mmol, 0.5 M in toluene) was slowly added to a solution of compound 13-4b (1.85 g, 5.29 mmol) in anhydrous tetrahydrofuran (60 mL) at approximately −78° C. After stirring at 0° C. for 1 h, the reaction mixture was cooled to −78° C. and a solution of 2-[N,N-bis(trifluoromethylsulfonyl)amino]-5-chloropyridine (2.49 g, 6.35 mmol) in anhydrous tetrahydrofuran (10 mL) was added. The reaction mixture was slowly warmed to ambient temperature overnight. The reaction mixture was cooled to −78° C., quenched and warmed to ambient temperature. The mixture was extracted twice with ethyl acetate and hexanes. The organic phase was washed with brine, dried (sodium sulfate) and concentrated in vacuo to give a crude residue. Purification of the crude residue by flash chromatography over silica gel (gradient elution; 5%-50% ethyl acetate/hexanes as eluent) afforded compound 13-5 as a white solid.

Step F: Preparation of (13-6)

A mixture of compound 13-5 (5.29 mmol from Step F), triethylamine (1.47 mL, 10.58 mmol), triphenylphosphine (0.554 g, 2.1 mmol), and palladium acetate (238 mg, 1.06 mmol) in ethanol (10 mL) and N,N-dimethylformamide (20 mL) was purged for 10 minutes with carbon monoxide. After stirring under an atmosphere of carbon monoxide for 4.5 days at ambient temperature, the volatiles were removed in vacuo and the reaction mixture was diluted with water and extracted with ethyl acetate. The organic phase was washed with water and brine, dried (sodium sulfate) and concentrated in vacuo to give a crude residue. Purification of the crude residue by flash chromatography over silica gel (gradient elution; 5%-50% ethyl acetate/hexanes as eluent) afforded compound 13-6 as a white solid.

Step G: Preparation of (13-7)

A mixture of compound 13-6 (0.96 g, 2.4 mmol) and 10% Pd on carbon (89 mg, 0.084 mmol) in ethyl acetate (30 mL) was hydrogenated at room temperature at 1 atmosphere for 1 h. The resulting mixture was filtered, and the filtrate was concentrated in vacuo to give compound 13-7 as a white solid.

Step H: Preparation of (13-8)

Methylmagnesium iodide (4.79 mL of a 3 M solution in diethyl ether, 14.4 mmol) was added to a solution of compound 13-7 (0.73 g, 1.80 mmol) in anhydrous diethyl ether (5 mL) at 0° C. The reaction mixture was heated to reflux for 1 h. The reaction mixture was cooled to 0° C. and quenched by dropwise addition of ammonium chloride saturated aqueous solution. The mixture was warmed to ambient temperature and extracted 4 times with dichloromethane. The combined organic layers were dried (sodium sulfate) and concentrated in vacuo to afford compound 13-8.

Step I: Preparation of (13-9a) and (13-9b)

Concentrated sulfuric acid (3.14 mL, 57.8 mmol) in acetonitrile (100 mL) was added to a solution of compound 13-8 (1.13 g, 3.86 mmol) in acetonitrile (300 mL) at ambient temperature. After stirring at ambient temperature for 48 h, the reaction mixture was quenched with water and ice, and then concentrated in vacuo to give a residue. A mixture of this residue, ice, 1,4-dioxane (20 mL), aqueous sodium hydroxide solution (5 M, 20 mL) and di-tert-butyl dicarbonate (1.68 g, 7.72 mmol) was stirred at ambient temperature overnight. Volatiles were removed and the residue was extracted with ethyl acetate. The combined organic layers were washed with brine, dried (sodium sulfate) and concentrated in vacuo to give a crude residue. Purification of the crude residue by flash chromatography over silica gel (gradient elution; 10%-100% ethyl acetate/hexanes as eluent) afforded a racemic mixture of 13-9a and 13-9b. The racemic mixture was resolved on high performance chromatography with ChiralPak OJ column (ChiralCel OJ 4.6×250 mm 10 u column, flow rate at 0.5 ml/min of 7% ethanol in heptane, and UV detection at 220 nM) to give two separate enantiomers 13-9a and 13-9b.

Step J: Preparation of (13-10a and 13-10b)

A solution of compound 13-9a (55 mg, 0.127 mmol) in dichloromethane (0.7 mL) was treated with hydrogen chloride (4 M in 1,4-dioxane, 2 mL) at ambient temperature. The resulting mixture was stirred at ambient temperature for 4 h. The mixture was concentrated in vacuo to give a residue. A mixture of this residue, 1-4 (47 mg, 0.165 mmol),) O-(7-azabenzotriazol-1-yl)-N,N,N',N'-tetramethyluronium hexafluorophosphate (HATU, 63 mg, 0.165 mmol), 1-hydroxyl-7-azabenzotriazole (HOAT, 22 mg, 0.165 mmol) and 4-methylmorpholine (56 μL, 0.508 mmol) in dichloromethane (5 mL) was stirred at ambient temperature overnight. The volatiles were removed to afford a residue, which was purified with high performance chromatography on C18 reversed phase column with a gradient of water (0.1% TFA) and acetonitrile (0.1% TFA) to afford compound 13-10a as a white solid. (m/z (ES) 600.4 (MH$^+$)). Compound 13-10b was prepared using a similar procedure to that used to prepare compound 13-10a. (m/z (ES) 600.4 (MH$^+$)).

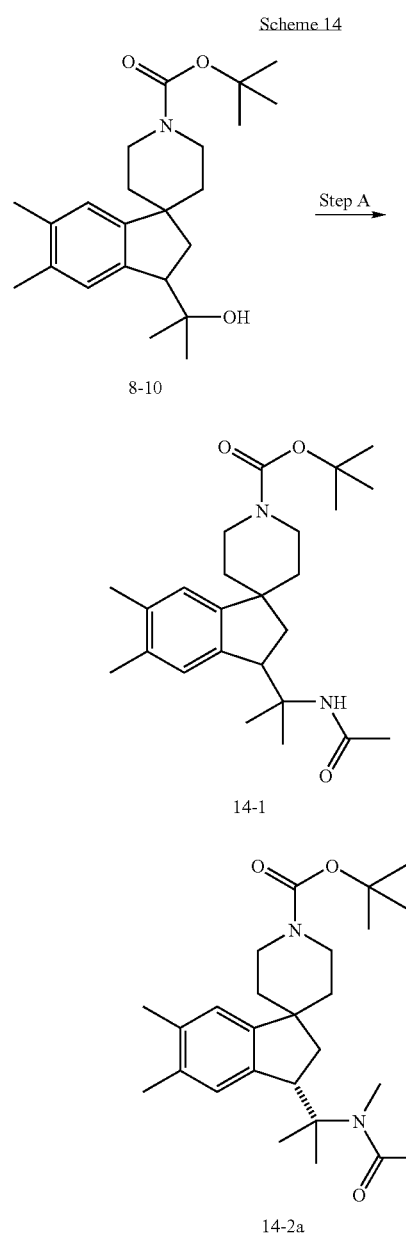

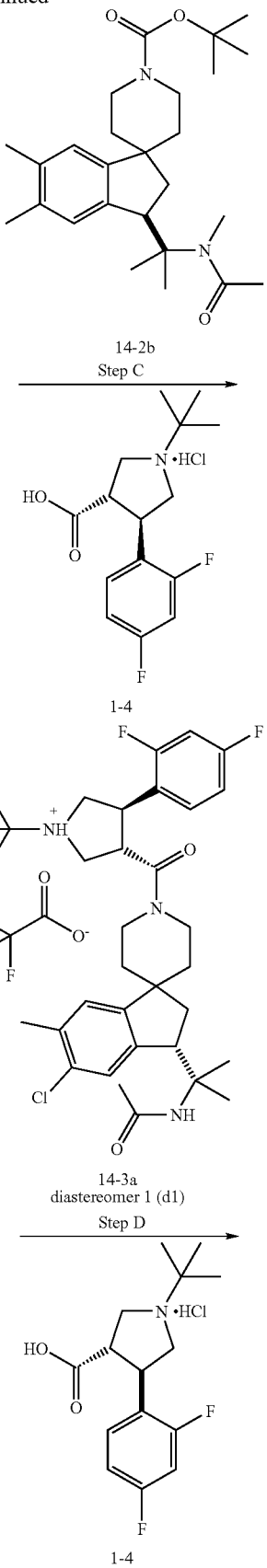

-continued

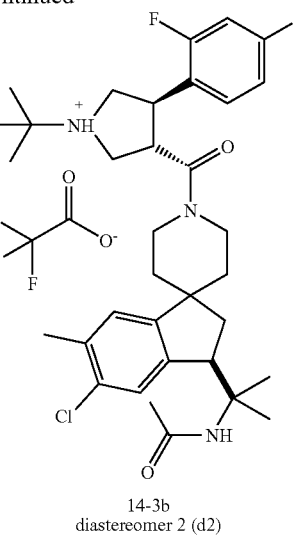

14-3b
diastereomer 2 (d2)

EXAMPLE 82

Preparation of (14-3a) and (14-3b)

Step A: Preparation of (14-1)

Compound 14-1 was prepared as a racemic mixture from 8-10 following a similar procedure to that described for compound 8-11.

Step B: Preparation of (14-2a) and (14-2b)

Compound 14-1 (30 mg, 0.072 mmol) was azeotroped twice with 5 mL of toluene to give a residue. A solution of this residue in anhydrous tetrahydrofuran (1 mL) was cooled to −78° C. Sodium bis(trimethylsilyl)amide (0.35 mL of a 1.0 M solution in tetrahydrofuran) was added, and the resulting solution was stirred at −78° C. for 1 h. Iodomethane (22.5 uL, 0.361 mmol) was added at −78° C., and the solution was stirred overnight while warming to room temperature. The reaction mixture was cooled to −78° C. and quenched by the dropwise addition of saturated aqueous sodium bicarbonate solution. The mixture was warmed to room temperature and extracted 3 times with ethyl acetate and hexanes (approximately 1:1). The combined organic layers were washed with brine, dried (sodium sulfate) and concentrated in vacua to give a crude residue. Purification of the crude residue by flash chromatography over silica gel (gradient elution; 20%-100% ethyl acetate/hexanes as eluent) afforded a racemic mixture of 14-2a and 14-2b. The racemic mixture was resolved on high performance chromatography with ChiralPak AD column (Chiral Pak AD-H 4.6×250 mm 5 u column, flow rate at 0.5 ml/min of 5% ethanol in heptane, and UV detection at 220 nM) to give two separate enantiomers 14-2a and 14-2b.

Steps C-D: Preparation of (14-3a) and (14-3b)

Compound 14-3a was prepared from compound 14-2a following a similar procedure to that described for compound 8-12. (m/z (ES) 594.7 (MH$^+$)).

Compound 14-3b was prepared from compound 14-2b following a similar procedure to that described for compound 8-12. (m/z (ES) 594.7 (MH$^+$)).

Scheme 15

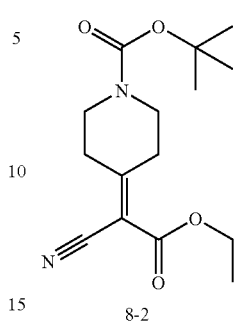

8-2

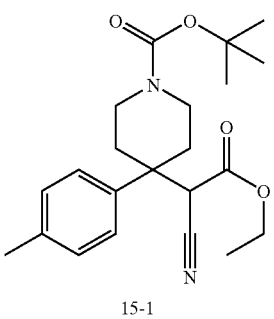

15-1

Step B

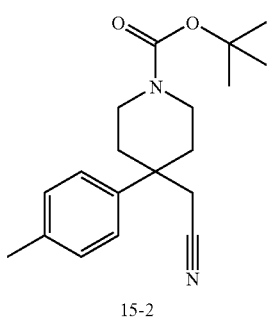

15-2

Step C

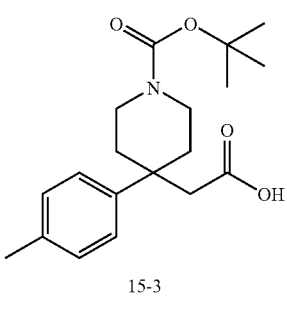

15-3

Step D

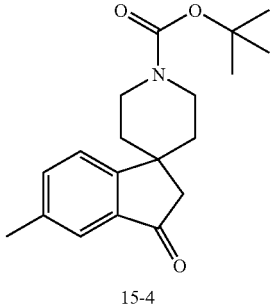

15-4

Step E

-continued
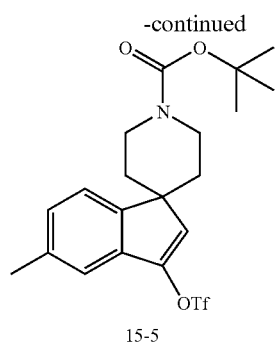
15-5
Step F →
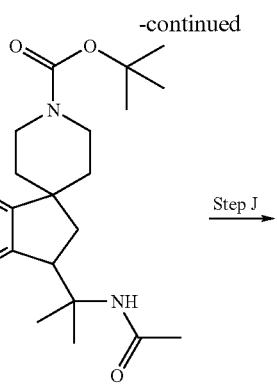
15-9
Step J →
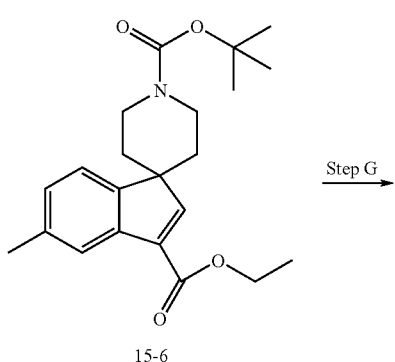
15-6
Step G →
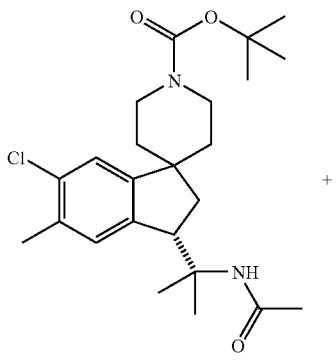
15-10a
+
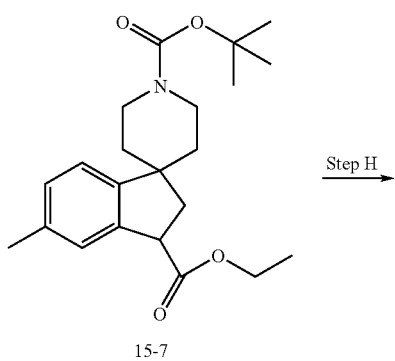
15-7
Step H →
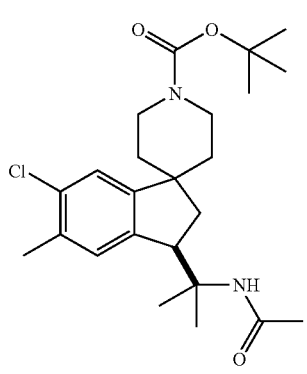
15-10b
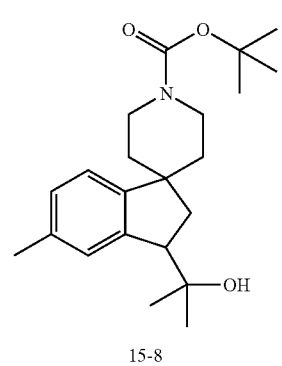
15-8
Step I →
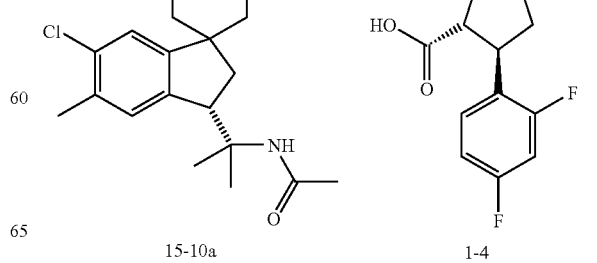
15-10a     1-4
Step K →

EXAMPLE 83

Preparation of (15-11a) and (15-11b)

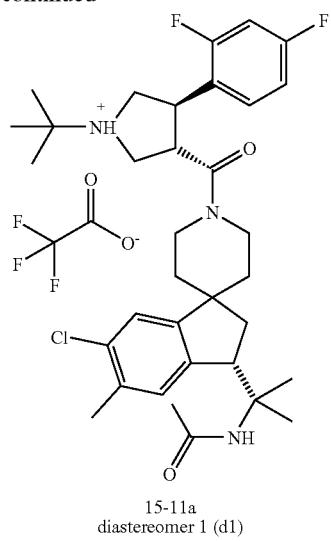

15-11a
diastereomer 1 (d1)

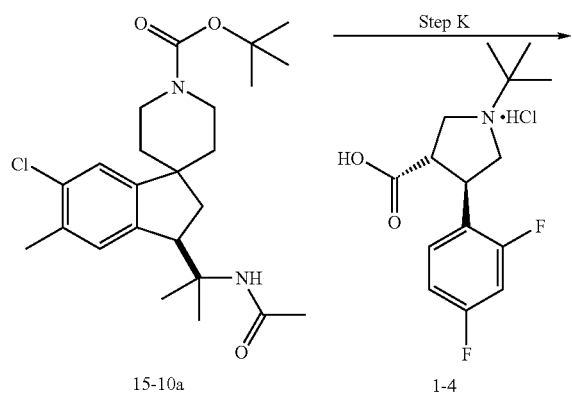

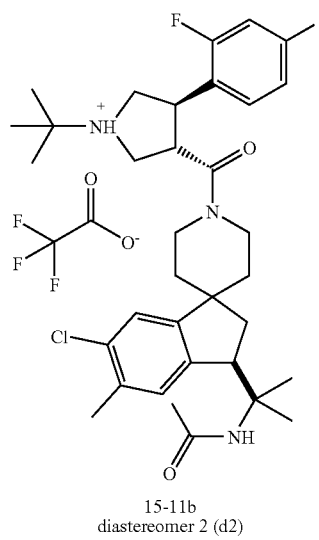

15-11b
diastereomer 2 (d2)

Step A: Preparation of (15-1)

p-Tolylmagnesium bromide (250 mL of a 1.0 M solution in diethyl ether) was added to a suspension of copper (I) cyanide (11.0 g, 122.4 mmol) in anhydrous tetrahydrofuran (150 mL) under nitrogen at approximately −50° C. After stirring at approximately −50° C. for 10 min, the reaction mixture was allowed to warm to ambient temperature over 1 h then recooled to approximately −50° C. A solution of tert-butyl 4-(1-cyano-2-ethoxy-2-oxoethylidene)piperidine-1-carboxylate 8-2 (30.0 g, 102 mmol) in tetrahydrofuran (50 mL) was added. The reaction mixture was allowed to warm to ambient temperature over 4 h. The reaction mixture was cooled to 0° C. and quenched with saturated aqueous ammonium chloride. The reaction mixture was extracted with ethyl acetate and hexanes. The organic layers were washed with brine, dried (sodium sulfate) and concentrated in vacuo to give compound 15-1 as an oil.

Step B: Preparation of (15-2)

Lithium chloride (8.65 g, 204 mmol) and water (14.7 mL) were added to a solution of 15-1 (102 mmol, crude from Step B) in dimethyl sulfoxide (200 mL). After stirring at approximately 160° C. for 4 h the reaction mixture was cooled to ambient temperature, poured into ice and extracted with ethyl acetate and hexanes (4×400 mL). The organic phase were washed with water, brine, dried (sodium sulfate) and concentrated in vacuo to give a crude residue. Purification of the crude residue by flash chromatography over silica gel with 25% ethyl acetate/hexanes as eluent afforded compound 15-2 as a white solid.

Step C: Preparation of (15-3)

A mixture of concentrated hydrochloric acid (200 mL) and 15-2 (28.0 g, 89 mmol) was heated to reflux overnight. The reaction mixture was concentrated in vacuo to give a crude residue. The residue was treated with aqueous sodium hydroxide (5 M, 45 mL) and the mixture was concentrated in vacuo. The residue was again treated with aqueous sodium hydroxide (5 M, 45 mL) and the mixture was concentrated in vacuo. The residue was treated with water (100 mL), 1,4-dioxane (100 mL) followed by di-tert-butyl dicarbonate (26.7 g, 122.4 mml). The mixture was stirred at ambient temperature overnight. The volatiles were removed in vacuo and the residue was extracted with ethyl acetate and hexanes. The organic layers were washed with brine and dried (sodium sulfate) and concentrated in vacuo to give a residue. Purification of the residue by flash chromatography over silica gel with 25% ethyl acetate/hexanes as eluent) afforded compound 15-3 as a white solid.

Step D: Preparation of (154)

Oxalyl chloride (4.0 mL, 46.1 mmol) was added to a solution of 15-3 (12.78 g, 38.4 mmol) and N,N-dimethylamide (20 mg) at 0° C. The mixture was warmed to ambient temperature and stirred for 2.5 h. Hydrogen chloride (4.0 M in 1,4-dioxane) was added and the mixture was concentrated in vacuo. The residue was left under high vacuum pump for 0.5 h. The residue was treated with dichloromethane (100 mL) and cooled to 0° C. To this suspension was added anhydrous aluminum chloride (12.8 g, 96 mmol). After 30 min at 0° C., the mixture was warm to ambient temperature and stirred for 1 h. The reaction mixture was poured into ice and aqueous sodium hydroxide (5 M, 50 mL). The pH of the mixture was adjusted to 9-10. The mixture was treated with 1,4-dioxane (200 mL) followed by di-tert-butyl dicarbonate (12.6 g, 57.6 mmol). The mixture was stirred at ambient temperature overnight. Volatiles were removed in vacuo and the residue was extracted with ethyl acetate and dichloromethane. The organic layers were washed with brine and dried (sodium sulfate) to afford a residue. Purification of the crude residue by flash chromatography over silica gel (gradient elution; 5%-25% ethyl acetate/hexanes as eluent) afforded compound 15-4 as a white solid.

Step E: Preparation of (15-5)

Sodium bis(trimethylsilyl)amide (14.3 mL, 14.3 mmol, 1.0 M in tetrahydrofuran) was slowly added to a solution of compound 15-4 (3.0 g, 9.52 mmol) in anhydrous tetrahydrofuran (60 mL) at approximately −78° C. After stirring at 0° C. for 1 h, the reaction mixture was cooled to −78° C. and a solution of 2-[N,N-bis(trifluoromethylsulfonyl)amino]-5-chloropyridine (4.12 g, 10.5 mmol) in anhydrous tetrahydrofuran (20 mL) was added. The reaction mixture was slowly warmed to ambient temperature overnight. The reaction mixture was cooled to −78° C., quenched by dropwise addition of saturated aqueous sodium hydrogen carbonate and warmed to ambient temperature. The mixture was extracted with ethyl acetate and hexanes twice. The organic phase was washed with brine, dried (sodium sulfate) and concentrated in vacuo to give a crude residue. Purification of the crude residue by flash chromatography over silica gel (gradient elution; 5%-12% ethyl acetate/hexanes as eluent) afforded compound 15-5 as a white solid.

Step F: Preparation of (15-6)

A mixture of compound 15-5 (4.27 g, 9.55 mmol), triethylamine (2.66 mL, 19.1 mmol), triphenylphosphine (1.00 g, 3.82 mmol), and palladium acetate (429 mg, 1.91 mmol) in ethanol (20 mL) and N,N-dimethylformamide (40 mL) was purged for 10 minutes with carbon monoxide. After stirring under an atmosphere of carbon monoxide for 40 h, the volatiles were removed in vacuo and the reaction mixture was diluted with water and extracted with ethyl acetate and hexanes. The organic phase was washed with water and brine, dried (sodium sulfate) and concentrated in vacuo to give a crude residue. Purification of the crude residue by flash chromatography over silica gel (15% ethyl acetate/hexanes as eluent) afforded compound 15-6 as a white solid.

Step G: Preparation of (15-7)

A mixture of compound 15-6 (2.5 g, 5.19 mmol) and 10% Pd on carbon (145 mg. 0.14 mmol) in ethyl acetate (50 mL) was hydrogenated with a hydrogen balloon at ambient temperature for 1 h. The resulting mixture was filtered and the filtrate was evaporated in vacuo to give compound 15-7 as a white solid.

Step H: Preparation of (15-8)

Methyllithium (35 mL of a 1.6 N solution in tetrahydrofuran, 56 mmol) was added to a solution of compound 15-7 (2.1 g, 5.6 mmol) in anhydrous tetrahydrofuran (65 mL) at approximately −78° C. After stirring at −78° C. for 2 h, additional methyllithium (10 mL of a 1.6 N solution in tetrahydrofuran, 16 mmol) was added to the solution at approximately −78° C. After stirring at −78° C. for 1 h the reaction mixture was quenched with saturated aqueous sodium hydrogen carbonate and extracted with ethyl acetate and hexanes. The organic phase was washed with brine, dried (sodium sulfate) and concentrated in vacuo to give a 15-8.

Step I: Preparation of (15-9)

Concentrated sulfuric acid (4.59 mL, 84 mmol) in acetonitrile (100 mL) was added to a solution of compound 15-8 (5.63 mmol) in acetonitrile (100 mL) at ambient temperature. After stirring at ambient temperature for 40 h, the reaction mixture was quenched with small amount of ice and water. Volatiles were removed in vacuo to give a crude residue. This residue was treated with ice, aqueous sodium hydroxide (5.0M, 40 mL), followed by 1,4-dioxane (100 mL) and di-ter-butyl dicarbonate (2.46 g, 11.26 mmol). The mixture was stirred at ambient temperature overnight. Volatiles were removed and the residue was extracted 3 times with ethyl acetate and hexanes. The combined organic layers were washed with brine, dried (sodium sulfate) and concentrated in vacuo to give a residue. Purification of the residue by flash chromatography over silica gel (75% ethyl acetate/hexanes as eluent) afforded a racemic mixture of compound 15-9.

Step J: Preparation of (15-10a) and (15-10b)

Solid N-chlorosuccinimide (88 mg, 0.66 mmol) was added to a solution of compound 15-9 (134 mg, 0.33 mmol) in DMF (1 mL) at ambient temperature. The mixture was heated in an oil bath (50° C.) for 1.5 h. The reaction mixture was cooled to 0° C. and quenched with saturated aqueous sodium hydrogen carbonate followed by saturated aqueous sodium thiosulfate. The mixture was extracted with ethyl acetate and hexanes. The organic phase was washed with brine, dried (sodium sulfate) and concentrated in vacuo to give a residue. Purification of the residue by flash chromatography over silica gel (gradient elution; 75%-100% ethyl acetate/hexanes as eluent) afforded a racemic mixture of 15-10a and 15-10b. The racemic mixture was resolved on high performance chromatography with ChiralPak AD column (Chiral Pak AD-H 4.6×250 mm 5 u column, flow rate at 0.5 ml/min of 7% ethanol in heptane, and UV detection at 220 nM) to afford two separate enantiomers 15-10a and 15-10b.

Step K: Preparation of (15-11a and 15-11b)

A solution of compound 15-10a (30 mg, 0.069 mmol) in dichloromethane (0.3 mL) was treated with hydrogen chloride (4 M in 1,4-dioxane, 1 mL) at ambient temperature. The resulting mixture was stirred at ambient temperature for 1 h. The mixture was concentrated in vacuo to give a crude residue. A mixture of this residue, 1-4 (25 mg, 0.090 mmol),) O-(7-azabenzotriazol-1-yl)-N,N,N',N',-tetramethyluronium hexafluorophosphate (HATU, 34 mg, 0.090 mmol), 1-hydroxyl-7-azabenzotriazole (HOAT, 12 mg, 0.090 mmol) and 4-methylmorpholine (30 μL 0.276 mmol) in dichloromethane (2 mL) was stirred at ambient temperature overnight. The volatiles were removed to afford a residue, which was purified with high performance chromatography on a C18 reversed phase column with a gradient of water (0.1% TFA) and acetonitrile (0.1% TFA) to afford compound 15-11a as a white solid (m/z (ES) 600.3 (MH$^+$)). Compound 15-11b was prepared using a similar procedure to that utilized for compound 15-11a.

Following procedures similar to that described above for Example 83 the following compounds were prepared.
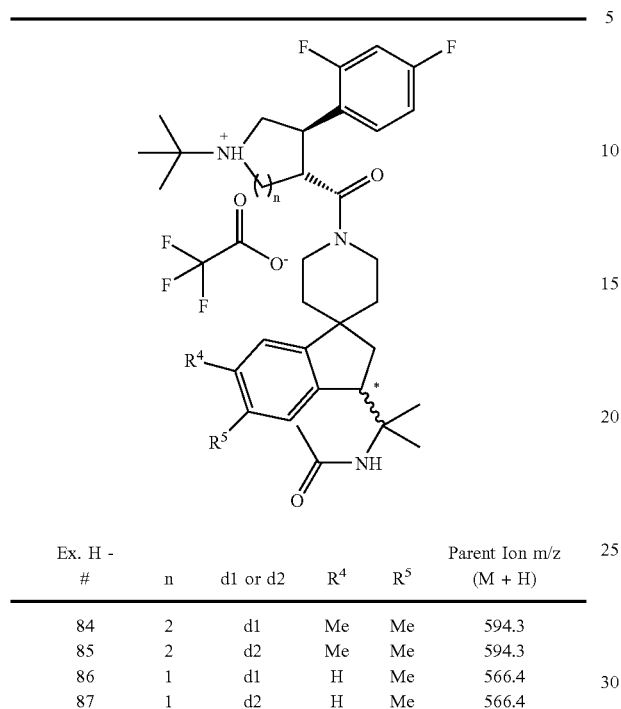
| Ex. # | H - n | d1 or d2 | R⁴ | R⁵ | Parent Ion m/z (M + H) |
|---|---|---|---|---|---|
| 84 | 2 | d1 | Me | Me | 594.3 |
| 85 | 2 | d2 | Me | Me | 594.3 |
| 86 | 1 | d1 | H  | Me | 566.4 |
| 87 | 1 | d2 | H  | Me | 566.4 |
* = diastereomer 1 (d1) and/or diastereomer 2 (d2)
Scheme 16
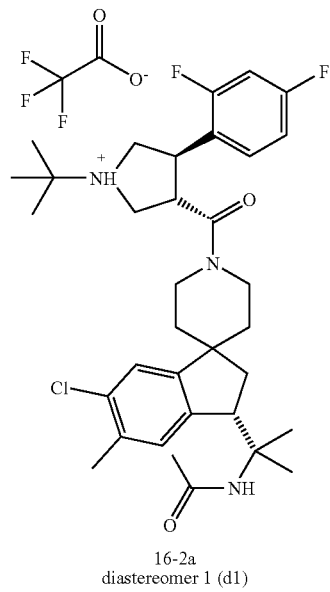
16-2a
diastereomer 1 (d1)
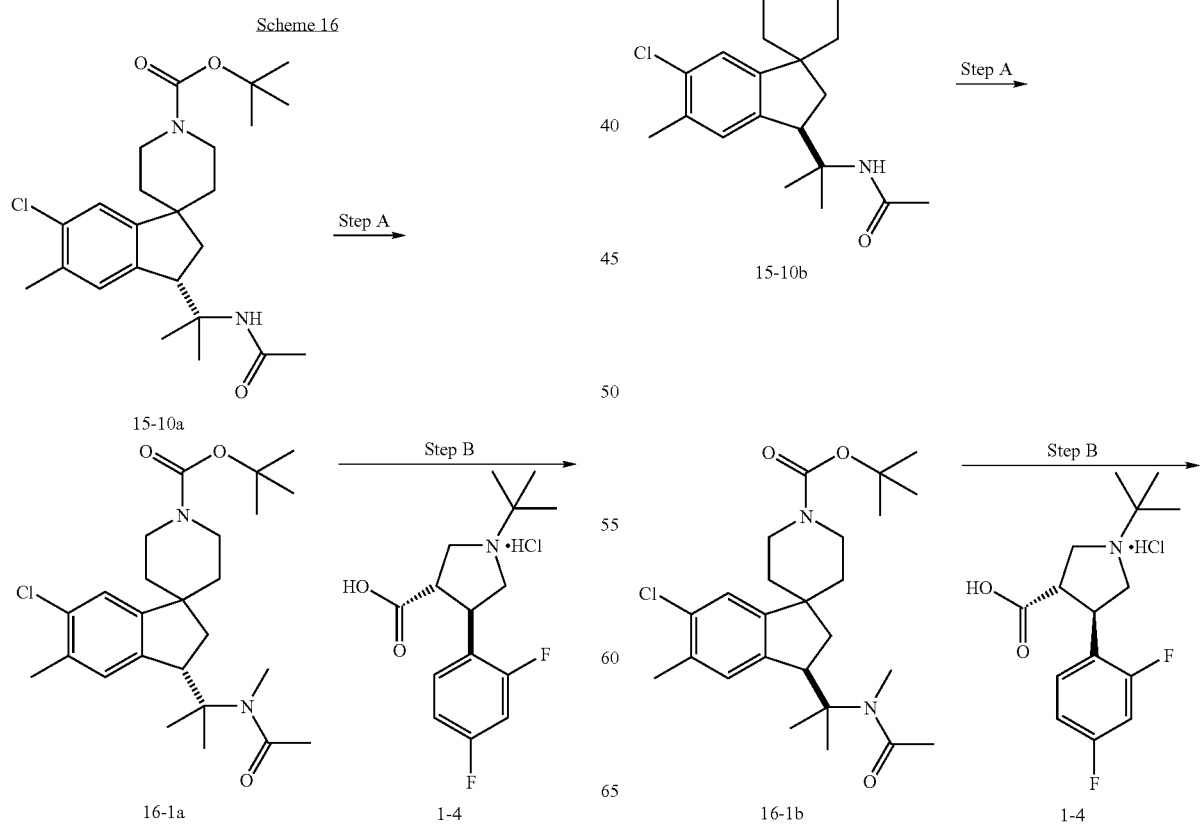

-continued

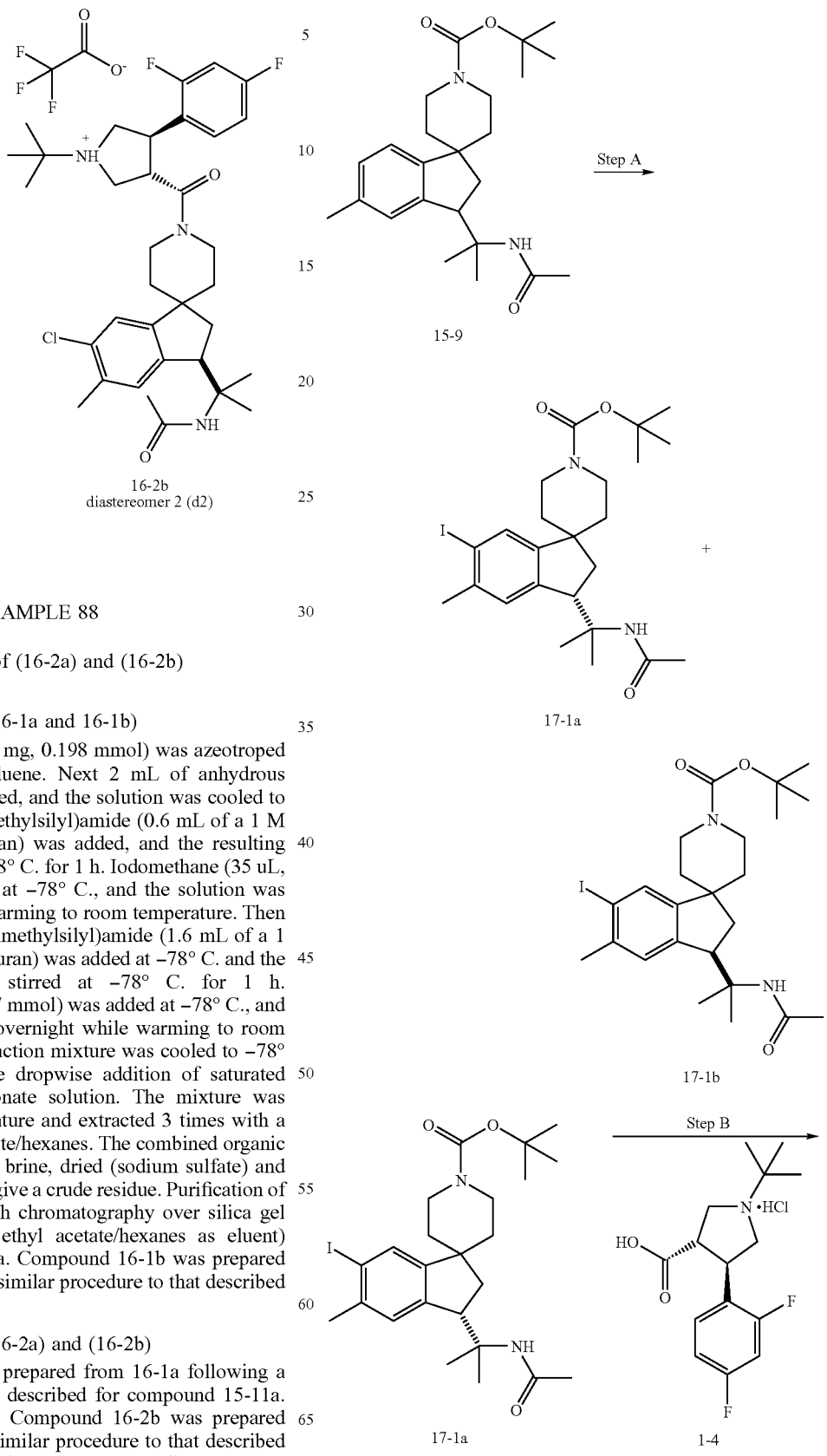

EXAMPLE 88

Preparation of (16-2a) and (16-2b)

Step A: Preparation of (16-1a and 16-1b)

Compound 15-10a (86 mg, 0.198 mmol) was azeotroped twice with 5 mL of toluene. Next 2 mL of anhydrous tetrahydrofuran were added, and the solution was cooled to −78° C. Sodium bis(trimethylsilyl)amide (0.6 mL of a 1 M solution in tetrahydrofuran) was added, and the resulting solution was stirred at −78° C. for 1 h. Iodomethane (35 uL, 0.562 mmol) was added at −78° C., and the solution was stirred overnight while warming to room temperature. Then additional sodium bis (trimethylsilyl)amide (1.6 mL of a 1 M solution in tetrahydrofuran) was added at −78° C. and the resulting solution was stirred at −78° C. for 1 h. Iodomethane (85 uL, 1.37 mmol) was added at −78° C., and the solution was stirred overnight while warming to room temperature. Then the reaction mixture was cooled to −78° C. and quenched by the dropwise addition of saturated aqueous sodium bicarbonate solution. The mixture was warmed to room temperature and extracted 3 times with a 1:1 mixture of ethyl acetate/hexanes. The combined organic layers were washed with brine, dried (sodium sulfate) and concentrated in vacuo to give a crude residue. Purification of the crude residue by flash chromatography over silica gel (isocratic elution; 75% ethyl acetate/hexanes as eluent) afforded compound 16-1a. Compound 16-1b was prepared from 15-10b following a similar procedure to that described for compound 16-1a.

Step B: Preparation of (16-2a) and (16-2b)

Compound 16-2a was prepared from 16-1a following a similar procedure to that described for compound 15-11a. (m/z (ES) 614.3 (MH+). Compound 16-2b was prepared from 16-1b following a similar procedure to that described for compound 15-11b. (m/z (ES) 614.3 (MH+).

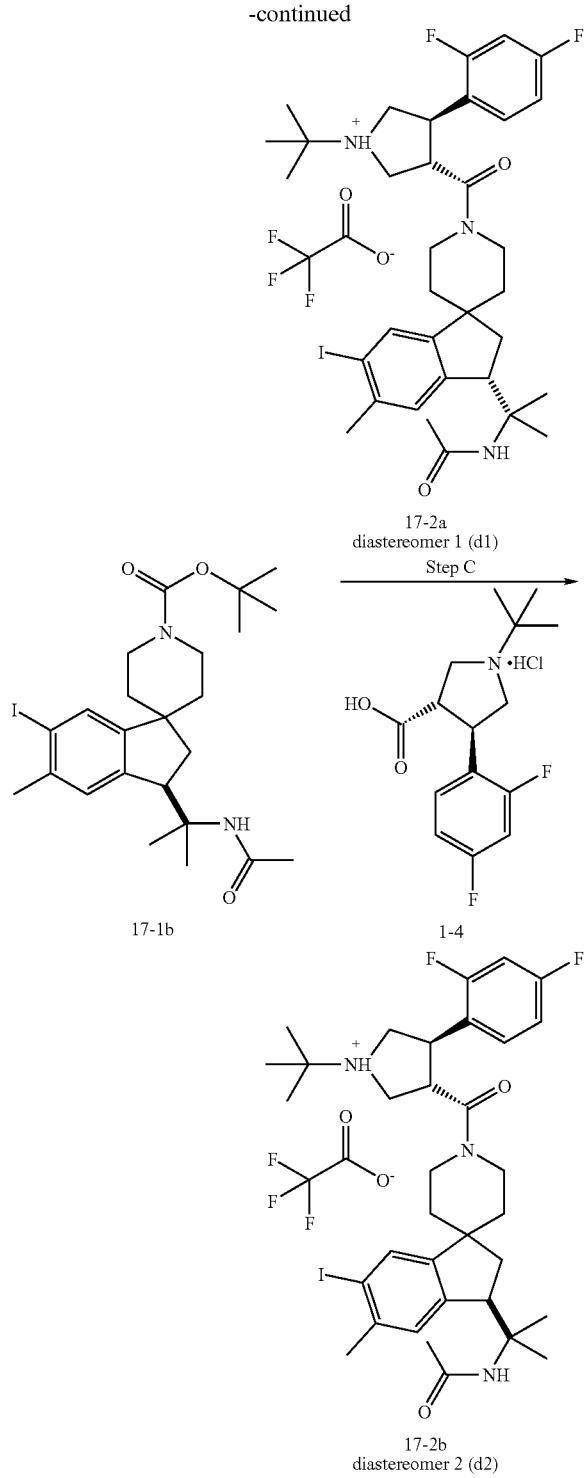

17-1b 17-2a
diastereomer 1 (d1)

Step C →

1-4

17-2b
diastereomer 2 (d2)

EXAMPLE 89

Preparation of (17-2a) and (17-2b)

Step A: Preparation of (17-1a) and (17-1b)

Compound 15-9 (140 mg, 0.35 mmol) was dissolved in 3 mL of trifluoroacetic acid, and the solution was stirred at room temperature for 20 minutes. N-Iodosuccinimide (80 mg, 0.355 mmol) was added, and the reaction was stirred in the dark at room temperature for 15 minutes. The reaction was quenched by the addition of solid sodium bicarbonate. The pH was adjusted to 10 with the addition of aqueous sodium hydroxide (5.0 M). Sodium thiosulfate (125 mg, 0.504 mmol), sodium thiosulfate saturated aqueous solution (1 mL) and aqueous sodium hydroxide (5.0 M, 2 mL) were added. The mixture was diluted with 1,4-dioxane (15 mL) and di-tert-butyl dicarbonate (150 mg, 0.687 mmol) was added. The mixture was stirred for approximately 4 hours and then extracted 4 times with ethyl acetate and hexanes (approximately 1:1). The combined organic layers were washed with brine, dried (sodium sulfate) and concentrated in vacuo to give a crude residue. Purification of the crude residue by flash chromatography over silica gel (gradient elution; 20%-100% ethyl acetate/hexanes as eluent) afforded a racemic mixture of 17-1a and 17-1b. The racemic mixture was resolved on high performance chromatography with ChiralPak AD column (Chiral Pak AD-H 4.6×250 mm 5 u column, flow rate at 0.5 ml/min 7% ethanol in heptane, and UV detection at 220 nM) to give two separate enantiomers 17-1a and 17-1b.

Steps B-C: Preparation of (17-2a) and (17-2b)

Compound 17-2a was prepared from compound 17-1a following a similar procedure to that described for compound 15-11a. (m/z (ES) 692.6 (MH+)). Compound 17-2b was prepared from compound 17-1b following a similar procedure to that described for compound 15-11b. (m/z (ES) 692.6 (MH$^+$)).

Scheme 18

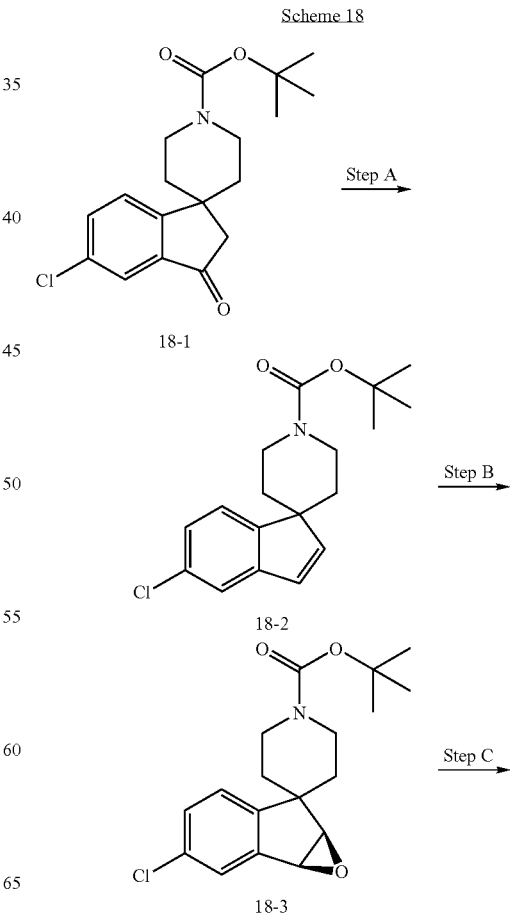

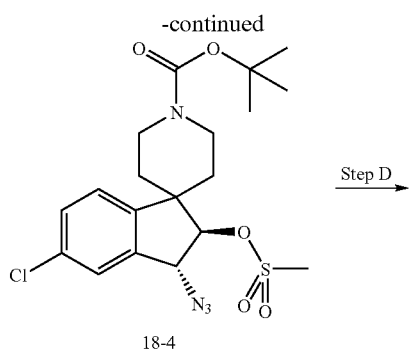
18-4
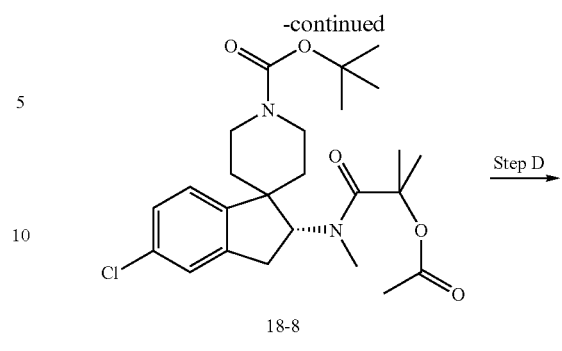
18-8
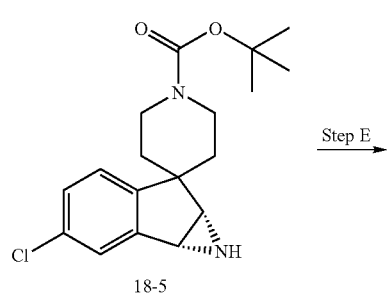
18-5
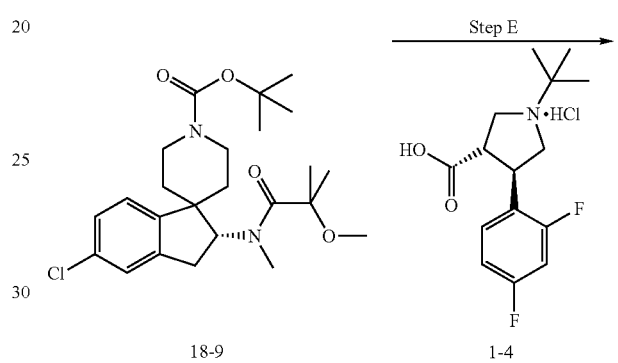
18-9          1-4
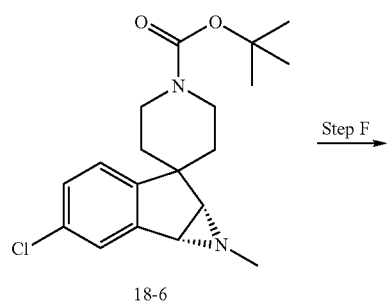
18-6
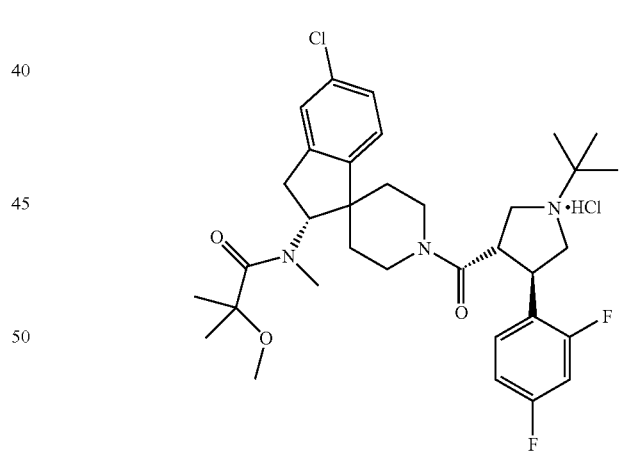
18-10
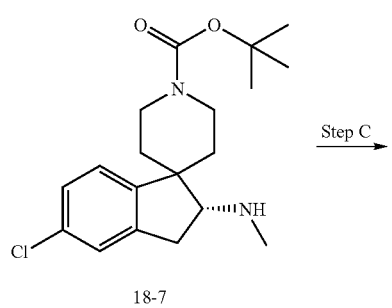
18-7
EXAMPLE 90
Preparation of Compound (18-10)
Step A: Preparation of (18-2)
Compound 18-1 was prepared following a similar procedure to that described for the preparation of 13-4. Sodium borohydride (0.704 g, 18.61 mmol) was added to a solution of 18-1 in methylene chloride (25 mL) and methanol (150 mL) at approximately 0° C. After stirring at approximately 0° C. for 10 min then at ambient temperature for 20 min, the reaction mixture was poured into 2N aqueous hydrochloric acid and ice. The resulting emulsion was extracted with ethyl acetate. The combined organic extracts were washed with aqueous saturated sodium bicarbonate and brine, dried (sodium sulfate) and concentrated in vacuo to give a crude residue. p-Toluenesulfonic acid (7.04 g, 37.01 mmol) was added to a solution of the crude alcohol in benzene (500 mL). After heating at reflux overnight, the reaction mixture was diluted with ethyl acetate, washed with 1N aqueous sodium hydroxide and brine, dried (sodium sulfate) and concentrated in vacuo to give a crude residue. Di-tert-butyl dicarbonate was added to a solution of the crude residue in 10% triethylamine/methanol (300 mL). After stirring at ambient temperature for 2 hr, the reaction mixture was concentrated in vacuo to give a crude residue. Purification of the crude residue by flash chromatography over silica gel (gradient elution; 0%-20% ethyl acetate/hexane as eluent) afforded compound 18-2 a white solid, (m/z (ES) 320 (MH+)).

Step B: Preparation of (18-3)

(S,S)-(+)-N,N'-Bis(3,5-Di-tert-butylsalicylidene)-1,2-cyclohexane diamino-manganese (III) chloride (0.44 g, 0.7 mmol) followed by 4-phenylpyridine N-oxide (707 mg, 4.12 mmol) were added to a stirred solution of compound 18-2 (4.4 g, 13.76 mmol) in methylene chloride (50.0 mL) at approximately 0° C. After stirring at ambient temperature for 10 min, sodium hypochlorite (8.6 mL of a 1.6 M aqueous solution, 13.76 mmol) was added. The reaction mixture was allowed to warm slowly to ambient temperature over 3 hr. The reaction mixture was then diluted with water and extracted with ethyl acetate. The organic phase was washed with aqueous saturated sodium sulfite and brine, dried (magnesium sulfate) and concentrated in vacuo to give a crude residue. Purification of the crude residue by flash chromatography over silica gel (gradient elution; 5%-55% ethyl acetate/hexanes as eluent) afforded compound 18-3 as a white solid (m/z (ES) 336 (MH+)).

Step C: Preparation of (18-4)

Ammonium chloride (1.47 g, 27.51 mmol) followed by sodium azide (4.07 g, 62.53 mmol) were added to a solution of 18-3 in methanol:water (8:1) (100 mL) at ambient temperature. After stirring at reflux overnight, the reaction mixture was cooled and concentrated in vacuo to half its original volume. The residue was diluted with cold water and extracted with methylene chloride. The combined organic extracts were washed with brine, dried (magnesium sulfate) and concentrated in vacuo to give a crude residue. Methanesulfonyl chloride (0.89 mL, 11.44 mmol) was added to a solution of the crude residue and triethylamine (2.90 mL, 20.80 mmol) in methylene chloride (200 mL) at approximately 0° C. After stirring at ambient temperature for 30 min, the reaction mixture was diluted with ethyl acetate, washed successively with aqueous 2N hydrochloric acid, aqueous saturated sodium bicarbonate and brine, dried (magnesium sulfate) and concentrated in vacuo to give compound 18-4 which was used without further purification (m/z (ES) 457 (MH+)).

Step D: Preparation of (18-5)

Triethylamine (2.81 mL, 20.13 mmol) followed by diphenyl-(2(1H,1H,2H,2H-perfluorodecyl)phenyl)phosphine (3.14 g, 4.43 mmol) were added to a solution of 18-4 (1.84 g, 4.03 mmol) in THF:water (10:1) (90 mL). After stirring at ambient temperature overnight, the reaction mixture was concentrated in vacuo, the residue was partitioned between ethyl acetate, brine and perfluorinated Hexanes (FC-72, ACROS). The uppermost organic phase was dried (sodium sulfate) and concentrated in vacuo to give a crude residue. Purification of the crude residue by flash chromatography over silica gel (gradient elution; 5%-50% acetone/methylene chloride as eluent) afforded compound 18-5 as an off-white solid (m/z (ES) 335 (MH+)).

Step E: Preparation of (18-6)

Potassium carbonate (0.15 g, 1.08 mmol) followed by methyl iodide (0.03 mL, 0.54 mmol) were added to a solution of compound 18-5 (0.12 g, 0.36 mmol) in acetone. After stirring at approximately 50° C. for 2 h, the reaction mixture was concentrated in vacuo. The residue was diluted with methylene chloride and washed with brine, dried (magnesium sulfate) and concentrated in vacuo to give a crude residue. Purification of the crude residue by flash chromatography over silica gel (gradient elution; 5%-55% acetone/methylene chloride as eluent) afforded compound 18-6 (m/z (ES) 349 (MH+)).

Step F: Preparation of (18-7)

p-Toluenesulfonic acid monohydrate (0.44 g, 2.34 mmol) followed by sodium cyanoborohydride (0.15 g, 2.34 mmol) were added in four portions over a period of 1 hr to a solution of 18-6 (0.37 g, 0.58 mmol) in tetrahydrofuran (15 mL) at ambient temperature. After stirring the reaction mixture at ambient temperature for a further 30 min, aqueous 5N sodium hydroxide (5 mL) was added and stirring continued for 30 min. The reaction mixture was concentrated in vacuo and extracted with ethyl acetate. The organic phase was washed with brine, dried (sodium sulfate) and concentrated in vacuo to give a crude residue. Purification of the crude residue by flash chromatography over silica gel (gradient elution; 20%-100% ethyl acetate/hexande as eluent) afforded 18-7 as a pale yellow solid (m/z (ES) 351 (MH+)).

Step G: Preparation of (18-8)

Dimethylaniline (0.235 mL, 1.85 mmol) was added to a solution of compound 18-7 (65 mg, 0.185 mmol) in methylene chloride (4 mL). After stirring at ambient temperature for 30 min, 2-acetoxyisobutyryl chloride (0.13 mL, 0.93 mmol) was added. After stirring the reaction mixture at ambient temperature overnight, dimethylaniline (0.235 mL, 1.85 mmol) and 2-acetoxyisobutyryl chloride (0.13 mL, 0.93 mmol) were added and stirring continued for 18 hr. Volatiles were removed in vacuo, the residue was diluted with ethyl acetate and washed successively with aqueous 2N hydrochloric acid, aqueous saturated sodium bicarbonate and brine, dried (sodium sulfate) and concentrated in vacuo to give a crude residue. Purification of the crude residue by flash chromatography over silica gel (gradient elution; 5%-40% acetone/methylene chloride as eluent) afforded compound 18-8 (m/z (ES) 479 (MH+)).

Step H: Preparation of (18-9)

Sodium methoxide (1.85 mL of a 0.5 M solution in methanol, 0.925 mmol) was added to a solution of compound 18-8 (88 mg, 0.185 mmol) in methanol (4 mL). After stirring at reflux overnight, the reaction was cooled, concentrated in vacuo and the residue was partitioned between water and methylene chloride. The organic phase was dried (magnesium sulfate) and concentrated in vacuo to give a crude residue. Sodium hydride (44 mg, 1.85 mmol) followed by methyl iodide (0.058 mL, 0.926 mmol) were added to a solution of crude alcohol in tetrahydrofuran:N,N-dimethyl formamide (10:1) (4 mL). After stirring at ambient temperature overnight, the reaction mixture was concentrated in vacuo and the residue was partioned between water and methylene chloride. The aqueous phase was extracted with methylene chloride; the combined organic extracts were dried (magnesium sulfate) and concentrated in vacuo to give a crude residue. Purification of the crude residue by flash chromatography over silica gel (gradient elution; 20%-60% acetone/methylene chloride as eluent) afforded compound 18-9 as a white solid (m/z (ES) 451 (MH+)).

Step I: Preparation of (18-10)

Compound 18-10 was prepared was prepared from compound 18-9 following a similar procedure to that described for compound 8-12 (m/z (ES) 616 (MH$^+$).

Following procedures similar to that described above for Example 90, the following compounds

| Ex. # | R1 | R2 | R3 | Parent Ion m/z (M + H) |
|---|---|---|---|---|
| 91 | Cl | H | COMe | 558 |
| 92 | Cl | H | SO2Me | 594 |
| 93 | Cl | H | SO2NH2 | 595 |
| 94 | Cl | Me | SO2Me | 608 |
| 95 | Cl | Me | COC(Me)2OMe | 630 |
| 96 | H | H | COMe | 524 |
| 97 | H | H | SO2Me | 560 |
| 98 | H | H | CO2Me | 540 |
| 99 | H | H | CO(cyclopropyl) | 540 |
| 100 | H | H | CO(cyclopropyl) | 550 |
| 101 | H | H | COiPr | 552 |
| 102 | F | H | COMe | 542 |
| 103 | F | H | SO2Me | 578 |
| 104 | F | Me | COMe | 556 |
| 105 | F | Me | SO2Me | 592 |
| 106 | H | H | COC(Me)2OH | 568 |
| 107 | H | H | COC(Me)2OMe | 582 |
| 108 | H | H | COCH2OH | 540 |
| 109 | H | H | COCH2OMe | 554 |
| 110 | H | H | COCH2C(Me)2OH | 582 |
| 111 | H | H | COCH2CH2OH | 554 |
| 112 | H | H | COCH2CH2Cl | 572 |
| 113 | H | H | COCHF2 | 560 |
| 114 | H | H | COCH=CH2 | 536 |

Following procedures similar to that described above for Example 51, the following compounds were prepared:

| Ex. # | R1 | R2 | R3 | Parent Ion m/z (M + H) |
|---|---|---|---|---|
| 115 | Cl | H | COMe | 586 |
| 116 | Cl | H | CO(cyclopropyl) | 612 |
| 117 | Cl | Me | COMe | 600 |
| 118 | Me | Me | COMe | 580 |
| 119 | Me | Me | CO(cyclopropyl) | 606 |
| 120 | Me | Me | COiPr | 608 |
| 121 | H | H | CO(cyclopropyl) | 578 |
| 122 | H | H | COiPr | 580 |
| 123 | F | H | COMe | 570 |
| 124 | F | Me | COMe | 584 |

Scheme 19

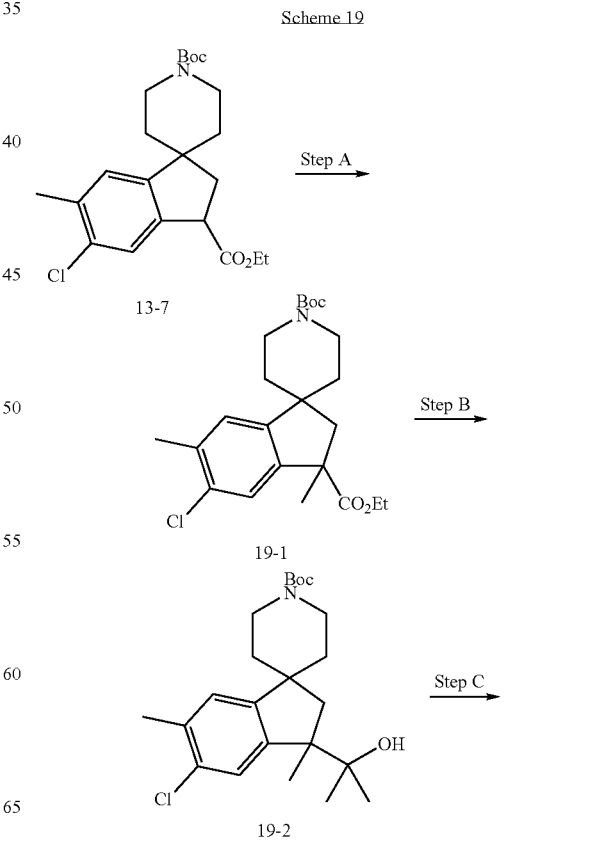

153
-continued
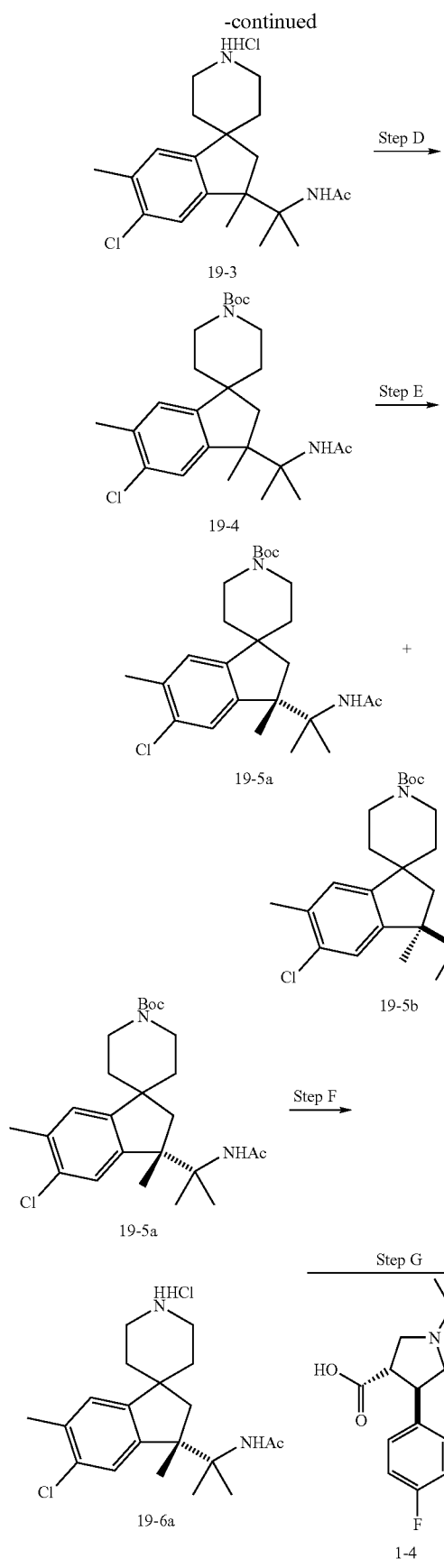
154
-continued
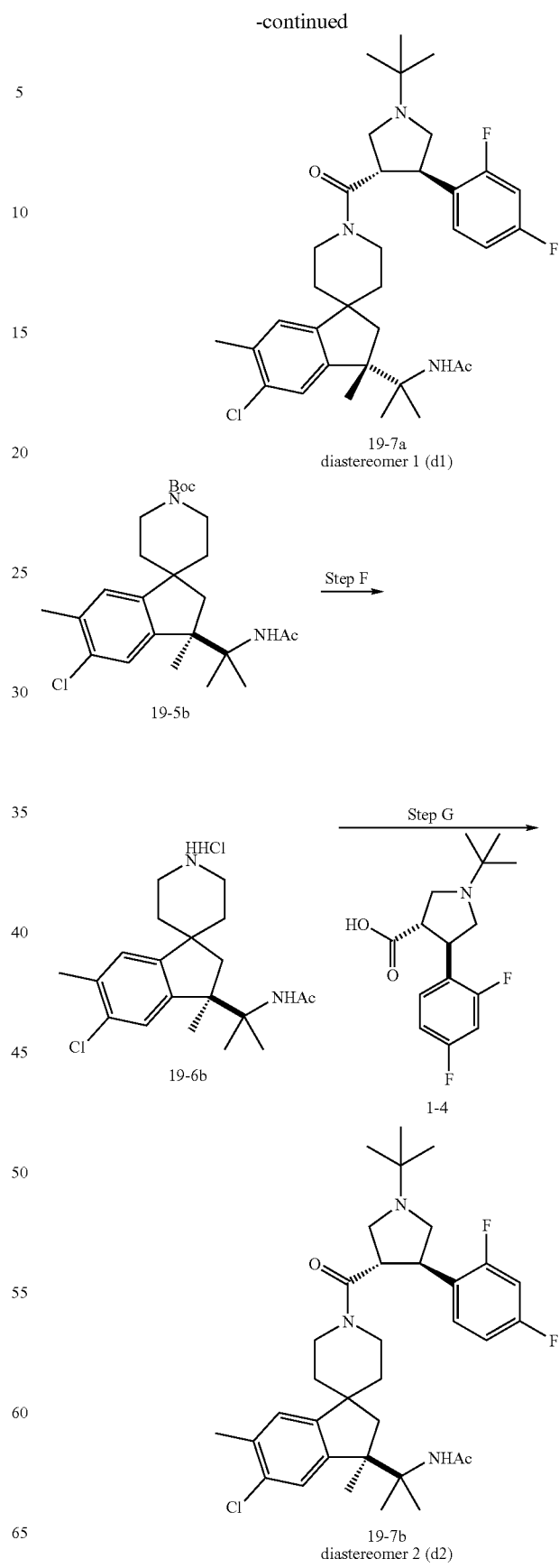

EXAMPLE 125

Preparation of Compound (19-7a and 19-7b)

Step A: Preparation of (19-1)

To the stirred solution of LDA (1.5 M in cyclohexane, Aldrich, 1.8 ml, 2.7 mmol) in dry THF (15 ml) was added compound 13-7 (725 mg, 1.77 mmol) in THF (5 ml) dropwise at −78° C. The mixture was stirred at −78° C. for 1 h, then MeI (553 µl, 8.85 mmol) was added. The reaction mixture was slowly warmed up to room temperature, and stirred overnight. To the reaction mixture was added cold 1N HCl aqueous (30 ml) and EtOAc (30 ml). The aqueous layer was extracted with EtOAc three times. The combined organic phases were dried over $MgSO_4$. MPLC purification using 0%-30% EtOAc in hexane as the eluting solvent afforded compound 19-1. Calc. for $C_{23}H_{32}ClNO_4$: 421; found by LC-MASS: M+Na=444.

Step B: Preparation of (19-2)

To the stirred solution of compound 19-1 (450 mg, 1.06 mmol) in dry THF (15 ml) at −78° C. was added MeLi (1.5 M in ether, 5 ml, 7.46 mmol) dropwise. The mixture was stirred at for 2 h, then quenched with 1N HCl in ether (8 ml). The mixture was poured to cold saturated aqueous $NaHCO_3$/EtOAc (30 ml/30 ml). The aqueous layer was extracted with EtOAc three times, the combined organic phases were dried over $MgSO_4$, and concentrated in vacuo to afford compound 19-2. Calc. for $C_{23}H_{34}ClNO_3$: 407; found by LC-MASS M+Na=430.

Step C: Preparation of (19-3)

Compound 19-2 (320 mg, 0.786 mmol) was dissolved in 15 ml dry acetonitrile, then concentrated $H_2SO_4$ (642 µl, 11.8 mmol) was added while the reaction flask was immersed in a cold water bath. The reaction was stirred at room temperature overnight. The volatiles were evaporated, and the residue was partitioned between cold NaOH (1N, 25 ml) and $CH_2Cl_2$ (25 ml). The aqueous layer was extracted with $CH_2Cl_2$ three times, and the combined organic phases were dried over $Na_2SO_4$, acidified to form the HCl salt using 1N HCl in ether and concentrated in vacuo to give compound 19-3. Calc. for $C_{20}H_{29}ClN_2O$: 348, found on LC-MASS M+1=349.

Step D: Preparation of (19-4)

To the stirred solution of compound 19-3 (250 mg, 0.65 mmol) in $CH_2Cl_2$ (20 ml) was added DIEA (226 µL, 1.3 mmol) and di-tert-butyl carbonate (184.4 mg, 0.845 mmol). The mixture was stirred at room temperature overnight, followed by aqueous work-up (washed with 1N HCl and saturated $NaHCO_3$) to afford compound 19-4. Calc. MW for $C_{25}H_{37}ClN_2O_3$: 448, found M+Na=471.

Step E: Preparation of (19-5a and 19-5b)

Chiral HPLC resolution of racemic mixture of compound 19-4 on Gilson chiral HPLC system afforded the individual enantiomers 19-a and 19-5b using ChiralPak AD-H column and 7% IPA/Heptane as eluting solvent. Calc. MW for $C_{25}H_{37}ClN_2O_3$: 448, found M+Na=471 for both 19-5a and 19-5b.

Step F: Preparation of (19-6a and 19-6b)

Compound 19-5a (65 mg) was dissolved in 4N HCl in dioxane (15 ml), and stirred at room temperature for 60 min, followed by evaporation to dryness to yield compound 19-6a. Calc. MW for $C_{20}H_{29}ClN_2O$: 348, found M+1=349 on LC-MASS. Compound 19-5b (70 mg) was dissolved in 4N HCl in dioxane (15 ml), and stirred at room temperature for 60 min, followed by evaporation to dryness to yield compound 19-6b. Calc. MW for $C_{20}H_{29}ClN_2O$: 348, found M+1=349 on LC-MASS.

Step G: Preparation of (19-7a and 19-7b)

To the stirred solution of compound 19-6a (35 mg, 0.091 mmol) in $CH_2Cl_2$ (2 ml) was added DIEA (63 µl, 0.365 mmol), compound 1-4 (31 mg, 0.109 mmol), HOAt (15 mg, 0.109 mmol) and HATU (69 mg, 0.182 mmol) at room temperature. The mixture was stirred at room temperature overnight. Preparative TLC purification using 10% MeOH in $CH_2Cl_2$ as an eluting solvent, followed by acidification using 1N HCl in ether to afford compound 19-7a as white solid. Calc. MW for $C_{35}H_{46}ClF_2N_3O_2$: 613; found on LC-MASS M+1=614. To the stirred solution of compound 19-6b (35 mg, 0.091 mmol) in $CH_2Cl_2$ (2 ml) was added DIEA (63 µl, 0.365 mmol), compound 1-4 (31 mg, 0.109 mmol), HOAt (15 mg, 0.109 mmol) and HATU (69 mg, 0.182 mmol) at room temperature. The mixture was stirred at room temperature overnight. Preparative TLC purification using 10% MeOH in $CH_2Cl_2$ as an eluting solvent, followed by acidification using 1N HCl in ether to afford compound 19-7b as white solid. Calc. MW for $C_{35}H_{46}ClF_2N_3O_2$: 613, found on LC-MSS M+1=614.

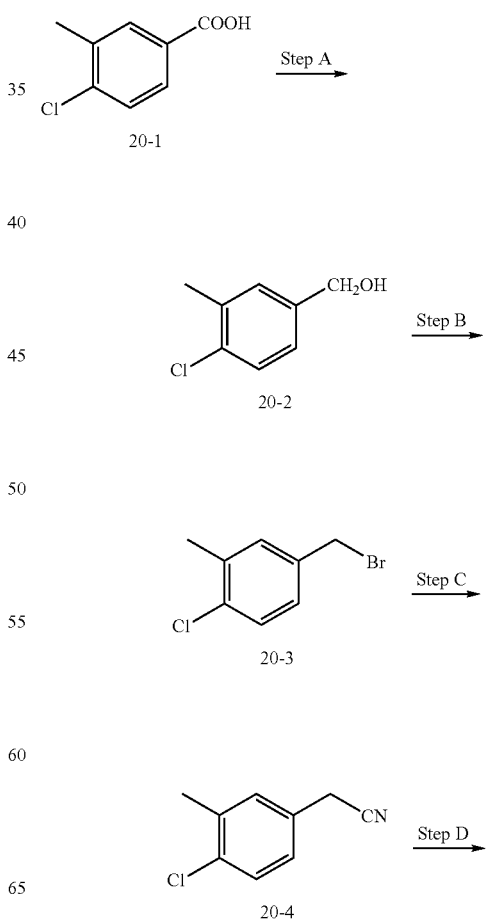

Scheme 20

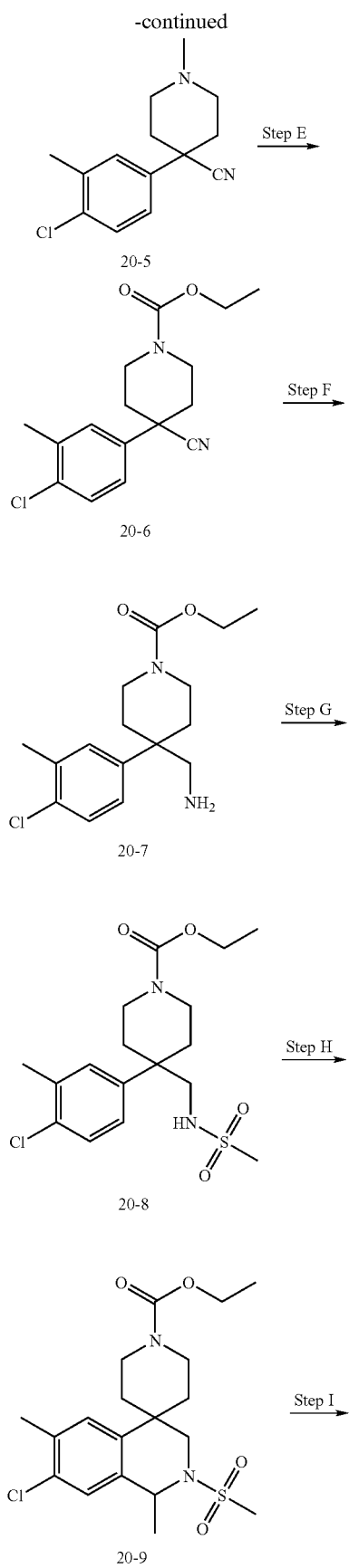
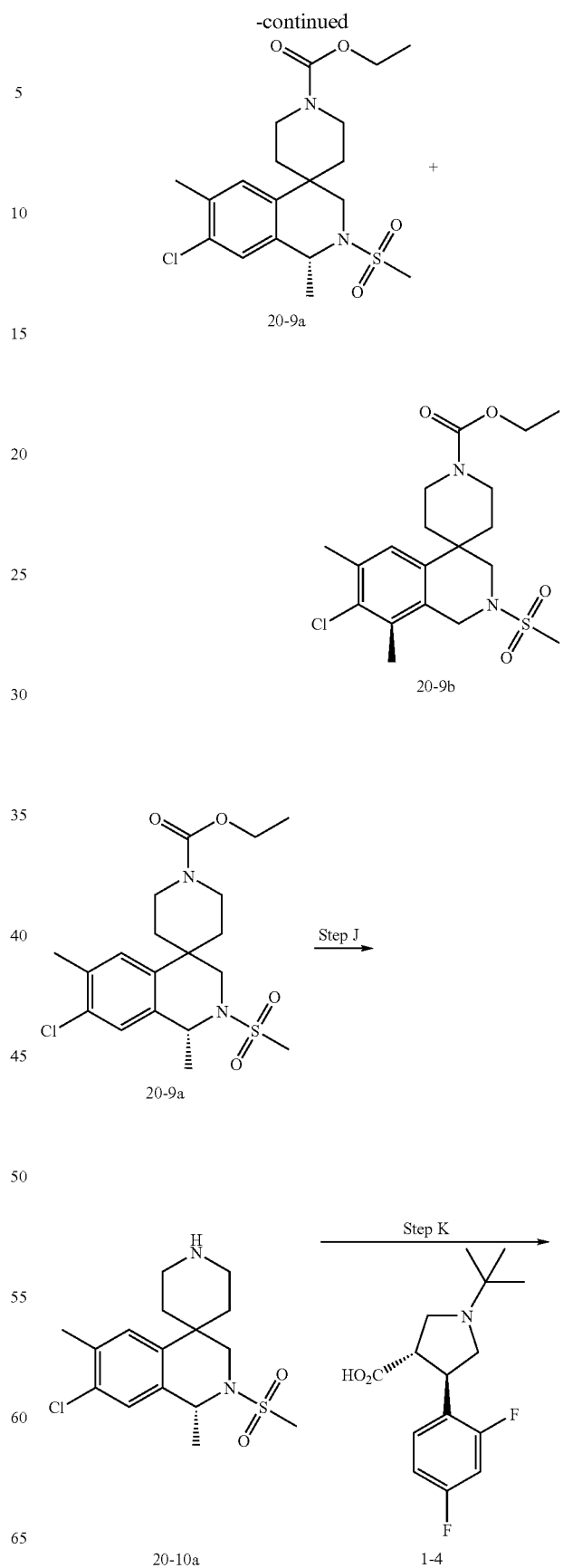

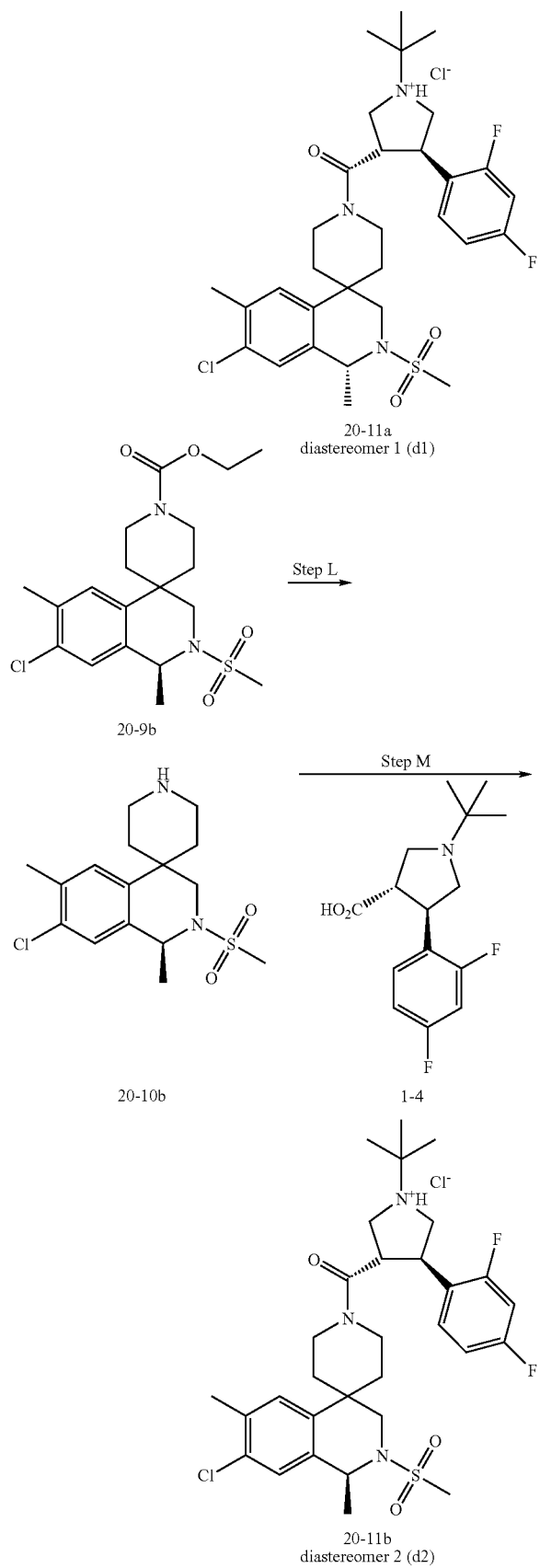

EXAMPLE 126

Preparation of Compound (20-11)

Step A: Preparation of (20-2)

4-Chloro-3-methyl benzoic acid 20-1 (8.40 g, 49.2 mmol) was dissolved in anhydrous tetrahydrofuran (100 mL), and the mixture was cooled to −78° C. in a dry ice-acetone bath. A solution of lithium aluminum hydride in tetrahydrofuran (1.0 M, 73.8 mL) was added dropwise to the reaction mixture over 30 min. The resulting mixture was stirred at −78° C. for 30 min and then at room temperature for 1 hr. Then the reaction was quenched by adding water (2.9 mL) slowly, NaOH (5N, 2.9 mL) and water (9 mL). The resulting slurry was stirred for 30 min, filtered, washed with ethyl acetate, and the filtrate was concentrated to afford 20-2.

Step B: Preparation of (20-3)

A solution of compound 20-2 (8.20 g, 52.4 mmol) in methylene chloride (100 mL) was cooled to 0° C. in an ice water bath. Under stirring, triphenyl phosphine (17.85 g, 68.06 mmol) was added slowly in small portions over 5 min, followed by the slow addition of carbon tetrabromide (22.57 g, 68.06 mmol) in small portions over 10 min. The resulting mixture was stirred at 0° C. for 1 h and then concentrated to give a residue. The residue was loaded to a 40M Biotage cartridge and eluted with ethyl acetate/hexanes (10%) to afford compound 20-3 mixed with bromoform, which was used for next step without further purification.

Step C: Preparation of (20-4)

To a solution of tetrabutylammonium chloride (43.65 g, 157.08 mmol), potassium cyanide (10.23 g, 157.08 mmol) in a mixture of acetonitrile (60 mL) and water (30 mL), was added dropwise over 20 minutes a solution of 20-3 in acetonitrile (50 mL). The resulting reaction mixture was stirred at room temperature for 15 h, and then quenched by adding water (50 mL). The organic phase was separated and the aqueous layer was extracted by ethyl acetate (3×100 mL). The combined organic phases were washed by water (2×) and brine, dried over $MgSO_4$, filtered and concentrated. The crude product was purified by MPLC (65M, ethyl acetate/hexanes from 0 to 10%) to afford compound 20-4 (m/z (ES) $(M+H)^+=166$).

Step D: Preparation of (20-5)

Compound 20-4 (6.48 g, 39.13 mmol) was charged in a 500 mL one necked round bottomed flask along with mechlorethamine hydrochloride (7.53 g, 39.13 mmol), tetrabutylammonium hydrosulfate (0.664 g, 1.96 mmol) and NaOH (50%, 60 mL). The mixture was stirred vigorously and heated to reflux in an oil bath of 100° C. for 3 h. After cooling to room temperature, the mixture was diluted with water (50 mL) and extracted by ethyl acetate (4×100 mL). The combined organic phases were washed by water (2×), brine, dried over $MgSO_4$, filtered and concentrated. The resulting crude was purified by MPLC (65M cartridge, ethyl acetate/hexanes from 10% to 100% and then 10% MeOH/ 0.1% $NH_3/CH_2Cl_2$) to afford product 20-5 (m/z (ES) $(M+H)^+=249$).

Step E: Preparation of (20-6)

Compound 20-5 (1.05 g, 4.22 mmol) was dissolved in 1,2-dichloroethane (9 mL) and ethyl chloroformate (0.916 g, 0.807 mL, 8.44 mmol). The mixture was stirred and heated to reflux for 19 h overnight. Then the mixture was concentrated and the resulting residue was purified by MPLC (25

M cartridge, ethyl acetate/hexanes from 0% to 25%) to afford product 20-6 (m/z (ES) (M+H)$^+$=307).

Step F: Preparation of (20-7)

To a solution of compound 20-6 (0.841 g, 2.74 mmol) in anhydrous tetrahydrofuran (5 mL) was added borane in tetrahydrofuran (1.5 M, 5.5 mL, 8.22 mmol) dropwise over 5 min. The resulting mixture was stirred at room temperature for 10 min and then at 40° C. for 3 h. After cooling to room temperature, the reaction was quenched by the slow addition of methanol (2 mL) and NaOH (1N, 5 mL). The organic layer was separated and the aqueous phase was extracted by ethyl acetate (3×). The combined organic phases were washed with water, brine, dried over MgSO$_4$, filtered and concentrated to afford compound 20-7 (m/z (ES) (M+H)$^+$=311).

Step G: Preparation of (20-8)

A mixture of compound 20-7 (2.74 mmol) in methylene chloride (6 mL) and triethyl amine (0.683 g, 0.886 mL, 6.85 mmol) was cooled to 0° C. in an ice water bath and methanesulfonyl chloride (0.408 g, 0.277 mL, 3.56 mmol) was added dropwise over 10 min. The reaction mixture was stirred at 0° C. for 10 min and then at room temperature for 2 h. The reaction was quenched by adding water (4 mL). The organic layer was separated and the aqueous phase was extracted with methylene chloride (3×). The combined organic phases were washed by water and brine, dried over MgSO$_4$, filtered and concentrated. The crude residue was purified by MPLC (25 S cartridge, ethyl acetate/hexanes from 10% to 50%) to give compound 20-8 (m/z (ES) (M+H)$^+$=389).

Step H: Preparation of (20-9)

Compound 20-8 (129.3 mg, 0.333 mmol) was dissolved in acetic acid (0.8 mL), then acetaldehyde (29.3 mg, 0.665 mmol) was added, followed by the dropwise addition of sulfuric acid (0.3 mL) over 5 min. The resulting mixture was stirred at room temperature for one and half hours. The reaction was quenched by diluting with water (2 mL) and extracted with ethyl acetate (4×). The combined organic phases were washed by water, saturated NaHCO$_3$, water, and brine, dried over MgSO$_4$, filtered and concentrated to give a residue. The residue was purified by preparation TLC (2000 nm, ethyl acetate:hexanes=2:3) to afford compound 20-9 (m/z (ES) (M+H)$^+$=415).

Step I: Preparation of (20-9a and 20-9b)

Chiral separation of the mixture of 20-9 (1 mg in 1 mL EtOH or isopropanol) on a preparative Chiral OD column using 4% to 40% EtOH in heptane gradient elution afforded two enantiomers 20-9a (m/z (ES) (M+H)$^+$=415) and 20-9b (m/z (ES) (M+H)$^+$=415).

Step J: Preparation of (20-10a)

Compound 20-9a was dissolved in a 38% solution of HBr in AcOH (1 mL). The mixture was stirred and heated in an oil bath of 95° C. for 1 hr, then the solvent was removed and the residue was purified by reverse phase HPLC using gradient elution of acetonitrile and water from 20% to 80% to afford compound 20-10a (m/z (ES) (M+H)$^+$=343), which was converted to its HCl salt.

Step K: Preparation of (20-11a)

To a solution of compound 20-10a (20.3 mg, 0.054 mmol), acid 1-4 (16.7 mg, 0.058 mmol) and methylene chloride (1 µL), was added diisopropylethyl amine (47 µL, 0.27 mmol). The mixture was stirred until the solid all dissolved. Then O-(7-azabenzotriazol-1-yl)-N,N,N',N',-tetramethyluronium hexafluorophosphate (HATU, 24.6 mg, 0.065 mmol), and 1-hydroxyl-7-azabenzotriazole (HOAT, 7.3 mg, 0.054 mmol) were added and the resulting mixture was stirred at room temperature for 2 h. The solvent was then removed and the residue was dissolved in methanol (1 mL) and filtered. The filtrate was concentrated and the resulting residue was purified by reverse phase HPLC (gradient 20% to 80% acetonitrile in water) to afford product 20-11a (m/z (ES) (M+H)$^+$=608), which was converted to its HCl salt.

Step L: Preparation of (20-10b)

A similar procedure to Step J was used for the preparation of 20-10b (m/z (ES) (M+H)$^+$=343) from 20-9b.

Step M: Preparation of (25-11b)

A similar procedure to Step K was used for the preparation of 20-11b (m/z (ES) (M+H)$^+$=608) from 20-10b.

Following the procedure described above in Example 126, the compounds shown below were prepared:

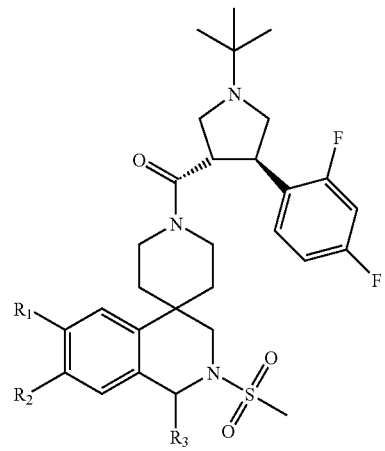

| Ex. # | R1 | R2 | R3 | d1 or d2 | Parent Ion m/z (M + H) |
|---|---|---|---|---|---|
| 127 | Me | Cl | H | | 594 |
| 128 | Me | Me | H | | 574 |
| 129 | Me | Me | Me | d1 | 588 |
| 130 | Me | Me | Me | d2 | 588 |
| 131 | Me | Me | Et | | 602 |
| 132 | H | Cl | H | | 580 |
| 133 | H | Me | H | | 560 |

Scheme 21

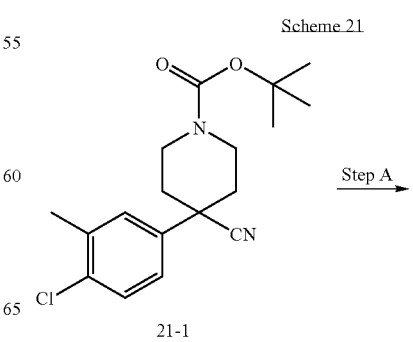

21-1

Step A

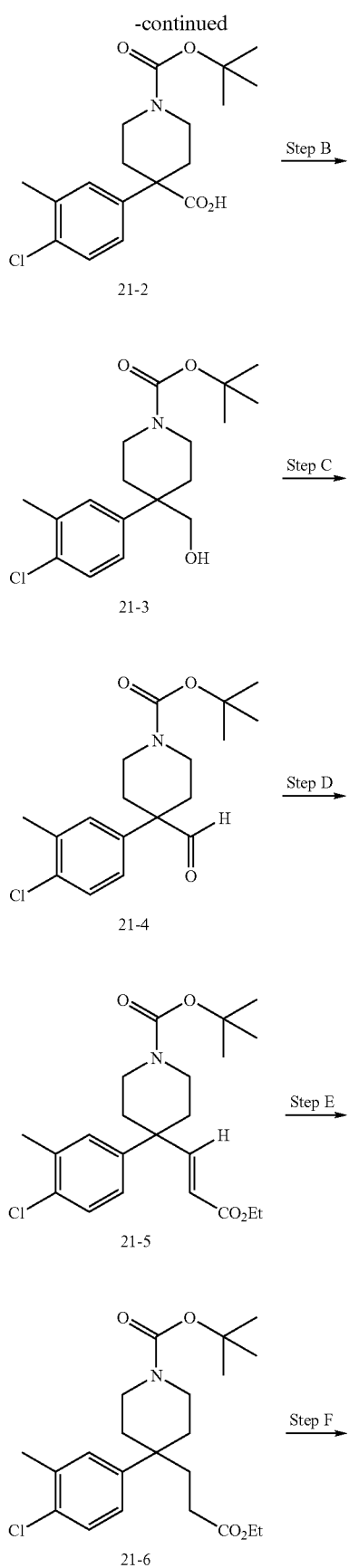
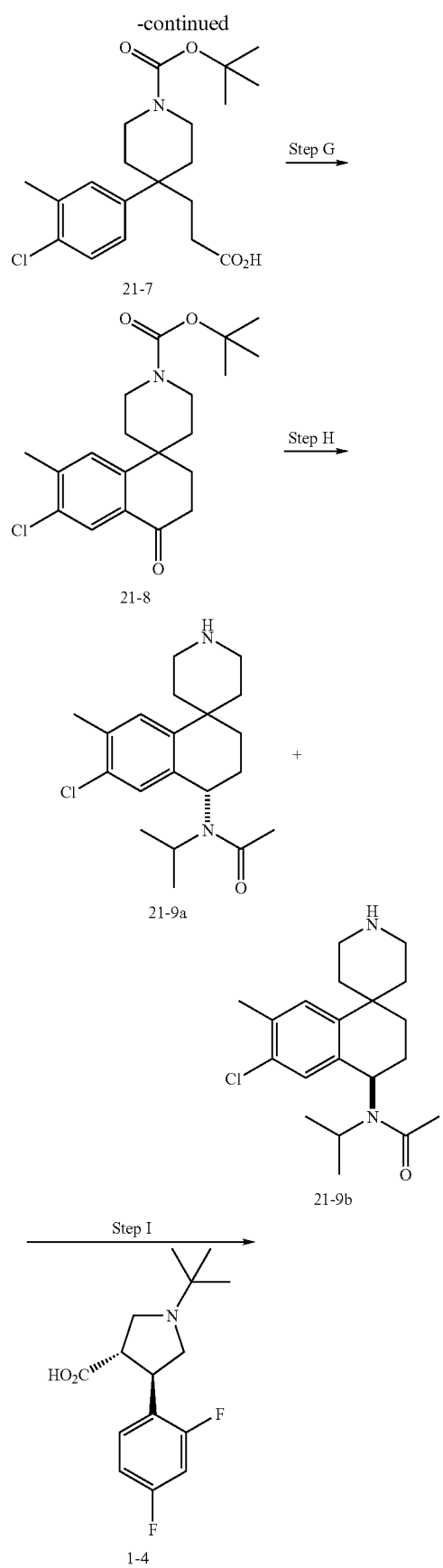

-continued

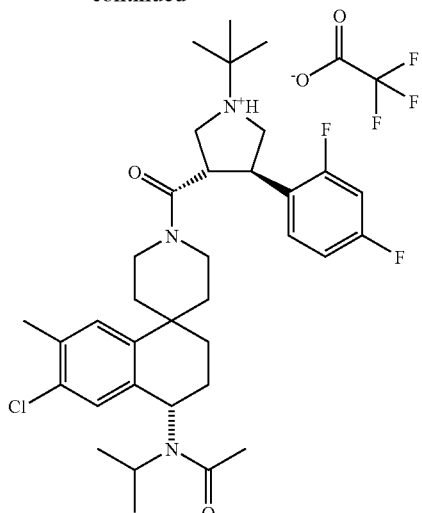

21-10a
diastereomer 1 (d1)

21-9b —Step J→

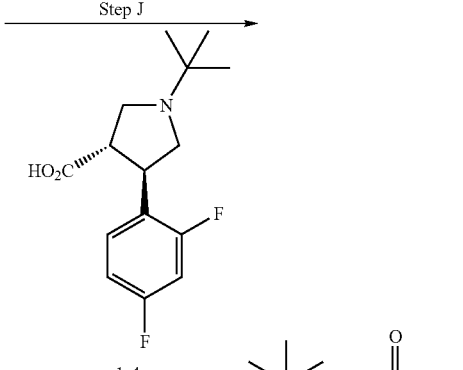

1-4

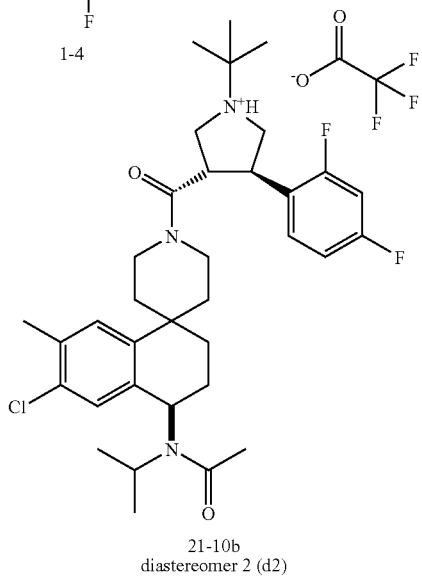

21-10b
diastereomer 2 (d2)

EXAMPLE 134

Preparation of Compound (21-10a and 21-10b)

Step A: Preparation of (21-2)

Compound 21-1 was prepared using a procedure similar to the procedure used to prepare compound 20-6. Compound 21-1 (1.77 g, 5.29 mmol) was charged in a sealed vessel along with concentrated HCl (30 mL). The vessel was sealed by a screw cap and the mixture was stirred and heated in an oil bath of 110° C. for 18 hr over night. After cooling to room temperature, the solvent was removed by rotary evaporation. The resulting residue was then transferred to a 250 mL one necked round bottomed flask by methylene chloride (50 mL), then TEA (1.07 g, 1.378 mL, 10.58 mmol) was added, followed by the addition of di-tert-butyl dicarbonate (1.50 g, 6.88 mmol). The resulting mixture was stirred at room temperature for 1 hr, then diluted by ethyl acetate (100 mL) and washed with cold HCl (2 N, 50 mL), water, brine, dried over $MgSO_4$, filtered and concentrated to afford compound 21-2 (m/z (ES) $(M+H)^+=354$).

Step B: Preparation of (21-3)

Compound 21-2 was dissolved in anhydrous tetrahydrofuran (20 mL). The mixture was cooled to −78° C. in a dry ice acetone bath, and a solution of borane in THF (1.5 M, 17.6 mL, 26.45 mmol) was added dropwise over 15 rain. The resulting mixture was stirred at −78° C. for 15 min, then at room temperature for 3 hr, and then quenched with methanol (3 mL) and water (10 mL). The aqueous layer was extracted with ethyl acetate (3×30 mL). The combined organic phases were washed with water, brine, dried over $MgSO_4$, filtered and concentrated. The resulting crude product was purified by MPLC (40S, ethyl acetate/hexanes from 0 to 30%) to afford compound 21-3 (m/z (ES) $(M+H)^+=340$).

Step C: Preparation of (21-4)

Compound 21-3 (1.8 g, 5.29 mmol) was dissolved in anhydrous methylene chloride (15 mL), then N-methylmorpholine N-oxide (NMO, 0.745 g, 6.35 mmol) and activated molecular sieves (4 A, 1 g) were added. The mixture was cooled to 0° C. in an ice water bath. Tetrapropylammonium perruthenate (TPAP, 93 mg, 0.265 mmol) was added in one portion. The resulting mixture was stirred at 0° C. for 30 min, and at room temperature for 1 hr. The reaction mixture was then filtered through a short silica gel stem (100 g) and washed with a mixture of ethyl acetate/hexanes (2:3, 250 mL). The filtrate was concentrated to afford compound 21-4 (m/z (ES) $(M+H)^+=338$).

Step D: Preparation of (21-5)

Compound 21-4 (1.62 g, 4.79 mmol) was charged in a 100 mL one necked round bottomed flask along with triethylphosphoroacetate (1.62 g, 7.19 mmol) and anhydrous tetrahydrofuran (15 mL). The mixture was cooled to 0° C. in an ice water bath, then NaH (326 mg, 8.15 mmol) was added in small portions over 10 min. The resulting reaction mixture was stirred at 0° C. for 1 hr, then quenched by water (5 mL). The aqueous layer was extracted with ethyl acetate (3×50 mL). The combined organic phases were washed with water, brine, dried over $MgSO_4$, filtered and concentrated. The resulting residue was purified by MPLC (40M, ethyl acetate/hexanes from 0 to 20%) to afford compound 21-5 (m/z (ES) $(M+H)^+=408$).

Step B: Preparation of (21-6)

Compound 21-5 (1.48 g, 3.63 mmol) was charged to a 100 mL one necked round bottomed flask along with platinum dioxide (100 mg) and ethanol (20 mL). The flask was connected to a hydrogen balloon. The system was vacuumed and refilled with hydrogen three times and then stirred under a hydrogen atmosphere for 3 h. The catalyst was filtered through a thin layer of celite and washed with ethanol. The filtrate was concentrated to afford compound 21-6 (m/z (ES) $(M+H)^+=410$).

Step F: Preparation of (21-7)

Compound 21-6 (1.18 g, 2.88 mmol) was dissolved in MeOH (6 µl), then a solution of NaOH (5 N in water, 4 mL) was added dropwise over 5 min. The resulting mixture was stirred at room temperature for 1 hr, then concentrated to give a residue. The residue was dissolved in ethyl acetate (60 mL) and acidified with HCl (2N) to pH 2. The aqueous layer was extracted with ethyl acetate (2×30 mL). The combined organic phases were washed with water, brine, dried over $MgSO_4$, filtered and concentrated to afford compound 21-7 (m/z (ES) $(M+H)^+=382$).

Step G: Preparation of (21-8)

Compound 21-7 (1.08 g, 2.88 mmol) was dissolved in anhydrous methylene chloride (10 mL), then oxalyl chloride (538 mg, 4.32 mmol) was added dropwise over 5 min. The reaction was initiated with one drop of DMF. The resulting mixture was stirred at room temperature for 30 then concentrated by rotary evaporation to provide the acyl chloride. The acyl chloride was dissolved in methylene chloride (10 mL), aluminum trichloride (845 mg, 6.34 mmol) was added in one portion. The resulting reaction mixture was stirred at room temperature for 2 h and then quenched with water (1 mL). The mixture was then diluted with ethyl acetate (50 mL) and neutralized with 2N NaOH until the solid all dissolved. The aqueous layer was extracted with ethyl acetate (3×20 mL). The combined organic phases were washed with water, brine, dried over $MgSO_4$, filtered and concentrated to afford an oil. The oil was dissolved in methylene chloride (10 mL), and triethylamine (TEA, 583 mg, 5.76 mmol) was added. The mixture was stirred while di-tert-butyl dicarbonate (943 mg, 4.32 mmol) was added in one portion. The resulting mixture was stirred at room temperature for 30 min. After the solvent was removed by rotary evaporation, the residue was purified by MPLC (25M, ethyl acetate/hexanes from 0 to 20%) to afford compound 21-8 (m/z (ES) $(M+H)^+=364$).

Step H: Preparation of (21-9a and 21-9b)

Compound 21-8 (124 mg, 0.341 mmol) was charged in a sealed tube along with sodium acetate (140 mg, 1.704 mmol), isopropyl amine (161.3 mg, 2.73 mmol), methanol (1.5 mL) and powder molecular sieves (3 A, 1 g). The tube was sealed by a screw cap and the reaction mixture was stirred and heated in an oil bath of 85° C. for 19 h. After cooling to room temperature, sodium borohydride (103 mg, 2.73 mmol) was added in one portion. The resulting mixture was stirred at room temperature for 30 min and then quenched. with water (1.5 mL). The resulting solid was filtered through a thin layer of celite and washed with methanol (3 mL). The filtrate was concentrated to afford the amine. The amine was dissolved in methylene chloride (2 mL) and TEA (173 mg, 1.71 mmol) was added, followed by the dropwise addition of acetyl chloride (40.1 mg, 0.512 mmol). The resulting reaction mixture was stirred at room temperature for 1 h, then quenched with ammonium chloride (saturated, 2 mL). The aqueous layer was extracted by methylene chloride (3×5 mL). The combined organic phases were washed with water, brine, dried over $MgSO_4$, filtered and concentrated. The resulting crude product was purified by preparative TLC (2×2000 nm, ethyl acetate:hexanes=2:3) to afford racemic amide (m/z (ES) $(M+H)^+=449$). The two enantiomers of the amide were separated using a chiral AD-H column with 7% isopropanol in heptane as eluting solvent and 220 nm as detecting wave length to give the Boc protected enantiomer of compound 21-9a (m/z (ES) $(M+H)^+=449$) and the Boc protected enantiomer of compound 21-9b (m/z (ES) $(M+H)^+=449$). The Boc protected enantiomer of compound 21-9a (31.o mg, 0.069 mmol) was treated with a mixture of concentrated HCl (0.5 mL) and methanol (1 mL) at 40° C. for 40 min. The mixture was then concentrated and the residue was co-evaporated with toluene twice to afford the HCl salt of compound 21-9a (m/z (ES) $(M+H)^+=349$). A similar procedure was used to prepare the HCl salt of compound 21-9b (m/z (ES) $(M+H)^+=349$).

Step I: Preparation of (21-10a)

Compound 21-9a (0.0691 mmol) was charged in a 15 mL one necked round bottomed flask along with acid 1-4 (21.5 mg, 0.076 mmol), anhydrous methylene chloride (1 mL), diisopropylethylamine (26.8 mg, 0.207 mmol). The mixture was stirred until the solid all dissolved. Then O-(7-azabenzotriazol-1-yl)-N,N,N',N',-tetramethyluronium hexafluorophosphate (HATU, 31.5 mg, 0.083 mmol) and 1-hydroxyl-7-azabenzotriazole (HOAT, 9.4 mg, 0.0691 mmol) were added subsequently. The resulting reaction mixture was stirred at room temperature for 1.5 hr until LC-MS showed complete reaction. The mixture was concentrated and the residue was purified by reverse phase HPLC using gradient elution (20% to 80% acetonitrile in water) to afford TFA salt of 21-10a (m/z (ES) $(M+H)^+=614$).

Step J: Preparation of (21-10b)

A similar procedure to Step I was utilized to the prepare compound 21-10b, as a TPA salt, from compound 21-9b. (m/z (ES) $(M+H)^+=614$).

Following the procedure in the Example 134, the compounds listed below were prepared:

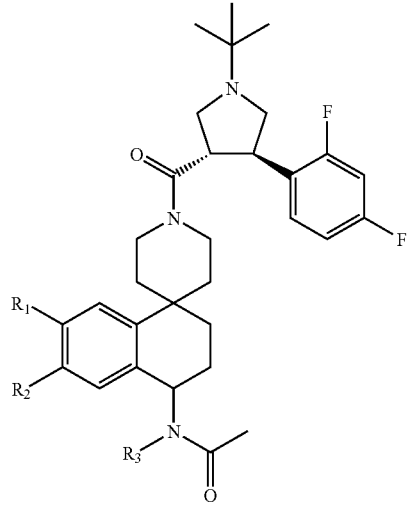

| Ex. # | R1 | R2 | R3 | d1 or d2 | Parent Ion m/z (M + H) |
|-------|----|----|----|----------|------------------------|
| 135 | Me | Cl | H | d1 | 572 |
| 136 | Me | Cl | H | d2 | 572 |
| 137 | Me | Me | H | d1 | 552 |
| 138 | Me | Me | H | d2 | 552 |
| 139 | Me | Me | $^i$Pr | d1 | 594 |
| 140 | Me | Me | $^i$Pr | d2 | 594 |

Biological Assays

A. Binding Assay

The membrane binding assay was used to identify competitive inhibitors of $^{125}$I-NDP-alpha-MSH binding to cloned human MCRs expressed in mouse L- or Chinese hamster ovary (CHO)-cells.

Cell lines expressing melanocortin receptors were grown in T-180 flasks containing selective medium of the composition: 1 L Dulbecco's modified Eagles Medium (DMEM) with 4.5 g L-glucose, 25 mM Hepes, without sodium pyruvate, (Gibco/BRl); 100 ml 10% heat-inactivated fetal bovine serum (Sigma); 10 mL 10,000 unit/mL penicillin & 10,000 µg/mL streptomycin (Gibco/BRl); 10 ml 200 mM L-glutamine (Gibco/BRl); 1 mg/mL geneticin (G418) (Gibco/BRl). The cells were grown at 37° C. with $CO_2$ and humidity control until the desired cell density and cell number was obtained.

The medium was poured off and 10 mls/monolayer of enzyme-free dissociation media (Specialty Media Inc.) was added. The cells were incubated at 37° C. for 10 min or until cells sloughed off when flask was banged against hand.

The cells were harvested into 200 mL centrifuge tubes and spun at 1000 rpm, 4° C., for 10 min. The supernatant was discarded and the cells were resuspended in 5 mls/monolayer membrane preparation buffer having the composition: 10 mM Tris pH 7.2-7.4; 4 µg/mL Leupeptin (Sigma); 10 µM Phosphoramidon (Boehringer Mannheim); 40 µg/mL Bacitracin (Sigma); 5 µm Aprotinin (Sigma); 10 mM Pefabloc (Boehringer Mannheim). The cells were homogenized with motor-driven dounce (Talboy setting 40), using 10 strokes and the homogenate centrifuged at 6,000 rpm, 4° C., for 15 min.

The pellets were resuspended in 0.2 mls/monolayer membrane prep buffer and aliquots were placed in tubes (500-1000 µL/tube) and quick frozen in liquid nitrogen and then stored at −80° C.

Test compounds or unlabelled NDP-α-MSH was added to 100 µL of membrane binding buffer to a final concentration of 1 µM. The membrane binding buffer had the composition: 50 mM Tris pH 7.2; 2 mM $CaCl_2$; 1 mM $MgCl_2$; 5 mM KCl; 0.2% BSA; 4 µg/mL Leupeptin (SIGMA); 10 µM Phosphoramidon (Boehringer Mannheim); 40 µg/mL Bacitracin (SIGMA); 5 µg/mL Aprotinin (SIGMA); and 10 mM Pefabloc (Boehringer Mannheim). One hundred µL of membrane binding buffer containing 10-40 µg membrane protein was added, followed by 100 µM 125I-NDP-α-MSH to final concentration of 100 pM. The resulting mixture was vortexed briefly and incubated for 90-120 min at room temp while shaking.

The mixture was filtered with Packard Microplate 196 filter apparatus using Packard Unifilter 96-well GF/C filter with 0.1% polyethyleneimine (Sigma). The filter was washed (5 times with a total of 10 mL per well) with room temperature of filter wash having the composition: 50 mM Tris-HCl pH 7.2 and 20 mM NaCl. The filter was dried, and the bottom sealed and 50 µL of Packard Microscint-20 was added to each well. The top was sealed and the radioactivity quantitated in a Packard Topcount Microplate Scintillation counter.

B. Functional Assay

Functional cell based assays were developed to discriminate melanocortin receptor agonists from antagonists.

Cells (for example, CHO- or L-cells or other eukaryotic cells) expressing a human melanocortin receptor (see e.g. Yang-Y K; Ollmann-M M; Wilson-B D; Dickinson-C; Yamada-T; Barsh-G S; Gantz-I; Mol-Endocrinol. 1997 March; 11(3): 274-80) were dissociated from tissue culture flasks by rinsing with Ca and Mg free phosphate buffered saline (14190-136, Life Technologies, Gaithersburg, Md.) and detached following 5 min incubation at 37° C. with enzyme free dissociation buffer (S-014-B, Specialty Media, Lavellette, N.J.). Cells were collected by centrifugation and resuspended in Earle's Balanced Salt Solution (14015-069, Life Technologies, Gaithersburg, Md.) with additions of 10 mM HEPES pH 7.5, 5 mM $MgCl_2$, 1 mM glutamine and 1 mg/ml bovine serum albumin. Cells were counted and diluted to 1 to $5 \times 10^6$/mL. The phosphodiesterase inhibitor 3-isobutyl-1-methylxanthine was added to cells to 0.6 mM.

Test compounds were diluted in dimethylsulfoxide (DMSO) ($10^{-5}$ to $10^{-10}$ M) and 0.1 volume of compound solution was added to 0.9 volumes of cell suspension; the final DMSO concentration was 1%. After room temperature incubation for 45 min, cells were lysed by incubation at 100° C. for 5 min to release accumulated cAMP.

cAMP was measured in an aliquot of the cell lysate with the Amersham (Arlington Heights, Ill.) cAMP detection assay (RPA556). The amount of cAMP production which resulted from an unknown compound was compared to that amount of cAMP produced in response to alpha-MSH which was defined as a 100% agonist. The $EC_{50}$ is defined as the compound concentration which results in half maximal stimulation, when compared to its own maximal level of stimulation.

Antagonist assay: Antagonist activity was defined as the ability of a compound to block cAMP production in response to alpha-MSH. Solution of test compounds and suspension of receptor containing cells were prepared and mixed as described above; the mixture was incubated for 15 min, and an $EC_{50}$ dose (approximately 10 nM alpha-MSH) was added to the cells. The assay was terminated at 45 min and cAMP quantitated as above. Percent inhibition was determined by comparing the amount of cAMP produced in the presence to that produced in the absence of test compound.

C. In Vivo Food Intake Models

1) Overnight food intake. Sprague Dawley rats are injected intracerebroventricularly with a test compound in 400 µL of 50% propylene glycol/artificial cerebrospinal fluid one hour prior to onset of dark cycle (12 hours). Food intake is determined using a computerized system in which each rat's food is placed on a computer monitored balance. Cumulative food intake for 16 h post compound administration is measured.

2) Food intake in diet induced obese mice. Male C57/B16J mice maintained on a high fat diet (60% fat calories) for 6.5 months from 4 weeks of age are are dosed intraperitoneally with test compound. Food intake and body weight are measured over an eight day period. Biochemical parameters relating to obesity, including leptin, insulin, triglyceride, free fatty acid, cholesterol and serum glucose levels are determined.

D. Rat Ex Copula Assay

Sexually mature male Caesarian Derived Sprague Dawley (CD) rats (over 60 days old) are used with the suspensory ligament surgically removed to prevent retraction of the penis back into the penile sheath during the ex copula evaluations. Animals receive food and water ad lib and are kept on a normal light/dark cycle. Studies are conducted during the light cycle.

1) Conditioning to Supine Restraint for Ex Copula Reflex Tests. This conditioning takes ~4 days. Day 1, the animals are placed in a darkened restrainer and left for 15-30 minutes. Day 2, the animals are restrained in a supine position in the restrainer for 15-30 minutes. Day 3, the animals are restrained in the supine position with the penile sheath retracted for 15-30 minutes. Day 4, the animals are restrained in the supine position with the penile sheath retracted until penile responses are observed. Some animals require additional days of conditioning before they are completely acclimated to the procedures; non-responders are removed from further evaluation. After any handling or evaluation animals are given a treat to ensure positive reinforcement.

2) Ex Copula Reflex Tests. Rats are gently restrained in a supine position with their anterior torso placed inside a cylinder of adequate size to allow for normal head and paw grooming. For a 400-500 gram rat, the diameter of the cylinder is approximately 8 cm. The lower torso and hind limbs are restrained with a non-adhesive material (vetrap). An additional piece of vetrap with a hole in it, through which the glans penis will be passed, is fastened over the animal to maintain the preputial sheath in a retracted position. Penile responses will be observed, typically termed ex copula genital reflex tests. Typically, a series of penile erections will occur spontaneously within a few minutes after sheath retraction. The types of normal reflexogenic erectile responses include elongation, engorgement, cup and flip. An elongation is classified as an extension of the penile body. Engorgement is a dilation of the glans penis. A cup is defined as an intense erection where the distal margin of the glans penis momentarily flares open to form a cup. A flip is a dorsiflexion of the penile body.

Baseline and or vehicle evaluations are conducted to determine how and if an animal will respond. Some animals have a long duration until the first response while others are non-responders altogether. During this baseline evaluation latency to first response, number and type of responses are recorded. The testing time frame is 15 minutes after the first response.

After a minimum of 1 day between evaluations, these same animals are administered the test compound at 20 mg/kg and evaluated for penile reflexes. All evaluations are videotaped and scored later. Data are collected and analyzed using paired 2 tailed t-tests to compared baseline and/or vehicle evaluations to drug treated evaluations for individual animals. Groups of a minimum of 4 animals are utilized to reduce variability.

Positive reference controls are included in each study to assure the validity of the study. Animals can be dosed by a number of routes of administration depending on the nature of the study to be performed. The routes of administration includes intravenous (IV), intraperitoneal (IP), subcutaneous (SC) and intracerebral ventricular (ICV).

E. Models of Female Sexual Dysfunction

Rodent assays relevant to female sexual receptivity include the behavioral model of lordosis and direct observations of copulatory activity. There is also a urethrogenital reflex model in anesthetized spinally transected rats for measuring orgasm in both male and female rats. These and other established animal models of female sexual dysfunction are described in McKenna K E et al, *A Model For The Study of Sexual Function In Anesthetized Male And Female Rats*, Am. J. Physiol. (Regulatory Integrative Comp. Physiol 30): R1276-R1285, 1991; McKenna K E et al, *Modulation By Peripheral Serotonin of The Threshold For Sexual Reflexes In Female Rats*, Pharm. Bioch. Behav., 40:151-156, 1991; and Takahashi L K et al, *Dual Estradiol Action In The Diencephalon And The Regulation Of Sociosexual Behavior In Female Golden Hamsters*, Brain Res., 359:194-207, 1985.

Representative compounds of the present invention were tested and found to bind to the melanocortin-4 receptor. These compounds were generally found to have $IC_{50}$ values less than 10 µM. Representative compounds of the present invention were also tested in the functional assay and found generally to activate the melanocortin-4 receptor with $EC_{50}$ values less than 5 µM.

Examples of Pharmaceutical Compositions

As a specific embodiment of an oral composition of a composition of the present invention, 5 mg of Example 1 is formulated with sufficient finely divided lactose to provide a total amount of 580 to 590 mg to fill a size O hard gelatin capsule.

As another specific embodiment of an oral composition of a compound of the present invention, 2.5 mg of Example 57 is formulated with sufficient finely divided lactose to provide a total amount of 580 to 590 mg to fill a size O hard gelatin capsule.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:
1. A compound of structural formula I:

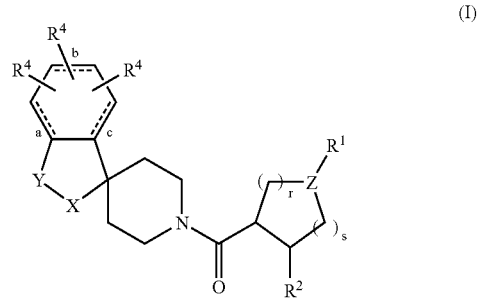

or a pharmaceutically acceptable salt thereof; wherein
a, b and c are all single bonds or all double bonds;
X and Y taken together form —C($R^6$)=C($R^6$)—, or
one of X and Y is C($R^6$)$_2$ and the other is selected from the group consisting of
(1) C($R^6$)$_2$,
(2) N($R^6$),
(3) C(O),
(4) C=N($R^6$)
(5) oxygen,
(6) sulfur,
(7) S(O), and
(8) S(O)$_2$, or one of X and Y is N(R$^9$) and the other is selected from the group consisting of
(1) C(R$^6$)$_2$,
(2) N(R$^9$),
(3) C(O),
(4) C=N(R$^6$)
(5) oxygen,
(6) sulfur,
(7) S(O), and
(8) S(O)$_2$,
or one of X and Y is C(O) and the other is selected from the group consisting of
(1) C(R$^6$)$_2$,
(2) N(R$^6$),
(3) C(O),
(4) C=N(R$^6$)
(5) oxygen, and
(6) sulfur;
Z is independently selected from the group consisting of
(1) CH,
(2) C(R$^1$), and
(3) N;
R$^1$ is selected from the group consisting of
(1) hydrogen,
(2) amidino,
(3) —(CH$_2$)$_n$—NR$^7$R$^8$,
(4) C$_{1-4}$ alkyliminoyl,
(5) C$_{1-10}$ alkyl,
(6) —(CH$_2$)$_n$—C$_{3-7}$ cycloalkyl,
(7) —(CH$_2$)$_n$-phenyl,
(8) —(CH$_2$)$_n$-naphthyl, and
(9) —(CH$_2$)$_n$-heteroaryl,
wherein phenyl, naphthyl, and heteroaryl are unsubstituted or substituted with one to three groups independently selected from R$^3$, and wherein alkyl and cycloalkyl are unsubstituted or substituted with one to three groups independently selected from R$^3$ and oxo;
R$^2$ is selected from the group consisting of
(1) phenyl,
(2) naphthyl, and
(3) heteroaryl,
wherein phenyl, naphthyl, and heteroaryl are unsubstituted or substituted with one to three groups independently selected from R$^3$;
each R$^3$ is independently selected from the group consisting of
(1) C$_{1-6}$ alkyl,
(2) —(CH$_2$)$_n$-phenyl,
(3) —(CH$_2$)$_n$-naphthyl,
(4) —(CH$_2$)$_n$-heteroaryl,
(5) —(CH$_2$)$_n$C$_{2-7}$ heterocycloalkyl,
(6) —(CH$_2$)$_n$C$_{3-7}$ cycloalkyl,
(7) halogen,
(8) OR$^5$,
(9) —(CH$_2$)$_n$N(R$^5$)$_2$,
(10) —(CH$_2$)$_n$C≡N,
(11) —(CH$_2$)$_n$CO$_2$R$^5$,
(12) NO$_2$,
(13) —(CH$_2$)$_n$NR$^5$S(O)$_p$R$^5$
(14) —(CH$_2$)$_n$S(O)$_p$N(R$^5$)$_2$,
(15) —(CH$_2$)$_n$S(O)$_p$R$^5$,
(16) —(CH$_2$)$_n$NR$^5$C(O)N(R$^5$)$_2$,
(17) —(CH$_2$)$_n$C(O)N(R$^5$)$_2$,
(18) —(CH$_2$)$_n$NR$^5$C(O)R$^5$,
(19) —(CH$_2$)$_n$NR$^5$CO$_2$R$^5$,
(20) —(CH$_2$)$_n$NR$^5$C(O)-heteroaryl,
(21) —(CH$_2$)$_n$C(O)NR$^5$N(R$^5$)$_2$,
(22) —(CH$_2$)$_n$C(O)NR$^5$NR$^5$C(O)R$^5$,
(23) O(CH$_2$)$_n$C(O)N(R$^5$)$_2$,
(24) CF$_3$,
(25) CH$_2$CF$_3$,
(26) OCF$_3$, and
(27) OCH$_2$CF$_3$,
wherein phenyl, naphthyl, and heteroaryl are unsubstituted or substituted with one to three substituents independently selected from halogen, hydroxy, C$_{1-4}$ alkyl, trifluoromethyl, and C$_{1-4}$ alkoxy, and wherein alkyl, cycloalkyl, heterocycloalkyl, and (CH$_2$) are unsubstituted or substituted with one to three substituents independently selected from halogen, hydroxy, oxo, C$_{1-4}$ alkyl, trifluoromethyl, and C$_{1-4}$ alkoxy, or wherein two substituents when on the same methylene (CH$_2$) group are taken together with the carbon atom to which they are attached to form a cyclopropyl group;
each R$^4$ is independently selected from the group consisting of
(1) hydrogen,
(2) C$_{1-8}$ alkyl,
(3) —(CH$_2$)$_n$-phenyl,
(4) —(CH$_2$)$_n$-naphthyl,
(5) —(CH$_2$)$_n$-heteroaryl,
(6) —(CH$_2$)$_n$C$_{2-7}$ heterocycloalkyl,
(7) —(CH$_2$)$_n$C$_{3-7}$ cycloalkyl,
(8) halogen,
(9) OR$^5$,
(10) —(CH$_2$)$_n$N(R$^5$)$_2$,
(11) —(CH$_2$)$_n$C≡N,
(12) —(CH$_2$)$_n$C(O)OR$^5$,
(13) —(CH$_2$)$_n$OC(O)R$^5$,
(14) NO$_2$,
(15) —(CH$_2$)$_n$NR$^5$S(O)$_p$R$^5$,
(16) —(CH$_2$)$_n$N(S(O)$_p$R$^5$)$_2$,
(17) —(CH$_2$)$_n$S(O)$_p$N(R$^5$)$_2$,
(18) —(CH$_2$)$_n$S(O)$_p$R$^5$,
(19) —(CH$_2$)$_n$NR$^5$C(O)N(R$^5$)$_2$,
(20) —(CH$_2$)$_n$C(O)N(R$^5$)$_2$,
(21) —(CH$_2$)$_n$NR$^5$C(O)R$^5$,
(22) —(CH$_2$)$_n$NR$^5$CO$_2$R$^5$,
(23) —(CH$_2$)$_n$NR$^5$C(O)-heteroaryl,
(24) —(CH$_2$)$_n$C(O)NR$^5$N(R$^5$)$_2$,
(25) —(CH$_2$)$_n$C(O)NR$^5$NR$^5$C(O)R$^5$,
(26) O(CH$_2$)$_n$C(O)N(R$^5$)$_2$,
(27) CF$_3$,
(28) CH$_2$CF$_3$,
(29) OCF$_3$, and
(30) OCH$_2$CF$_3$,
wherein phenyl, naphthyl, and heteroaryl are unsubstituted or substituted with one to three substituents independently selected from halogen, hydroxy, C$_{1-4}$ alkyl, trifluoromethyl, and C$_{1-4}$ alkoxy, and wherein alkyl, cycloalkyl, heterocycloalkyl, and (CH$_2$) are unsubstituted or substituted with one to three substituents independently selected from halogen, hydroxy, oxo, C$_{1-4}$ alkyl, trifluoromethyl, and C$_{1-4}$ alkoxy, or wherein two substituents when on the same methylene (CH$_2$) group are taken together with the carbon atom to which they are attached to form a cyclopropyl group;
each R$^5$ is independently selected from the group consisting of
(1) hydrogen,
(2) C$_{1-8}$ alkyl,
(3) —(CH$_2$)$_n$C$_{3-7}$ cycloalkyl,
(4) —(CH$_2$)$_n$C$_{2-7}$ heterocycloalkyl,
(5) —(CH$_2$)$_n$-phenyl, (6) —(CH$_2$)$_n$-naphthyl,
(7) —(CH$_2$)$_n$-heteroaryl, and
(8) —(CH$_2$)$_n$C$_{3-7}$ bicycloalkyl, wherein alkyl, phenyl, heteroaryl, heterocycloalkyl, naphthyl, cycloalkyl, bicycloalkyl and (CH$_2$) are unsubstituted or substituted with one to three groups independently selected from halogen, C$_{1-4}$ alkyl, hydroxy, and C$_{1-4}$ alkoxy, or wherein two R$^5$ groups together with the atom to which they are attached form a 4- to 8-membered mono- or bicyclic ring system optionally containing an additional heteroatom selected from O, S, and —NC$_{1-4}$ alkyl;

each R$^6$ is independently selected from the group consisting of
(1) hydrogen,
(2) C$_{1-6}$ alkyl,
(3) —(CH$_2$)$_n$C$_{3-7}$ cycloalkyl,
(4) —(CH$_2$)$_n$C$_{2-7}$ heterocycloalkyl,
(5) —(CH$_2$)$_n$-phenyl,
(6) —(CH$_2$)$_n$-naphthyl,
(7) —(CH$_2$)$_n$-heteroaryl,
(8) —(CH$_2$)$_n$C(O)R$^5$,
(9) —(CH$_2$)$_n$C(O)OR$^5$,
(10) —(CH$_2$)$_n$C(OH)R$^5$,
(11) —(CH$_2$)$_n$C(O)(CH$_2$)$_n$—N(R$^5$)$_2$,
(12) —(CH$_2$)$_n$C(O)(CH$_2$)$_n$—NR$^7$R$^8$,
(13) —(CH$_2$)$_n$—OR$^5$,
(14) —(CH$_2$)$_n$—OC(O)R$^5$,
(15) —(CH$_2$)$_n$—O—(CH$_2$)$_n$—N(R$^5$)$_2$,
(16) —(CH$_2$)$_n$CN,
(17) —(CH$_2$)$_n$N(R$^5$)$_2$,
(18) —(CH$_2$)$_n$N(R$^5$)C(O)R$^5$,
(19) —(CH$_2$)$_n$N(C(O)R$^5$)$_2$,
(20) —(CH$_2$)$_n$N(R$^5$)C(O)OR$^5$,
(21) —(CH$_2$)$_n$N(C(O)OR$^5$)$_2$,
(22) —(CH$_2$)$_n$N(R$^5$)C(O)(CH$_2$)$_n$N(R$^5$)$_2$,
(23) —(CH$_2$)$_n$N(R$^5$)—S(O)—C$_{1-8}$ alkyl,
(24) —(CH$_2$)$_n$N(R$^5$)S(O)$_2$—C$_{1-8}$ alkyl,
(25) —(CH$_2$)$_n$—S—R$^5$,
(26) —(CH$_2$)$_n$—S(O)—R$^5$, and
(27) —(CH$_2$)$_n$—S(O)$_2$—R$^5$, wherein phenyl, naphthyl, and heteroaryl are unsubstituted or substituted with one to three groups independently selected from R$^3$, and wherein alkyl, cycloalkyl and heterocycloalkyl are unsubstituted or substituted with one to three groups independently selected from R$^3$ and oxo, and wherein any methylene (CH$_2$) in R$^6$ is unsubstituted or substituted with one to two groups independently selected from halogen, hydroxy, and C$_{1-4}$ alkyl, or wherein two R$^6$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from R$^3$ and oxo;

each R$^7$ and R$^8$ is independently selected from the group consisting of
(1) hydrogen,
(2) amidino,
(3) C$_{1-4}$ alkyliminoyl,
(4) C$_{1-10}$ alkyl,
(5) —(CH$_2$)$_n$—C$_{3-7}$ cycloalkyl,
(6) —(CH$_2$)$_n$-phenyl,
(7) —(CH$_2$)$_n$-naphthyl, and
(8) —(CH$_2$)$_n$-heteroaryl, wherein phenyl, naphthyl, and heteroaryl are unsubstituted or substituted with one to three groups independently selected from R$^3$, and wherein alkyl and cycloalkyl are unsubstituted or substituted with one to three groups independently selected from R$^3$ and oxo;

each R$^9$ is independently selected from the group consisting of
(1) hydrogen,
(2) C$_{1-6}$ alkyl,
(3) —(CH$_2$)$_n$C$_{3-7}$ cycloalkyl,
(4) —(CH$_2$)$_n$C$_{2-7}$ heterocycloalkyl,
(5) —(CH$_2$)$_n$-phenyl,
(6) —(CH$_2$)$_n$-naphthyl,
(7) —(CH$_2$)$_n$-heteroaryl,
(8) —(CH$_2$)$_n$C(O)R$^5$,
(9) —(CH$_2$)$_n$C(O)OR$^5$,
(10) —(CH$_2$)$_n$C(OH)R$^5$,
(11) —(CH$_2$)$_n$C(O)(CH$_2$)$_n$—N(R$^5$)$_2$,
(12) —(CH$_2$)$_n$C(O)(CH$_2$)$_n$—NR$^7$R$^8$,
(13) —(CH$_2$)$_m$—OR$^5$,
(14) —(CH$_2$)$_m$—OC(O)R$^5$,
(15) —(CH$_2$)$_m$—O—(CH$_2$)$_n$—N(R$^5$)$_2$,
(16) —(CH$_2$)$_m$CN,
(17) —(CH$_2$)$_m$N(R$^5$)$_2$,
(18) —(CH$_2$)$_m$N(R$^5$)C(O)R$^5$,
(19) —(CH$_2$)$_m$N(C(O)R$^5$)$_2$,
(20) —(CH$_2$)$_m$N(R$^5$)C(O)OR$^5$,
(21) —(CH$_2$)$_m$N(C(O)OR$^5$)$_2$,
(22) —(CH$_2$)$_m$N(R$^5$)C(O)(CH$_2$)$_n$N(R$^5$)$_2$,
(23) —(CH$_2$)$_m$N(R$^5$)—S(O)—C$_{1-8}$ alkyl,
(24) —(CH$_2$)$_m$N(R$^5$)—S(O)$_2$—C$_{1-8}$ alkyl,
(25) —(CH$_2$)$_m$—S—R$^5$,
(26) —(CH$_2$)$_n$—S(O)—R$^5$, and
(27) —(CH$_2$)$_n$—S(O)$_2$—R$^5$, wherein phenyl, naphthyl, and heteroaryl are unsubstituted or substituted with one to three groups independently selected from R$^3$, and wherein alkyl, cycloalkyl and heterocycloalkyl are unsubstituted or substituted with one to three groups independently selected from R$^3$ and oxo, and wherein any methylene (CH$_2$) in R$^9$ is unsubstituted or substituted with one to two groups independently selected from halogen, hydroxy, and C$_{1-4}$ alkyl; or wherein two R$^9$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from R$^3$ and oxo;

r is 1 or 2;
s is 1 or 2;
n is 0, 1, 2, or 3;
m is 1, 2, or 3; and
p is 0, 1, or 2.

2. The compound of claim 1 wherein R$^1$ is selected from the group consisting of hydrogen, C$_{1-6}$ alkyl, —(CH$_2$)$_{0-1}$—C$_{3-6}$ cycloalkyl, —(CH$_2$)$_{0-1}$-phenyl, and —(CH$_2$)$_{0-1}$—NR$^7$R$^8$, wherein phenyl is unsubstituted or substituted with one to three groups independently selected from R$^3$, and wherein alkyl and cycloalkyl are optionally substituted with one to three groups independently selected from R$^3$ and oxo, and pharmaceutically acceptable salts thereof.

3. The compound of claim 1 wherein R$^2$ is phenyl or thienyl optionally substituted with one to three groups independently selected from R$^3$, and pharmaceutically acceptable salts thereof.

4. The compound of claim 3 wherein $R^2$ is phenyl optionally substituted with one to three groups independently selected from $R^3$, and pharmaceutically acceptable salts thereof.

5. The compound of claim 4 wherein X and Y are independently selected from the group consisting of $C(R^6)_2$, $N(R^9)$, and C(O), or X and Y taken together form —$C(R^6)$=$C(R^6)$—, and pharmaceutically acceptable salts thereof.

6. The compound of claim 5 wherein $R^4$ is selected from the group consisting of hydrogen, $C_{1-6}$ alkyl, halogen, $OR^5$, —$(CH_2)_nN(R^5)_2$, —$(CH_2)_nC\equiv N$, —$(CH_2)_nNR^5SO_2R^5$, —$(CH_2)_nN(S(O)_2R^5)_2$, and —$(CH_2)_nNR^5C(O)R^5$, wherein alkyl and $(CH_2)$ are unsubstituted or substitute with one to three substituents independently selected from halogen, hydroxy, oxo, $C_{1-4}$ alkyl, trifluoromethyl, and $C_{1-4}$ alkoxy, or wherein two substituents when on the same methylene ($CH_2$) group are taken together with the carbon atom to which they are attached to form a cyclopropyl group, and pharmaceutically acceptable salts thereof.

7. The compound of claim 5 wherein Z is CH.

8. The compound of claim 6 wherein Z is N.

9. The compound of claim 1 of structural formula IIa or IIb of the indicated trans relative stereochemical configuration:

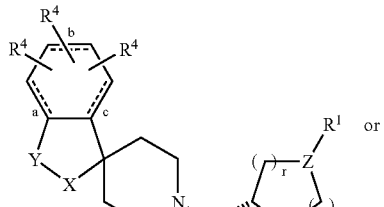

(IIa)

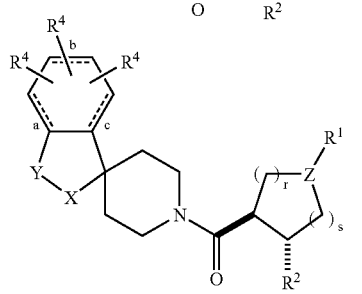

(IIb)

or a pharmaceutically acceptable salt thereof; wherein
a, b and c are all single bonds or all double bonds;
X and Y taken together form —$C(R^6)$=$C(R^6)$—, or
one of X and Y is $C(R^6)_2$ and the other is selected from the group consisting of
  (1) $C(R^6)_2$,
  (2) $N(R^6)$,
  (3) C(O),
  (4) C=$N(R^6)$
  (5) oxygen,
  (6) sulfur,
  (7) S(O), and
  (8) $S(O)_2$,
or one of X and Y is $N(R^9)$ and the other is selected from the group consisting of
  (1) $C(R^6)_2$,
  (2) $N(R^9)$,
  (3) C(O),
  (4) C=$N(R^6)$
  (5) oxygen,
  (6) sulfur,
  (7) S(O), and
  (8) $S(O)_2$,
or one of X and Y is C(O) and the other is selected from the group consisting of
  (1) $C(R^6)_2$,
  (2) $N(R^6)$,
  (3) C(O),
  (4) C=$N(R^6)$
  (5) oxygen, and
  (6) sulfur;
Z is independently selected from the group consisting of
  (1) CH,
  (2) $C(R^1)$, and
  (3) N;
$R^1$ is selected from the group consisting of hydrogen, amidino, $C_{1-4}$ alkyliminoyl, $C_{1-6}$ alkyl, $C_{5-6}$ cycloalkyl, —$(CH_2)_{0-1}$ phenyl, —$(CH_2)_{0-1}$ heteroaryl, and —$(CH_2)_{0-1}$—$NR^7R^8$, wherein phenyl and heteroaryl are unsubstituted or substituted with one to three groups independently selected from $R^3$, and wherein alkyl and cycloalkyl are unsubstituted or substituted with one to three groups independently selected from $R^3$ and oxo;
$R^2$ is phenyl or thienyl optionally substituted with one to three groups independently selected from $R^3$;
each $R^3$ is independently selected from the group consisting of
  (1) $C_{1-6}$ alkyl,
  (2) —$(CH_2)_n$-phenyl,
  (3) —$(CH_2)_n$-naphthyl,
  (4) —$(CH_2)_n$-heteroaryl,
  (5) —$(CH_2)_nC_{2-7}$ heterocycloalkyl,
  (6) —$(CH_2)_nC_{3-7}$ cycloalkyl,
  (7) halogen,
  (8) $OR^5$,
  (9) —$(CH_2)_nN(R^5)_2$,
  (10) —$(CH_2)_nC\equiv N$,
  (11) —$(CH_2)_nCO_2R^5$,
  (12) $NO_2$,
  (13) —$(CH_2)_nNR^5S(O)_pR^5$
  (14) —$(CH_2)_nS(O)_pN(R^5)_2$,
  (15) —$(CH_2)_nS(O)_pR^5$,
  (16) —$(CH_2)_nNR^5C(O)N(R^5)_2$,
  (17) —$(CH_2)_nC(O)N(R^5)_2$,
  (18) —$(CH_2)_nNR^5C(O)R^5$,
  (19) —$(CH_2)_nNR^5CO_2R^5$,
  (20) —$(CH_2)_nNR^5C(O)$-heteroaryl,
  (21) —$(CH_2)_nC(O)NR^5N(R^5)_2$,
  (22) —$(CH_2)_nC(O)NR^5NR^5C(O)R^5$,
  (23) $O(CH_2)_nC(O)N(R^5)_2$,
  (24) $CF_3$,
  (25) $CH_2CF_3$,
  (26) $OCF_3$, and
  (27) $OCH_2CF_3$,
wherein phenyl, naphthyl, and heteroaryl are unsubstituted or substituted with one to three substituents independently selected from halogen, hydroxy, $C_{1-4}$ alkyl, trifluoromethyl, and $C_{1-4}$ alkoxy, and wherein alkyl, cycloalkyl, heterocycloalkyl, and ($CH_2$) are unsubstituted or substituted with one to three substituents independently selected from halogen, hydroxy, oxo, $C_{1-4}$ alkyl, trifluoromethyl, and $C_{1-4}$ alkoxy, or wherein two substituents when on the same methylene ($CR^2$) group are taken together with the carbon atom to which they are attached to form a cyclopropyl group;

each $R^4$ is independently selected from the group consisting of
(1) hydrogen,
(2) $C_{1-8}$ alkyl,
(3) —$(CH_2)_n$-phenyl,
(4) —$(CH_2)_n$-naphthyl,
(5) —$(CH_2)_n$-heteroaryl,
(6) —$(CH_2)_nC_{2-7}$ heterocycloalkyl,
(7) —$(CH_2)_nC_{3-7}$ cycloalkyl,
(8) halogen,
(9) $OR^5$,
(10) —$(CH_2)_nN(R^5)_2$,
(11) —$(CH_2)_nC\equiv N$,
(12) —$(CH_2)_nC(O)OR^5$,
(13) —$(CH_2)_nOC(O)R^5$,
(14) $NO_2$,
(15) —$(CH_2)_nNR^5S(O)_pR^5$,
(16) —$(CH_2)_nN(S(O)_pR^5)_2$,
(17) —$(CH_2)_nS(O)_pN(R^5)_2$,
(18) —$(CH_2)_nS(O)_pR^5$,
(19) —$(CH_2)_nNR^5C(O)N(R^5)_2$,
(20) —$(CH_2)_nC(O)N(R^5)_2$,
(21) —$(CH_2)_nNR^5C(O)R^5$,
(22) —$(CH_2)_nNR^5CO_2R^5$,
(23) —$(CH_2)_nNR^5C(O)$-heteroaryl,
(24) —$(CH_2)_nC(O)NR^5N(R^5)_2$,
(25) —$(CH_2)_nC(O)NR^5NR^5C(O)R^5$,
(26) $O(CH_2)_nC(O)N(R^5)_2$,
(27) $CF_3$,
(28) $CH_2CF_3$,
(29) $OCF_3$, and
(30) $OCH_2CF_3$,
wherein phenyl, naphthyl, and heteroaryl are unsubstituted or substituted with one to three substituents independently selected from halogen, hydroxy, $C_{1-4}$ alkyl, trifluoromethyl, and $C_{1-4}$ alkoxy, and wherein alkyl, cycloalkyl, heterocycloalkyl, and $(CH_2)$ are unsubstituted or substituted with one to three substituents independently selected from halogen, hydroxy, oxo, $C_{1-4}$ alkyl, trifluoromethyl, and $C_{1-4}$ alkoxy, or wherein two substituents when on the same methylene $(CH_2)$ group are taken together with the carbon atom to which they are attached to form a cyclopropyl group;
each $R^5$ is independently selected from the group consisting of
(1) hydrogen,
(2) $C_{1-8}$ alkyl,
(3) —$(CH_2)_nC_{3-7}$ cycloalkyl,
(4) —$(CH_2)_nC_{2-7}$ heterocycloalkyl,
(5) —$(CH_2)_n$-phenyl,
(6) —$(CH_2)_n$-naphthyl,
(7) —$(CH_2)_n$-heteroaryl, and
(8) —$(CH_2)_nC_{3-7}$ bicycloalkyl,
wherein alkyl, phenyl, heteroaryl, heterocycloalkyl, naphthyl, cycloalkyl, bicycloalkyl and $(CH_2)$ are unsubstituted or substituted with one to three groups independently selected from halogen, $C_{1-4}$ alkyl, hydroxy, and $C_{1-4}$ alkoxy, or wherein two $R^5$ groups together with the atom to which they are attached form a 4- to 8-membered mono- or bicyclic ring system optionally containing an additional heteroatom selected from O, S, and —$NC_{1-4}$ alkyl;
each $R^6$ is independently selected from the group consisting of
(1) hydrogen,
(2) $C_{1-6}$ alkyl,
(3) —$(CH_2)_nC_{3-7}$ cycloalkyl,
(4) —$(CH_2)_nC_{2-7}$ heterocycloalkyl,
(5) —$(CH_2)_n$-phenyl,
(6) —$(CH_2)_n$-naphthyl,
(7) —$(CH_2)_n$-heteroaryl,
(8) —$(CH_2)_nC(O)R^5$,
(9) —$(CH_2)_nC(O)OR^5$,
(10) —$(CH_2)_nC(OH)R^5$,
(11) —$(CH_2)_nC(O)(CH_2)_n$—$N(R^5)_2$,
(12) —$(CH_2)_nC(O)(CH_2)_n$—$NR^7R^8$,
(13) —$(CH_2)_n$—$OR^5$,
(14) —$(CH_2)_n$—$OC(O)R^5$,
(15) —$(CH_2)_n$—O—$(CH_2)_n$—$N(R^5)_2$,
(16) —$(CH_2)_nCN$,
(17) —$(CH_2)_nN(R^5)_2$,
(18) —$(CH_2)_nN(R^5)C(O)R^5$,
(19) —$(CH_2)_nN(C(O)R^5)_2$,
(20) —$(CH_2)_nN(R^5)C(O)OR^5$,
(21) —$(CH_2)_nN(C(O)OR^5)_2$,
(22) —$(CH_2)_nN(R^5)C(O)(CH_2)_nN(R^5)_2$,
(23) —$(CH_2)_nN(R^5)$—S(O)—$C_{1-8}$ alkyl,
(24) —$(CH_2)_nN(R^5)$—$S(O)_2$—$C_{1-8}$ alkyl,
(25) —$(CH_2)_n$—S—$R^5$,
(26) —$(CH_2)_n$—S(O)—$R^5$, and
(27) —$(CH_2)_n$—$S(O)_2$—$R^5$,
wherein phenyl, naphthyl, and heteroaryl are unsubstituted or substituted with one to three groups independently selected from $R^3$, and wherein alkyl, cycloalkyl and heterocycloalkyl are unsubstituted or substituted with one to three groups independently selected from $R^3$ and oxo, and wherein any methylene $(CH_2)$ in $R^6$ is unsubstituted or substituted with one to two groups independently selected from halogen, hydroxy, and $C_{1-4}$ alkyl, or wherein two $R^6$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from $R^3$ and oxo;
each $R^7$ and $R^8$ is independently selected from the group consisting of
(1) hydrogen,
(2) amidino,
(3) $C_{1-4}$ alkyliminoyl,
(4) $C_{1-10}$ alkyl,
(5) —$(CH_2)_n$—$C_{3-7}$ cycloalkyl,
(6) —$(CH_2)_n$-phenyl,
(7) —$(CH_2)_n$-naphthyl, and
(8) —$(CH_2)_n$-heteroaryl,
wherein phenyl, naphthyl, and heteroaryl are unsubstituted or substituted with one to three groups independently selected from $R^3$, and wherein alkyl and cycloalkyl are unsubstituted or substituted with one to three groups independently selected from $R^3$ and oxo;
each $R^9$ is independently selected from the group consisting of
(1) hydrogen,
(2) $C_{1-6}$ alkyl,
(3) —$(CH_2)_nC_{3-7}$ cycloalkyl,
(4) —$(CH_2)_nC_{2-7}$ heterocycloalkyl,
(5) —$(CH_2)_n$-phenyl,
(6) —$(CH_2)_n$-naphthyl,
(7) —$(CH_2)_n$-heteroaryl,
(8) —$(CH_2)_nC(O)R^5$, (9) —(CH$_2$)$_n$C(O)OR$^5$,
(10) —(CH$_2$)$_n$C(OH)R$^5$,
(11) —(CH$_2$)$_n$C(O)(CH$_2$)$_n$—N(R$^5$)$_2$,
(12) —(CH$_2$)$_n$C(O)(CH$_2$)$_n$—NR$^7$R$^8$,
(13) —(CH$_2$)$_m$—OR$^5$,
(14) —(CH$_2$)$_m$—OC(O)R$^5$,
(15) —(CH$_2$)$_m$—O—(CH$_2$)$_n$—N(R$^5$)$_2$,
(16) —(CH$_2$)$_m$CN,
(17) —(CH$_2$)$_m$N(R$^5$)$_2$,
(18) —(CH$_2$)$_m$N(R$^5$)C(O)R$^5$,
(19) —(CH$_2$)$_m$N(C(O)R$^5$)$_2$,
(20) —(CH$_2$)$_m$N(R$^5$)C(O)OR$^5$,
(21) —(CH$_2$)$_m$N(C(O)OR$^5$)$_2$,
(22) —(CH$_2$)$_m$N(R$^5$)C(O)(CH$_2$)$_n$N(R$^5$)$_2$,
(23) —(CH$_2$)$_m$N(R$^5$)—S(O)—C$_{1-8}$ alkyl,
(24) —(CH$_2$)$_m$N(R$^5$)—S(O)$_2$—C$_{1-8}$ alkyl,
(25) —(CH$_2$)$_m$—S—R$^5$,
(26) —(CH$_2$)$_n$—S(O)—R$^5$, and
(27) —(CH$_2$)$_n$—S(O)$_2$—R$^5$, wherein phenyl, naphthyl, and heteroaryl are unsubstituted or substituted with one to three groups independently selected from R$^3$, and wherein alkyl, cycloalkyl and heterocycloalkyl are unsubstituted or substituted with one to three groups independently selected from R$^3$ and oxo, and wherein any methylene (CH$_2$) in R$^9$ is unsubstituted or substituted with one to two groups independently selected from halogen, hydroxy, and C$_{1-4}$ alkyl; or wherein two R$^9$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from R$^3$ and oxo;

r is 1 or 2;
s is 1 or 2;
n is 0, 1, 2, or 3;
m is 1, 2 or 3; and
p is 0, 1, or 2.

10. The compound of claim 1 of structural formula IIIa or IIIb of the indicated trans relative stereochemical configuration:

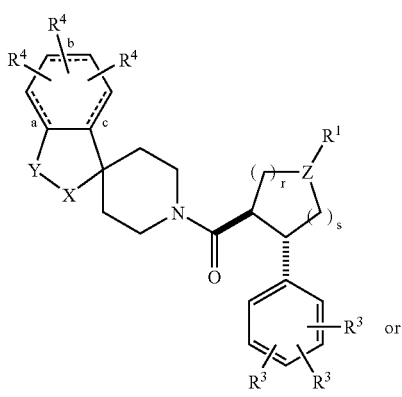

(IIIa)

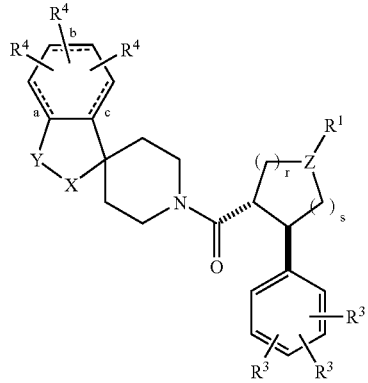

(IIIb)

or a pharmaceutically acceptable salt thereof; wherein
a, b and c are all single bonds or all double bonds;
X and Y taken together form —C(R$^6$)=C(R$^6$)—, or one of X and Y is C(R$^6$)$_2$ and the other is selected from the group consisting of
(1) C(R$^6$)$_2$,
(2) N(R$^6$),
(3) C(O),
(4) C=N(R$^6$)
(5) oxygen,
(6) sulfur,
(7) S(O), and
(8) S(O)$_2$,
or one of X and Y is N(R$^9$) and the other is selected from the group consisting of
(1) C(R$^6$)$_2$,
(2) N(R$^9$),
(3) C(O),
(4) C=N(R$^6$)
(5) oxygen,
(6) sulfur,
(7) S(O), and
(8) S(O)$_2$,
or one of X and Y is C(O) and the other is selected from the group consisting of
(1) C(R$^6$)$_2$,
(2) N(R$^6$),
(3) C(O),
(4) C=N(R$^6$)
(5) oxygen, and
(6) sulfur;
Z is independently selected from the group consisting of
(1) CH,
(2) C(R$^1$), and
(3) N;
R$^1$ is selected from the group consisting of hydrogen, C$_{1-4}$ alkyl, —(CH$_2$)$_{0-1}$-phenyl, and —(CH$_2$)$_{0-1}$—NR$^7$R$^8$;
each R$^3$ is independently selected from the group consisting of
(1) C$_{1-6}$ alkyl,
(2) —(CH$_2$)$_{0-1}$-phenyl,
(3) —(CH$_2$)$_{0-1}$-naphthyl,
(4) —(CH$_2$)$_{0-1}$-heteroaryl,
(5) —(CH$_2$)$_{0-1}$—C$_{2-7}$ heterocycloalkyl,
(6) —(CH$_2$)$_{0-1}$—C$_{3-7}$ cycloalkyl,
(7) halogen,
(8) OR$^5$,
(9) —(CH$_2$)$_{0-1}$—N(R$^5$)$_2$,

(10) —$(CH_2)_{0-1}$—C≡N,
(11) —$(CH_2)_{0-1}$—$CO_2R^5$,
(12) $NO_2$,
(13) —$(CH_2)_{0-1}$—$NR^5S(O)_{1-2}R^5$,
(14) —$(CH_2)_{0-1}$—$S(O)_{1-2}N(R^5)_2$,
(15) —$(CH_2)_{0-1}$—$S(O)_{0-2}R^5$,
(16) —$(CH_2)_{0-1}$—$NR^5C(O)N(R^5)_2$,
(17) —$(CH_2)_{0-1}$—$C(O)N(R^5)_2$,
(18) —$(CH_2)_{0-1}$—$NR^5C(O)R^5$,
(19) —$(CH_2)_{0-1}$—$NR^5CO_2R^5$,
(20) —$(CH_2)_{0-1}$—$NR^5C(O)$-heteroaryl,
(21) —$(CH_2)_{0-1}$—$C(O)NR^5N(R^5)_2$,
(22) —$(CH_2)_{0-1}$—$C(O)NR^5NR^5C(O)R^5$,
(23) $O(CH_2)_{0-1}$—$C(O)N(R^5)_2$,
(24) $CF_3$,
(25) $CH_2CF_3$,
(26) $OCF_3$, and
(27) $OCH_2CF_3$,
wherein phenyl, naphthyl, and heteroaryl are unsubstituted or substituted with one to three substituents independently selected from halogen, hydroxy, $C_{1-4}$ alkyl, trifluoromethyl, and $C_{1-4}$ alkoxy, and wherein alkyl, cycloalkyl, heterocycloalkyl, and ($CH_2$) are unsubstituted or substituted with one to three substituents independently selected from halogen, hydroxy, oxo, $C_{1-4}$ alkyl, trifluoromethyl, and $C_{1-4}$ alkoxy, or wherein two substituents when on the same methylene ($CH_2$) group are taken together with the carbon atom to which they are attached to form a cyclopropyl group;

each $R^4$ is independently selected from the group consisting of
(1) hydrogen,
(2) $C_{1-8}$ alkyl,
(3) —$(CH_2)_{0-1}$-phenyl,
(4) —$(CH_2)_{0-1}$-naphthyl,
(5) —$(CH_2)_{0-1}$-heteroaryl,
(6) —$(CH_2)_{0-1}$—$C_{2-7}$ heterocycloalkyl,
(7) —$(CH_2)_{0-1}$—$C_{3-7}$ cycloalkyl,
(8) halogen,
(9) $OR^5$,
(10) —$(CH_2)_{0-1}$—$N(R^5)_2$,
(11) —$(CH_2)_{0-1}$—C≡N,
(12) —$(CH_2)_{0-1}$—$C(O)OR^5$,
(13) —$(CH_2)_{0-1}$—$OC(O)R^5$,
wherein alkyl, phenyl, heteroaryl, heterocycloalkyl, naphthyl, cycloalkyl, bicycloalkyl and ($CH_2$) are unsubstituted or substituted with one to three groups independently selected from halogen, $C_{1-4}$ alkyl, hydroxy, and $C_{1-4}$ alkoxy, or wherein two $R^5$ groups together with the atom to which they are attached form a 4- to 8-membered mono- or bicyclic ring system optionally containing an additional heteroatom selected from O, S, and —$NC_{1-4}$ alkyl;

each $R^6$ is independently selected from the group consisting of
(1) hydrogen,
(2) $C_{1-6}$ alkyl,
(3) —$(CH_2)_{0-1}$—$C_{3-7}$ cycloalkyl,
(4) —$(CH_2)_{0-1}$—$C_{2-7}$ heterocycloalkyl,
(5) —$(CH_2)_{0-1}$-phenyl,
(6) —$(CH_2)_{0-1}$-naphthyl,
(7) —$(CH_2)_{0-1}$-heteroaryl,
(8) —$(CH_2)_{0-1}$—$C(O)R^5$,
(9) —$(CH_2)_{0-1}$—$C(O)OR^5$,
(10) —$(CH_2)_{0-1}$—$C(OH)R^5$,
(11) —$(CH_2)_{0-1}$—$C(O)(CH_2)_{0-1}$—$N(R^5)_2$,
(12) —$(CH_2)_{0-1}$—$C(O)(CH_2)_{0-1}$—$NR^7R^8$,
(13) —$(CH_2)_{0-1}$—$OR^5$,
(14) —$(CH_2)_{0-1}$—$OC(O)R^5$,
(15) —$(CH_2)_{0-1}$—O—$(CH_2)_{1-2}$—$N(R^5)_2$,
(16) —$(CH_2)_{0-1}$—CN,
(17) —$(CH_2)_{0-3}$—$N(R^5)_2$,
(18) —$(CH_2)_{0-3}$—$N(R^5)C(O)R^5$,
(19) —$(CH_2)_{0-3}$—$N(C(O)R^5)_2$,
(20) —$(CH_2)_{0-3}$—$N(R^5)C(O)OR^5$,
(21) —$(CH_2)_{0-1}$—$N(C(O)OR^5)_2$,
(22) —$(CH_2)_{0-1}$—$N(R^5)C(O)(CH_2)_{0-1}N(R^5)_2$,
(23) —$(CH_2)_{0-3}$—$N(R^5)$—S(O)—$C_{1-8}$ alkyl,
(24) —$(CH_2)_{0-3}$—$N(R^5)$—$S(O)_2$—$C_{1-8}$ alkyl,
(25) —$(CH_2)_{0-1}$—S—$R^5$,
(26) —$(CH_2)_{0-1}$—S(O)—$R^5$, and
(27) —$(CH_2)_{0-1}$—$S(O)_2$—$R^5$,
(14) $NO_2$,
(15) —$(CH_2)_{0-1}$—$NR^5S(O)_{1-2}$—$R^5$,
(16) —$(CH_2)_{0-1}$—$N(S(O)_{1-2}$—$R^5)_2$,
(17) —$(CH_2)_{0-1}$—$S(O)_{1-2}$—$N(R^5)_2$,
(18) —$(CH_2)_{0-1}$—$S(O)_{0-2}$—$R^5$,
(19) —$(CH_2)_{0-1}$—$NR^5C(O)N(R^5)_2$,
(20) —$(CH_2)_{0-1}$—$C(O)N(R^5)_2$,
(21) —$(CH_2)_{0-1}$—$NR^5C(O)R^5$,
(22) —$(CH_2)_{0-1}$—$NR^5CO_2R^5$,
(23) —$(CH_2)_{0-1}$—$NR^5C(O)$-heteroaryl,
(24) —$(CH_2)_{0-1}$—$C(O)NR^5N(R^5)_2$,
(25) —$(CH_2)_{0-1}$—$C(O)NR^5NR^5C(O)R^5$,
(26) $O(CH_2)_{0-1}$—$C(O)N(R^5)_2$,
(27) $CF_3$,
(28) $CH_2CF_3$,
(29) $OCF_3$, and
(30) $OCH_2CF_3$,
wherein phenyl, naphthyl, and heteroaryl are unsubstituted or substituted with one to three substituents independently selected from halogen, hydroxy, $C_{1-4}$ alkyl, trifluoromethyl, and $C_{1-4}$ alkoxy, and wherein alkyl, cycloalkyl, heterocycloalkyl, and ($CH_2$) are unsubstituted or substituted with one to three substituents independently selected from halogen, hydroxy, oxo, $C_{1-4}$ alkyl, trifluoromethyl, and $C_{1-4}$ alkoxy, or wherein two substituents when on the same methylene ($CH_2$) group are taken together with the carbon atom to which they are attached to form a cyclopropyl group;

each $R^5$ is independently selected from the group consisting of
(1) hydrogen,
(2) $C_{1-8}$ alkyl,
(3) —$(CH_2)_{0-1}$—$C_{3-7}$ cycloalkyl,
(4) —$(CH_2)_{0-1}$—$C_{2-7}$ heterocycloalkyl,
(5) —$(CH_2)_{0-1}$-phenyl,
(6) —$(CH_2)_{0-1}$-naphthyl,
(7) —$(CH_2)_{0-1}$-heteroaryl, and
(8) —$(CH_2)_{0-1}$—$C_{3-7}$ bicycloalkyl,
wherein phenyl, naphthyl, and heteroaryl are unsubstituted or substituted with one to three groups independently selected from $R^3$, and wherein alkyl, cycloalkyl and heterocycloalkyl are unsubstituted or substituted with one to three groups independently selected from $R^3$ and oxo, and wherein any methylene ($CH_2$) in $R^6$ is unsubstituted or substituted with one to two groups independently selected from halogen, hydroxy, and $C_{1-4}$ alkyl, or wherein two $R^6$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from $R^3$ and oxo;

each $R^7$ and $R^8$ is independently selected from the group consisting of
(1) hydrogen,
(2) amidino,
(3) $C_{1-4}$ alkyliminoyl,
(4) $C_{1-10}$ alkyl,
(5) —$(CH_2)_{0-1}$—$C_{3-7}$ cycloalkyl,
(6) —$(CH_2)_{0-1}$-phenyl,
(7) —$(CH_2)_{0-1}$-naphthyl, and
(8) —$(CH_2)_{0-1}$-heteroaryl,
wherein phenyl, naphthyl, and heteroaryl are unsubstituted or substituted with one to three groups independently selected from $R^3$, and wherein alkyl and cycloalkyl are unsubstituted or substituted with one to three groups independently selected from $R^3$ and oxo;

each $R^9$ is independently selected from the group consisting of
(1) hydrogen,
(2) $C_{1-6}$ alkyl,
(3) —$(CH_2)_{0-1}$—$C_{3-7}$ cycloalkyl,
(4) —$(CH_2)_{0-1}$—$C_{2-7}$ heterocycloalkyl,
(5) —$(CH_2)_{0-1}$-phenyl,
(6) —$(CH_2)_{0-1}$-naphthyl,
(7) —$(CH_2)_{0-1}$-heteroaryl,
(8) —$(CH_2)_{0-1}$—$C(O)R^5$,
(9) —$(CH_2)_{0-1}$—$C(O)OR^5$,
(10) —$(CH_2)_{0-1}$—$C(OH)R^5$,
(11) —$(CH_2)_{0-1}$—$C(O)(CH_2)_{0-1}$—$N(R^5)_2$,
(12) —$(CH_2)_{0-1}$—$C(O)(CH_2)_{0-1}$—$NR^7R^5$,
(13) —$(CH_2)_{1-3}$—$OR^5$,
(14) —$(CH_2)_{1-3}$—$OC(O)R^5$,
(15) —$(CH_2)_{1-3}$—O—$(CH_2)_{1-2}$—$N(R^5)_2$,
(16) —$(CH_2)_{1-3}$—CN,
(17) —$(CH_2)_{1-3}$—$N(R^5)_2$,
(18) —$(CH_2)_{1-3}$—$N(R^5)C(O)R^5$,
(19) —$(CH_2)_{1-3}$—$N(C(O)R^5)_2$,
(20) —$(CH_2)_{1-3}$—$N(R^5)C(O)OR^5$,
(21) —$(CH_2)_{1-3}$—$N(C(O)OR^5)_2$,
(22) —$(CH_2)_{1-3}$—$N(R^5)C(O)(CH_2)_{0-1}N(R^5)_2$,
(23) —$(CH_2)_{1-3}$—$N(R^5)$—$S(O)$—$C_{1-8}$ alkyl,
(24) —$(CH_2)_{1-3}$—$N(R^5)$—$S(O)_2$—$C_{1-8}$ alkyl,
(25) —$(CH_2)_{1-3}$—S—$R^5$,
(26) —$(CH_2)_{0-1}$—$S(O)$—$R^5$, and
(27) —$(CH_2)_{0-1}$—$S(O)_2$—$R^5$,
wherein phenyl, naphthyl, and heteroaryl are unsubstituted or substituted with one to three groups independently selected from $R^3$, and wherein alkyl, cycloalkyl and heterocycloalkyl are unsubstituted or substituted with one to three groups independently selected from $R^3$ and oxo, and wherein any methylene ($CH_2$) in $R^9$ is unsubstituted or substituted with one to two groups independently selected from halogen, hydroxy, and $C_{1-4}$ alkyl; or wherein two $R^9$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from $R^3$ and oxo;

r is 1 or 2; and
s is 1 or 2.

11. The compound of claim 10 selected from the group consisting of:

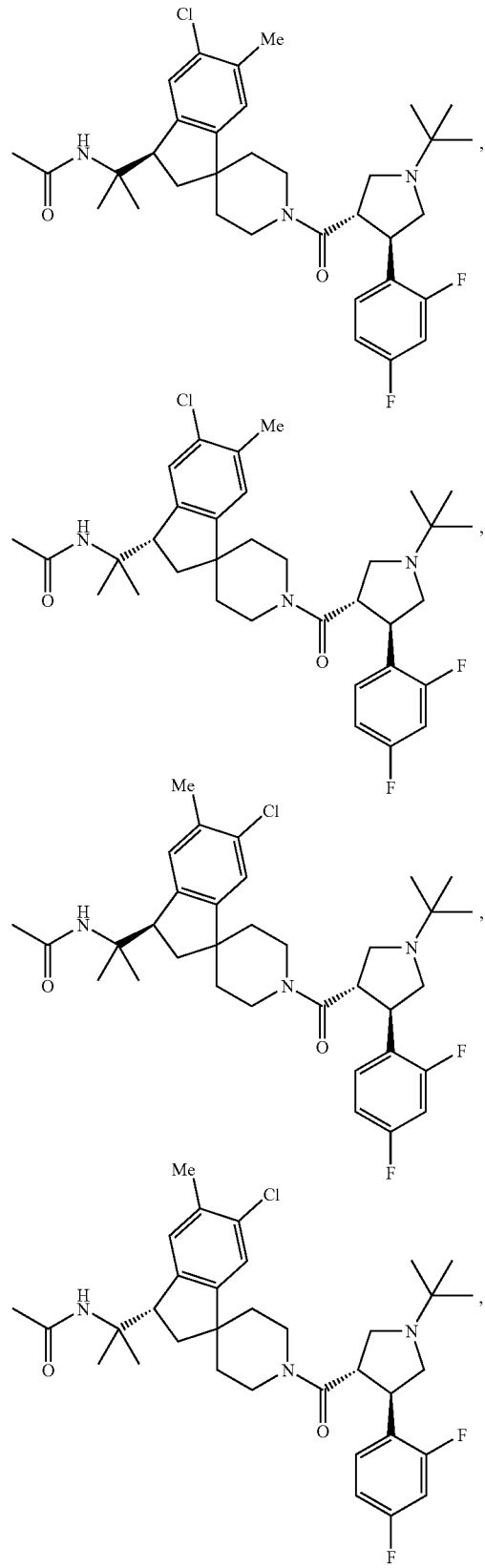

-continued
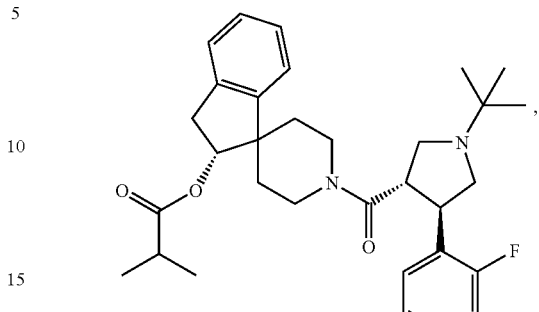
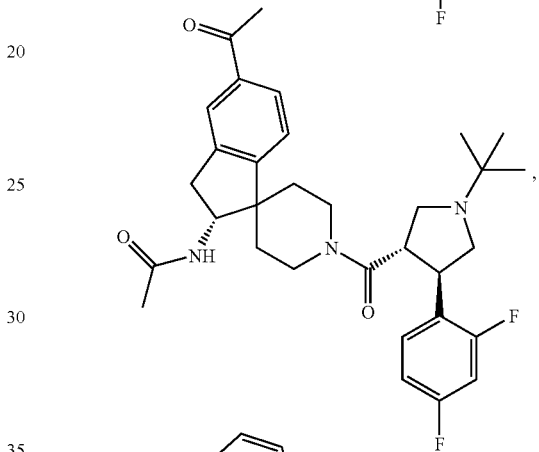
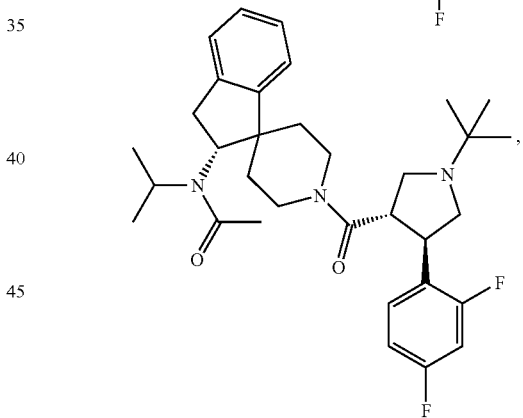
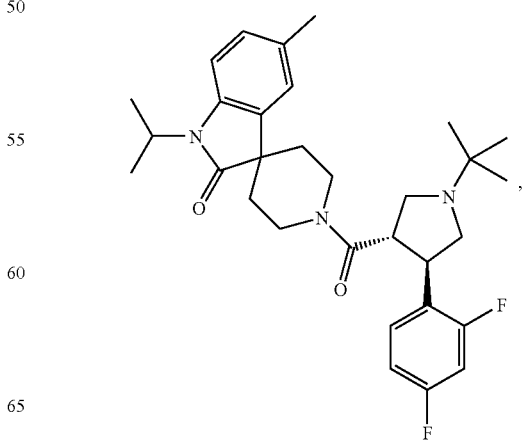
or a pharmaceutically acceptable salt thereof.
12. The compound of claim 10 selected from the group consisting of:

189
-continued
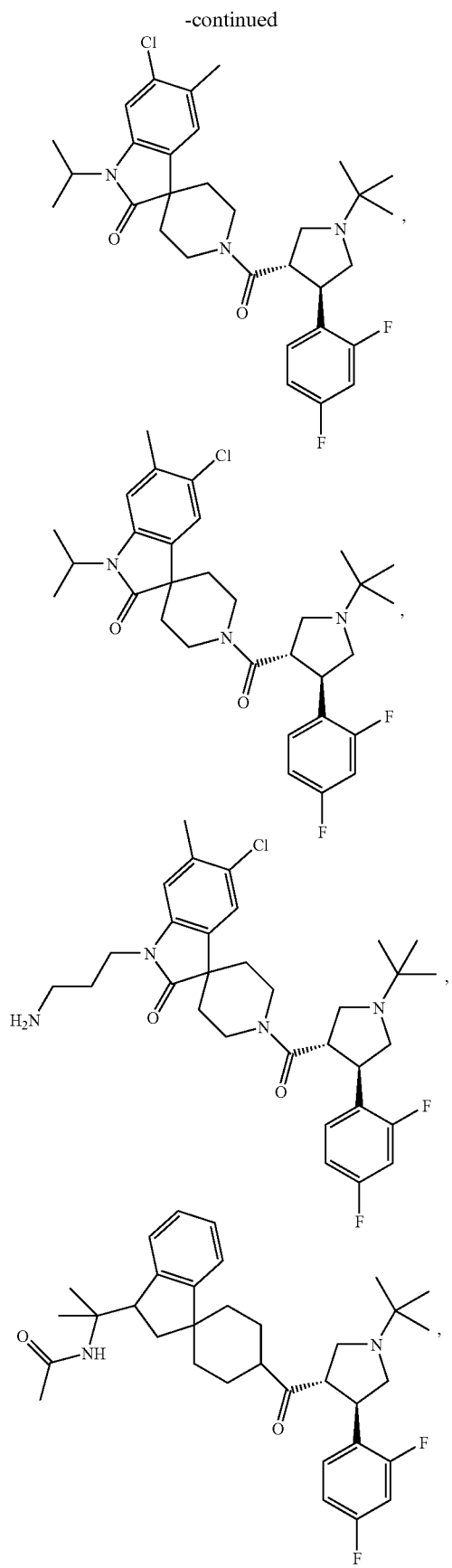
190
-continued
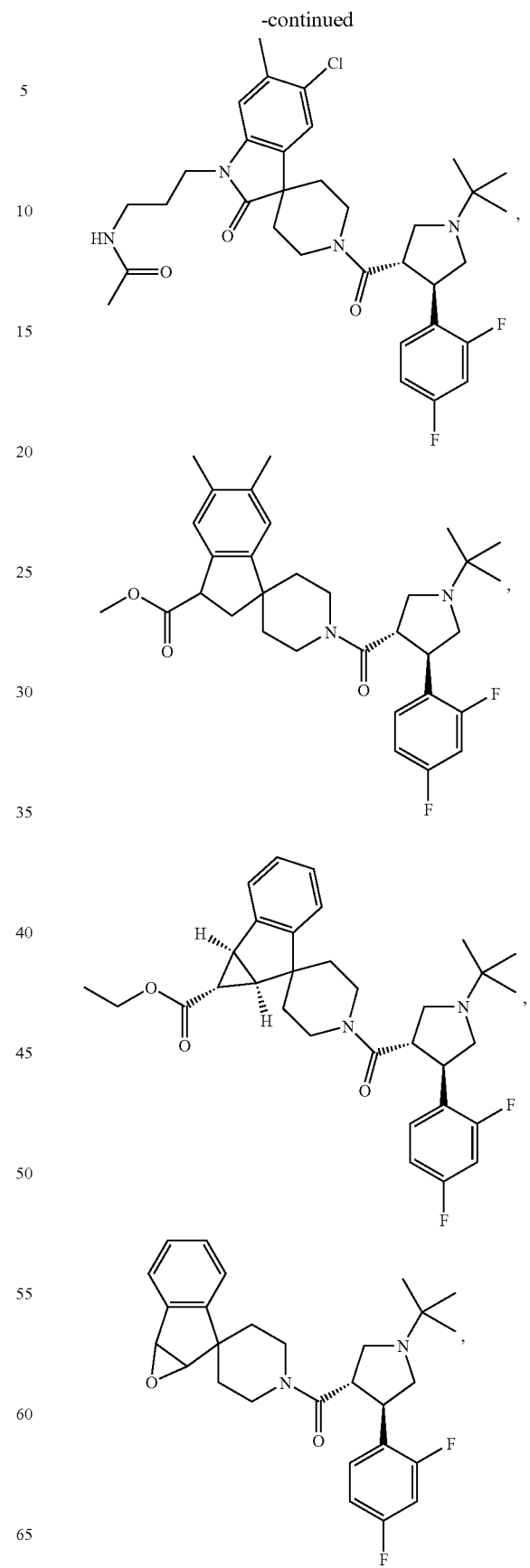

191
-continued
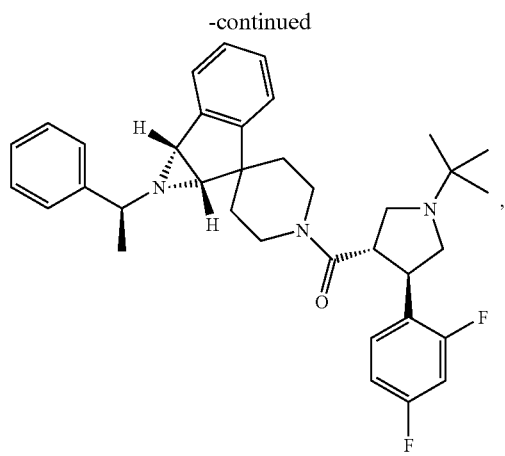
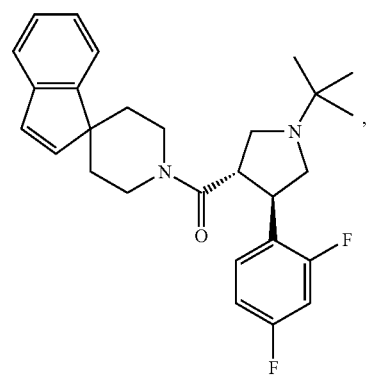
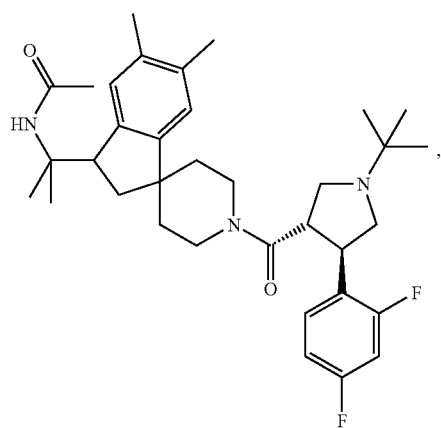
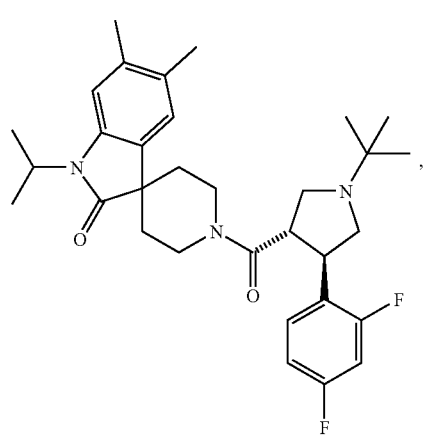
192
-continued
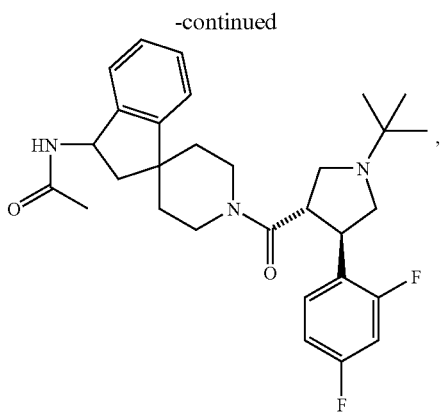
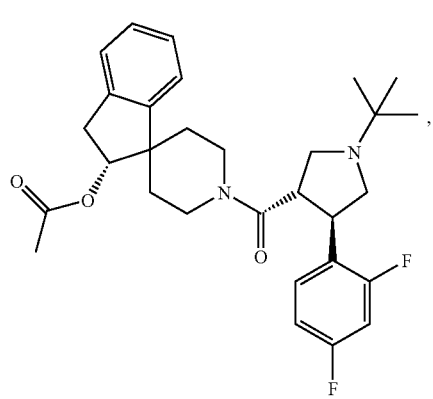
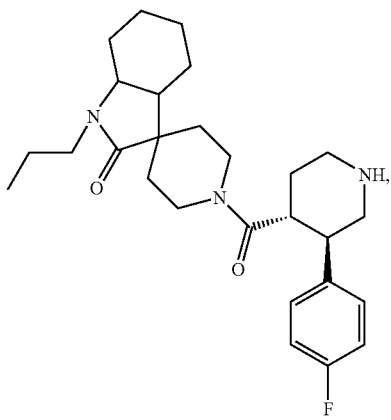
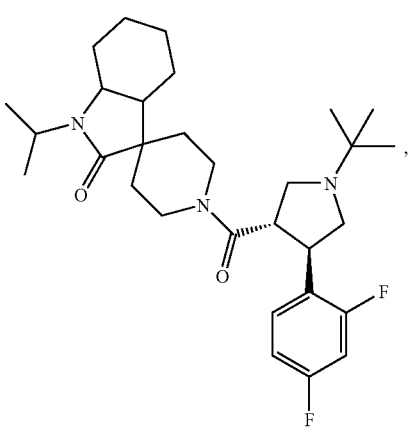

-continued
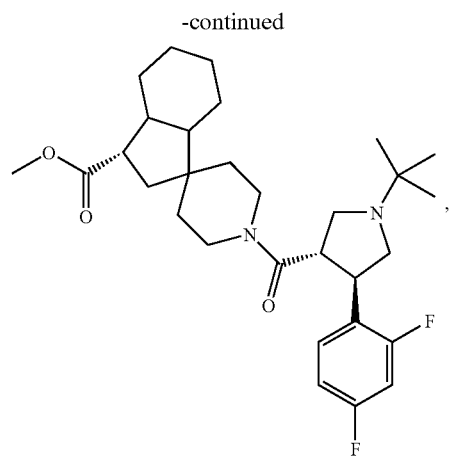
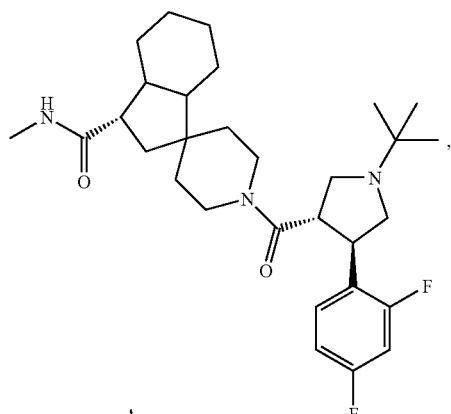
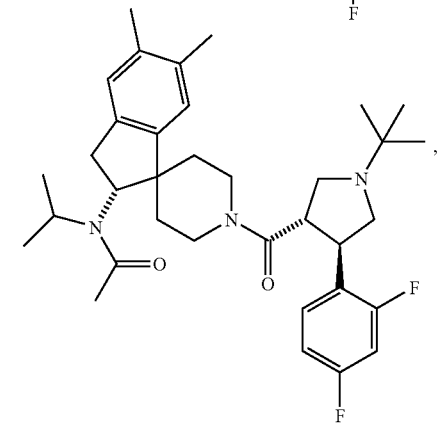
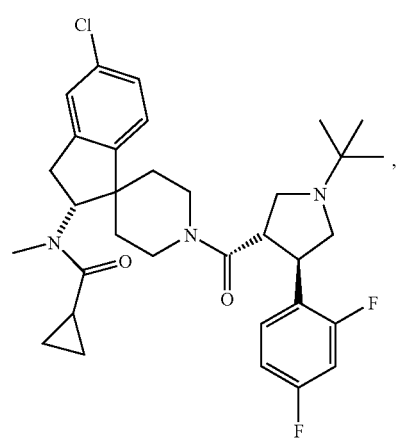
-continued
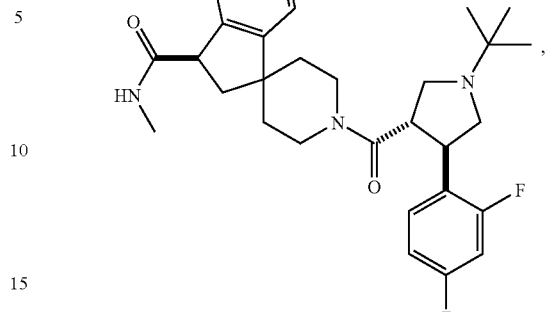
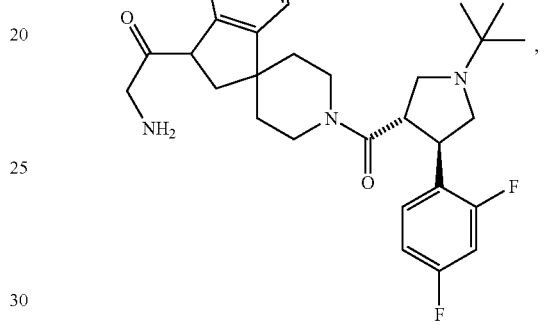
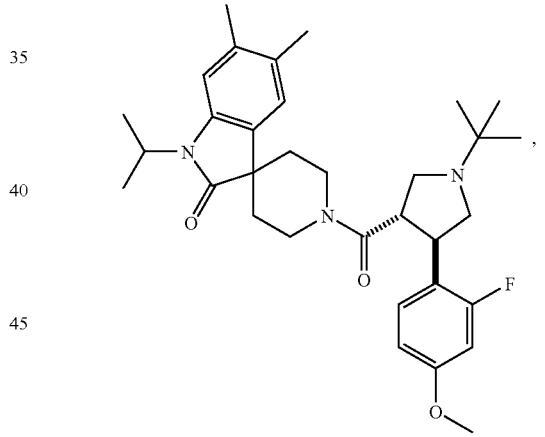
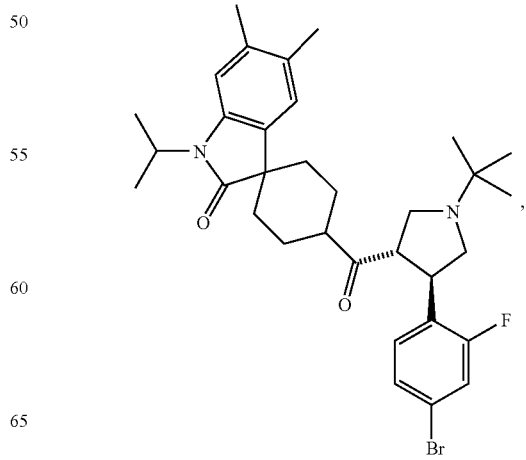

-continued
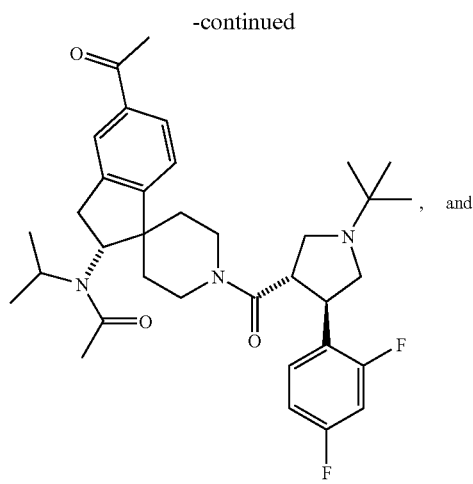
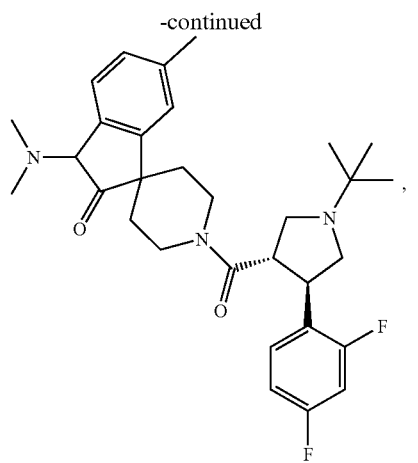
or a pharmaceutically acceptable salt thereof.
13. The compound of claim 12 which is selected from the group consisting of:
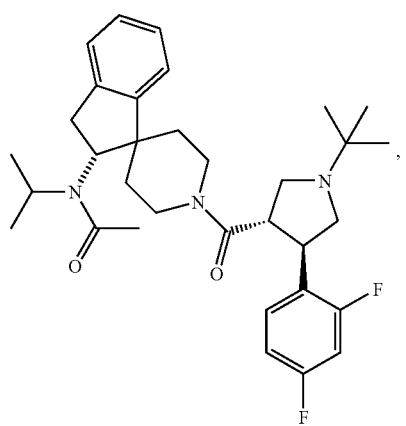
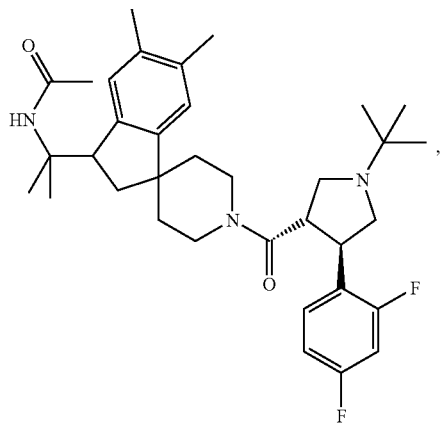

-continued
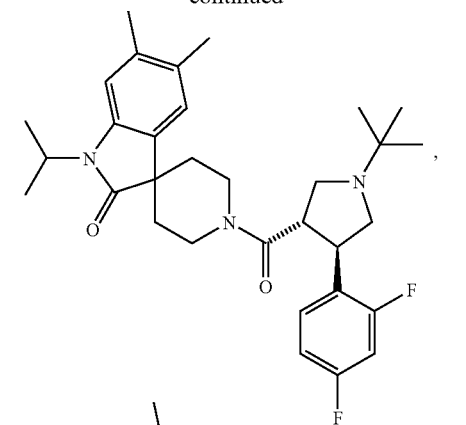
,
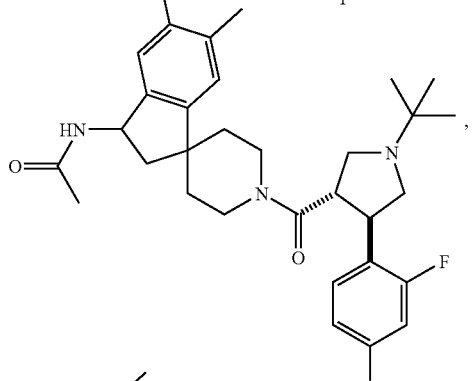
,
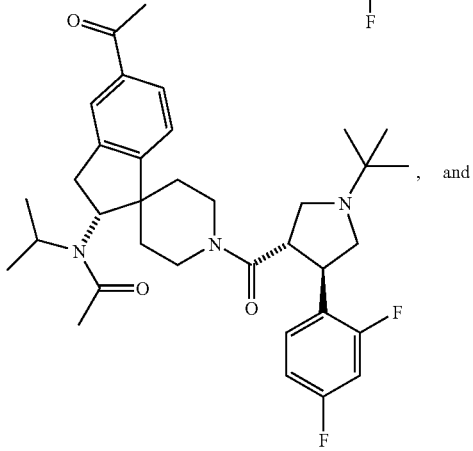
, and
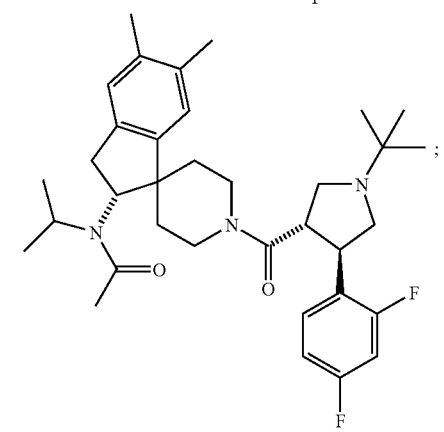
;
or a pharmaceutically acceptable salt thereof.
14. The compound of claim 13 which is:
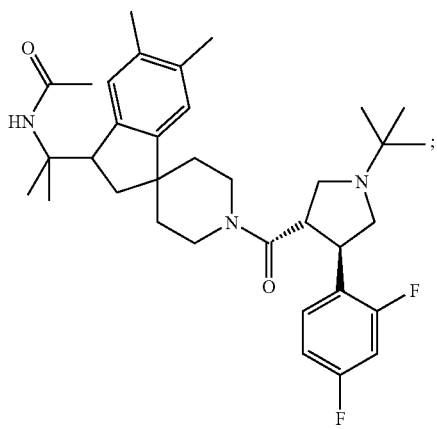
;
or a pharmaceutically acceptable salt thereof.
15. The compound of claim 13 which is:
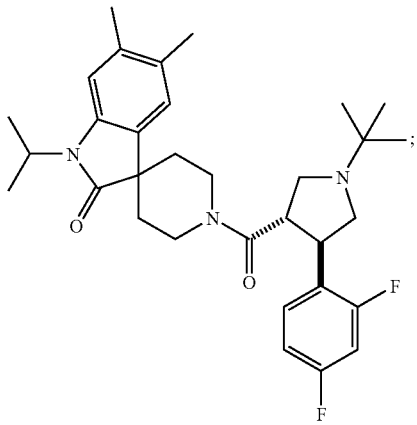
;
or a pharmaceutically acceptable salt thereof.
16. The compound of claim 13 which is:
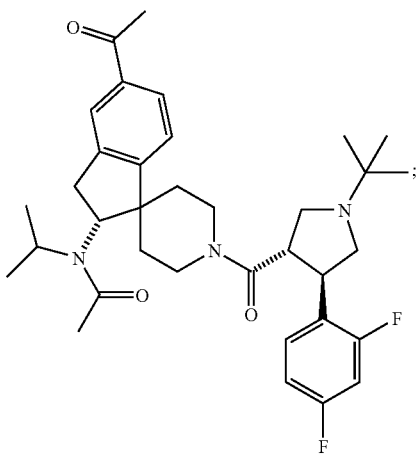
;
or a pharmaceutically acceptable salt thereof.

17. The compound of claim 13 which is:

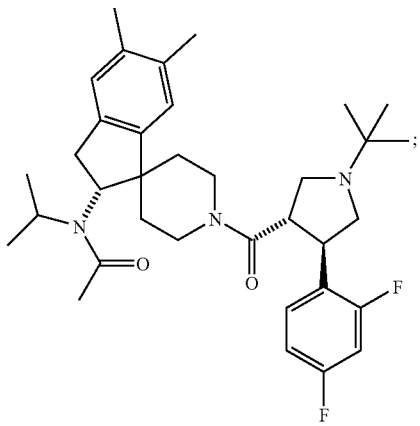

or a pharmaceutically acceptable salt thereof.

18. A compound of structural formula VI:

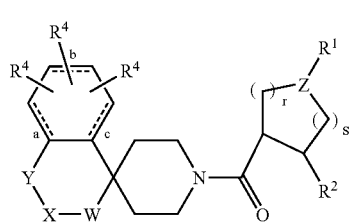

(VI)

or a pharmaceutically acceptable salt thereof; wherein
a, b and c are all single bonds or all double bonds;
W is independently selected from the group consisting of
(1) C(O),
(2) N($R^{10}$), and
(3) C($R^{10}$)$_2$;
X and Y taken together form —C($R^6$)═C($R^6$)—, or
one of X and Y is C($R^6$)$_2$ and the other is selected from the group consisting of
(1) C($R^6$)$_2$,
(2) N($R^6$),
(3) C(O),
(4) C═N($R^6$)
(5) oxygen,
(6) sulfur,
(7) S(O), and
(8) S(O)$_2$,
or one of X and Y is N($R^9$) and the other is selected from the group consisting of
(1) C($R^6$)$_2$,
(2) C(O),
(3) C═N($R^6$)
(4) S(O), and
(5) S(O)$_2$,
or one of X and Y is C(O) and the other is selected from the group consisting of
(1) C($R^6$)$_2$,
(2) N($R^6$),
(3) oxygen, and
(4) sulfur;
Z is independently selected from the group consisting of
(1) CH,
(2) C($R^1$), and
(3) N;

$R^1$ is selected from the group consisting of
(1) hydrogen,
(2) amidino,
(3) —(CH$_2$)$_n$—NR$^7$R$^8$,
(4) C$_{1-4}$ alkyliminoyl,
(5) C$_{0-10}$ alkyl,
(6) —(CH$_2$)$_n$—C$_{3-7}$ cycloalkyl,
(7) —(CH$_2$)$_n$-phenyl,
(8) —(CH$_2$)$_n$-naphthyl, and
(9) —(CH$_2$)$_n$-heteroaryl,
wherein phenyl, naphthyl, and heteroaryl are unsubstituted or substituted with one to three groups independently selected from $R^3$, and wherein alkyl and cycloalkyl are unsubstituted or substituted with one to three groups independently selected from $R^3$ and oxo;
$R^2$ is selected from the group consisting of
(1) phenyl,
(2) naphthyl, and
(3) heteroaryl,
wherein phenyl, naphthyl, and heteroaryl are unsubstituted or substituted with one to three groups independently selected from $R^3$;
each $R^3$ is independently selected from the group consisting of
(1) C$_{1-6}$ alkyl,
(2) —(CH$_2$)$_n$-phenyl,
(3) —(CH$_2$)$_n$-naphthyl,
(4) —(CH$_2$)$_n$-heteroaryl,
(5) —(CH$_2$)$_n$C$_{2-7}$ heterocycloalkyl,
(6) —(CH$_2$)$_n$C$_{3-7}$ cycloalkyl,
(7) halogen,
(8) OR$^5$,
(9) —(CH$_2$)$_n$N(R$^5$)$_2$,
(10) —(CH$_2$)$_n$C≡N,
(11) —(CH$_2$)$_n$CO$_2$R$^5$,
(12) NO$_2$,
(13) —(CH$_2$)$_n$NR$^5$S(O)$_p$R$^5$,
(14) —(CH$_2$)$_n$S(O)$_p$N(R$^5$)$_2$,
(15) —(CH$_2$)$_n$S(O)$_p$R$^5$,
(16) —(CH$_2$)$_n$NR$^5$C(O)N(R$^5$)$_2$,
(17) —(CH$_2$)$_n$C(O)N(R$^5$)$_2$,
(18) —(CH$_2$)$_n$NR$^5$C(O)R$^5$,
(19) —(CH$_2$)$_n$NR$^5$CO$_2$R$^5$,
(20) —(CH$_2$)$_n$NR$^5$C(O)-heteroaryl,
(21) —(CH$_2$)$_n$C(O)NR$^5$N(R$^5$)$_2$,
(22) —(CH$_2$)$_n$C(O)NR$^5$NR$^5$C(O)R$^5$,
(23) O(CH$_2$)$_n$C(O)N(R$^5$)$_2$,
(24) CF$_3$,
(25) CH$_2$CF$_3$,
(26) OCF$_3$, and
(27) OCH$_2$CF$_3$,
wherein phenyl, naphthyl, and heteroaryl are unsubstituted or substituted with one to three substituents independently selected from halogen, hydroxy, C$_{1-4}$ alkyl, trifluoromethyl, and C$_{1-4}$ alkoxy, and wherein alkyl, cycloalkyl, heterocycloalkyl, and (CH$_2$) are unsubstituted or substituted with one to three substituents independently selected from halogen, hydroxy, oxo, C$_{1-4}$ alkyl, trifluoromethyl, and C$_{1-4}$ alkoxy, or wherein two substituents when on the same methylene (CH$_2$) group are taken together with the carbon atom to which they are attached to form a cyclopropyl group;
each $R^4$ is independently selected from the group consisting of
(1) hydrogen,
(2) C$_{1-8}$ alkyl,
(3) —(CH$_2$)$_n$-phenyl, (4) —$(CH_2)_n$-naphthyl,
(5) —$(CH_2)_n$-heteroaryl,
(6) —$(CH_2)_nC_{2-7}$ heterocycloalkyl,
(7) —$(CH_2)_nC_{3-7}$ cycloalkyl,
(8) halogen,
(9) $OR^5$,
(10) —$(CH_2)_nN(R^5)_2$,
(11) —$(CH_2)_nC\equiv N$,
(12) —$(CH_2)_nC(O)OR^5$,
(13) —$(CH_2)_nOC(O)R^5$,
(14) $NO_2$,
(15) —$(CH_2)_nNR^5S(O)_pR^5$,
(16) —$(CH_2)_nN(S(O)_pR^5)_2$,
(17) —$(CH_2)_nS(O)_pN(R^5)_2$,
(18) —$(CH_2)_nS(O)_pR^5$,
(19) —$(CH_2)_nNR^5C(O)N(R^5)_2$,
(20) —$(CH_2)_nC(O)N(R^5)_2$,
(21) —$(CH_2)_nNR^5C(O)R^5$,
(22) —$(CH_2)_nNR^5CO_2R^5$,
(23) —$(CH_2)_nNR^5C(O)$-heteroaryl,
(24) —$(CH_2)_nC(O)NR^5N(R^5)_2$,
(25) —$(CH_2)_nC(O)NR^5NR^5C(O)R^5$,
(26) $O(CH_2)_nC(O)N(R^5)_2$,
(27) $CF_3$,
(28) $CH_2CF_3$,
(29) $OCF_3$, and
(30) $OCH_2CF_3$,
wherein phenyl, naphthyl, and heteroaryl are unsubstituted or substituted with one to three substituents independently selected from halogen, hydroxy, $C_{1-4}$ alkyl, trifluoromethyl, and $C_{1-4}$ alkoxy, and wherein alkyl, cycloalkyl, heterocycloalkyl, and $(CH_2)$ are unsubstituted or substituted with one to three substituents independently selected from halogen, hydroxy, oxo, $C_{1-4}$ alkyl, trifluoromethyl, and $C_{1-4}$ alkoxy, or wherein two substituents when on the same methylene $(CH_2)$ group are taken together with the carbon atom to which they are attached to form a cyclopropyl group;

each $R^5$ is independently selected from the group consisting of
(1) hydrogen,
(2) $C_{1-8}$ alkyl,
(3) —$(CH_2)_nC_{3-7}$ cycloalkyl,
(4) —$(CH_2)_nC_{2-7}$ heterocycloalkyl,
(5) —$(CH_2)_n$-phenyl,
(6) —$(CH_2)_n$-naphthyl,
(7) —$(CH_2)_n$-heteroaryl, and
(8) —$(CH_2)_nC_{3-7}$ bicycloalkyl,
wherein alkyl, phenyl, heteroaryl, heterocycloalkyl, naphthyl, cycloalkyl, bicycloalkyl and $(CH_2)$ are unsubstituted or substituted with one to three groups independently selected from halogen, $C_{1-4}$ alkyl, hydroxy, and $C_{1-4}$ alkoxy, or wherein two $R^5$ groups together with the atom to which they are attached form a 4- to 8-membered mono- or bicyclic ring system optionally containing an additional heteroatom selected from O, S, and —$NC_{1-4}$ alkyl;

each $R^6$ is independently selected from the group consisting of
(1) hydrogen,
(2) $C_{1-6}$ alkyl,
(3) —$(CH_2)_nC_{3-7}$ cycloalkyl,
(4) —$(CH_2)_nC_{2-7}$ heterocycloalkyl,
(5) —$(CH_2)_n$-phenyl,
(6) —$(CH_2)_n$-naphthyl,
(7) —$(CH_2)_n$-heteroaryl,
(8) —$(CH_2)_nC(O)R^5$,
(9) —$(CH_2)_nC(O)OR^5$,
(10) —$(CH_2)_nC(OH)R^5$,
(11) —$(CH_2)_nC(O)(CH_2)_n$—$N(R^5)_2$,
(12) —$(CH_2)_nC(O)(CH_2)_n$—$NR^7R^8$,
(13) —$(CH_2)_n$—$OR^5$,
(14) —$(CH_2)_n$—$OC(O)R^5$,
(15) —$(CH_2)_n$—O—$(CH_2)_n$—$N(R^5)_2$,
(16) —$(CH_2)_nCN$,
(17) —$(CH_2)_nN(R^5)_2$,
(18) —$(CH_2)_nN(R^5)C(O)R^5$,
(19) —$(CH_2)_nN(C(O)R^5)_2$,
(20) —$(CH_2)_nN(R^5)C(O)OR^5$,
(21) —$(CH_2)_nN(C(O)OR^5)_2$,
(22) —$(CH_2)_nN(R^5)C(O)(CH_2)_nN(R^5)_2$,
(23) —$(CH_2)_nN(R^5)S(O)$—$C_{1-8}$ alkyl,
(24) —$(CH_2)_nN(R^5)$—$S(O)_2$—$C_{1-8}$ alkyl,
(25) —$(CH_2)_n$—S—$R^5$,
(26) —$(CH_2)_n$—S(O)—$R^5$, and
(27) —$(CH_2)_n$—$S(O)_2$—$R^5$,
wherein phenyl, naphthyl, and heteroaryl are unsubstituted or substituted with one to three groups independently selected from $R^3$, and wherein alkyl, cycloalkyl and heterocycloalkyl are unsubstituted or substituted with one to three groups independently selected from $R^3$ and oxo, and wherein any methylene $(CH_2)$ in $R^6$ is unsubstituted or substituted with one to two groups independently selected from halogen, hydroxy, and $C_{1-4}$ alkyl, or wherein two $R^6$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from $R^3$ and oxo;

each $R^7$ and $R^8$ is independently selected from the group consisting of
(1) hydrogen,
(2) amidino,
(3) $C_{1-4}$ alkyliminoyl,
(4) $C_{1-10}$ alkyl,
(5) —$(CH_2)_n$—$C_{3-7}$ cycloalkyl,
(6) —$(CH_2)_n$-phenyl,
(7) —$(CH_2)_n$-naphthyl, and
(8) —$(CH_2)_n$-heteroaryl,
wherein phenyl, naphthyl, and heteroaryl are unsubstituted or substituted with one to three groups independently selected from $R^3$, and wherein alkyl and cycloalkyl are unsubstituted or substituted with one to three groups independently selected from $R^3$ and oxo;

each $R^9$ is independently selected from the group consisting of
(1) hydrogen,
(2) $C_{1-6}$ alkyl,
(3) —$(CH_2)_nC_{3-7}$ cycloalkyl,
(4) —$(CH_2)_nC_{2-7}$ heterocycloalkyl,
(5) —$(CH_2)_n$-phenyl,
(6) —$(CH_2)_n$-naphthyl,
(7) —$(CH_2)_n$-heteroaryl,
(8) —$(CH_2)_nC(O)R^5$,
(9) —$(CH_2)_nC(O)OR^5$,
(10) —$(CH_2)_nC(OH)R^5$,
(11) —$(CH_2)_nC(O)(CH_2)_n$—$N(R^5)_2$,
(12) —$(CH_2)_nC(O)(CH_2)_n$—$NR^7R^8$,
(13) —$(CH_2)_m$—$OR^5$,
(14) —$(CH_2)_m$—$OC(O)R^5$,
(15) —$(CH_2)_m$—O—$(CH_2)_n$—$N(R^5)_2$,
(16) —$(CH_2)_mCN$,

(17) —(CH$_2$)$_m$N(R$^5$)$_2$,
(18) —(CH$_2$)$_m$N(R$^5$)C(O)R$^5$,
(19) —(CH$_2$)$_m$N(C(O)R$^5$)$_2$,
(20) —(CH$_2$)$_m$N(R$^5$)C(O)OR$^5$,
(21) —(CH$_2$)$_m$N(C(O)OR$^5$)$_2$,
(22) —(CH$_2$)$_m$N(R$^5$)C(O)(CH$_2$)$_n$N(R$^5$)$_2$,
(23) —(CH$_2$)$_m$N(R$^5$)—S(O)—C$_{1-8}$ alkyl,
(24) —(CH$_2$)$_m$N(R$^5$)—S(O)$_2$—C$_{1-8}$ alkyl,
(25) —(CH$_2$)$_m$—S—R$^5$,
(26) —(CH$_2$)$_n$—S(O)—R$^5$, and
(27) —(CH$_2$)$_n$—S(O)$_2$—R$^5$, wherein phenyl, naphthyl, and heteroaryl are unsubstituted or substituted with one to three groups independently selected from R$^3$, and wherein alkyl, cycloalkyl and heterocycloalkyl are unsubstituted or substituted with one to three groups independently selected from R$^3$ and oxo, and wherein any methylene (CH$_2$) in R$^9$ is unsubstituted or substituted with one to two groups independently selected from halogen, hydroxy, and C$_{1-4}$ alkyl; or wherein two R$^9$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from R$^3$ and oxo;

each R$^{10}$ is independently selected from the group consisting of
(1) hydrogen,
(2) —C$_{1-6}$ alkyl,
(3) —C(O)—C$_{1-6}$ alkyl, and
(4) —S(O)$_2$—C$_{1-6}$ alkyl;

r is 1 or 2;
s is 1 or 2;
n is 0, 1, 2, or 3;
m is 1, 2, or 3; and
p is 0, 1, or 2.

19. A pharmaceutical composition which comprises a compound of claim 1 and a pharmaceutically acceptable carrier.

20. The compound of claim 11 wherein the pharmaceutically acceptable salt thereof is the hydrochloride salt.

21. The compound of claim 11 wherein the pharmaceutically acceptable salt thereof is the trifluoroacetic acid salt.

22. The compound of claim 11 which is:

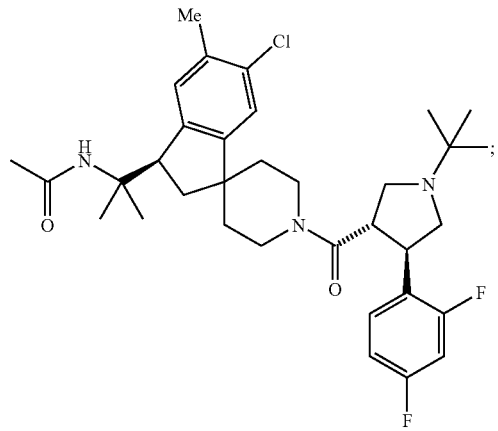

or a pharmaceutically acceptable salt thereof.

* * * * *